US007964207B2

(12) United States Patent  (10) Patent No.: US 7,964,207 B2
Deslauriers et al.  (45) Date of Patent: Jun. 21, 2011

(54) METHODS OF PERFORMING MEDICAL PROCEDURES THAT PROMOTE BONE GROWTH, METHOD OF MAKING COMPOSITIONS THAT PROMOTE BONE GROWTH, AND APPARATUS FOR USE IN SUCH METHODS

(75) Inventors: Richard Deslauriers, Woodbury, CT (US); Aisa Sendijarevic, Troy, MI (US)

(73) Assignee: Doctor's Research Group, Inc., Wolcott, CT (US)

( * ) Notice: Subject to any disclaimer, the term of this patent is extended or adjusted under 35 U.S.C. 154(b) by 1087 days.

(21) Appl. No.: 11/089,489

(22) Filed: Mar. 24, 2005

(65) Prior Publication Data

US 2005/0220771 A1    Oct. 6, 2005

Related U.S. Application Data

(63) Continuation-in-part of application No. 10/808,188, filed on Mar. 24, 2004, which is a continuation-in-part of application No. 10/395,001, filed on Mar. 24, 2003.

(60) Provisional application No. 60/366,335, filed on Mar. 22, 2002.

(51) Int. Cl.
    *A61F 2/00*    (2006.01)
(52) U.S. Cl. ........................................................ 424/423
(58) Field of Classification Search .................. None
    See application file for complete search history.

(56) References Cited

U.S. PATENT DOCUMENTS

| | | |
|---|---|---|
| 3,030,951 A | 4/1962 | Mandarino |
| 3,112,743 A | 12/1963 | Cochran et al. |
| 4,256,617 A | 3/1981 | Kroplinski et al. ............. 260/18 |
| 4,267,299 A | 5/1981 | Oechsle, III et al. ........... 528/48 |
| 4,440,750 A | 4/1984 | Glowacki et al. |
| 4,477,604 A | 10/1984 | Oechsle, III ................... 523/116 |
| 4,502,479 A * | 3/1985 | Garwood et al. .................. 602/8 |
| 4,515,930 A | 5/1985 | Omura et al. .................. 526/276 |
| 4,525,493 A | 6/1985 | Omura et al. .................. 523/116 |
| 4,539,382 A | 9/1985 | Omura et al. .................. 526/276 |
| 4,570,270 A | 2/1986 | Oechsle, III .................... 623/18 |
| 4,598,136 A | 7/1986 | Wick .............................. 528/56 |
| 4,612,384 A | 9/1986 | Omura et al. .................. 558/198 |
| 4,625,722 A | 12/1986 | Murray ........................... 128/92 |
| 4,627,434 A | 12/1986 | Murray .......................... 128/303 |
| 4,650,847 A | 3/1987 | Omura et al. .................. 526/276 |
| 4,698,318 A | 10/1987 | Vogel et al. ..................... 501/10 |
| 4,731,394 A | 3/1988 | Vogel et al. .................... 523/115 |
| 4,814,423 A | 3/1989 | Huang et al. ................... 528/230 |
| 4,844,259 A | 7/1989 | Glowczewskie, Jr. et al. |
| 4,898,734 A | 2/1990 | Mathiowitz et al. ........... 424/426 |
| 4,938,769 A | 7/1990 | Shaw ........................ 623/20.15 |
| 4,994,030 A | 2/1991 | Glowczewskie, Jr. et al. |
| 5,009,666 A | 4/1991 | Van Syckle et al. ....... 623/23.28 |
| 5,019,096 A | 5/1991 | Fox, Jr. et al. ................. 600/36 |
| 5,061,286 A | 10/1991 | Lyle |
| 5,073,373 A | 12/1991 | O'Leary et al. |
| 5,084,051 A | 1/1992 | Tormala et al. .................. 606/77 |
| 5,236,456 A | 8/1993 | O'Leary et al. |
| 5,270,300 A | 12/1993 | Hunziker ......................... 514/12 |
| 5,284,655 A | 2/1994 | Bogdansky et al. |
| 5,290,558 A | 3/1994 | O'Leary et al. |
| 5,298,254 A | 3/1994 | Prewett et al. |
| 5,314,476 A | 5/1994 | Prewett et al. |
| 5,326,532 A | 7/1994 | Taylor ........................... 422/100 |
| 5,399,665 A | 3/1995 | Barrera et al. ................. 528/354 |
| 5,405,390 A | 4/1995 | O'Leary et al. |
| 5,439,684 A | 8/1995 | Prewett et al. |
| 5,443,514 A | 8/1995 | Steffee |
| 5,461,124 A | 10/1995 | Ritter et al. ..................... 526/84 |
| 5,484,601 A | 1/1996 | O'Leary et al. |
| 5,507,813 A | 4/1996 | Dowd et al. |
| 5,510,396 A | 4/1996 | Prewett et al. |
| 5,514,378 A | 5/1996 | Mikos ........................... 424/425 |
| 5,525,648 A | 6/1996 | Aasen et al. .................. 523/116 |
| 5,607,474 A | 3/1997 | Athanasiou ..................... 623/11 |
| 5,626,861 A | 5/1997 | Laurencin .................... 424/426 |
| 5,676,146 A | 10/1997 | Scarborough |
| 5,681,872 A | 10/1997 | Erbe .............................. 523/114 |
| 5,735,900 A | 4/1998 | Barrett et al. ................. 128/898 |
| 5,800,899 A * | 9/1998 | Sandvig et al. ................. 428/96 |
| 5,846,484 A | 12/1998 | Scarborough et al. |
| 5,849,331 A | 12/1998 | Ducheyne .................... 424/484 |
| 5,885,234 A * | 3/1999 | Sandvig et al. .................. 602/8 |
| 5,895,426 A | 4/1999 | Scarborough et al. |
| 5,899,939 A | 5/1999 | Boyce et al. |
| 5,913,899 A | 6/1999 | Barrett et al. ................... 623/18 |
| 5,914,356 A | 6/1999 | Erbe .............................. 523/114 |
| 5,919,473 A | 7/1999 | Elkhoury ...................... 424/422 |
| 5,980,948 A | 11/1999 | Goedemoed et al. |
| 6,022,887 A | 2/2000 | Gasper et al. ................. 514/451 |
| 6,048,346 A | 4/2000 | Reiley et al. .................... 606/92 |
| 6,110,484 A | 8/2000 | Sierra ........................... 424/426 |
| 6,123,731 A | 9/2000 | Boyce et al. |
| 6,136,029 A | 10/2000 | Johnson et al. ................. 623/16 |

(Continued)

FOREIGN PATENT DOCUMENTS

BR    MU 7802499-4 U    6/2000

(Continued)

OTHER PUBLICATIONS http://www.merriam-webster.com/dictionary/porosity, accessed Nov. 29, 2008.*

(Continued)

*Primary Examiner* — Michael G Hartley
*Assistant Examiner* — Paul Dickinson
(74) *Attorney, Agent, or Firm* — Fish & Richardson P.C.

(57) ABSTRACT

Methods of performing medical procedures, and methods of making bone-growth-promoting compositions useful in performing medical procedures are provided. Apparatus useful both in methods of performing medical procedures, and in methods of making bone-growth-promoting compositions useful in performing medical procedures, are provided. The bone-growth-promoting compositions made according to the disclosed methods are biocompatible, and are adapted to stimulate bone growth when positioned in contact with, or in the vicinity of, a bone of a mammal.

16 Claims, 134 Drawing Sheets

U.S. PATENT DOCUMENTS

| | | | |
|---|---|---|---|
| 6,140,452 A | 10/2000 | Felt et al. | |
| 6,143,354 A | 11/2000 | Koulik et al. | 427/2.24 |
| 6,162,258 A | 12/2000 | Scarborough et al. | |
| 6,277,149 B1 | 8/2001 | Boyle et al. | |
| 6,277,394 B1 | 8/2001 | Sierra | 424/426 |
| 6,280,456 B1 | 8/2001 | Scribner et al. | 606/192 |
| 6,294,187 B1 | 9/2001 | Boyce et al. | |
| 6,296,667 B1 | 10/2001 | Johnson et al. | 623/23 |
| 6,299,448 B1 | 10/2001 | Zdrahala et al. | 433/173 |
| 6,303,179 B1 | 10/2001 | Koulik et al. | 427/2.26 |
| D450,240 S | 11/2001 | Haag et al. | |
| 6,332,779 B1 | 12/2001 | Boyce et al. | |
| 6,348,055 B1 | 2/2002 | Preissman | 606/94 |
| 6,368,322 B1 | 4/2002 | Luks et al. | |
| 6,376,742 B1 | 4/2002 | Zdrahala et al. | |
| 6,383,519 B1 | 5/2002 | Sapieszko et al. | 424/489 |
| 6,387,391 B1 | 5/2002 | Shikinami et al. | 424/426 |
| 6,426,186 B1 | 7/2002 | Jones et al. | 435/6 |
| 6,428,579 B1 | 8/2002 | Valentini | 623/23.76 |
| 6,436,138 B1 | 8/2002 | Dowd et al. | |
| 6,458,162 B1 | 10/2002 | Koblish et al. | 623/23.51 |
| 6,478,825 B1 | 11/2002 | Winterbottom et al. | 623/23.63 |
| 6,482,871 B1 | 11/2002 | Aasen et al. | 523/116 |
| 6,485,737 B1 | 11/2002 | Mao et al. | 424/426 |
| 6,508,841 B2 | 1/2003 | Martin et al. | 623/23 |
| 6,520,964 B2 | 2/2003 | Tallarida et al. | 606/71 |
| 6,521,246 B2 | 2/2003 | Sapieszko et al. | 424/423 |
| 6,547,823 B2 | 4/2003 | Scarborough et al. | |
| 6,576,263 B2 | 6/2003 | Truong | 424/489 |
| 6,582,446 B1 | 6/2003 | Marchosky | 606/167 |
| 6,585,992 B2 | 7/2003 | Pugh | 424/422 |
| 6,586,009 B1 | 7/2003 | Lidgren | 424/489 |
| 6,599,448 B1 | 7/2003 | Ehrhard, Jr. et al. | 252/582 |
| 6,599,520 B2 | 7/2003 | Scarborough et al. | |
| 6,607,544 B1 | 8/2003 | Boucher et al. | 606/192 |
| 6,610,067 B2 | 8/2003 | Tallarida et al. | 606/102 |
| 6,613,054 B2 | 9/2003 | Scribner et al. | 606/93 |
| 6,616,698 B2 | 9/2003 | Scarborough | |
| 6,622,864 B1 | 9/2003 | Debbs et al. | |
| 6,626,945 B2 | 9/2003 | Simon et al. | 623/17.19 |
| 6,632,235 B2 | 10/2003 | Weikel et al. | 606/192 |
| 6,632,246 B1 | 10/2003 | Simon et al. | 623/14.12 |
| 6,641,587 B2 | 11/2003 | Scribner et al. | 606/93 |
| 6,641,831 B1 | 11/2003 | Schierholz | 424/422 |
| 6,645,213 B2 | 11/2003 | Sand et al. | 606/92 |
| 6,669,730 B2 | 12/2003 | Ralph et al. | 623/17.13 |
| 6,679,917 B2 | 1/2004 | Ek | 623/20.14 |
| 6,696,073 B2 | 2/2004 | Boyce et al. | 424/422 |
| 6,706,067 B2 | 3/2004 | Shimp et al. | |
| 6,716,216 B1 | 4/2004 | Boucher et al. | 606/86 |
| 6,719,761 B1 | 4/2004 | Reiley et al. | 606/92 |
| 6,726,691 B2 | 4/2004 | Osorio et al. | 606/94 |
| 6,752,831 B2 | 6/2004 | Sybert et al. | |
| 6,755,862 B2 | 6/2004 | Keynan | 623/16.11 |
| 6,814,736 B2 | 11/2004 | Reiley et al. | 606/92 |
| 6,827,743 B2 | 12/2004 | Eisermann et al. | 623/23.54 |
| 6,852,125 B2 | 2/2005 | Simon et al. | 623/16.11 |
| 6,855,167 B2 | 2/2005 | Shimp et al. | |
| 6,863,694 B1 | 3/2005 | Boyce et al. | |
| 6,863,899 B2 | 3/2005 | Koblish et al. | 424/423 |
| 6,899,713 B2 | 5/2005 | Shaolian et al. | 606/61 |
| 6,899,719 B2 | 5/2005 | Reiley et al. | 606/192 |
| 6,921,264 B2 | 7/2005 | Mayer et al. | 433/173 |
| 6,989,830 B2 | 1/2006 | Stollnitz et al. | 345/420 |
| 6,991,803 B2 | 1/2006 | Sapieszko et al. | 424/423 |
| 7,001,431 B2 | 2/2006 | Bao et al. | 623/17.12 |
| 7,008,226 B2 | 3/2006 | Mayer et al. | 433/173 |
| 7,077,865 B2 | 7/2006 | Bao et al. | |
| 2002/0016636 A1 | 2/2002 | Ricci et al. | 623/23.51 |
| 2002/0044888 A1 | 4/2002 | Morris et al. | |
| 2002/0072550 A1 | 6/2002 | Brady et al. | 521/155 |
| 2002/0095213 A1 | 7/2002 | Bakker et al. | |
| 2002/0128717 A1 | 9/2002 | Alfaro et al. | |
| 2003/0009235 A1 | 1/2003 | Manrique et al. | |
| 2003/0060825 A1 | 3/2003 | Alfaro et al. | |
| 2003/0083747 A1 | 5/2003 | Winterbottom et al. | |
| 2003/0097182 A1 | 5/2003 | Buchman et al. | 623/18.11 |
| 2003/0099630 A1 | 5/2003 | DiBenedetto et al. | 424/94.64 |
| 2003/0104069 A1 | 6/2003 | Higham | 424/494 |
| 2003/0105530 A1 | 6/2003 | Pirhonen et al. | 623/23.72 |
| 2003/0108589 A1 | 6/2003 | Lacout et al. | 424/423 |
| 2003/0114552 A1 | 6/2003 | Schacht | 523/113 |
| 2003/0114936 A1 | 6/2003 | Sherwood et al. | 623/23.58 |
| 2003/0143258 A1 | 7/2003 | Knaack et al. | |
| 2004/0024457 A1 | 2/2004 | Boyce et al. | |
| 2004/0052829 A1 | 3/2004 | Shimp | |
| 2004/0146543 A1 | 7/2004 | Shimp et al. | |
| 2004/0243242 A1 | 12/2004 | Sybert et al. | |
| 2004/0249327 A1 * | 12/2004 | Sendijarevic et al. | 602/8 |
| 2004/0259966 A1 * | 12/2004 | Lovette | 521/82 |
| 2005/0008620 A1 | 1/2005 | Shimp et al. | |
| 2005/0008672 A1 | 1/2005 | Winterbottom et al. | |
| 2005/0013793 A1 * | 1/2005 | Beckman et al. | 424/78.27 |
| 2005/0027033 A1 * | 2/2005 | Knaack et al. | 523/115 |
| 2005/0251267 A1 | 11/2005 | Winterbottom et al. | |
| 2006/0216323 A1 | 9/2006 | Knaack et al. | |

FOREIGN PATENT DOCUMENTS

| | | |
|---|---|---|
| BR | 7900159 | 9/2000 |
| BR | MU 7900159-9 U | 9/2000 |
| BR | 7900158 | 10/2000 |
| BR | MU 7900158-0 U | 10/2000 |
| BR | PI 0006544-7 A | 6/2001 |
| DE | 268 114 A3 | 5/1989 |
| DE | 268 119 A3 | 5/1989 |
| DE | 268 130 A3 | 5/1989 |
| DE | 295 827 AS | 11/1991 |
| EP | 0 867 422 A2 | 9/1998 |
| WO | WO 94/09048 | 4/1994 |
| WO | WO 96/39201 | 12/1996 |
| WO | WO 2004009227 A2 * | 1/2004 |
| WO | WO 2004/085508 | 10/2004 |

OTHER PUBLICATIONS

Ruy Alberto Corrêa Altafim, et al., "The Effects of Fillers on Polyurethane Resin-Based Electrical Insulators," Materials Research, vol. 6, No. 2, pp. 187-191, 2003.

A. Seth Greenwald, D. Phil, et al., "Bone-Graft Substitutes: Facts, Fictions & applications," The American Academy of Orthopaedic Surgeons, Feb. 13-17, 2002.

S. N. Parikh, "Bone Graft Substitutes: Past, Present, Future," Journal of Postgraduate Medicine, vol. 48, Issue 2, pp. 142-148, 2002.

Patrick McGee, "Bone Substitutes Are More Plentiful But Barriers Remain," Orthopedics Today, Oct. 2001.

Sylwester Gogolewki, "Nonmetallic Materials for Bone Substitutes," European Cells and Materials, vol. 1, Suppl. 2, pp. 54-55, 2001.

Daniel Klempner, et al., "Handbook of Polymeric Foams and Foam Technology," Hanser Publishers, pp. 12-15, 47-72, 73-94, and 95-134, 1991.

Salvador Claro Neto, "Thesis for Doctor'S Degree," pp. 117-120 (in English and Portuguese), Estimated 1997.

Helencar Ignácio, et al., "The Use of a Polyurethane Derived From Castor Oil to Fill Segmental Diaphyseal Defects in Radii; An Experimental Study in Rabbits," Rev. Bras. Ortop., vol. 32, N. 10, Oct. 1997.

Renata Hinhug Vilarinho, et al., "Implant of Vegetable Polyurethane in the Anterior Chamber of the Mouse Eye," Odonto 2000—Odontologia Do Seculo XXI-VI, N. 00, 1996.

Salvador Claro Neto, et al., "Caracterizacão Mecãnica De Poliuretano Utilizado Para Implante Osseo", Undated.

Mission Impossible—Inconceivable Surgeries Successfully Accomplished, www.3dsystems.com/appsolutions/casestudies/PDF/CS_styles.PDF, 2003.

Examiner Abigail Manda Cotton, Office Action, U.S. Appl. No. 10/395,001, mailed Mar. 29, 2007, 30 pages.

Examiner Deirdre Renee Claytor, Final Office Action, U.S. Appl. No. 10/395,001, mailed Dec. 18, 2007, 9 pages.

Examiner Deirdre Renee Claytor, Office Action, U.S. Appl. No. 10/395,001, mailed May 29, 2008, 10 pages.

Examiner Deirdre Renee Claytor, Final Office Action, U.S. Appl. No. 10/395,001, mailed Jan. 23, 2009, 10 pages.

Examiner Randall English, Examiner's First Report, Australian Application Serial No. 2004223841, mailed Jul. 15, 2008, 6 pages.

Examiner Frank Heidenhain, Communication pursuant to Article 94(3) EPC, European Application No. 04 758 101.2, mailed Dec. 13, 2007, 3 pages.

Examiner Frank Heidenhain, Communication pursuant to Article 94(3) EPC, European Application No. 04 758 101.2, mailed Aug. 8, 2008, 4 pages.

Examiner Rachael E. Welter, Requirement for Restriction/Election, U.S. Appl. No. 10/808,188, mailed Jul. 1, 2008, 7 pages.

Examiner Rachael E. Welter, Requirement for Restriction/Election, U.S. Appl. No. 10/808,188, mailed Nov. 14, 2008, 14 pages.

Examiner Eszter Dudás, Supplementary European Search Report in EP 05 73 3196 mailed Nov. 30, 2009, 3 pages.

Redey et al., "Osteoclast adhesion and activity on synthetic hydroxyapatite, carbonated hydroxyapatite, and natural calcium carbonate: Relationship to surface energies," *J Biomed Mater Res*, 1999, 45:140-147.

Combes et al., "Calcium carbonate-calcium phosphate mixed cement compositions for bone reconstruction," *J Biomed Mater Res*, 2006, 79A:318-328.

Ohgushi et al., "Bone formation process in porous calcium carbonate and hydroxyapatite," *J Biomed Mater Res*, 1992, 26:885-895.

Goss et al., "Determination of calcium salt solubility with changes in pH and $P_{CO2}$, simulating varying gastrointestinal environments," *Journal of Pharmacy and Pharmacology*, 2007, pp. 1485-1492.

Karageorgiou et al., "Porosity of 3D biomaterial scaffolds and osteogenesis," *Biomaterials*, 26, 2005; pp. 5474-5491.

Monchau et al., "In vitro studies of human and rat osteoclast activity on hydroxyapatite, β-tricalcium phosphate, calcium carbonate," *Biomolecular Engineering*, 19, 2002; pp. 143-152.

Neto, Salvador Claro, "Thesis for Doctor's Degree," (est. 1997), pp. 117-120 (English Translation).

Spence et al., "Osteoclastogenesis on hydroxyapatite ceramics: The effect of carbonate substitution," *Wiley Periodicals, Inc.*, 2009; pp. 1292-1300.

\* cited by examiner

METHODS OF PERFORMING MEDICAL PROCEDURES THAT PROMOTE BONE GROWTH, METHOD OF MAKING COMPOSITIONS THAT PROMOTE BONE GROWTH, AND APPARATUS FOR USE IN SUCH METHODS

CROSS-REFERENCE TO RELATED APPLICATION

The present application is a continuation-in-part application of U.S. patent application Ser. No. 10/808,188, entitled "Methods of Performing Medical Procedures Which Promote Bone Growth, Compositions Which Promote Bone Growth, and Methods of Making Such Compositions," which was filed on Mar. 24, 2004, and which is a continuation-in-part application of U.S. patent application Ser. No. 10/395,001, entitled "Methods of Performing Medical Procedures Which Promote Bone Growth, Compositions Which Promote Bone Growth, and Methods of Making Such Compositions," which was filed on Mar. 24, 2003, and claims priority from U.S. Provisional Patent Application No. 60/366,335, entitled "Three Part Biodegradable Osteoconductive Polymer and Dispensing System," and filed on Mar. 22, 2002, the disclosures of which are incorporated herein by reference in their entirety.

BACKGROUND OF THE INVENTION

The present invention relates generally to methods of performing medical procedures, methods of making compositions useful in such medical procedures, and apparatus useful in such methods. In particular, the present invention is directed towards methods of making compositions useful in certain medical procedures, and methods of performing medical procedures in which a composition promotes bone growth when the composition is positioned in the vicinity of a bone of a mammal. The present invention also is directed towards apparatus that are useful in making such compositions, and in performing such medical procedures.

Human bone includes a solid mineral phase and an organic matrix that is between 90% and 95% type I collagen. The mineral phase includes, inter alia, calcium and phosphate. The mechanical properties of bone are related to its specific type of construction and internal architecture. Although bone may be relatively light, it also may have a relatively high tensile strength. This combination of high strength coupled with relatively low weight results from, inter alia, the hollow, tubular shape of bone, the layering of bone tissue, and the internal buttressing within the organic matrix. Bone tissue may supplant membranous or fibrous tissue by a mechanism referred to as "intramembranous ossification." Bone tissue only grows by appositional growth, e.g., the deposition of a new organic matrix on the surface of the bone by adjacent surface cells. A damaged bone repairs itself through a multiphase process. Initially, bone repair begins with an inflammatory phase, involving extensive tearing of the membrane surrounding the bone (the periosteum), rupturing of blood vessels and extensive hemorrhaging. Typically, this leads to a secondary inflammatory response of white blood cells (e.g., polymorphonuclear leukocytes, macrophages, and mononuclear cells), in an effort to prevent infection. Pluripotential mesenchymal cells from the soft tissue and within the bone marrow give rise to the osteoblast cells that synthesize bone.

Known bone replacement technologies can be divided into three transitional matrix categories. The first category relies on replacing bone with either autogenous, homologous, heterologous, or decalcified bone, followed by remodeling. As referred to herein, the term "remodeling" will be understood to mean the process by which bone is continually built and resorbed within the body. This first category may be problematic, however, because of difficulties inherent in harvesting the replacement bone, as well as the risk of transmitting blood-borne pathogens into the body of the recipient. The second category involves synthetic bone replacement, e.g., replacing bone with a bone-like mineral (e.g., crystalline hydroxyapatite or calcium pyrophosphate), followed by remodeling. Conventional synthetic bone replacement may be problematic, however, because the replacement material may have poor tensile strength and may adhere poorly to the surrounding bone. The third category relies on replacing bone with a composition that maintains its chemical and mechanical properties without change or subsequent remodeling (e.g., titanium, stainless steel, PMMA); nevertheless, this category is problematic because, inter alia, it does not allow for the growth of new bone.

Conventional biological materials (e.g., those comprising poly(lactic acid)) also have been considered for use in bone replacement procedures. However, such materials may degrade over a particular period of time, irrespective of whether new bone has formed in the vicinity of the material, thereby leaving undesirable voids that may limit the stability of surrounding structures within the body of the mammal.

Additionally, certain conventional bone replacement materials may produce a substantial exotherm once placed in the body of a mammal. Generally, the exotherm is caused by curing (e.g., continued polymerization) of the conventional bone replacement material within the body. The exotherm produced by certain conventional bone replacement materials may reach temperatures above 45° C., which may, inter alia, cause adjacent tissue to necrose. Rapid-cure conventional bone replacement materials (e.g., conventional bone replacement materials that may be cured within the body within 1-5 minutes after exposure to an energy source that facilitates curing) are particularly likely to produce such undesirable exotherms reaching such undesirably high temperatures.

Traditional methods for preparation of conventional bone replacement materials often involve the use of glass ampoules, within which are disposed certain chemical components. The ampoules are cracked to release the components, which subsequently are reacted to form the conventional bone replacement material. Glass ampoules are problematic for a number of reasons. First, they must be cracked in order to release the compounds stored within, which poses a safety hazard in that the cracked glass may puncture the skin of the technician handling the ampoule. Moreover, the cracking of the glass creates glass fragments that may fall back into the ampoule, which may cause them to become incorporated within the bone replacement material. Further, because the ampoules lack a dispensing means capable of positively displacing the compound stored therein, the ampoules must be inverted and poured. Often, this is a time-consuming process, because the stored compounds may be quite viscous. Air bubbles also may become entrained in the stored compounds during the pouring process. Additionally, some portion of the stored compounds generally will remain within the ampoule at the completion of the pouring process, and cannot be displaced. In addition to wasting material, this is undesirable because proper formulation of conventional bone replacement materials often requires mixing of the entirety of the contents of the ampoules; if a portion of one or more components remains within the ampoule, the resulting bone replacement material will not be properly formulated.

Further, conventional methods of preparing bone replacement material often involve elaborate vapor containment measures. Such measures commonly are employed because, inter alia, certain bone replacement materials that are PMMA-based may be extremely toxic. Furthermore, certain blood-based products may create a risk of blood-borne-pathogen transmission or contamination. This may be problematic, because not all operating rooms are equipped with vacuum apparatus, and because expensive accessory equipment may be required.

SUMMARY

Certain embodiments of the present invention provide methods of making compositions useful in certain medical procedures. These compositions initially may be prepared in a liquid state, and then may cure into a solid state. For example, the compositions may cure into a solid in an oxygen environment and/or a hydrophilic environment. Certain embodiments of the compositions may pass through a "taffy-like" state while curing from a liquid to a solid.

A technical advantage of the compositions that may be made according to the methods of the present invention is that such compositions may be positioned in the vicinity of a bone of a mammal, e.g., in the vicinity of a damaged portion of the bone, and the compositions promote bone growth. The compositions made according to the methods of the present invention may be placed in the vicinity of a bone of a mammal in a variety of ways. For example, the compositions can be applied to an exterior surface of the bone, dispensed in an opening formed within or through the bone, injected into the bone, positioned between two pieces of bone, or the like, without necessitating exposure of the bone, (e.g., the compositions may be positioned in the vicinity of a bone by injecting the compositions through the skin using a syringe). The compositions also may be molded into an implant, a screw, a plate, a prosthetic member, or the like, which may be inserted in or positioned on the bone.

As noted above, the compositions made according to the methods of the present invention promote bone growth. When placed within the body of a mammal according to the methods of the present invention, the compositions made according to the methods of the present invention may degrade through a cyclic AMP regulated lipase hydrolysis reaction process that generally maintains a 1-to-1 conversion (e.g., the compositions generally are replaced or converted to bone while maintaining regional structural stability). The compositions may be used to reconstruct bone, fuse bones (intravertebroinfusions), reduce or eliminate bone fractures or otherwise damaged bones, and/or regenerate missing bone, e.g., generate bone growth that fills a void within a bone. The compositions also may be used to make plates, screws, prosthetic joints, or the like, and/or may act as an anchor for a suture inserted in an opening in a bone, preventing the suture from falling out of the opening after insertion. Moreover, the compositions made according to the methods of the present invention also may be used as a base of a substrate in order to dilate compressed structures, e.g., vertebral disks, intramedullary nails, and in angioplasty-type procedures. The newly generated bone has an internal rigid fixation similar to that of bone already present in the body, such that the generated bone is not readily damaged.

The compositions made according to the methods of the present invention are biocompatible, and are adapted to stimulate bone growth when positioned in contact with, or in the vicinity of, a bone of a mammal. One feature of certain embodiments of these compositions that may particularly adapt them to stimulate bone growth is their porosity. Certain embodiments of the methods of the present invention may be used to make compositions that may have an average porosity in the range of from about 5 to about 500 microns in some embodiments, and from about 5 to about 100 microns in other embodiments. Certain embodiments may have a smaller average porosity, e.g., an average porosity in the range of at least about 1.5 microns. Certain embodiments may have an average porosity that is greater, e.g., an average porosity in the range of from about 500 microns to about 700 microns, or greater. Porosity may be created within the compositions made according to the methods of the present invention through the inclusion in the compositions of, inter alia, water, surfactants, and/or cell openers. Though certain embodiments of the compositions made according to the methods of the present invention may be considered to have a closed cellular matrix, these compositions support osteoclasts in growth through local degradations that create micro-open-cellular matrices. Such micro-open-cellular matrices support osteoclast and osteoblast activity, e.g., the osteoclast metabolic activities create an open-cell matrix.

The desirable porosity demonstrated by certain embodiments of the compositions that may be made according to the methods of the present invention is accompanied, and complemented, by desirable post-cure physical properties. Certain embodiments of the compositions have been found to demonstrate a compressive strength of at least about 50 MPa, a tensile strength of at least about 40 MPa, and/or a Young's Modulus of Elasticity of at least about 1,500 MPa. Certain other embodiments may demonstrate greater or lesser compressive strength, tensile strength, and/or Young's Modulus.

The compositions that may be made according to the methods of the present invention also are resilient. Certain embodiments of the compositions are resistant to thermal degradation up to temperatures of about 150° C. Certain embodiments of the compositions are resistant to degradation from superheated steam at multiple atmospheres. Certain embodiments may be capable of withstanding traditional autoclave sterilization cycles. For example, certain embodiments of the compositions repeatedly may be sterilized in an autoclave without substantially affecting their mechanical properties. Moreover, the chemical properties of certain embodiments of the compositions are substantially unaffected when the composition is exposed to gamma sterilization.

Certain embodiments of the compositions may be adhesive and cohesive, and certain embodiments may be bacterial static and bactericidal. Certain embodiments of the compositions also may be osteoinductive or osteoconductive. Certain embodiments of the compositions may be suitable for use as a USP Class VI medical adhesive. Certain embodiments of the compositions also may be biodegradable (depending upon, inter alia, the biodegradability of the reactants used to make the compositions, e.g., whether the composition was produced by a reaction involving a degradable isocyanate, and/or a degradable polyol, for example).

Certain embodiments of the compositions may expand in volume after mixing of all components. In certain embodiments, such expansion may begin when the composition is in a liquid state, and may continue for a period of time while the composition cures; during at least a portion of this time, the composition may be in a "taffy-like" state. In certain embodiments of the compositions that expand in volume while curing, such expansion generally terminates before the composition achieves a final, cured state. Certain embodiments of the compositions may expand in volume in the range of from about 5% to about 15%, as measured by ASTM D1622 "Apparent Density of Rigid Cellular Plastics."

The compositions made according to the methods of the present invention generally reside in a moldable state at room temperature for a desired time. Certain embodiments of the compositions may reside in a moldable state at room temperature for up to about 20 minutes after all components have been added; certain other embodiments may reside in a moldable state at room temperature for a longer or shorter period of time. Absent supplemental heating or cooling, certain embodiments of the compositions may attain a solid state at room temperature, or at body temperature (e.g., the temperature that may be measured within the body of a mammal within which the composition is to be placed), at a time within about 20 minutes to about 30 minutes after all components of the compositions have been combined.

Upon attaining a solid state at room temperature or body temperature within about 20-30 minutes after combination of all components, certain embodiments of the compositions may comprise unreacted isocyanate groups in an amount of about 15-30% by weight; these unreacted isocyanate groups may continue to react thereafter. In certain embodiments, these unreacted isocyanate groups may continue to react during a time period in which the composition may reside within the body of a mammal. A particularly beneficial feature of the present invention is that these unreacted isocyanate groups are encapsulated within the solid composition, and are not leachable therethrough. Furthermore, when a composition made according to the methods of the present invention comprising about 15% to about 30% unreacted isocyanate groups by weight is placed within the body of a mammal, the composition does not exotherm above about 45° C., and therefore does not imperil adjacent tissue. Within about 24 to 48 hours after all components have been combined, certain embodiments of the compositions may attain a final, cured state (e.g., a state at which all components have fully reacted); certain other embodiments of the compositions may attain a final, cured state at an earlier time.

The compositions made according to the methods of the present invention may be formulated to have a desired pH. For example, certain embodiments of the compositions made according to the methods of the present invention may have a physiological pH, e.g., the compositions may have a pH of about 7.4. Certain other embodiments of the compositions may be acidic or basic. For example, the pH of certain embodiments comprising calcium carbonate may be in the range of from about 8.7 to about 9.5. The acid profile of certain embodiments of the compositions made according to the methods of the present invention may be particularly compatible with inclusion of bone morphogenic proteins in the compositions. Moreover, the methods of making compositions described herein do not involve an excessively high exotherm that otherwise could possibly denature certain bone morphogenic proteins.

Another aspect of the present invention facilitates ready preparation of the compositions disclosed herein prior to their use in a medical procedure. According to an exemplary embodiment of the present invention, an example of an apparatus that is useful in preparing a composition to be used in a medical procedure comprises a sealed container comprising an internal cavity; one or more dividers for partitioning the internal cavity into a plurality of adjacent compartments; and a plurality of compounds useful in preparing the composition, wherein each compartment in the internal cavity has disposed therein at least one of the plurality of compounds. The one or more dividers may be externally affixed to the sealed container, or may be disposed internally within the internal cavity of the sealed container. Where the one or more dividers are externally affixed to the sealed container, the one or more dividers are capable of being removed without affecting the integrity of the sealed container. Where the one or more dividers are internally disposed within the internal cavity of the sealed container, the one or more dividers may be displaced within the sealed container without affecting its integrity. When a divider partitioning adjacent compartments is removed or displaced, communication is permitted among the compounds disposed in the adjacent compartments.

Another example of an apparatus of the present invention that is useful in preparing a composition to be used in a medical procedure comprises a sealed outer container comprising an internal cavity; a sealed inner container comprising an internal cavity; one or more dividers for partitioning the internal cavity within the sealed inner container into a plurality of compartments; and a plurality of compounds useful in preparing the composition, wherein each compartment has at least one compound disposed therein. The sealed inner container is disposed within the internal cavity within the sealed outer container. The one or more dividers may be externally affixed to the sealed container, or may be disposed internally within the internal cavity of the sealed container. Where the one or more dividers are externally affixed to the sealed inner container, the one or more dividers are capable of being removed without affecting the integrity of the sealed inner container. Where the one or more dividers are internally disposed within the internal cavity of the sealed inner container, the one or more dividers may be displaced within the sealed inner container without affecting its integrity. When a divider partitioning adjacent compartments is removed or displaced, communication is permitted among the compounds disposed in the adjacent compartments.

Among other benefits, the apparatus of the present invention may facilitate improved preparation of the bone-growth-promoting compositions made according to the present invention. For example, the individual components placed within the apparatus will be reacted therein; accordingly, no portion of the components will be lost prior to reacting to form the composition (in contrast, conventional methods of preparing conventional bone replacement materials may be significantly affected by loss of component material prior to reaction, e.g., conventional methods involving components disposed in glass ampoules may suffer from undesirable adherence of component material to the walls of their respective ampoules before the components are mixed). The apparatus of the present invention may facilitate improved preparation of bone-growth-promoting compositions, as the component materials that are reacted together within the apparatus are present in their stoichiometric amounts, with no loss of component materials prior to reaction.

The apparatus of the present invention further facilitate improved preparation of bone-growth-promoting compositions, because certain embodiments of the compositions may be prepared entirely within the confines of the apparatus, thereby reducing or preventing the possibility of contamination. Moreover, the apparatus may be sterilized with gamma radiation at a desired time after the placement of component materials within the apparatus; in this way, a plurality of component materials may be sterilized conveniently at one time.

Still further, preparation of certain embodiments of the compositions within the confines of the apparatus of the present invention may be more forgiving than if the compositions were conventionally prepared by combining a number of components in separate containers (e.g., separate beakers). Consider, for example, an operator who uses an apparatus of the present invention to form a prepolymer that later will be combined with another component (for example, a crosslinker or chain-extender), but fails to wait until the prepolymer is fully formed, and prematurely combines the not-fully-formed prepolymer (comprising some amount of unreacted components) with the other component within the apparatus of the present invention. Because the not-fully-formed prepolymer and the other component are all contained within the apparatus of the present invention, no adverse consequence may occur, as the unreacted components within the prepolymer will continue reacting as desired within the apparatus of the present invention.

Furthermore, the apparatus of the present invention demonstrate improved convenience, in that the compositions prepared within the apparatus may be heated while reacting, cooled while reacting, and conveniently transported while reacting simply by heating, cooling, and/or transporting the apparatus while the mixture of components disposed therein is reacting.

Another aspect of the present invention facilitates improved delivery, within the body of a mammal, of therapeutic substances (e.g., antibiotics, bone morphogenic proteins, and the like). According to an exemplary embodiment of the present invention, a composition may be made according to the methods of the present invention, and one or more therapeutic substances optionally may be incorporated within the composition. Upon curing of the composition, either inside or outside the body of a mammal, the one or more therapeutic substances may become encapsulated within the cured composition, thereby temporarily impairing or preventing the release within the body of the one or more therapeutic substances. As the cured composition is converted to bone within the body over time, the one or more therapeutic substances may gradually be released within the body, over time. Among other benefits, this may permit a physician to place, within the body of a mammal, a greater quantity of a therapeutic substance than otherwise would be possible, in view of, inter alia, the half-life of the therapeutic substance and the maximum recommended bolus dose of the therapeutic substance.

Another aspect of the present invention involves improved methods for performing medical procedures. According to an exemplary embodiment of the present invention, an apparatus of the present invention may be used that comprises a sealed container comprising a plurality of compartments, that each may store one or more of a plurality of components that may be reacted (within the apparatus) to form a bone-growth-promoting composition. At a desired time (e.g., after the reacting components within the apparatus have been mixed for about 10 minutes, in certain embodiments) the apparatus may be frozen (e.g., by immersion in liquid nitrogen), thereby suspending the reaction. In certain embodiments, the frozen apparatus (comprising the mixed and partially-reacted components disposed therein) may be packaged in, e.g., dry ice, and transported to a medical operating room. The frozen apparatus may be thawed at a desired time before or during a medical operation (e.g., in certain embodiments, the desired time may be about 10 minutes before implantation of the composition is desired), and an operator may continue to mix the components disposed within the thawed apparatus, which may cause the suspended reaction to resume and proceed towards completion. When the reaction has proceeded to a desired degree, the composition may be dispensed from the apparatus, and placed within the body of the mammal, where the composition may finish reacting. Because the majority of the reaction between the components in the apparatus may occur before the composition is placed within the body of a mammal, the majority of the exotherm generated by this reaction may occur outside the body of a mammal. For example, in one embodiment, 50% of the components in the apparatus may become reacted before the apparatus is frozen, and 40% of the components in the apparatus may become reacted after the frozen apparatus is thawed and further mixed for a desired time, while only the remaining 10% of the components may be left to react once the composition is dispensed and placed within the body of a mammal. Among other benefits, this aspect of the present invention may provide a composition that cures quickly within the body of a mammal. Moreover, among other benefits, this aspect of the present invention may provide a desirable combination of curing quickly within the body of a mammal without exotherming in a such a way that might expose tissue of the mammal to a significant temperature increase.

Other features, and advantages of the present invention will be apparent to persons of ordinary skill in the art in view of the following detailed description of the invention and the accompanying drawings.

BRIEF DESCRIPTION OF THE DRAWINGS

For a more complete understanding of the present invention, needs satisfied thereby, and objects, features, and advantages thereof, reference now is made to the following descriptions taken in connection with the accompanying drawings.

Figure 1A:
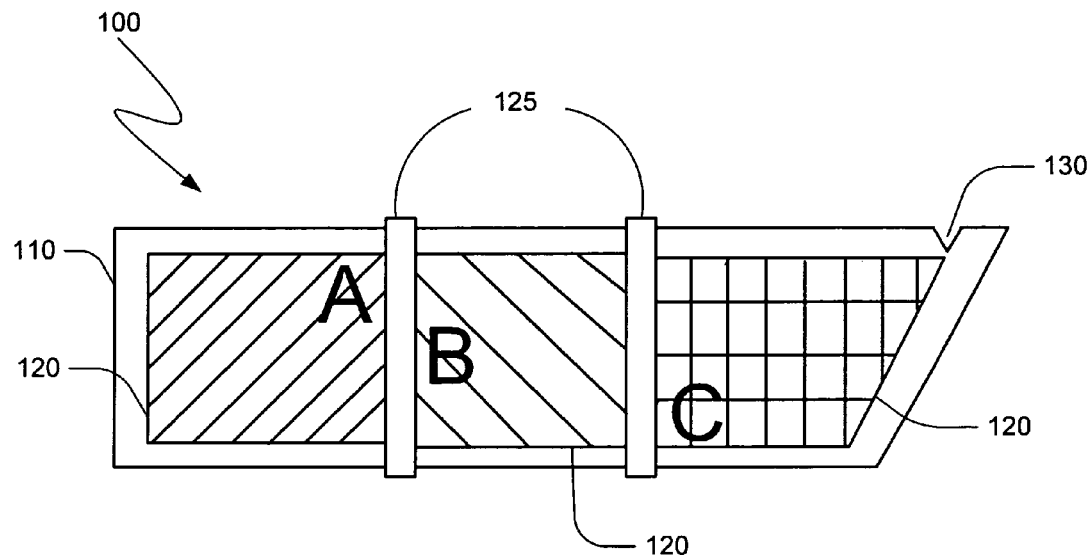
FIG. 1A illustrates an exemplary embodiment of an apparatus of the present invention.

While the present invention is susceptible to various modifications and alternative forms, specific embodiments thereof have been shown in the drawings and are herein described. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The present invention is directed towards methods of making compositions useful in certain medical procedures, and methods of performing medical procedures in which the composition promotes bone growth when the composition is positioned in the vicinity of a bone of a mammal. The present invention also is directed towards apparatus that are useful in making such compositions, and in performing such medical procedures. Embodiments of the present invention and their advantages may be understood by referring to FIGS. 1A-36, like numerals being used for like corresponding parts in the various drawings.

I. Compositions for Promoting Bone Growth

The present invention provides methods for making a variety of compositions that promote bone growth when used in certain medical procedures. Certain embodiments of these compositions comprise an isocyanate and a polyol and/or a polyamine. Certain embodiments of these compositions further may comprise water. Certain embodiments of these compositions that comprise an isocyanate and a polyol and/or a polyamine further may comprise at least one filler material, at least one catalyst, and other additives (e.g., surfactants, proteins, and the like). As referred to herein, the term "additives" will be understood to include reactive materials (e.g., water) as well as nonreactive materials (e.g., filler material). In certain embodiments of the present invention, a composition may be formed by reacting individual components—e.g., reacting an isocyanate or an isocyanate prepolymer with a polyol and/or a polyamine, and optionally with water—and the composition produced by such reaction (and optional additives that may be added to such composition) may be used in a medical procedure to promote bone growth.

In certain embodiments of the present invention, methods are provided for making compositions that comprise biocompatible polyurethane/polyurea components, which compositions may be used in medical procedures to promote bone growth. For example, the present invention provides methods that involve combining an isocyanate with one or more polyols and/or polyamines, along with optional additives (e.g., water, filler material), and permitting them to react to form a composition that comprises biocompatible polyurethane/polyurea components. As referred to herein, the term "biocompatible polyurethane/polyurea components" includes, inter alia, biocompatible polyester urethanes, biocompatible polyether urethanes, biocompatible poly(urethane-ureas), biocompatible polyureas, and the like, and mixtures thereof.

As noted above, the compositions comprising biocompatible polyurethane/polyurea components further may comprise optional additives, (e.g., at least one filler material, at least one catalyst, surfactants, proteins, and the like), as will be described further hereinbelow. Certain embodiments of the compositions made according to the present invention may comprise biocompatible polyurethane/polyurea components present in an amount in the range of from about 40% to about 90% by weight of the composition, with the balance comprising additives, such as those that have been described above and those that will be described below. Certain embodiments of the compositions made according to the present invention may comprise biocompatible polyurethane/polyurea components present in an amount in the range of from about 50% to about 70% by weight of the composition, with the balance comprising additives. In certain embodiments of the present invention, the biocompatible polyurethane/polyurea components may include non-saturated polyester urethanes.

In other embodiments of the present invention, methods are provided for making compositions that comprise poly(urethane-isocyanurate) components, along with poly(urethane-urea-isocyanurate) components and poly(urethane-carbodiimide) components, all of which compositions may be biocompatible and may be used in medical procedures to promote bone growth. For example, the present invention provides methods that involve combining an isocyanate prepolymer with a polyol or chain-extender, and a catalyst, along with optional additives (e.g., filler material), and permitting them to react to form a composition that comprises biocompatible poly(urethane-isocyanurate) components. In certain embodiments, the isocyanate prepolymer may react with a polyol, water, and a catalyst to form a composition that comprises biocompatible poly(urethane-urea-isocyanurate) components; optional additives also may be included in the composition. As another example, the present invention provides methods that involve combining an isocyanate prepolymer with a catalyst and a polyol or chain-extender, along with optional additives (e.g., filler material), and permitting them to react to form a composition that comprises biocompatible poly(urethane-carbodiimide) components.

The individual components that may be included in the compositions that may be made according to the present invention now will be described in greater detail.

The Isocyanate Component

A broad variety of isocyanates may be suitable for use in the compositions made according to the methods of the present invention. In certain embodiments of the present invention, the isocyanate may be, e.g., an aromatic isocyanate, an aliphatic isocyanate, a cycloaliphatic isocyanate, an adduct of an isocyanate, or the like. Examples of suitable adducts of isocyanate include, inter alia, a hexamethylene diisocyanate trimer that is commercially available from Bayer AG under the trade name DESMODUR N-3390, and a hexamethylene diisocyanate biuret that is commercially available from Bayer AG under the trade name DESMODUR N-100. An example of a suitable aromatic isocyanate is diphenylmethane diisocyanate, also known as "MDI." Commercially available examples of diphenylmethane diisocyanate include, but are not limited to, mixtures of 2,4-diphenylmethane diisocyanate and 4,4-diphenylmethane diisocyanate isomers, such as those that are commercially available from Dow Chemical Company under the trade name ISONATE 50 OP, and those that are commercially available from Huntsman under the trade name RUBINATE 9433; these mixtures of 2,4- and 4,4-diphenylmethane diisocyanate isomers generally will be liquids at room temperature. Diphenylmethane diisocyanate is also commercially available, inter alia, in its pure 4,4-diphenylmethane diisocyanate form from Bayer AG under the trade name MONDUR M, and from Huntsman Corporation under the trade name RUBINATE 44; these compounds generally will be solids at room temperature. In certain embodiments of the present invention, liquid diphenylmethane diisocyanate may be particularly suitable, as it possesses excellent strength properties, and may react relatively quickly at lower temperatures. Other examples of suitable aromatic isocyanates include, but are not limited to, polymeric isocyanates, such as those that are commercially available from Dow Chemical Company under the trade names ISONATE 143L, ISONATE PAPI 901, ISONATE PAPI 27, and the like.

In certain embodiments, cycloaliphatic isocyanates may be particularly desirable. Cycloaliphatic isocyanates offer a desirable combination of properties, including, inter alia, excellent strength properties. Examples of suitable cycloaliphatic isocyanates include, but are not limited to, isophorone diisocyanate and dicyclohexylmethane diisocyanate. Isophorone diisocyanate is commercially available from Bayer Corporation under the trade name DESMODUR I. Dicyclohexyl methane diisocyanate is commercially available from Bayer Corporation under the trade name DESMODUR W. Examples of suitable aliphatic isocyanates include, inter alia, 1,6 hexylmethylene diisocyanate.

In certain embodiments of the present invention, an isocyanate may be chosen that may be a liquid at room temperature, and that may be used to produce a bone-growth-promoting composition having desired flexural properties. For example, an embodiment of a composition of the present invention made from an isocyanate prepolymer that comprises ISONATE PAPI 901 may demonstrate a given flexural strength at a given strain (e.g., flexural strength of 64.9 MPa at 5.5% strain (no yield), for example), while another embodiment of a composition of the present invention made from an isocyanate prepolymer that comprises ISONATE 50 OP may exhibit different flexural properties (e.g., flexural strength of 57.4 MPa at 7.0% strain (yield), for example). Furthermore, the quantity of isocyanate that may be included also may depend on factors including, inter alia, the desired flexural properties of the composition. For example, in certain embodiments of the present invention, isocyanate prepolymers may be used that comprise an isocyanate in an amount in the range of from about 30% to about 80% by weight of the isocyanate prepolymer, and, in certain embodiments, from about 30% to about 70% by weight of the isocyanate prepolymer. In certain other embodiments of the present invention, isocyanate prepolymers may be used that comprise less than about 30% isocyanate by weight of the prepolymer, or more than about 80% isocyanate by weight of the isocyanate prepolymer. One of ordinary skill in the art, with the benefit of this disclosure, will be able to identify a suitable amount of isocyanate to include for a particular application.

The Polyol/Polyamine Component

The compositions of the present invention further may comprise a polyol and/or a polyamine. A broad variety of polyols may be suitable for use in the present invention, including, but not limited to, naturally occurring polyols and biocompatible, synthetic polyols, and mixtures thereof. In certain embodiments, the polyols used in the present invention may comprise at least one ester group. In certain embodiments, a polyol used in the present invention may comprise in the range of from about 2 to 3 ester groups. In certain embodiments, a polyol used in the present invention may comprise in the range of from about 5 to 10 ester groups.

As referred to herein, the term "naturally occurring polyols" will be understood to include, inter alia, naturally occurring polyols as well as polyols that are derived from various vegetable oils. Generally, the naturally occurring polyols that are suitable for use in the present invention are those that have at least one hydroxyl group. In certain embodiments, naturally occurring polyols may be used that have two or more hydroxyl groups. Examples of naturally occurring polyols include, but are not limited to, castor oil, safflower oil, lesquerella oil, the polyols that may be obtained by chemical modification of naturally occurring vegetable oils (e.g., castor oil, olive oil, sesame oil, corn oil), naturally occurring oils that have been trans-esterified (e.g., a modified castor oil polyol that has been prepared by the transesterification reaction of natural castor oil with suitable crosslinkers (e.g., glycerol, trimethylolpropane, and the like) or with acids such as adipic acid), naturally occurring oils that have been hydrogenated, and the like. In certain embodiments of the present invention, a naturally-occurring polyol may be used that is derived from a naturally occurring saturated fatty acid. Examples of suitable naturally occurring polyols include, inter alia: a difunctional castor-oil-based polyol that is commercially available from CasChem, Inc., under the trade name CASPOL® 5001; a trifunctional castor-oil-based polyol that is commercially available from CasChem, Inc., under the trade name CASPOL® 1962; a quadrifunctional castor-oil-based polyol that is commercially available from CasChem, Inc., under the trade name CASPOL® 5004; and the like As referred to herein, the term "biocompatible, synthetic polyols" will be understood to include, inter alia, biocompatible synthetic polyols that are derived from crude oil. Examples of suitable biocompatible, synthetic polyols include, but are not limited to, polycaprolactone polyols, polyester polyols, polyadipate polyols (e.g., poly(hexane-adipate) diol, poly(butane-adipate) diol, poly(ethylene/propylene-adipate) diol, poly(hexane/adipate/isophthalate diol)), polyols that have been derived from a synthetic acid (e.g., isophthalic acid, maleic acid), and the like. In certain embodiments, the biocompatible, synthetic polyol may be biodegradable. An example of a suitable biocompatible synthetic polyol is a polycaprolactone diol that is commercially available from Dow Chemical under the trade name TONE 32 B8.

In certain embodiments of the present invention wherein a polyether urethane component is generated, suitable biocompatible, synthetic polyols may include, inter alia, poly(oxypropylene) glycols, poly(oxytetramethylene) glycols, poly(oxyethylene) glycols, and the like. Generally, polyols such as those described above (e.g., polyols that may be used to generate a polyether urethane component) may not be biodegradable; accordingly, if the resultant polyether urethane component is to be biodegradable, a biodegradable isocyanate may be chosen to react with the polyol.

In certain embodiments of the present invention, an isocyanate prepolymer may be reacted with a polyamine to form a poly(urethane-urea) according to a method of the present invention. Among other things, polyamines may react more quickly than polyols; in certain embodiments of the present invention, a polyamine may be reacted with, e.g., an isocyanate prepolymer, and may become about 70% to about 80% polymerized within about 8 to about 10 minutes, without supplemental heating. In certain embodiments, the composition may attain a "taffy-like" or "hard-taffy-like" state when about 70% to about 80% polymerized. In certain embodiments, the composition made from reaction of a polyamine with an isocyanate prepolymer may become fully polymerized within about 24 hours. Additionally, a poly(urethane-urea) formed by reaction of, e.g., a polyamine and an isocyanate prepolymer, may have greater strength than a polyurethane formed by reaction of, e.g., a polyol and an isocyanate prepolymer. In certain embodiments, a polyamine may be used that is a product of a chemical transformation of a naturally occurring polyol. In certain embodiments, the polyamine may be a primary or secondary di-amine, or a hindered amine. Examples of suitable polyamines include, but are not limited to, hindered diamine (e.g., isophorone diamine, "IPDA"), 1,4-cyclohexyl diamine, 1,3-pentane diamine, and aliphatic secondary diamines, and the like, and mixtures thereof. In certain embodiments of the present invention, aliphatic diamines and cycloaliphatic diamines may be particularly suitable, and may offer improved biocompatibility. Commercially available examples of suitable polyamines include, inter alia, those that are available from Dorf Ketal under the trade name CLEARLINK 1000.

The choice of a particular polyol or polyamine for use in accordance with the present invention may depend on factors including, inter alia, the desired flexural properties of the compositions that are to be produced from the particular polyol or polyamine. The use of a relatively short-chain polyol or polyamine will tend to impart less flexibility to the composition than will the use of a relatively long-chain polyol or polyamine. One of ordinary skill in the art, with the benefit of this disclosure, will be able to identify a suitable polyol or polyamine for a particular application.

In certain embodiments of the present invention, a polyol or polyamine may be present in an isocyanate prepolymer in an amount in the range of from about 10% to about 50% by weight of the isocyanate prepolymer, and, in certain embodiments, in an amount in the range of from about 20% to about 35% by weight of the isocyanate prepolymer. In certain other embodiments of the present invention, isocyanate prepolymers may be used that comprise less than about 10% polyol or polyamine by weight of the prepolymer, or more than about 50% polyol or polyamine by weight of the isocyanate prepolymer. One of ordinary skill in the art, with the benefit of this disclosure, will also be able to identify a suitable amount of polyol or polyamine to include for a particular application.

The Chain-Extender/Crosslinker Component

Certain embodiments of the present invention contemplate the use of chain-extenders and crosslinkers. In certain embodiments, a suitable chain-extender or crosslinker may be a naturally-occurring polyol, such as those that have been previously described herein. Examples of suitable naturally-occurring polyols that may be used as crosslinkers include, inter alia, CASPOL® 1962 and CASPOL® 5004.

Certain embodiments of the compositions that may be made according to the methods of the present invention may comprise chain-extenders or crosslinkers that are not biodegradable. In certain embodiments of the present invention, a nonbiodegradable crosslinker may be used that possesses a functionality in the range of from about 2 to about 6. In certain embodiments, the nonbiodegradable crosslinker functionality may be in the range of from about 3 to about 4. Examples of suitable nonbiodegradable crosslinkers include, but are not limited to, triethanolamine ("TEA"), trimethylolpropane, QUADROL (commercially available from BASF), and the like.

Examples of suitable nonbiodegradable chain-extenders include, but are not limited to, 1,4-butanediol, 1,6-hexanediol, diethylene glycol, and the like.

In certain embodiments of the present invention, a chain-extender or crosslinker may be present in an isocyanate prepolymer in an amount in the range of about 50% to about 80% by weight of the isocyanate prepolymer, and, in certain embodiments, in an amount in the range of about 60% to about 70% by weight of the isocyanate prepolymer In certain other embodiments of the present invention, isocyanate prepolymers may be used that do not comprise chain-extenders or crosslinkers, or that comprise less than about 50% chain-extender or crosslinker by weight of the prepolymer, or more than about 80% chain-extender or crosslinker by weight of the isocyanate prepolymer.

Water

Optionally, a water source may be used in the methods of the present invention. The water may be incorporated in a variety of ways. For example, certain commercially-available polyols often comprise a mixture of polyol and a small portion of water; when such polyols are used in the methods of the present invention, they may provide a source of water in certain embodiments of the present invention. As another example, certain types of filler materials (e.g., calcium carbonate) that optionally may be used in the methods of the present invention also may comprise water that is bound to the filler material; this may provide a source of water in certain embodiments of the present invention. As another example, formulating the compositions in an atmosphere that contains moisture may incorporate water within the compositions being prepared according to the methods of the present invention. In certain embodiments of the present invention, the compositions prepared according to the methods of the present invention may be prepared under a nitrogen purge that comprises a desired amount of moisture. As another example, an operator may inject a desired amount of water during formulation of the compositions; for example, an operator may inject a desired amount of water into a mixture that has been dispensed from an apparatus of the present invention, and that continues to react after having been dispensed therefrom.

In certain embodiments of the present invention wherein compositions are prepared with the use of an apparatus of the present invention that comprises a plurality of compartments in which, e.g., polyols, isocyanates and the like may be disposed, water may be incorporated in a variety of ways. For example, a polyol component may be placed in a compartment while in an environment comprising a desired amount of moisture, which may cause water to become incorporated into the compositions being made according to the methods of the present invention (however, compartments in which isocyanate compounds are to be disposed generally may be filled with isocyanate under a dry nitrogen purge). Exemplary embodiments of apparatus of the present invention are further described later in this application.

Because water is known to react with isocyanate to produce carbon dioxide, certain methods of the present invention that permit an isocyanate to react with water may generate a sufficient amount of carbon dioxide to impart a degree of porosity to the compositions of the present invention. In certain embodiments of the present invention, water may be present in an amount sufficient to provide a bone-growth-promoting composition having a desired porosity. In certain embodiments, water may be present in the compositions being made according to the methods of the present invention in an amount in the range of from at least about 0.05% by weight of the composition, and, in certain embodiments, water may be present in an amount in the range of from about 0.1% to about 1% by weight of the composition. One of ordinary skill in the art, with the benefit of this disclosure, will be able to identify an appropriate amount of water, if any, to incorporate into the compositions being made according to the methods of the present invention, for a particular application.

When water is incorporated within the compositions being made according to the methods of the present invention, an additional amount of isocyanate often may be required. EQUATION 1 below illustrates the general reaction that may occur between an isocyanate component and an alcohol, in which a urethane component may be formed:

$$RNCO + R'CH_2OH \rightarrow RHNCOOCH_2R' \qquad \text{EQUATION 1}$$

Furthermore, EQUATION 2 illustrates a reaction that may occur between water and an isocyanate component, in which carbamic acid (generally an unstable intermediate) may be formed:

$$RNCO + HOH \rightarrow RHNCO_2H \quad \text{EQUATION 2}$$

As carbamic acid generally is thermally unstable, it often spontaneously may decompose into an amine and carbon dioxide, as illustrated by EQUATION 3:

$$RHNCO_2H \rightarrow CO_2 + RNH_2 \quad \text{EQUATION 3}$$

The amine that may be generated further may react with isocyanate to form a urea component, as illustrated by EQUATION 4:

$$R''NCO + RNH_2 \rightarrow R''HNCONHR \quad \text{EQUATION 4}$$

In view of the competition that may occur between the above-described reactions, the addition of an increased amount of isocyanate, when water is present, ensures that sufficient isocyanate is present to provide the desired balance of urethane-forming and urea-forming reactions, and to prevent having unreacted hydroxyl groups (e.g., polyols) left over.

For example, in certain embodiments of the present invention wherein an aromatic isocyanate prepolymer, a naturally occurring polyol, and water are combined to form polyurethane/polyurea components, the quantity of aromatic isocyanate prepolymer may vary with the water concentration in the following manner:

TABLE 1

| | Sample Composition 1 | Sample Composition 2 | Sample Composition 3 | Sample Composition 4 |
|---|---|---|---|---|
| Isocyanate prepolymer (80 wt % Caspol 5001, 20 wt % Isonate 50 OP) | 100 | 102.3 | 111.66 | 123.3 |
| Caspol 1962 | 68.5 | 68.5 | 68.5 | 68.5 |
| Water | 0 | 0.1 | 0.5 | 1.0 |

As another example, in certain embodiments of the present invention wherein a prepolymer (comprising a naturally occurring polyol and a cycloaliphatic isocyanate), water, a polyamine and a naturally occurring polyol, are combined to form polyurethane/polyurea components, the quantity of prepolymer may vary with the water concentration in the following manner:

TABLE 2

| | Sample Composition 5 | Sample Composition 6 | Sample Composition 7 | Sample Composition 8 |
|---|---|---|---|---|
| Isocyanate prepolymer (19.7 wt % wt % Caspol 5001, 81.3 wt % Desmodur W) | 100 | 102.4 | 118.7 | 123.7 |
| Caspol 5004 | 42.5 | 42.5 | 42.5 | 42.5 |
| PolyQ 40-800 | 17.4 | 17.4 | 17.4 | 17.4 |
| Water | 0 | 0.1 | 0.5 | 1.0 |

In certain embodiments of the present invention where the presence of water in the composition may be determined to be undesirable, the compositions prepared according to the methods of the present invention may be prepared in a controlled environment, e.g., under a dry nitrogen purge.

The Optional Filler Material Component

A broad variety of optional filler materials may be suitable for use in the compositions made according to the methods of the present invention, including, but not limited to, calcium carbonate, bone (e.g., demineralized bone, allograft bone, and/or autogenous bone), calcium phosphate, calcium pyrophosphate, hydroxyapatite, poly methyl methacrylate, glass-ionomer, calcium sulfate, tricalcium phosphate (e.g., beta tricalcium phosphate), or any combination thereof, or the like. In certain embodiments, the filler material may be chosen so as to impart a desired degree of porosity to the compositions. Generally, the greater the adhesion between the filler material and other components in the composition, the lower the composition's porosity; and vice versa. Where included, the filler material may be present in the compositions in an amount sufficient to modify the compositions' mechanical properties (e.g., Young's Modulus of Elasticity, flexural strength, and the like). In certain embodiments, the optional filler material may be present in the compositions made according to the methods of the present invention in an amount in the range of from about 0.01% to about 55% by weight of the composition, and, in certain embodiments, from about 25% to about 35% by weight of the composition. In certain embodiments, the optional filler material may be present in the compositions in an amount greater than about 55% by weight of the composition.

In certain embodiments, the filler material may comprise calcium carbonate. In certain of these embodiments, the filler material may comprise calcium carbonate in an amount sufficient to provide free calcium to a body of a mammal and enhance osteoconductivity. In certain embodiments, the filler material may comprise at least about 98% pure calcium carbonate by weight of the filler material. In certain embodiments, the calcium carbonate may be implantable grade calcium carbonate. In certain embodiments, the calcium carbonate may have a particle size distribution that is capable of enhancing resorption of calcium within the body of a mammal, and/or a particle size distribution that may further enhance bone remodeling.

Another example of a suitable filler material is poly ether ether ketone (often referred to as "PEEK"). A commercially-available example of a suitable filler material is available from Cortek, Inc., of Dedham, Mass., under the trade name "Replace™."

Figure 36:
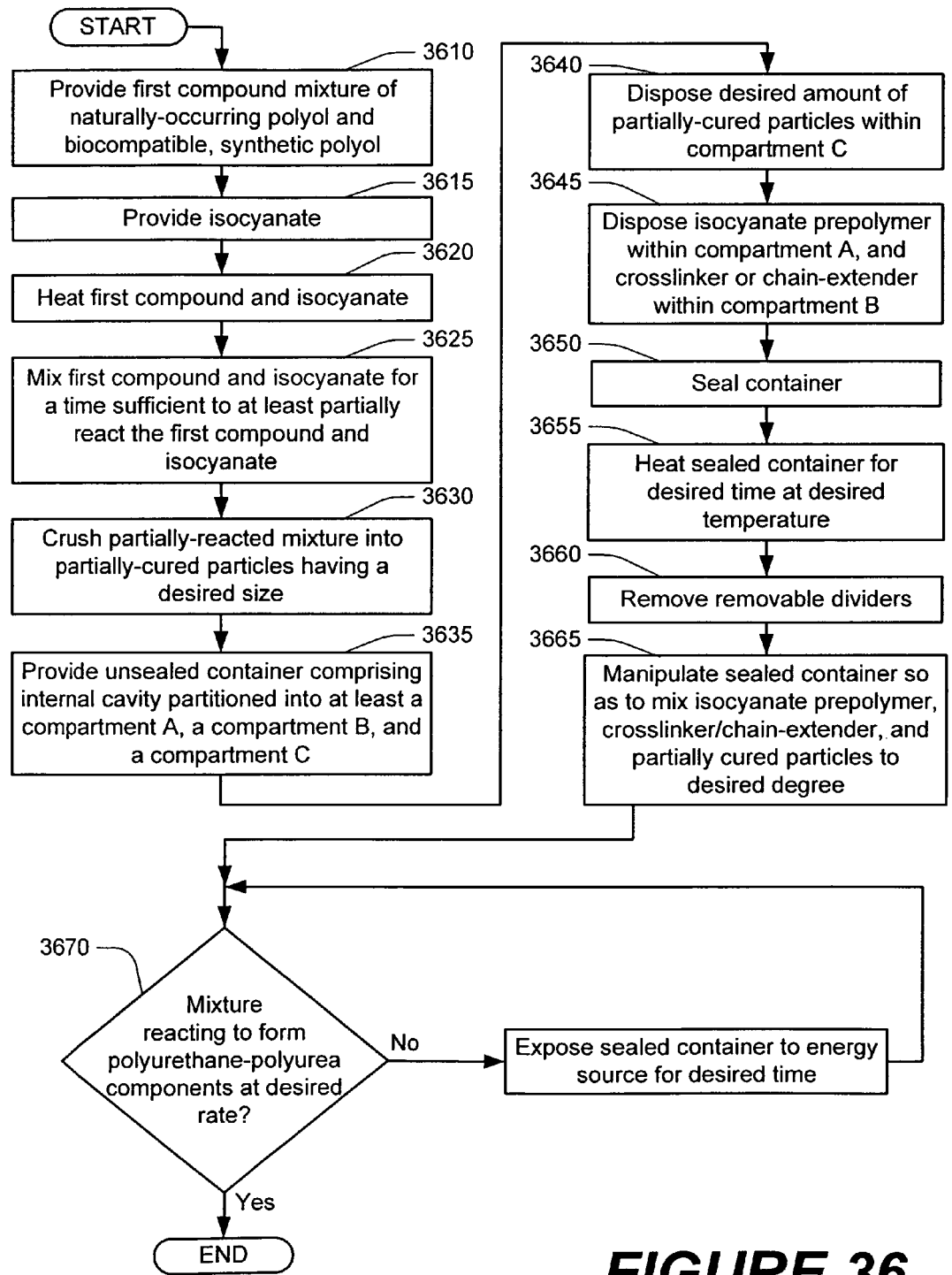
FIG. 36 is a top level flow-chart depicting an exemplary method for making compositions that promote bone growth, according to exemplary embodiments of the methods of the present invention.

In certain embodiments of the present invention, the optional filler material may comprise particles of partially-cured compositions that already have been prepared according to the methods of the present invention. (A nonlimiting example of a method of the present invention that employs partially-cured particles is illustrated in FIG. 36.) Among other things, the inclusion of these partially-cured particles as optional filler materials in the compositions made according to the present invention may increase the viscosity of the compositions and may facilitate providing a more uniform pour density. Moreover, the compositions that include partially-cured particles may cure rapidly (because, inter alia, they comprise particles that already have cured at least partially), and may produce a lower-temperature exotherm when permitted to cure within the body of a mammal. Among other benefits, the compositions made according to the present invention that include partially-cured particles may demonstrate a hybrid pore size (e.g., the compositions comprising partially-cured particles may have pore spaces of different sizes, in view of the presence of (i) porosity originating due to the presence therein of the partially-cured particles, and (ii) porosity originating from reaction of, e.g., water and isocyanate). The inclusion of partially-cured particles may permit greater, and more direct, control of expansion of the compositions made according to the methods of the present invention, because, inter alia, the inclusion of greater amounts of partially-cured particles within the compositions correspondingly may reduce the extent to which the compositions subsequently expand. In certain embodiments, the inclusion of partially-cured particles in a composition may reduce the composition's adhesive properties. In certain embodiments of the present invention, the partially-cured particles may be present as filler material in an amount in the range of from about 5% to about 80% by weight of the composition. For example, a composition may be made that weighs 20 grams and that includes partially-cured particles; such composition may comprise, for example, ten grams of partially-cured particles and ten grams of liquid components (e.g., an isocyanate, a polyol or a polyamine, a chain-extender or crosslinker, or the like).

Certain embodiments of the compositions made according to the methods of the present invention optionally may comprise filler materials that may be referred to as "porous fillers," which may be used, inter alia, to create or enhance porosity within the compositions. Nonlimiting examples of porous filler materials include EXPANCEL particles, commercially available from Akzo Nobel. Certain porous fillers may expand when heated, thereby increasing porosity within the compositions. Certain porous fillers may be chosen to rupture at a certain temperature, which may release a gas (e.g., air) disposed within the porous filler, thereby creating or enhancing porosity within the compositions.

The Optional Catalyst Component

Optionally, certain embodiments of the compositions made according to the methods of the present invention further may comprise at least one catalyst. In certain embodiments of the present invention where a catalyst is used, the catalyst may be used by, e.g., adding the catalyst to a polyol that may be mixed into the compositions. The inclusion of the catalyst in the compositions made according to the methods of the present invention may permit an operator to control, inter alia, certain polymerization reactions that occur during the formulation of the compositions (e.g., a polymerization reaction between a polyol and a isocyanate prepolymer that comprises an isocyanate). In certain embodiments of the present invention, at least one catalyst may be present in the compositions in an amount sufficient to ensure that such polymerization reactions have proceeded to completion before the compositions are placed within the body of a mammal. This may ensure, inter alia, that the isocyanate that may be present within the compositions, at the time of their placement within the body of a mammal, is not free to react while within the body.

A broad variety of optional catalysts may be used, including, but not limited to, a tertiary amine, and organometallic compounds such as, for example, stannous octoate, and dibutyl tin dilaurate. In certain embodiments wherein the catalyst is an organometallic catalyst, the presence of the organometallic catalyst in the compositions made according to the methods of the present invention will not adversely impact the radiotransparency or radiopacity of the composition. An example of a suitable tertiary amine is commercially available from Air Products, Inc., under the trade name DABCO 33LV. An example of a suitable source of dibutyl tin dilaurate is commercially available from Air Products, Inc., under the trade name DABCO T12. A tertiary amine may be preferred in, inter alia, certain embodiments of the present invention wherein a catalyst is to be used during preparation of a composition that may be placed within a body of a mammal while in liquid form.

In certain embodiments of the compositions made according to the methods of the present invention that comprise a catalyst, the catalyst may remain in the composition after its formulation and curing, e.g., as a monomer that is present in the matrix of the cured composition. Among other benefits, the permanent attachment of such catalyst within the cured composition may prevent or impair leaching of the catalyst from the composition. A non-limiting example of such catalyst is N,N,N'-Tri(2-hydroxylpropyl)-N'-hydroxyethyl ethylene diamine, which is commercially available from Arch Chemicals, Inc., under the trade name POLY-Q-40-800.

In certain embodiments of the present invention where a catalyst is added to a polyol that may be mixed into the compositions, the catalyst may be present in the polyol in an amount in the range of from about 0.05% to about 0.5% by weight of the polyol, and, in certain embodiments, from about 0.15% to about 0.4% by weight of the polyol. One of ordinary skill in the art, with the benefit of this disclosure, will be able to identify a suitable catalyst, and a suitable amount for inclusion, for a particular application.

In certain embodiments of the present invention, the optional catalyst component may be present in a compartment of an apparatus of the present invention in which, inter alia, any liquid component (e.g., an isocyanate, a polyol or a polyamine, a chain-extender or crosslinker, or the like) is disposed.

The Optional Surfactant Component

Optionally, certain embodiments of the compositions made according to the methods of the present invention further may comprise at least one surfactant. The inclusion of the at least one surfactant may, inter alia, impart a desired degree of porosity to the composition, and may permit an operator to control, inter alia, the size and/or the shape of pores within the composition. A broad variety of surfactants may be suitable for inclusion in the compositions. Commercially available examples of suitable surfactants include, but are not limited to, DABCO DC 193 and DABCO DC 5241, both of which are commercially available from Air Products, Inc., as well as copolymerizable surfactants with phosphate ester functionality that are available under the trade names "MAXEMUL 6106" and "MAXEMUL 6112" from Uniqema, and silicone surfactants that are commercially available from Struktol Corporation. One of ordinary skill in the art, with the benefit of this disclosure, will be able to identify an appropriate amount of optional surfactant to include for a particular application.

In certain embodiments of the present invention, the optional surfactant component may be present in a compartment of an apparatus of the present invention in which, inter alia, any liquid component (e.g., an isocyanate, a polyol or a polyamine, a chain-extender or crosslinker, or the like), or any solid component (e.g., an optional filler material, or the like) is disposed.

The Optional Radiotransparent/Radiopaque Component

Optionally, the compositions made according to the methods of the present invention also may comprise at least one radiotransparent substance or at least one radiopaque substance. The inclusion of such radiotransparent or radiopaque substances may be useful, inter alia, when a composition comprising such substance has been placed in contact with, or in the vicinity of, a bone of a mammal, and a physician subsequently seeks to determine the condition or location of the composition or the bone through the use of, inter alia, X-ray photographs. When an embodiment of the compositions made according to the methods of the present invention includes an optional radiotransparent substance (e.g., air, nitrogen gas, carbon dioxide, oxygen gas, or the like), the attenuation of the composition in the X-ray decreases. Consequently, a physician more readily may visualize the extent to which the underlying damaged bone has been repaired by the bone growth facilitated by treatment with the compositions made according to the methods of the present invention. Similarly, when an embodiment of the compositions includes an optional radiopaque substance (e.g., insoluble zirconium oxide, a radioactive tracer, a Barium Sulfate contrast media, a gadolinium contrast media, a water-soluble Iodinated contrast media, an oily Iodinated contrast media, an implantable metal (e.g., a chip, flake, or the like comprising a metal such as titanium, cobalt, or chromium), or the like), the attenuation of the composition in the X-ray increases. Consequently, the physician more readily may visualize the adequacy of the coverage of the compositions on the damaged bone.

Moreover, the at least one radiotransparent substance and/or the at least one radiopaque substance may be non-reactive substances, such that they may be included within the compositions made according to the methods of the present invention at any time during the process of manufacturing the compositions. Where included, the optional at least one radiotransparent substance and/or the optional at least one radiopaque substance may be present in the compositions in an amount in the range of from about 5% to about 30% by weight of the composition, and, in certain embodiments, from about 10% to about 20% by weight of the composition. Examples of commercially available radiopaque substances include "LIPIODOL," "HYPAQUE," and "OMNIPAQUE."

In certain embodiments of the present invention, an optional radiopaque or radiotransparent component that comprises a liquid (e.g., a liquid opacifier) may be present in a compartment of an apparatus of the present invention in which, inter alia, any liquid component (e.g., an isocyanate, a polyol or a polyamine, a chain-extender or crosslinker, or the like) is disposed. In certain embodiments of the present invention, an optional radiopaque or radiotransparent component that comprises a solid may be present in a compartment of an apparatus of the present invention in which, inter alia, any solid component (e.g., an optional filler material, or the like) is disposed.

The Optional Protein Component

Optionally, the compositions made according to the methods of the present invention further may comprise at least one protein. In certain embodiments of the present invention, the optional at least one protein may stimulate bone growth. In certain embodiments of the present invention, the optional at least one protein may be used to control the rate of bone regrowth, e.g., the type of protein may be selected, such that the protein increases or decreases the rate of bone growth relative to when the at least one protein is not present in the composition. For example, when a physician wishes to closely monitor the bone growth produced by treatment with the compositions made according to the methods of the present invention, the physician may opt to include within the compositions at least one protein that tends to decrease the rate of bone growth, relative to when the at least one protein is not present in the composition. Moreover, the at least one protein may be non-reactive, such that the at least one protein optionally may be included in the compositions made according to the methods of the present invention at any time during the manufacture of the composition. Examples of suitable proteins include, but are not limited to, collagen, OP1 (commercially available from Stryker Homedica), INFUSE (commercially available from Medtronic Corporation), or any recombinant bone morphogenic protein.

Bone morphogenic proteins may be incorporated within the compositions made according to the methods of the present invention in at least three ways. As a first example, bone morphogenic proteins may be mixed into the compositions during their preparation (e.g., mixed in with the isocyanate compound, the polyol/polyamine, the optional water component, and the like). In this way, the bone morphogenic protein may become fully impregnated within the compositions. This may be particularly desirable in embodiments wherein a slow release of the bone morphogenic protein within the body of a mammal is desired. As a second example, bone morphogenic proteins may be added to the compositions after all other components have been mixed together; e.g., the bone morphogenic proteins may be added to the compositions at a time in the range of from about 10 minutes to about 45 minutes after commencement of mixing of all other components. The compositions generally are very adhesive at this stage of their preparation, and may be rolled amongst bone morphogenic protein particles in a manner that causes the bone morphogenic protein particles to adhere to an outer surface of the composition. As a third example, the individual components from which a composition is to be made may be reacted together and allowed to cure, then may be ground up into granules, and mixed with bone morphogenic protein particles; the mixture of granules and particles then may be placed within the body of a mammal (e.g., in a void within the body of a mammal).

The Optional Light- or Photo-Initiators

Certain embodiments of the compositions made according to the methods of the present invention optionally may comprise light- or photo-initiators. Examples of suitable optional light- or photo-initiators include, but are not limited to, those that are available from Loctite Corporation under the trade designation "24650-42-8." The inclusion of optional photo- or light-initiators may be particularly suitable for compositions of the present invention that are made from unsaturated reactants, e.g., compositions that are made from, for example: isocyanate prepolymers having one or more double bonds; or from polyols having double bonds; or from adducts formed from reactions between isocyanates and acrylates; and the like. The inclusion of optional photo- or light-initiators in certain compositions made according to the methods of the present invention may be useful for a variety of purposes, and particularly may be useful, inter alia, in accelerating the curing (e.g., solidification) of the compositions. Such acceleration may be accomplished, inter alia, by exposing the compositions comprising the optional photo- or light-initiators to a suitable light source. Generally, the greater the intensity of the suitable light source, the faster the curing may be accelerated. Examples of suitable light sources include, but are not limited to, those that are commercially available from Doctor's Research Group, Inc., of Plymouth, Conn., under the trade name "SoftBeam." Generally, any light source having a wave spectrum matching the requirements of the photo- or light-initiator (e.g., blue light or white light of various intensities) may be used. In certain embodiments of the present invention, the suitable light source may be a fiber optic light source.

The optional photo- or light-initiators may be incorporated into the compositions in a variety of ways. In certain embodiments of the present invention, the optional photo- or light initiators may be present in a compartment of an apparatus of the present invention in which, inter alia, any liquid compound (e.g., an isocyanate, a polyol or polyamine, a chain-extender or crosslinker, or the like) is disposed.

In certain embodiments, the inclusion of optional photo- or light-initiators in the compositions made according to the methods of the present invention may accelerate the curing (e.g., solidification) of the compositions such that the compositions may cure "on demand." For example, a composition comprising optional light- or -photo-initiators may be in a liquid state (including, for example, a "taffy-like" state), and subsequently may cure in the range of from about 1 minute to about 5 minutes after exposure to a suitable energy source (e.g., a suitable light source). The present invention contemplates that on-demand curing may occur in vivo. For example, a composition comprising optional light- or -photo-initiators may be placed in the body of a mammal, and therein may be exposed to a suitable light source (for example, a fiber optic light source), that may cause it to cure on demand in vivo.

Generally, in embodiments of the present invention wherein optional photo- or light initiators may be present in a compartment of an apparatus of the present invention, the apparatus may be light-impermeable; inter alia, this may prevent premature curing of the compositions of the present invention within the apparatus.

Other Optional Additives

Optionally, the compositions of the present invention may comprise compounds that may be referred to as "cell openers." An example of a cell opener is commercially available from Goldschmidt under the trade name ORTOGEL 501. Another example of a cell opener is commercially available from Specialty Polymers & Services, of Valencia, Calif., under the trade name "X-AIR." Where included, the optional cell openers may be present in the compositions of the present invention in an amount in the range of from about 0.1% to about 5.0% by weight of the composition, and, in certain embodiments, from about 1% to about 3% by weight of the composition.

Optionally, the compositions of the present invention may comprise antibiotics, or any other therapeutic compound desired to be delivered within the body of a mammal. Examples of suitable antibiotics include, but are not limited to, broad spectrum antibiotics (e.g., gentamycin, clindamycin, erythromycin, and the like), as well as the gram-positive and gram-negative families of antibiotics (including, for example, ampicillin), and further including a broad variety of additional antibiotics. The antibiotics may be in a variety of forms, including, inter alia, powdered or bead form. Addition of antibiotics to the compositions of the present invention may be desirable for a variety of reasons, including, inter alia, the fact that the compositions of the present invention, when placed within the body of a mammal, desirably may degrade over time in a controlled fashion, which may promote a controlled, slow release of antibiotics within the mammal.

In certain embodiments of the present invention, antioxidant compounds optionally may be included in the compositions of the present invention. Examples of suitable antioxidants include, inter alia, those that are commercially available from Ciba Geigy under the trade names IRGANOX 1010 and IRGANOX 1035, as well as those that are commercially available from Cytec Industries under the trade names CYANOX 1790 and CYANOX 2777, and the like. In certain embodiments of the present invention wherein optional antioxidant compounds are included, the antioxidant compounds may be present in an amount in the range of from about 0.01% to about 0.5% by weight of the composition.

In certain embodiments, at least one steroid-based intracellular messenger optionally may be included in the compositions of the present invention, inter alia, to modulate the rate of bone growth. In certain embodiments, progenitor cells optionally may be included in the compositions of the present invention.

Optional Embodiments Involving Poly(Urethane-Isocyanurates) or Poly(Urethane-Carbodiimides)

The present invention also provides methods of making compositions that involve poly(urethane-isocyanurates), or poly(urethane-carbodiimides). Regarding compositions of the present invention that produce poly(urethane-isocyanurate)s, EQUATION 5 below illustrates a reaction that may occur so as to convert isocyanate groups to an isocyanurate:

EQUATION 5

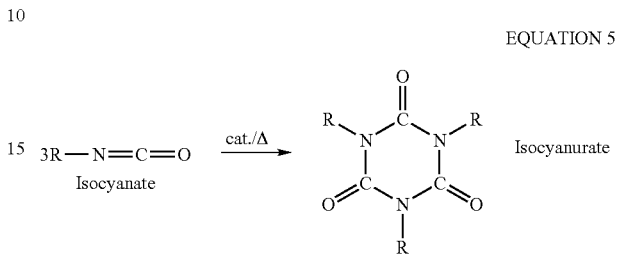

As a matter of convenience, EQUATION 5 demonstrates an exemplary reaction involving monoisocyanate groups; EQUATION 5 does not depict exemplary reactions that could occur involving polyisocyanate groups, which will be readily understood by those of ordinary skill in the art, with the benefit of this disclosure. As illustrated in EQUATION 5, three isocyanate groups may, after contact with a catalyst (and, optionally, heat), react to form an isocyanurate. Examples of suitable catalysts include, inter alia, potassium carboxylates, quaternary ammonium carboxylates, tertiary amines, and the like. Commercially available examples of suitable catalysts include, inter alia, DABCO T45 and DABCO TMR-2, which are commercially available from Air Products. These catalysts may be added in amounts in the range of from about 0.2% to about 7% by weight of the composition, and in certain embodiments, may be added in the range of from about 2% to about 5% by weight of the composition. In certain embodiments of the present invention wherein heat is applied during the formation of an isocyanurate, the temperature may be chosen to be in the range of from about room temperature to about 150° C. Heating time may vary from a few seconds (at about 150° C., for example) to up to about 1 hour (at about room temperature, or slightly above, for example).

Regarding compositions of the present invention that produce poly(urethane-carbodiimide)s, EQUATION 6 below illustrates a reaction that may occur so as to convert isocyanate groups to a carbodiimide:

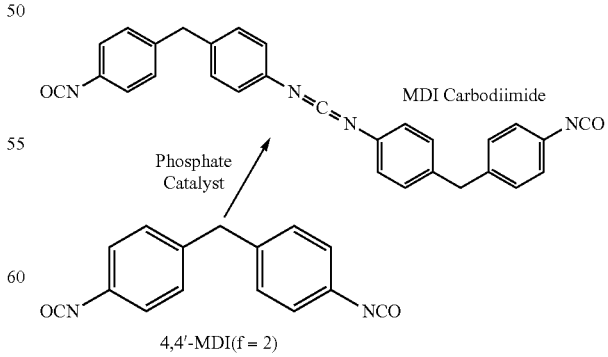

As will be understood by those of ordinary skill in the art, with the benefit of this disclosure, Equation 6 does not illustrate complete polymerization. Moreover, the exemplary reaction depicted in Equation 6 also will liberate carbon dioxide. Among other things, the exemplary reaction depicted in Equation 6 may generate porosity within the compositions made according to the methods of the present invention, without including water in the composition. This may be particularly useful, inter alia, when an apparatus of the present invention comprising components useful in making the compositions described herein is to be stored at elevated temperatures (exemplary apparatus are further described hereinbelow). Examples of suitable phosphate catalysts that may be used to convert isocyanate groups to polycarbodiimides include, inter alia, triphenylphosphine oxide, hexamethylphosphoric triamide, and the like.

II. Apparatus of the Present Invention

FIG. 1A illustrates an exemplary embodiment of an apparatus of the present invention, denoted generally by the number 100. Apparatus 100 comprises sealed container 110. In certain embodiments of the present invention, sealed container 110 is made from medical-grade material. In certain embodiments, sealed container 110 may be impermeable to moisture. Certain embodiments of sealed container 110 also may be light-impermeable. Certain embodiments of sealed container 110 also may resist heat degradation. In certain embodiments of the present invention, sealed container 110 may be made from polyethylene; in certain embodiments, the polyethylene may have a thickness in the range of from about 3 mils to about 5 mils. The present invention also contemplates that sealed container 110 may be made from glass. Sealed container 110 comprises within it internal cavity 120.

Figure 1B:
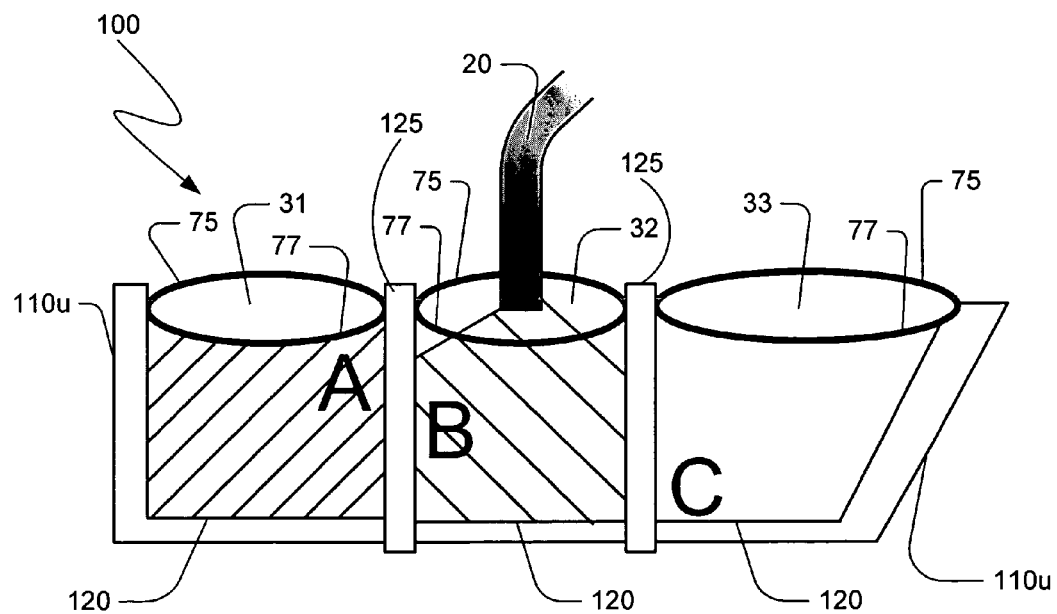
FIG. 1B illustrates an exemplary embodiment of the apparatus of FIG. 1A, while it is being made.

Sealed container 110 may be prepared (e.g., filled with desired components, and sealed) as follows. Referring now to FIG. 1B, an unsealed container 110*u* is illustrated therein. Dividers 125 may be affixed externally to unsealed container 110*u*. Dividers 125 function to partition internal cavity 120 into a plurality of compartments, so as to prevent communication between adjacent compartments, until divider 125 is removed. In certain embodiments of the present invention wherein embodiments of dividers 125 may be internally disposed within internal cavity 120, such internally-disposed dividers 125 partition internal cavity 120 into a plurality of compartments and prevent communication between adjacent compartments until internally-disposed dividers 125 are displaced within internal cavity 120, which displacement of internally-disposed dividers 125 may permit fluid communication between adjacent compartments that formerly were separated from each other by internally-disposed dividers 125. Though FIG. 1B illustrates the use of two dividers 125 to partition internal cavity 120 into three compartments, one of ordinary skill in the art having the benefit of this disclosure will recognize that a different quantity of dividers 125 may be used (e.g., three dividers 125, for example) to partition internal cavity into a different number of compartments (e.g., four compartments, for example).

As illustrated in FIG. 1B, dividers 125 partition internal cavity 120 to form a plurality of individual, unsealed compartments (e.g., compartments A, B, and C). Each compartment has an opening (31, 32, or 33, for example) through which desired components may be placed. As illustrated in FIG. 1B, opening 31 is bounded by lips 75 and 77, by a divider 125 and by the left-most edge of internal cavity 120; opening 32 is bounded by lips 75 and 77, and by two dividers 125; and opening 33 is bounded by lips 75 and 77, by a divider 125 and by the right-most edge of internal cavity 120. Each compartment then may be filled with the desired components (e.g, by flowing a component into a compartment through a conduit, such as conduit 20, for example). In certain embodiments of the present invention, the filling of compartments comprising isocyanate components may occur in a dry nitrogen atmosphere. In certain embodiments of the present invention, the filling of compartments in which non-isocyanate compounds (e.g., polyols and the like) are to be disposed may occur in a dry atmosphere, or alternatively, in a moist atmosphere (including a nitrogen atmosphere in which moisture may be present, e.g., in a controlled amount). After the desired components have been placed within unsealed container 110*u*, it may be sealed (e.g., by heat-sealing the openings through which the desired components were placed within unsealed container 110*u*), to form sealed container 110.

Figure 6A:
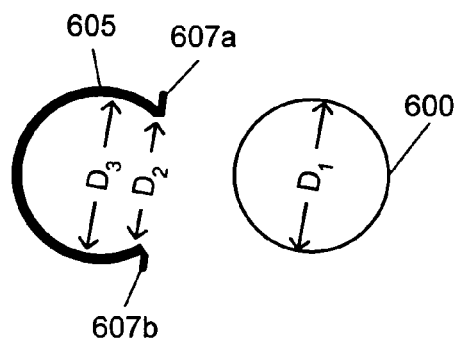
FIGS. 6A-6C illustrate exemplary embodiments of dividers that may be used with exemplary embodiments of apparatus of the present invention.

Dividers 125 may be made from any suitable material. In certain embodiments of the present invention, dividers 125 are made from a rigid plastic material. In certain embodiments, dividers 125 may be breakable dividers. The behavior of dividers 125 may be better understood with reference to FIGS. 6A through 6G. In one embodiment, dividers 125 comprise two components, rod 600 and collar 605. Referring now to FIG. 6A, rod 600 and collar 605 are depicted in the embodiment illustrated therein. Collar 605 comprises legs 607*a* and 607*b*. Rod 600 is depicted having diameter D1, while collar 605 has minor inner diameter D2 and major inner diameter D3. Generally, major inner diameter D3 of collar 605 will closely approximate (and will be only slightly larger than) diameter D1 of rod 600. Generally, minor inner diameter D2 of collar 605 will be smaller than diameter D1 of rod 600 (e.g., D2 may be in the range of from about 75% to about 95% of D1, in certain embodiments of the present invention; in other embodiments, D2 may be less than about 75% of D1).

Figure 6B:
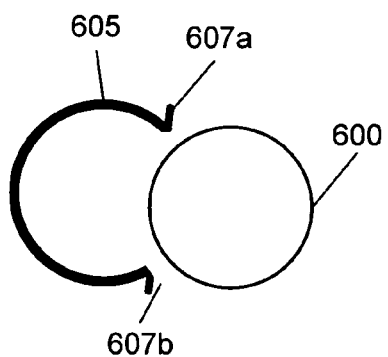
Figure 6C:
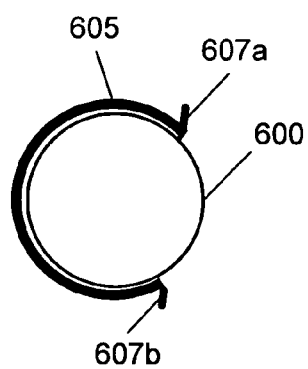

FIG. 6B depicts rod 600 in close proximity to collar 605. In the embodiment illustrated therein, when rod 600 engages collar 605, legs 607*a* and 607*b* will be displaced slightly outwardly; rod 600 then will be securely positioned within collar 605, as depicted in the embodiment illustrated in FIG. 6C.

Figure 6D:
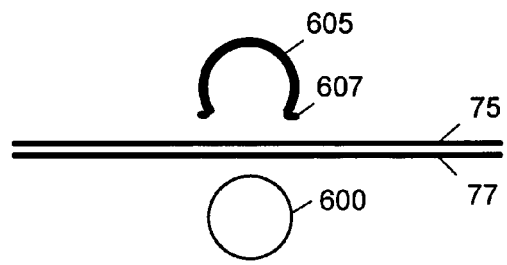
FIGS. 6D-6F illustrate exemplary embodiments of the use of exemplary dividers with exemplary embodiments of apparatus of the present invention.
Figure 6E:
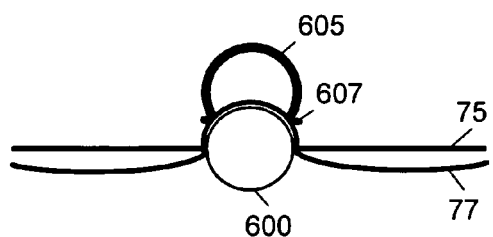
Figure 6F:
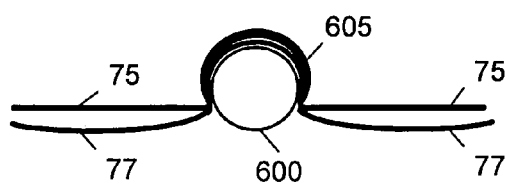
Figure 6G:
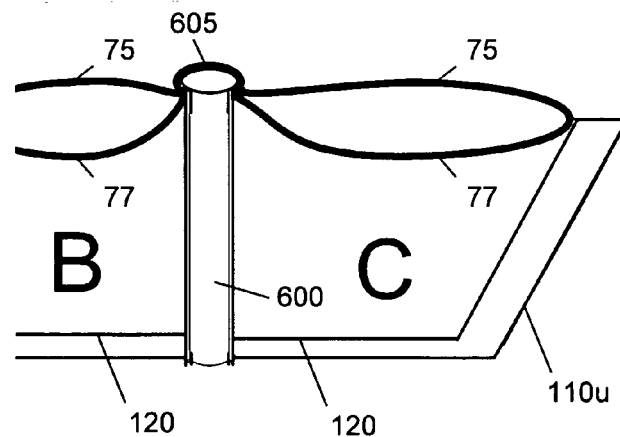
FIG. 6G illustrates another view of FIG. 6F.

FIGS. 6D through 6G illustrate an exemplary manner in which exemplary embodiments of dividers 125 (comprising rod 600 and collar 605) may be used to partition internal cavity 120 of unsealed container 110*u* into separate compartments. Referring now to FIG. 6D, rod 600 and collar 605 are shown separated from each other by unsealed container 110*u* (depicted in views 6D through 6F by lip 75 and lip 77). FIG. 6E depicts rod 600 having contacted lip 77 and pushed it into contact with lip 75, causing lip 75 to contact collar 605. FIG. 6F depicts rod 600 and lips 75 and 77 securely disposed within collar 605 (e.g., rod 600 and lips 75 and 77 having "snapped" into position within collar 605). FIG. 6G is an alternate view of FIG. 6F, and illustrates how dividers 125 (comprising rod 600 and collar 605) have partitioned internal cavity 120 into compartments B and C.

Referring now to the embodiment illustrated in FIG. 1A, two dividers 125 are shown partitioning internal cavity 120 into three compartments A, B, and C. Compartments A, B, and C generally will have disposed within them compounds useful in preparing compositions according to the methods of the present invention. For example, in an embodiment of the present invention wherein a biocompatible, synthetic polyol is to be mixed with an isocyanate and at least one filler material, the biocompatible, synthetic polyol may be disposed within, for example, Compartment A, the at least one filler material may be disposed within Compartment B, and the isocyanate may be disposed within Compartment C. Different orientations of the above-described compounds within the compartments A, B, and C are possible, as will be recognized by one of ordinary skill in the art, with the benefit of this disclosure.

Where the dividers 125 are externally affixed to sealed container 110, dividers 125 may be removed from sealed container 110 without compromising the integrity of sealed container 110. In certain embodiments of the present invention, dividers 125 may be removed by "unsnapping" rod 600 (shown in FIG. 6G) from its position within collar 605 (shown in FIG. 6G), or by sliding rod 600 out from its position within collar 605, or the like. In certain embodiments of the present invention, dividers 125 may be internally disposed within sealed container 110, and, at a desired time, may be displaced within sealed container 110 without compromising the integrity of sealed container 110.

In embodiments wherein dividers 125 are externally affixed to sealed container 110, removal of dividers 125 will permit communication between the compounds in adjacent compartments. In embodiments wherein dividers 125 are internally disposed within sealed container 110, displacement of dividers 125 within sealed container 110 will permit communication between the compounds in adjacent compartments. After the removal or displacement of dividers 125, sealed container 110 may be manipulated (e.g., manually manipulated) so as to mix the compounds in compartments A, B, and C to a desired degree, as may be discerned from FIG. 2.

Figure 2:
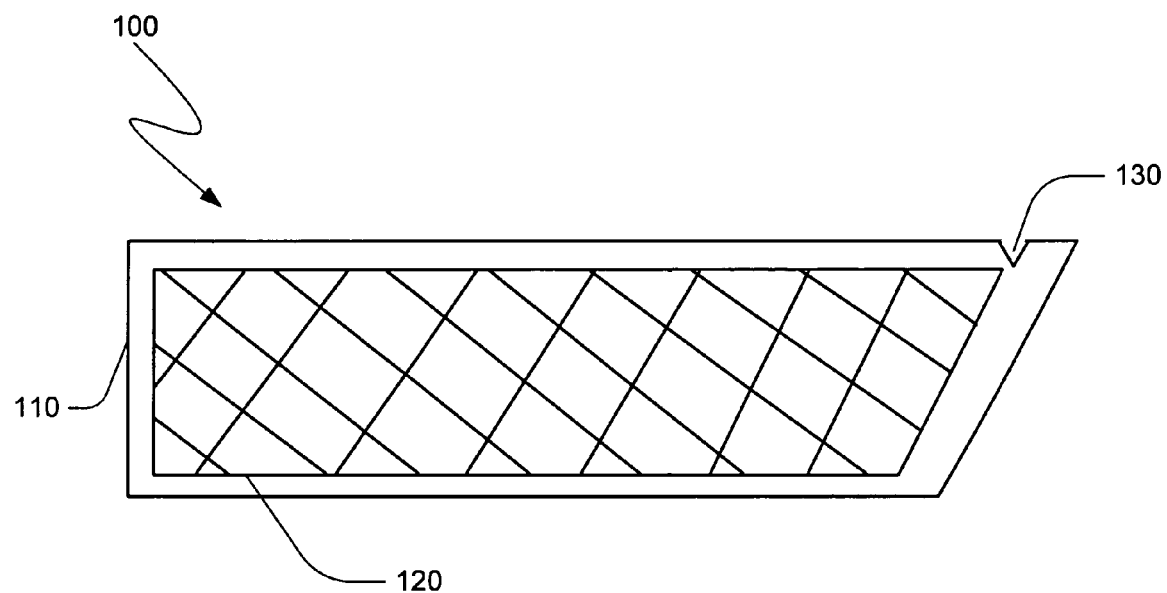
FIG. 2 illustrates another view of the apparatus of FIG. 1A.

FIG. 2 illustrates apparatus 100 after the removal of dividers 125 (shown in FIG. 1A) from sealed container 110, and after the compounds formerly segregated in compartments A, B, and C have been mixed to a desired degree. After the desired mixing has occurred, the contents of sealed container 110 may be dispensed (e.g., by dispensing the contents through an opening that may be provided in sealed container 110 that permits flow therethrough). In certain embodiments, optional tear notch 130 may facilitate dispensing of the contents of sealed container 110.

Figure 3A:
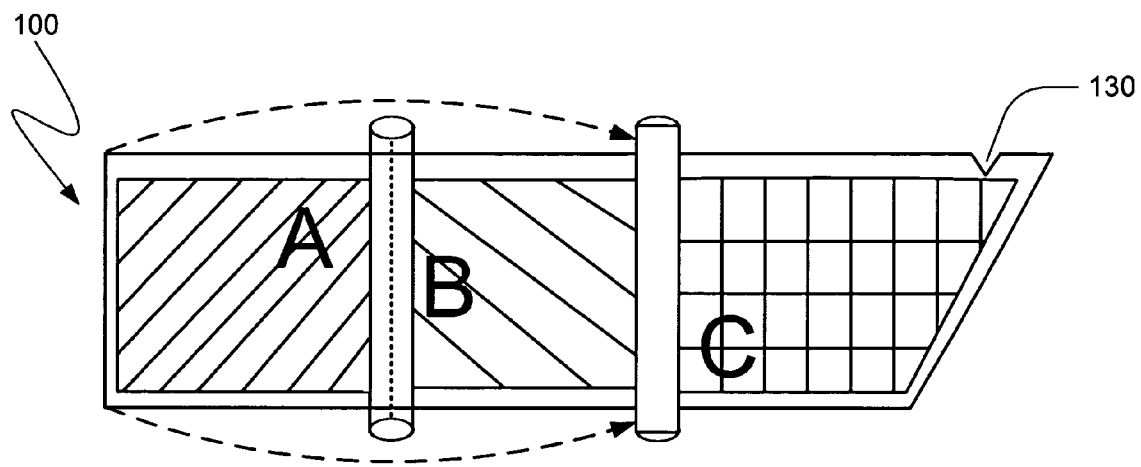
FIG. 3A illustrates another exemplary embodiment of an apparatus of the present invention.
Figure 3B:
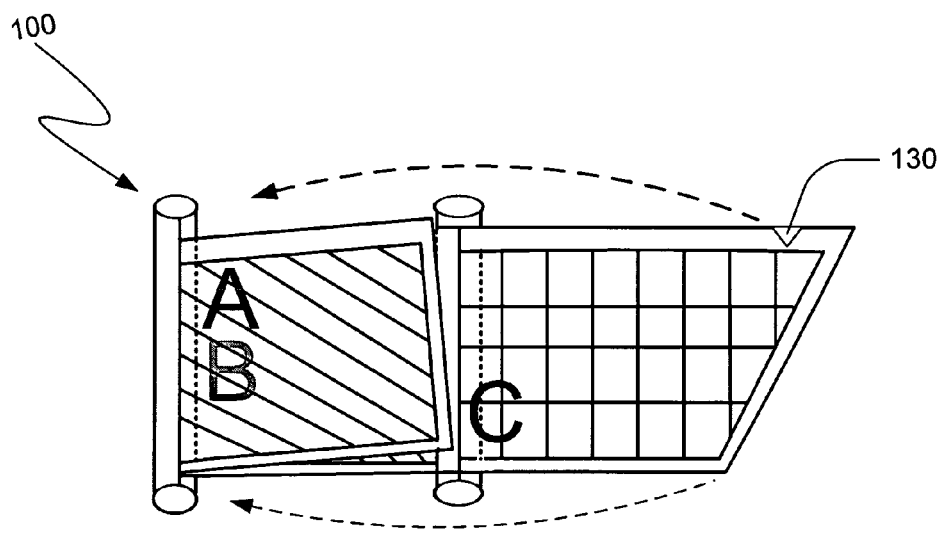
FIG. 3B illustrates another view of the apparatus of FIG. 3A.
Figure 3C:
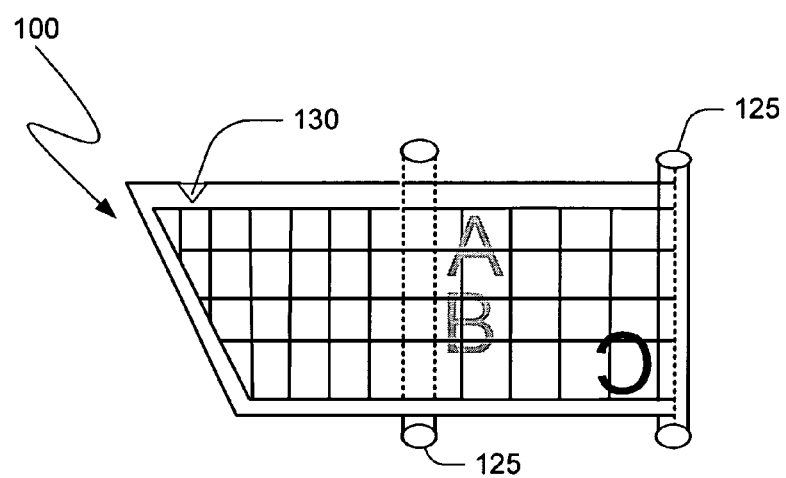
FIG. 3C illustrates another view of the apparatus of FIGS. 3A and 3B.

In certain embodiments of the present invention, apparatus 100 may be folded, e.g., for convenient storage. FIGS. 3A-3C illustrate embodiments of apparatus 100 in various stages of folding.

Figure 4A:
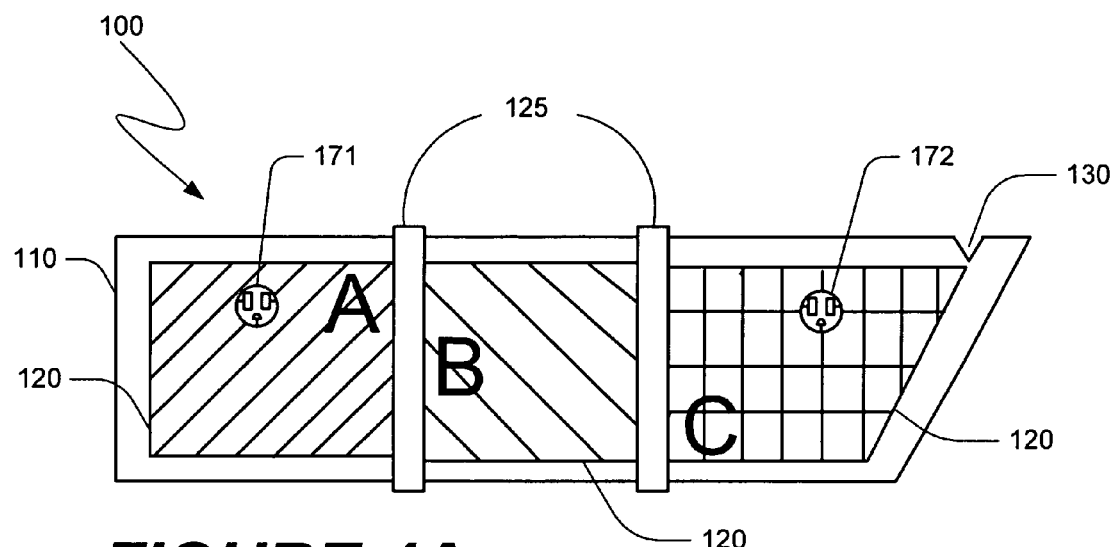
FIG. 4A illustrates another exemplary embodiment of an apparatus of the present invention.
Figure 4B:
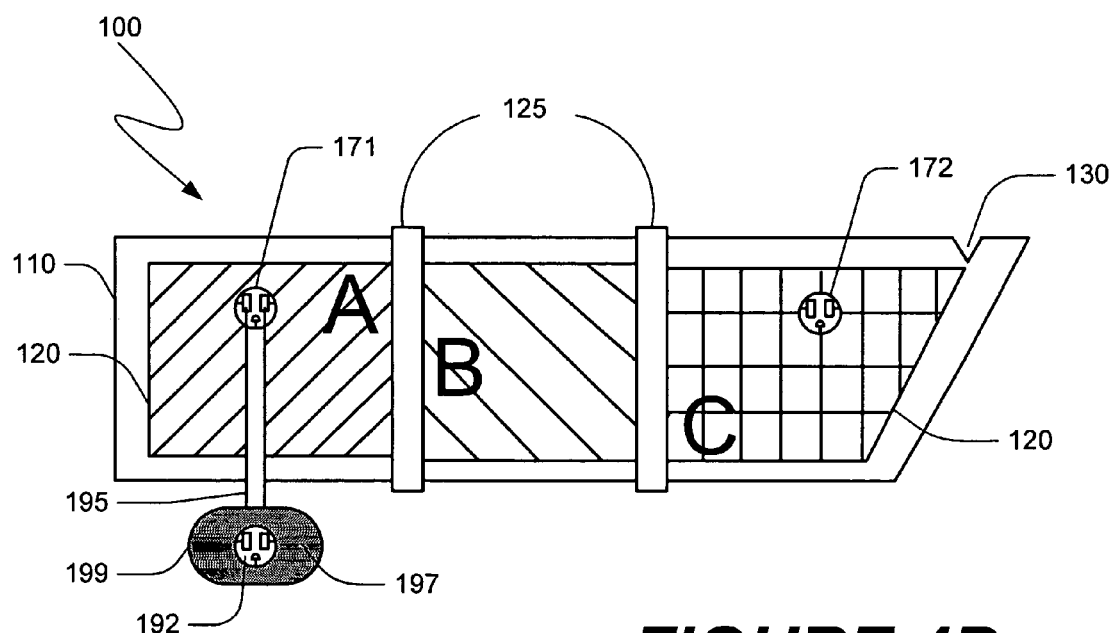
FIG. 4B illustrates another view of the apparatus of FIG. 4A.

Apparatus 100 also may be adapted to connect to a standard medical interface, e.g., a Luhr lock. Referring now to FIG. 4A, an exemplary embodiment of apparatus 100 is depicted therein, showing optional fitting 171 connected to compartment A, and optional fitting 172 connected to compartment C. Optional fittings 171 and 172 may be any suitable fittings that may enhance the compatibility of apparatus 100 with standard medical interfaces. In certain embodiments, optional fittings 171 and 172 may be male or female connectors. In certain embodiments, optional fittings 171 and 172 may be Luhr lock connectors. In certain embodiments, optional fittings 171 and 172 may be male connectors adapted to fit to a female Luhr lock connector. Among other things, the addition of one or more optional fittings to one or more compartments of apparatus 100 may be particularly useful when an operator desires to provide certain heat-sensitive additives (e.g., progenitor cells, proteins, antibiotics, a pH buffering solution, or the like) in separate reservoirs apart from apparatus 100, and additionally desires to combine such additives with the compounds disposed within apparatus 100 (or with a particular compound disposed within a particular compartment within apparatus 100). For example, FIG. 4B depicts the connection of one end of conduit 195 to fitting 171, with the other end of conduit 195 connecting to fitting 192 of reservoir 199. Reservoir 199 is filled with compound 197, which may comprise any additive desired to be provided separately from the compounds initially provided within apparatus 100. For example, in certain embodiments compound 197 may comprise, inter alia, progenitor cells, or pH buffering solution; in certain other embodiments, compound 197 may comprise proteins and/or antibiotics, for example. In certain other embodiments, compound 197 may comprise an isocyanate prepolymer that has been prepared in advance, which isocyanate prepolymer has then been placed within reservoir 199, to be combined at a desired time with the compounds disposed in apparatus 100. Compound 197 may be incorporated within compartment A in a variety of ways, including, for example, elevating and inverting reservoir 199 so as to permit compound 197 to gravity flow through conduit 195 into compartment A.

Figure 4C:
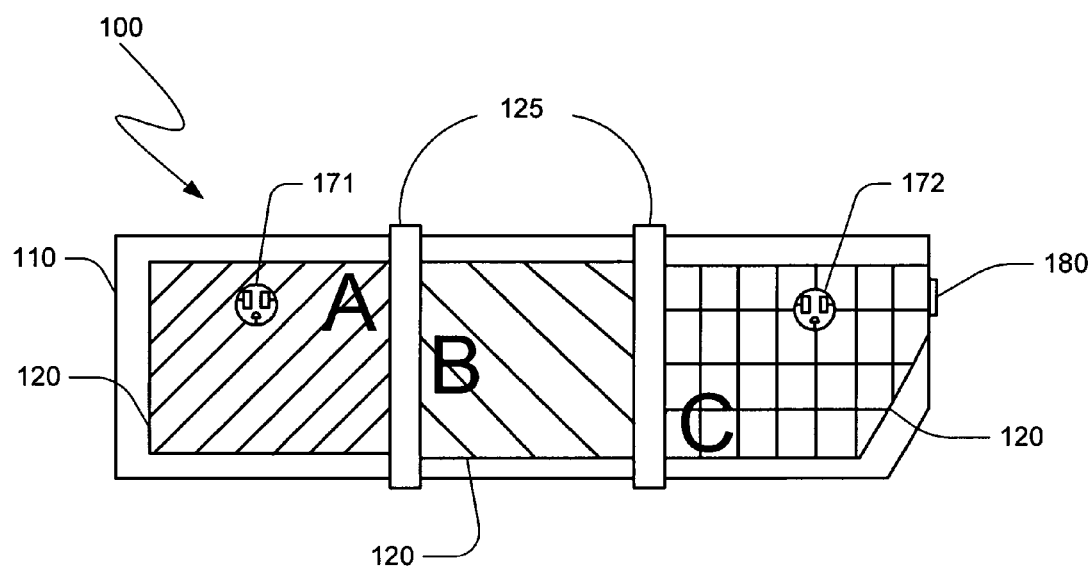
FIG. 4C illustrates another view of the apparatus of FIG. 4A.

FIG. 4C depicts an exemplary embodiment of apparatus 100 having optional fitting 180 disposed at one end. Optional fitting 180 may be any suitable fitting that may enhance the compatibility of apparatus 100 with standard medical interfaces. In certain embodiments, optional fitting 180 may be a Luhr lock connector. Among other things, the use of optional fitting 180 may reduce the possibility of contamination, and permit greater ease of use.

Table 3 below illustrates some of the possible combinations of compounds that may be disposed within compartments within sealed inner container 110. The combinations set forth in Table 3 are exemplary only, and in no way should be read so as to limit, or to define, the present invention.

TABLE 3

| | Compartment A | Compartment B | Compartment C |
|---|---|---|---|
| Embodiment 1 | Naturally occurring polyol | Biocompatible, synthetic polyol | Isocyanate |
| Embodiment 2 | Mixture of naturally occurring polyol and biocompatible, synthetic polyol | Filler material and/or certain other optional additives | Isocyanate |
| Embodiment 3 | Isocyanate | Filler material and/or certain other optional additives | Naturally occurring polyol |
| Embodiment 4 | Biocompatible, synthetic polyol | Isocyanate | Filler material and/or certain other optional additives |
| Embodiment 5 | Chain-extender | Isocyanate | Biocompatible, synthetic polyol |
| Embodiment 6 | Isocyanate | Biocompatible, synthetic polyol | Cross-linker |
| Embodiment 7 | Filler material and/or certain other optional additives | Cross-linker | Isocyanate prepolymer (e.g., prepolymer that has been previously-prepared, then placed within Compartment C) |

As noted above, the combinations listed in Table 3 are exemplary only, and numerous other combinations may be prepared in accordance with the teachings of the present invention. Moreover, the present invention does not require the inclusion within sealed container 110 of all compounds desired to be reacted to form a particular composition. Rather, the present invention contemplates that certain additives may be incorporated into a composition at a time after the contents of all compartments within sealed container 110 have been mixed, and dispensed from sealed container 110. For example, in certain embodiments, sealed container 110 may comprise, e.g., an isocyanate, a polyol, and a filler material, which may be heated, and mixed within sealed container 110 to a desired degree, after which the contents of sealed container 110 may be dispensed into a mold that comprises, for example, an anterior cruciate ligament and progenitor cells disposed therein. Alternatively, the compounds disposed within sealed container 110 may be heated and mixed to a desired degree, after which the contents of a separate reservoir (e.g., reservoir 199) may be flowed into sealed container 110, as described earlier.

Figure 5:
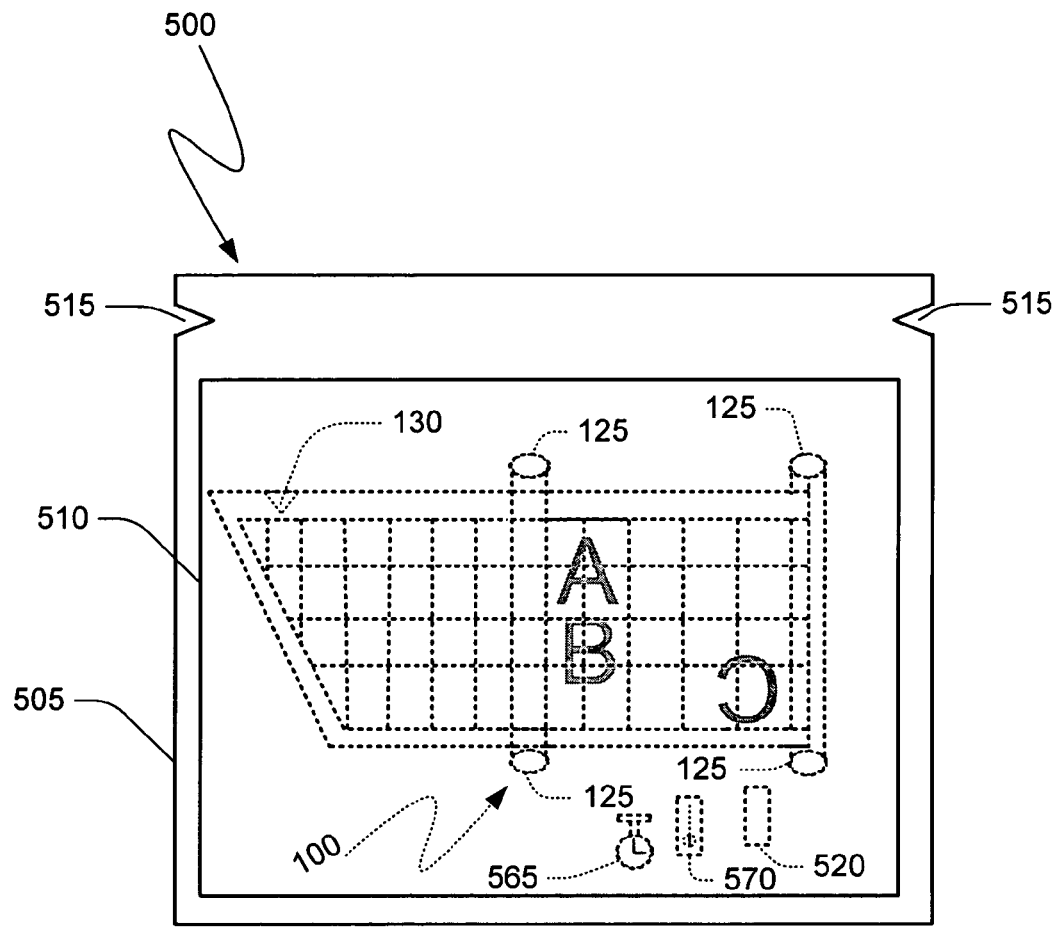
FIG. 5 illustrates another exemplary embodiment of an apparatus of the present invention.

FIG. 5 illustrates another embodiment of an apparatus of the present invention, denoted generally by the reference numeral 500. Apparatus 500 comprises sealed outer container 505, which comprises inner cavity 510. Sealed inner container 100 is disposed within sealed outer container 505. Generally, sealed outer container 505 is impermeable to moisture. In certain embodiments of the present invention, sealed outer container 505 may be made from medical grade material. In certain embodiments of the present invention, sealed outer container 505 is made from a moisture-resistant material (e.g., aluminum). In certain optional embodiments of the present invention, additional items may be disposed within inner cavity 510, such as, for example, desiccant 520, stopwatch 565, and thermometer 570. In certain embodiments of the present invention, sealed outer container 505 may comprise tear notches 515.

In certain embodiments of the methods of the present invention, apparatus 500 may be heated for a desired time at a desired temperature, after which sealed inner container 100 may be removed from sealed outer container 505. One or more dividers 125 (for example, a divider 125 separating compartments A and B) then may be separated from sealed inner container 100 (or may be displaced within sealed inner container 100, in embodiments wherein dividers 125 are internally disposed within sealed inner container 100), and sealed inner container 100 may be manipulated (e.g., manually manipulated) so as to mix compounds disposed within compartments adjacent the removed (or displaced) or more dividers 125. Sealed inner container 100 then may be heated for a desired time at a desired temperature. Any dividers 125 that remain affixed to sealed inner container 100 may be removed (or, any dividers 125 that remain internally disposed within sealed inner container 100 may be displaced), and any heretofore unmixed compounds disposed within sealed inner container 100 may be mixed for a desired time. Sealed inner container 100 then may be opened (e.g., by tearing sealed inner container 100 at optional tear notches 130), and the mixture of compounds may be dispensed. In certain embodiments of the present invention, the mixture of compounds may be dispensed directly into the body of a mammal. In certain embodiments of the present invention, the mixture of compounds may be dispensed into a mold or the like.

The apparatus of the present invention may be used to prepare a broad variety of bone-growth-promoting compositions, including those disclosed herein, as well as others, including such bone-growth-promoting compositions as may become known in the future. The present invention contemplates that a broad variety of components that usefully may be combined to form bone-growth-promoting compositions may be disposed within the apparatus of the present invention, and permitted to react therein to form bone-growth-promoting compositions.

III. Methods of the Present Invention

The present invention provides methods of making compositions that may be suitable for use in medical procedures; exemplary embodiments of these methods will be further described with reference to FIGS. 7A through 27F, and FIG. 36. The present invention also provides methods of performing medical procedures; exemplary embodiments of these methods will be further described with reference to FIGS. 28-35.

Certain embodiments of the methods of making compositions provided by the present invention involve, inter alia, reacting an isocyanate and polyols/polyamines to form compositions that comprise polyurethane/polyurea components. Certain other embodiments of the methods of making compositions provided by the present invention involve, inter alia, reacting an isocyanate and polyols/polyamines to form an isocyanate prepolymer, and reacting the isocyanate prepolymer with other compounds to form compositions that comprise polyurethane/polyurea components. Certain other embodiments of the methods of making compositions provided by the present invention involve, inter alia, reacting isocyanate prepolymers with polyol and a catalyst to form poly(urethane-isocyanurate) components. Certain other embodiments of the methods of making compositions provided by the present invention involve, inter alia, reacting isocyanate prepolymers with a polyol, catalyst, and water to form poly(urethane-urea-isocyanurate) components. Still other embodiments of the methods of making compositions provided by the present invention involve, inter alia, reacting isocyanate prepolymers with a polyol and a catalyst to form poly(urethane-carbodiimide) components.

Certain of these methods of making compositions involve the use of apparatus of the present invention (exemplary embodiments of which previously have been described with reference to FIGS. 1A through 6G). Exemplary embodiments of the methods of making compositions that involve the use of apparatus of the present invention will be further described with reference to FIGS. 7A-27F.

A. Modified "One-Shot" Embodiments

Figure 7A:
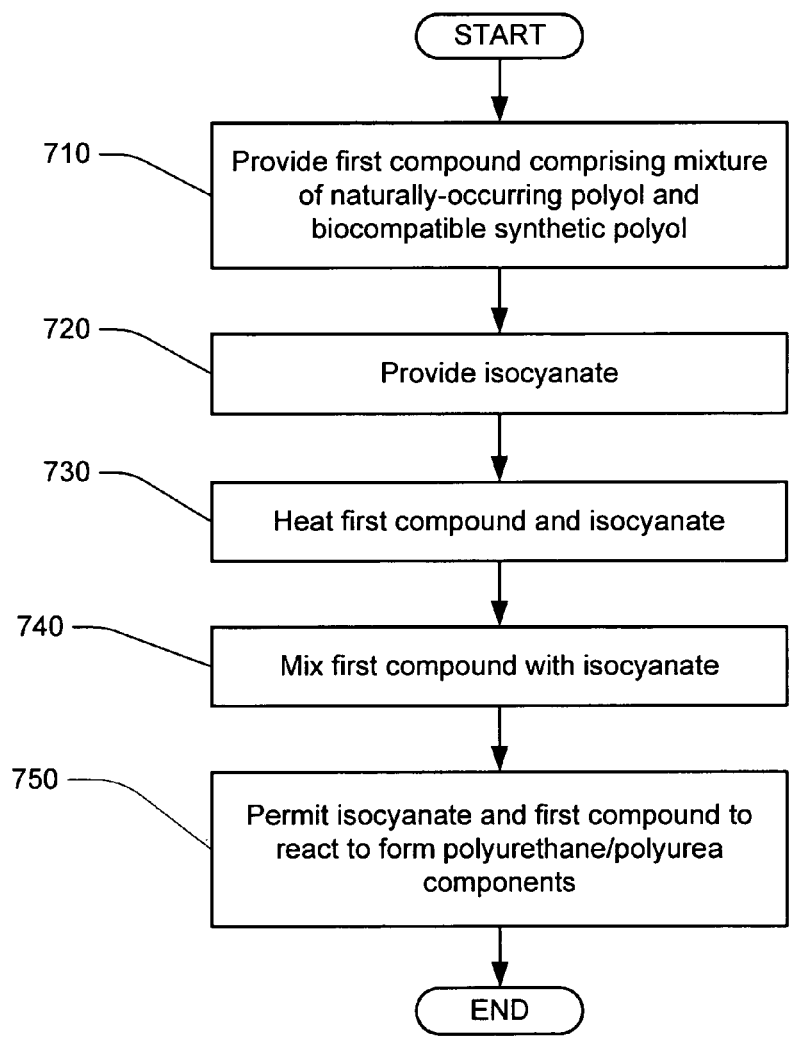
FIGS. 7A-27F are top level flow-charts depicting exemplary methods for making compositions that promote bone growth, according to exemplary embodiments of the methods of the present invention.
Figure 7B:
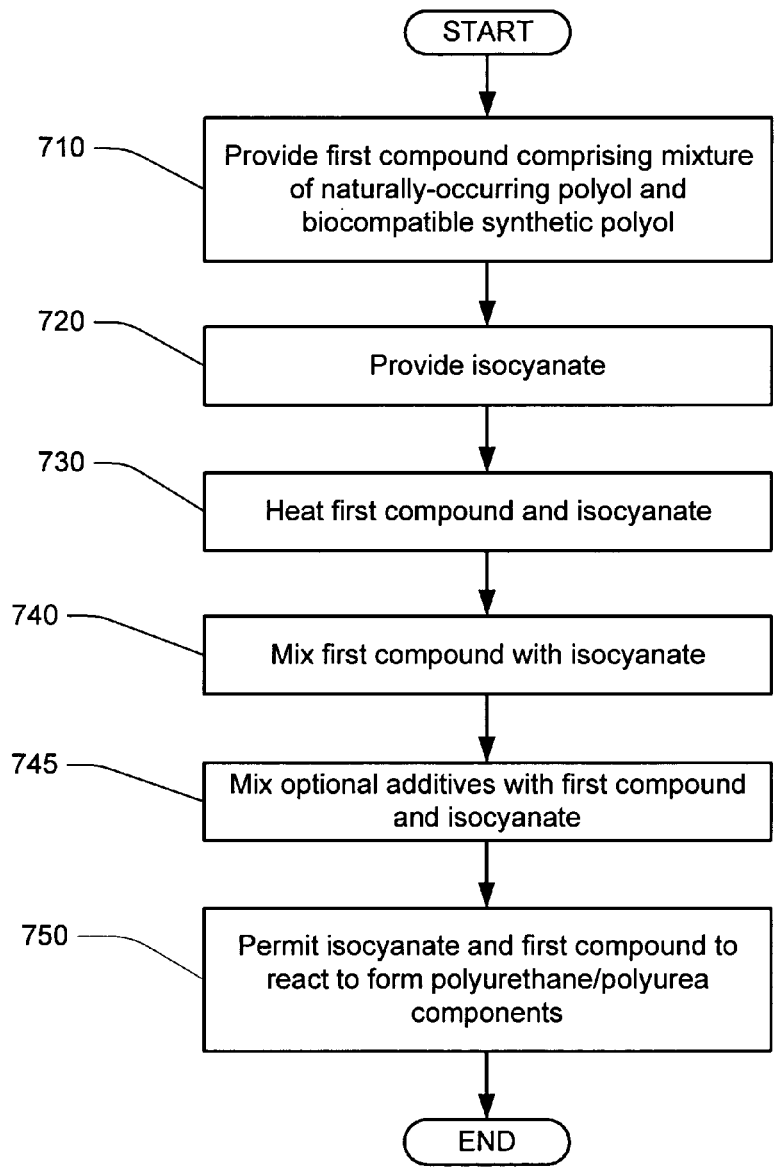

FIGS. 7A through 9D set forth exemplary embodiments of methods of the present invention that comprise reacting isocyanates and polyols/polyamines to form compositions that comprise polyurethane/polyurea components. Referring now to FIG. 7A, a first compound comprising a mixture of a naturally-occurring polyol and a biocompatible, synthetic polyol is provided in step 710. In step 720, an isocyanate is provided. In certain embodiments, the isocyanate and the first compound both may be liquids at room temperature. In step 730, the first compound and the isocyanate are heated to a desired temperature. In certain embodiments of the present invention, the desired temperature may be in the range of from about room temperature to about 150 degrees Celsius, but other temperatures may be selected, as will be recognized by one of ordinary skill in the art, with the benefit of this disclosure. In certain embodiments of the present invention, the desired temperature may be in the range of from about 50 degrees Celsius to about 100 degrees Celsius. In step 740, the first compound and the isocyanate are mixed to a desired degree. In step 750, the first compound and the isocyanate are permitted to react to form polyurethane/polyurea components. In the exemplary method illustrated in FIG. 7A, polyurea components may be formed if, inter alia, water was present in either or both of the naturally-occurring polyol and the biocompatible, synthetic polyol; absent the presence of water or a polyamine, only polyurethane components would be produced by the exemplary method illustrated in FIG. 7A.

In certain embodiments of the present invention, the mixture formed in step 740 further may be mixed in a step 745 (shown in FIG. 7B) with optional additives including, but not limited to, water, at least one filler material, a surfactant, at least one radio transparent substance, at least one radiopaque substance, and/or at least one protein, and the like, after which point the process then proceeds to step 750. As an alternative, these optional additives may be added earlier, e.g., in a step 725 (shown in FIG. 7D) before step 730, in which case optional step 745 would not be performed, and the process would proceed from step 740 to step 750, as illustrated in FIG. 7D. Certain optional additives (e.g., proteins, antibiotics, progenitor cells, and the like) may be heat-sensitive; in certain embodiments, an operator may elect to add heat-sensitive additives after step 730.

Figure 7C:
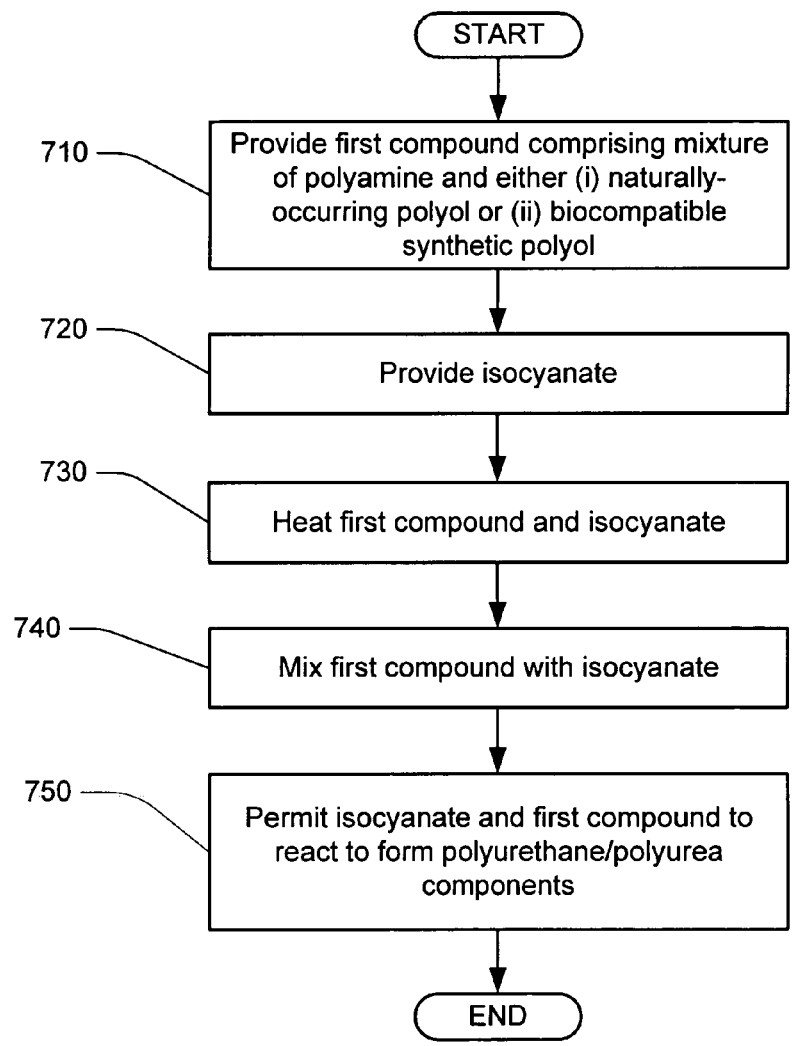
Figure 7D:
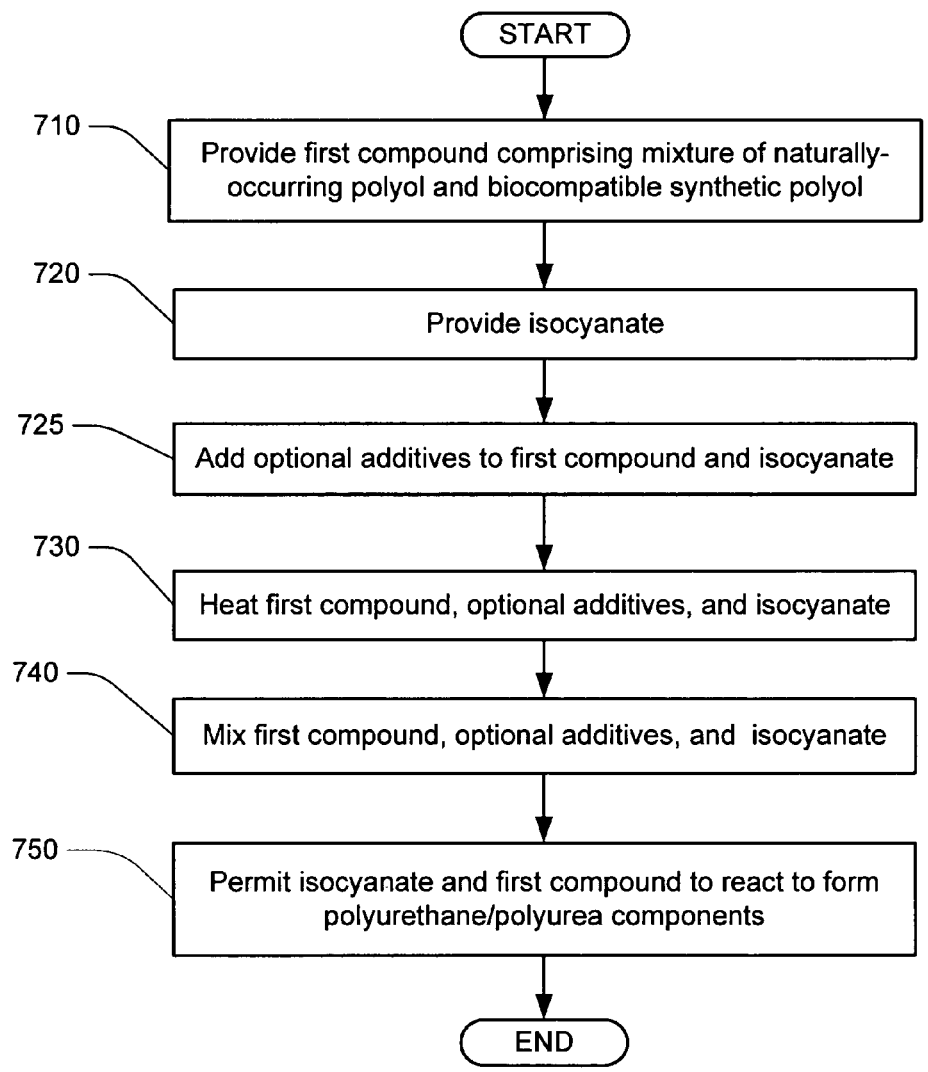

In certain embodiments of the present invention, a polyamine may be used in place of either the biocompatible, synthetic polyol or the naturally occurring polyol, as illustrated in FIG. 7C, and polyurethane/polyurea components may be produced.

FIGS. 8A through 9D illustrate additional exemplary methods of the present invention that comprise reacting isocyanates and polyols/polyamines to form compositions that comprise polyurethane/polyurea components. Because certain features and advantages of these embodiments of the present invention are substantially similar to certain features and advantages of the embodiments described with reference to FIGS. 7A-7D, such similar features and advantages are not discussed further with respect to the embodiments of the present invention illustrated in FIGS. 8A through 9D.

Figure 8A:
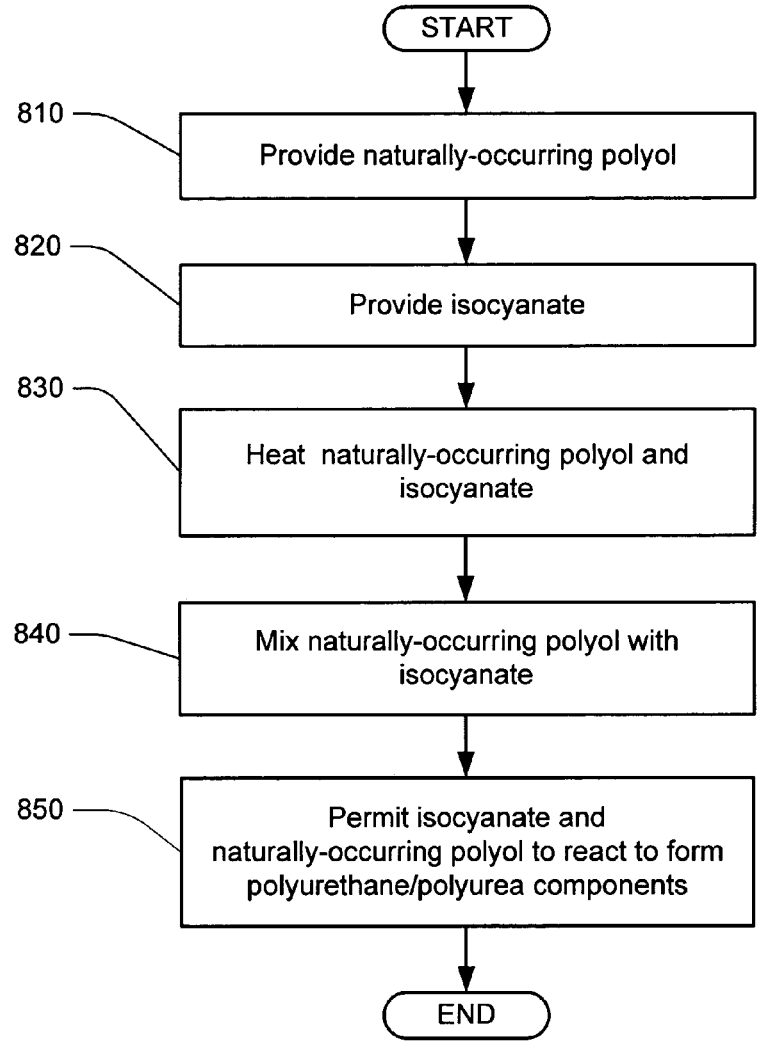
Figure 8B:
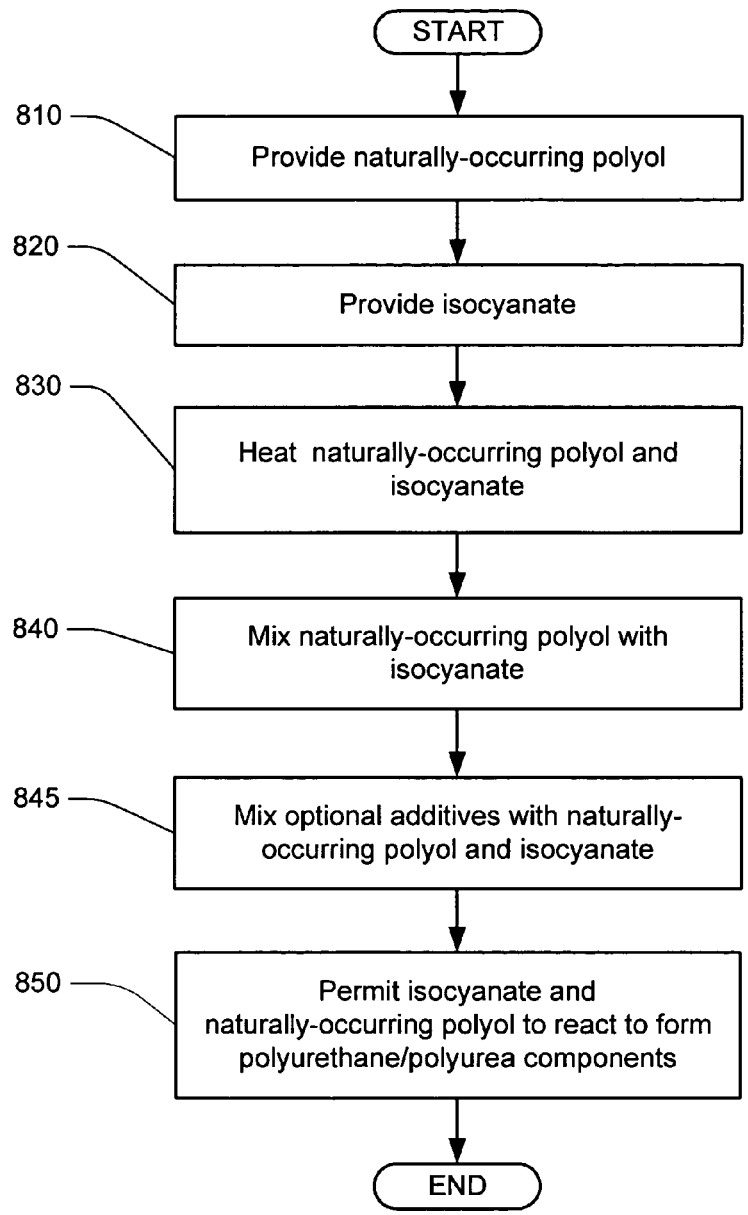
Figure 8C:
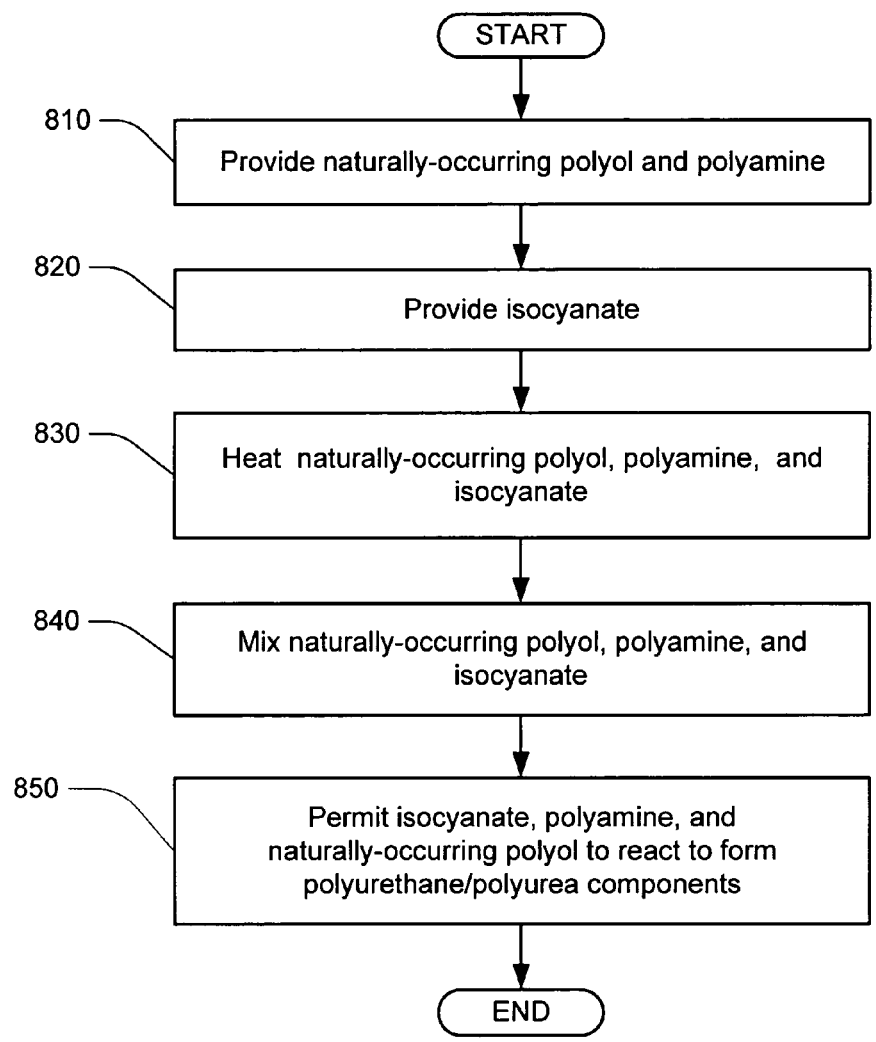
Figure 8D:
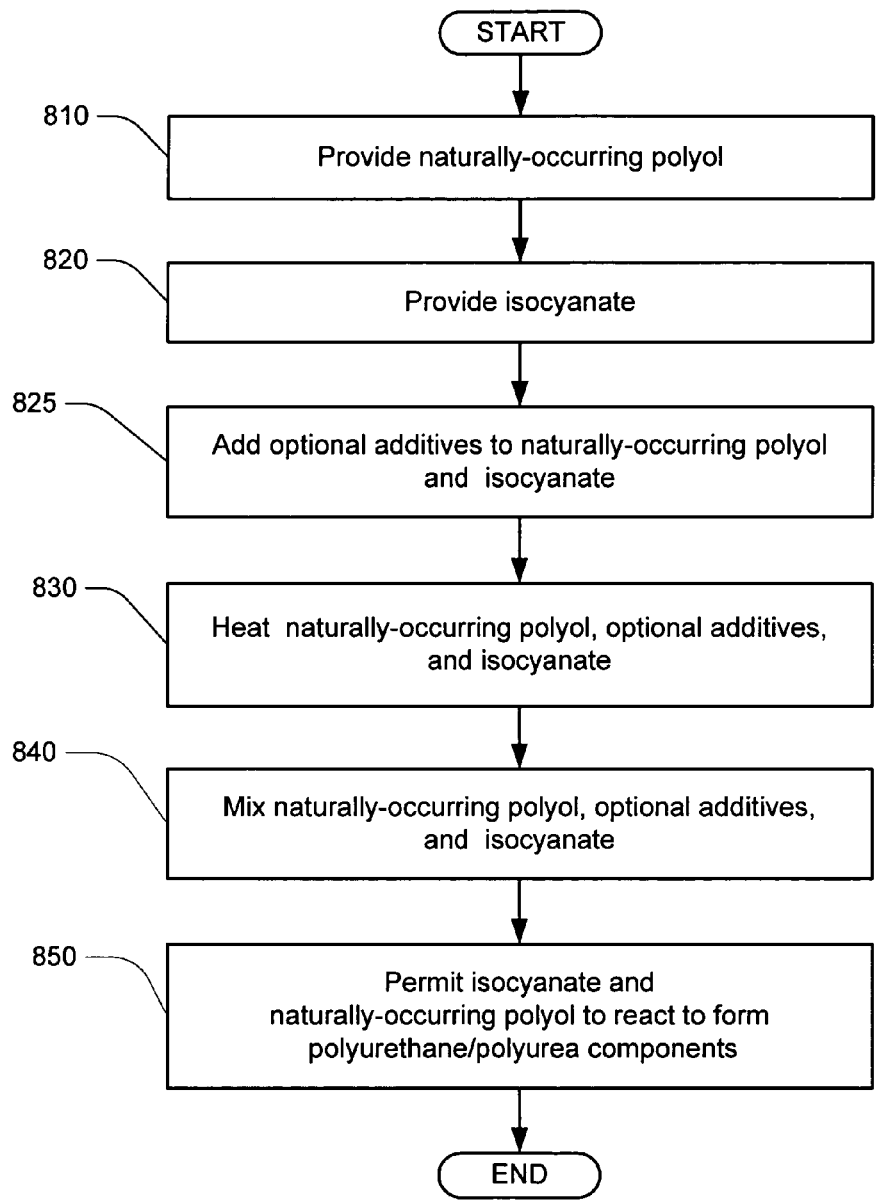

Referring now to FIG. 8A, in step 810, a naturally occurring polyol is provided. In step 820, an isocyanate is provided. In certain embodiments, the isocyanate and the naturally occurring polyol both may be liquids at room temperature. Exemplary steps that may be used to react these compounds to form a composition that comprises polyurethane/polyurea components are set forth in FIGS. 8A-8D; these steps are substantially similar to corresponding steps that have been described in FIGS. 7A-7D and will not be further elaborated upon here. In certain embodiments of the present invention, optional additives may be incorporated into the composition; suitable additives, and the ways in which they may become incorporated, have been previously described in greater detail herein with reference to the discussion of FIGS. 7B-7D (including, inter alia, the discussion of optional steps such as step 745, and the like).

Figure 9A:
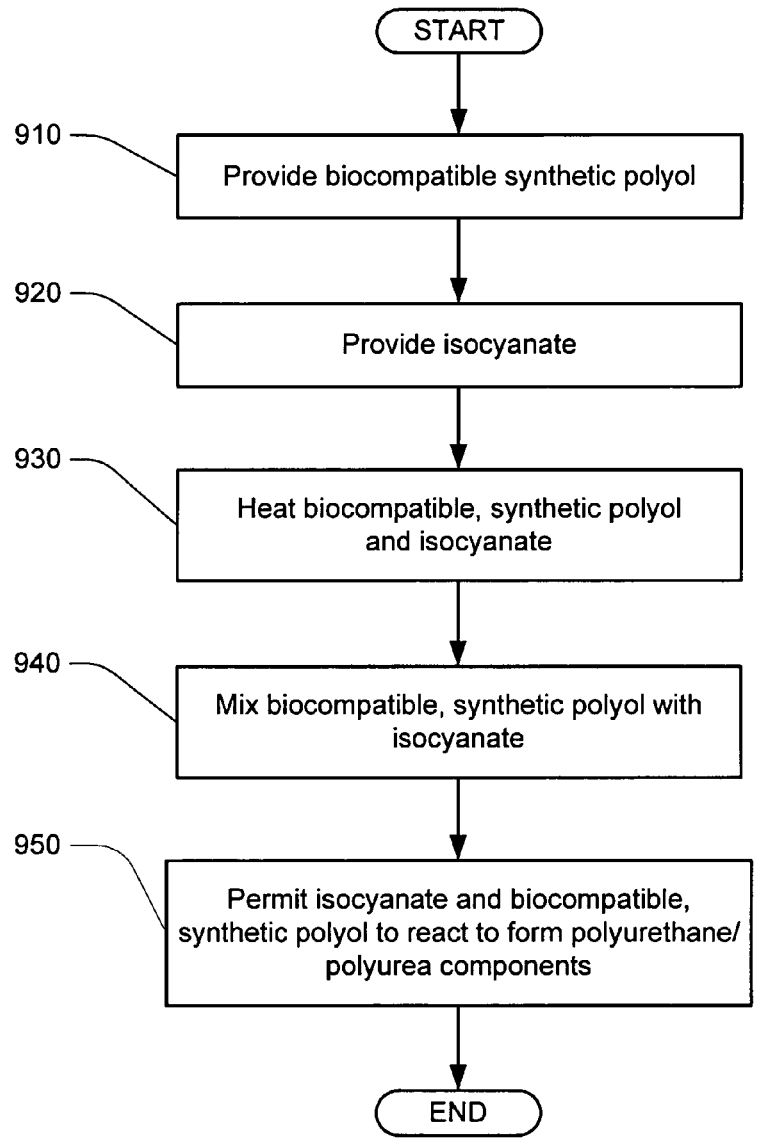
Figure 9B:
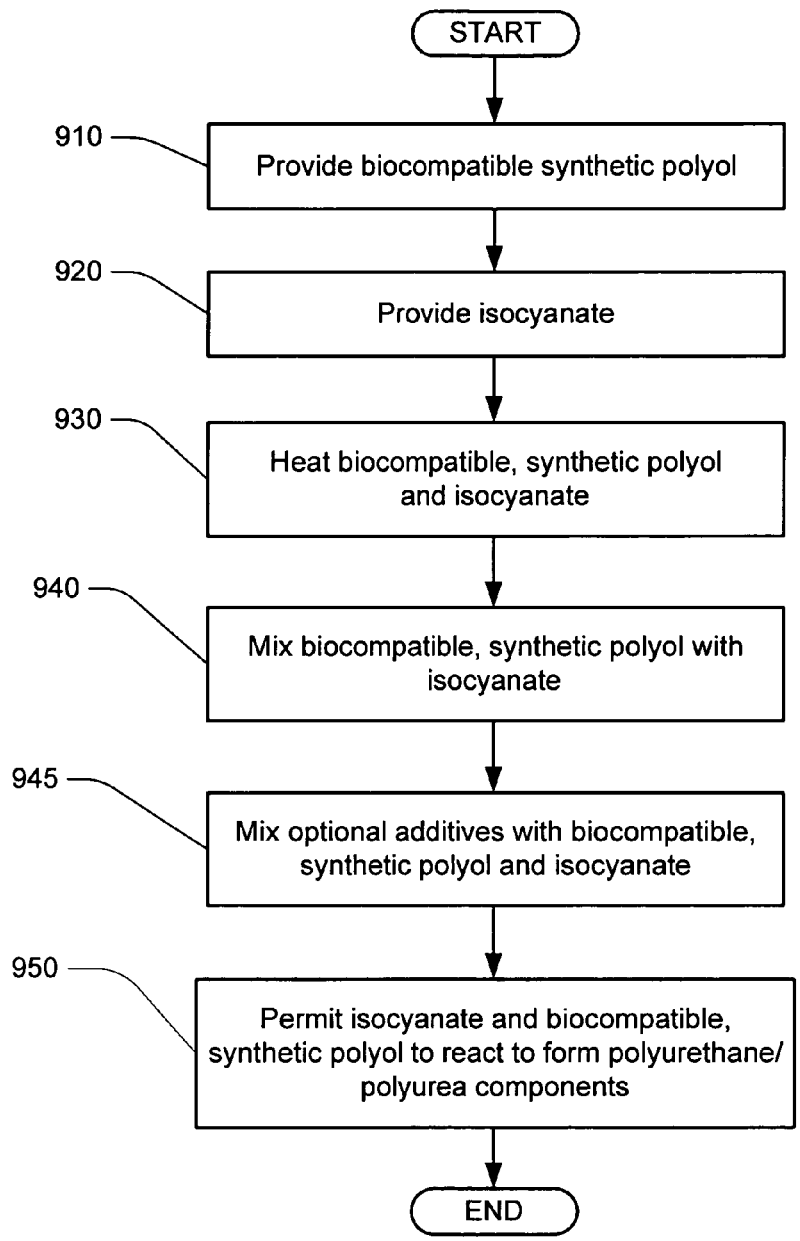
Figure 9C:
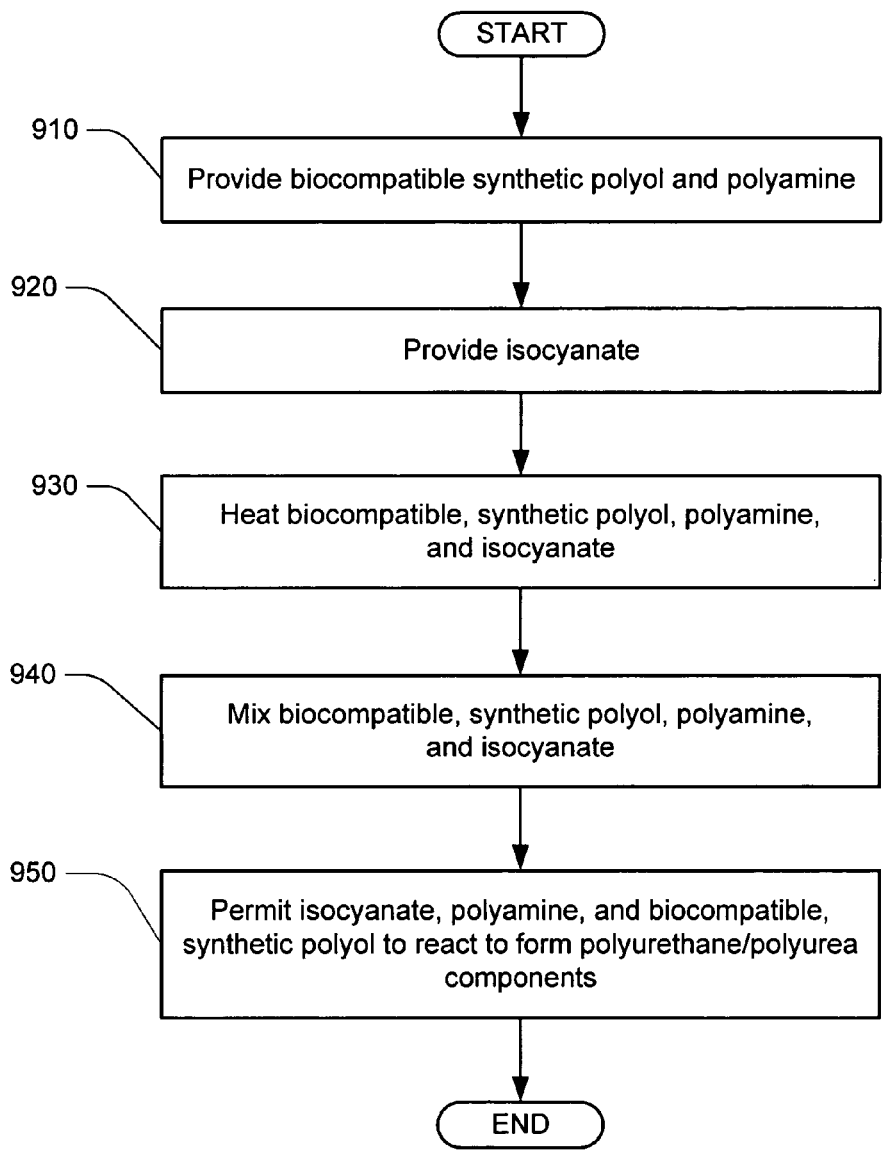
Figure 9D:
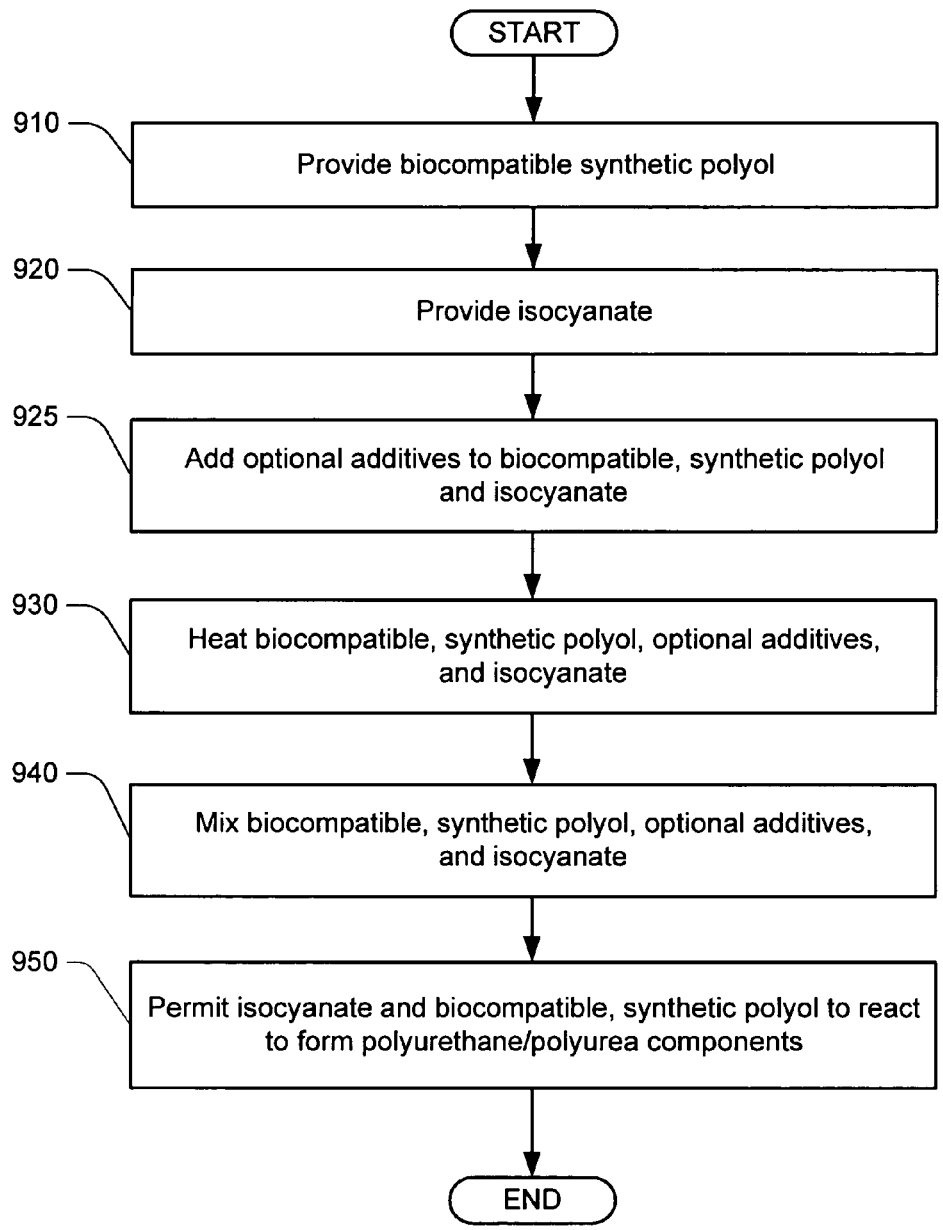

Referring now to FIG. 9A, in step 910, a biocompatible, synthetic polyol is provided. In step 920, an isocyanate is provided. In certain embodiments, the isocyanate and the biocompatible, synthetic polyol both may be liquids at room temperature. Exemplary steps that may be used to react these compounds to form a composition that comprises polyurethane/polyurea components are set forth in FIGS. 9A-9D; these steps are substantially similar to corresponding steps that have been described in FIGS. 7A-7D and will not be further elaborated upon here. In certain embodiments of the present invention, optional additives may be incorporated into the composition; suitable additives, and the ways in which they may become incorporated, have been previously described in greater detail herein with reference to the discussion of FIGS. 7B-7D (including, inter alia, the discussion of optional steps such as step 745, and the like).

B. Modified "One-Shot" Embodiments Employing Apparatus of the Present Invention

FIGS. 10A-12F describe exemplary embodiments of methods of the present invention comprising reacting isocyanates and polyols/polyamines to form compositions that comprise polyurethane/polyurea components. Moreover, the methods described in FIGS. 10A-12F employ embodiments of apparatus of the present invention.

1. Sealed Container

Figure 10A:
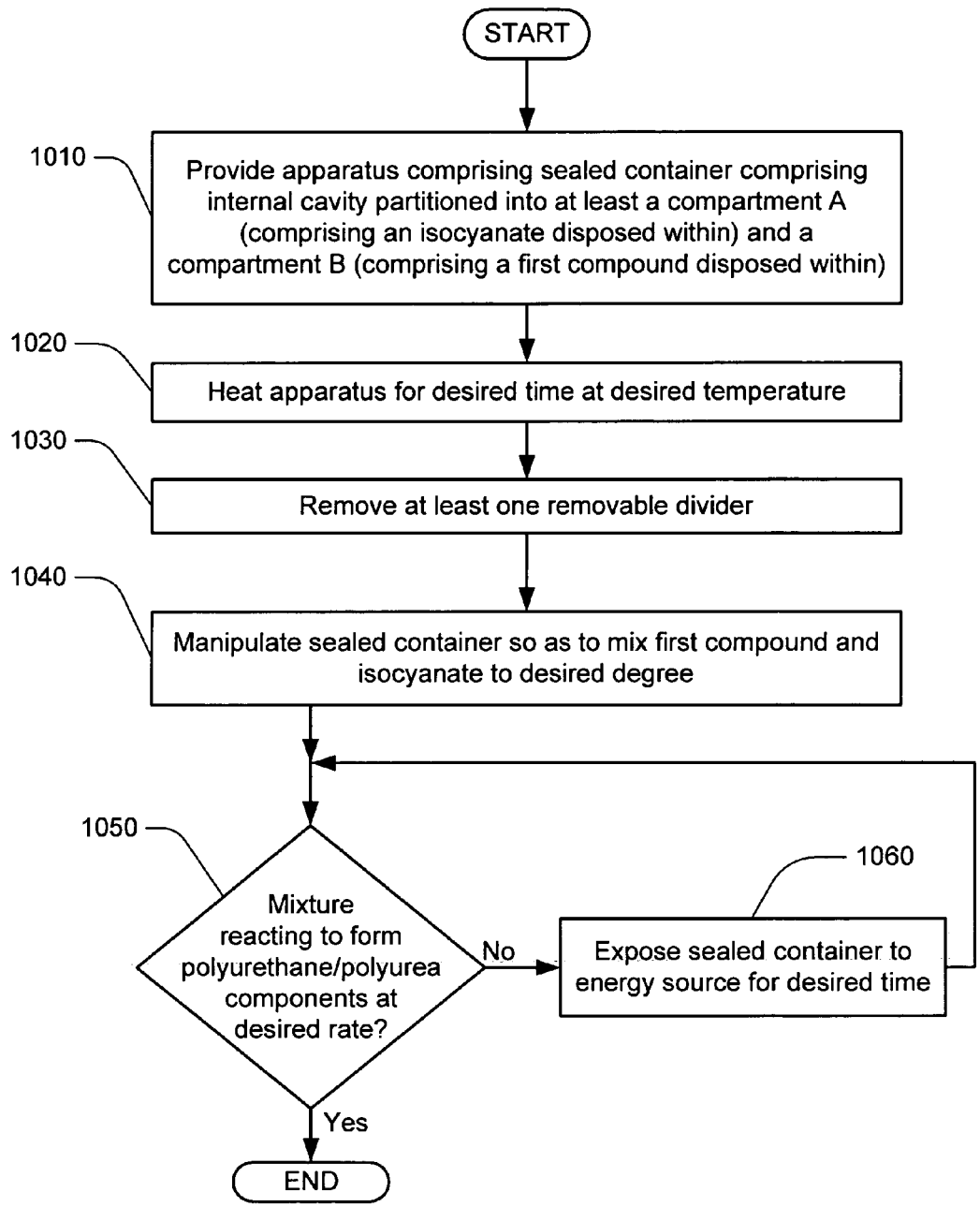
Figure 10B:
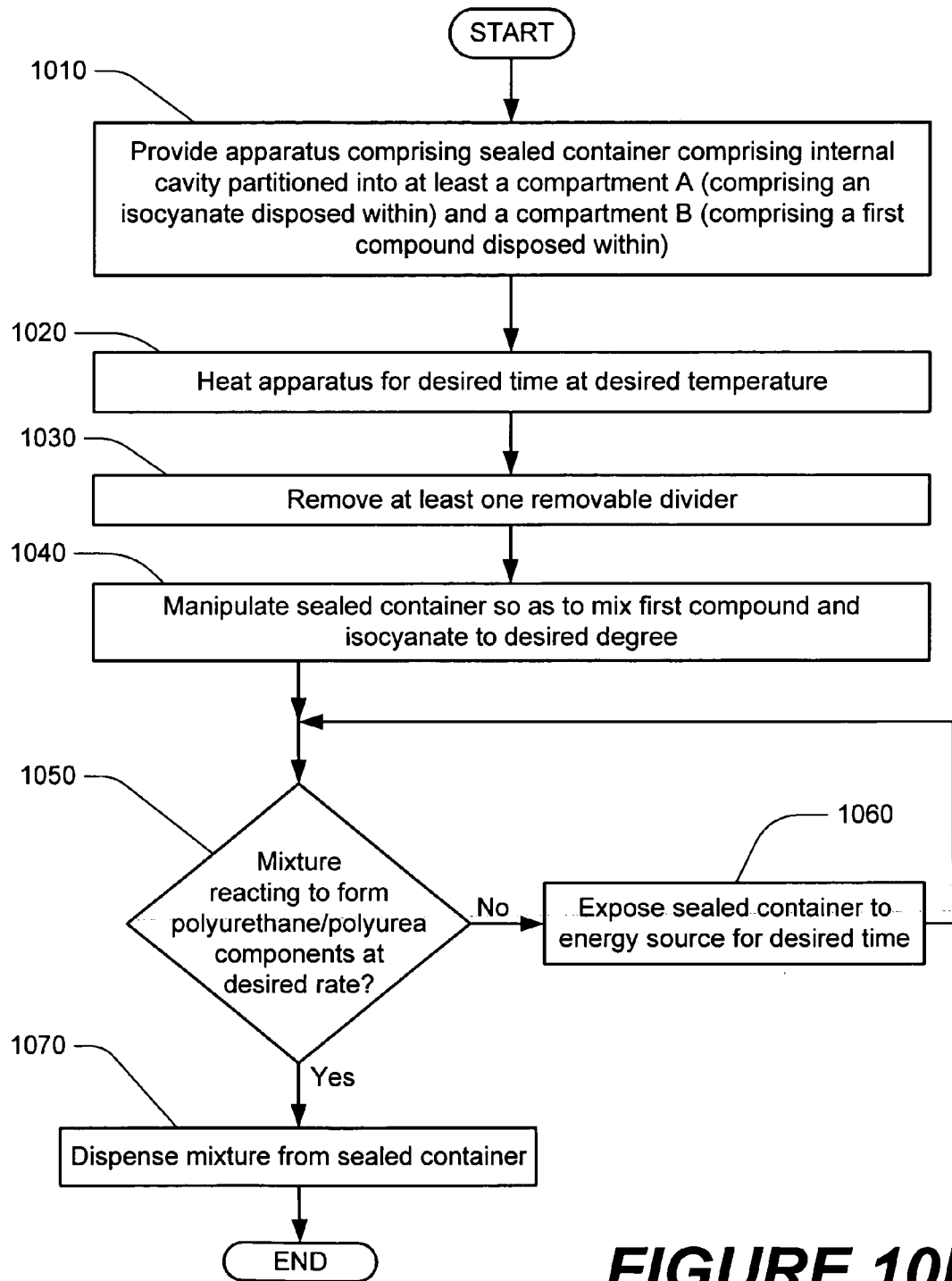
Figure 10C:
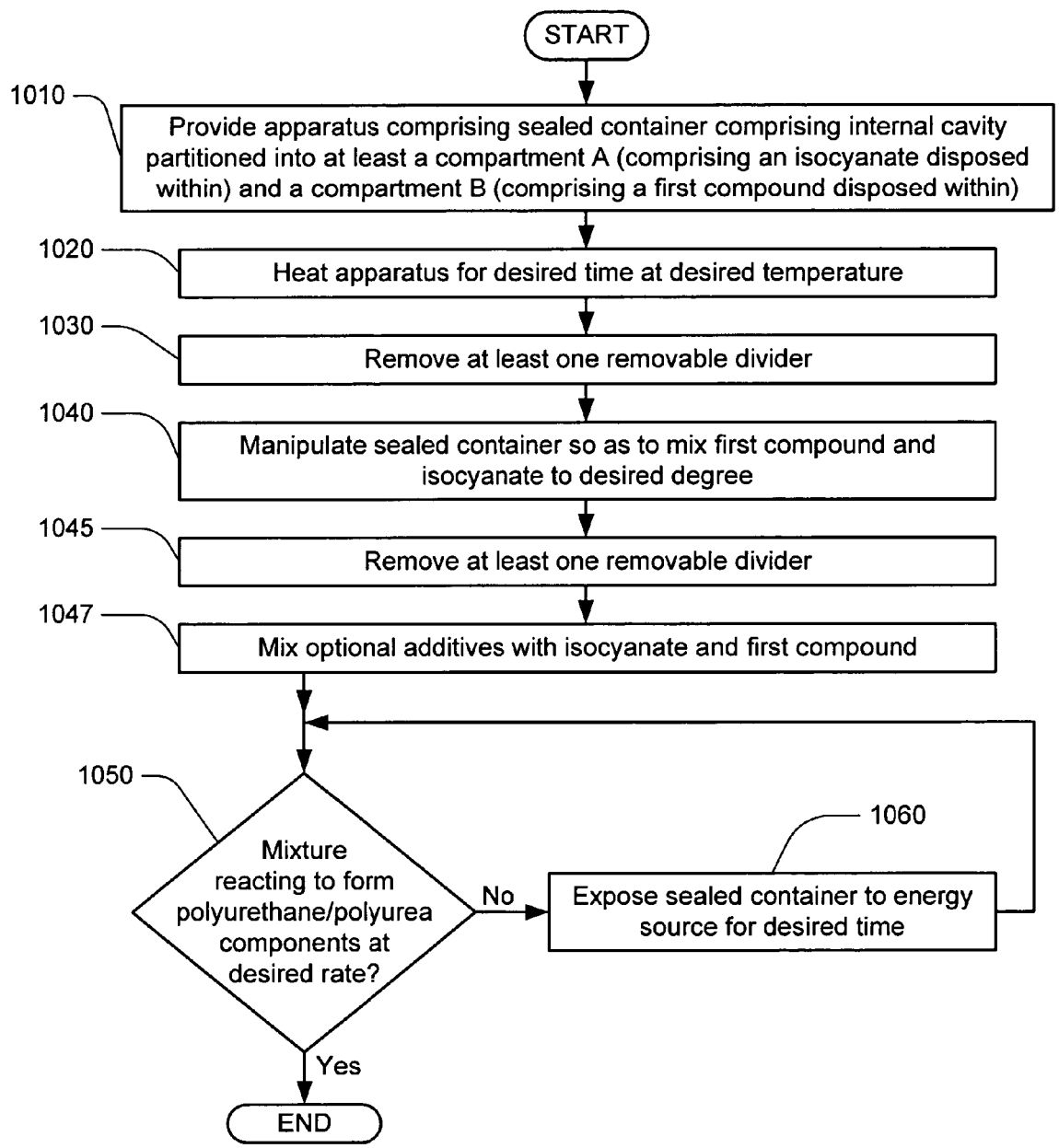
Figure 10D:
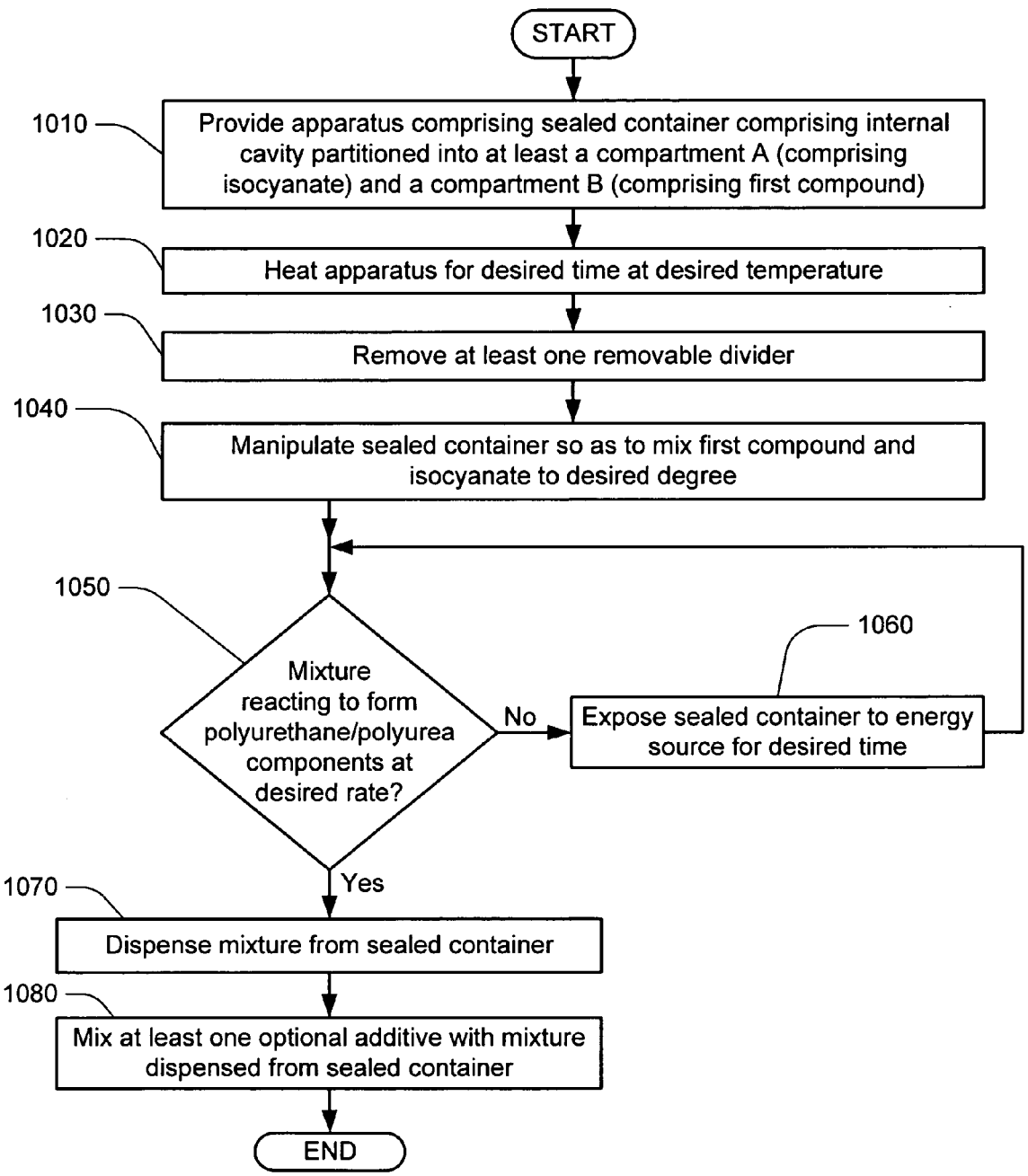

Referring now to FIG. 10A, in step 1010, an apparatus of the present invention is provided that comprises a sealed container comprising an internal cavity, the internal cavity being separated by at least one removable divider into at least a compartment A and at least a compartment B, an isocyanate being disposed in compartment A and a first compound comprising a mixture of a naturally occurring polyol and a biocompatible, synthetic polyol being disposed in compartment B. In certain embodiments of the present invention, the first compound also may comprise a polyamine. As referred to herein, the phrases "separated by at least one removable divider," "partitioned by at least one removable divider," "separated by a plurality of removable dividers," and "partitioned by a plurality of removable dividers" will be understood to include partitioning within the sealed container that may be provided by the use of removable dividers that may be externally-affixed to the sealed container, and, for embodiments of apparatus of the present invention that may employ internally-disposed dividers (e.g., dividers disposed internally within a sealed container rather than, or in combination with, externally-affixed dividers), these phrases also will be understood to include partitioning within the sealed container that may be provided by the use of internally-disposed displaceable dividers, so as to impede or prevent fluid communication between compartments located adjacent to the dividers when the dividers are in place.

In step 1020, the sealed container is heated for a desired time at a desired temperature (e.g., in the range of from about room temperature to about 150° Celsius, for certain embodiments). In certain embodiments of the present invention, the sealed container may be heated in boiling water for a desired time (e.g., for a time in the range of from about 30 seconds to about 90 seconds); alternatively, for example, the sealed container may be heated on "HIGH" in a microwave oven for a time in the range of from about 30 seconds to about 90 seconds. The desired time and temperature to which the sealed container is heated will depend on how rapidly the operator desires the compounds within the sealed container to react (after having been combined) to form polyurethane/polyurea components. Generally, the closer the temperature of the components approaches 150° C., the faster the reaction will proceed. The desired time and temperature to which the sealed container is heated also may depend on the temperature limitations of the material used to form the sealed container and the removable dividers; if, for example, either the sealed container or the removable dividers are made from a material that may degrade at about 150° C., then the sealed container may be heated to a lower temperature at which the sealed container or removable divider may not degrade (e.g., about 140° C., for example).

In step 1030, a removable divider is removed. As referred to herein, the phrases "a removable divider is removed," "remove a removable divider," "remove at least one removable divider," and "remove at least one remaining removable divider" will be understood to include removal from the sealed container of at least one removable divider that may be externally-affixed to the sealed container, and, for embodiments of apparatus of the present invention that may employ internally-disposed dividers (e.g., dividers disposed internally within a sealed container rather than, or in combination with, externally-affixed dividers), these phrases also will be understood to include displacing such internally-disposed displaceable dividers, so as to permit fluid communication between compartments located adjacent to, and previously separated by, the removed (or displaced) divider.

In step 1040, the sealed container is manipulated (e.g., manually manipulated) so as to mix the first compound and the isocyanate to a desired degree (e.g., for a time period in the range of from about one minute to about 30 minutes). The time period during which the sealed container may be manually manipulated may depend on factors including, inter alia, the temperature to which the sealed container may have been heated, whether an optional catalyst has been included, and the type of isocyanate used. For example, if an aromatic isocyanate has been used, the mixture within the sealed container may exotherm and react relatively quickly. Alternatively, if a cycloaliphatic isocyanate has been used, the reaction time may take longer.

In step 1050, a determination may be made whether the mixture of the first compound and the isocyanate is reacting to form polyurethane/polyurea components at a desired rate. For example, the progress of the reaction may be assessed through tactile feedback, as the viscosity of the mixture within the sealed container may be felt to increase, and as the mixture may be felt, and seen, to progress towards, and through, a "taffy-like" state. If the mixture is reacting at a desired rate, the process proceeds to end. Alternatively, in certain optional embodiments of the present invention, after a determination is made in step 1050 that the mixture of the first compound and the isocyanate is reacting at a desired rate, the process may proceed from step 1050 to an optional step 1070 (shown in FIG. 10B) wherein, at a desired time, the contents of the sealed container may be dispensed, after which the process may proceed to end. In certain embodiments of the present invention, an FTIR probe may be used to determine the desired time when the contents of the sealed container may be dispensed. In such embodiments, the FTIR probe may transmit a signal that may be monitored with a computer bearing suitable software; the software may interpret the signal from the FTIR probe so as to provide a quantitative measure of the concentration of isocyanate groups within the contents of the sealed container. As isocyanate groups continue reacting within the sealed container, their concentration will decrease correspondingly. When the isocyanate concentration decreases to a desired value (e.g., when the peak of the isocyanate signal decreases to about 10%, for example, of the peak originally measured at the beginning of the process), the contents of the sealed container may be dispensed. Alternatively, other means of determining the desired time for dispensing the contents of the sealed container may be used. For example, the sealed container may be placed on a relatively flat surface, and a small weight (e.g., a small magnet, for example) may be placed atop the bag. In certain embodiments, when such weight is placed atop the bag, and causes a depression having a depth of less than or about 2 millimeters, the contents of the sealed container may be dispensed.

If, however, the determination is made in step 1050 that the mixture is not reacting at a desired rate, then the process may proceed to step 1060, wherein the sealed container may be exposed to an energy source for a desired time at a desired temperature (e.g., the sealed container may be heated in boiling water for a time in the range of from about 30 seconds to about 90 seconds, or may be heated in a microwave for a similar time, or the like). In certain embodiments wherein the mixture comprises optional photo- or light-initiators and other suitable components (e.g., adducts of isocyanates, double-bond-containing isocyanates, double-bond-containing polyols, and the like), the sealed container may be exposed to a suitable light source for a desired time (e.g., in the range of from a few seconds to about 5 minutes, depending on factors including, inter alia, the intensity of the light source, the concentration of light- or photo-initiators, the concentration of double-bond containing components in the composition, and the type of light source). The process then returns to the determination made in step 1050, which has previously been described.

In certain optional embodiments of the present invention, a variety of optional additives may be incorporated into the process. For example, the inner cavity optionally further may be separated by removable dividers into at least a compartment A, a compartment B, and a compartment C, wherein one of these compartments (e.g., compartment C) may comprise optional additives including, but not limited to, those that have been previously disclosed herein (e.g., at least one filler material, and/or at least one protein, and the like). In certain of these embodiments wherein optional additives are disposed within one or more compartments, the process may comprise optional step 1045 (shown in FIG. 10C) wherein a removable divider is removed, and optional step 1047 (shown in FIG. 10C) wherein the sealed container is manipulated (e.g., manually manipulated) so as to mix the optional additives with the mixture of the first compound and the isocyanate. The process then may proceed from optional step 1047 to step 1050, which previously has been described. As an alternative, in certain embodiments of the present invention, certain of the optional additives may be introduced outside the sealed container, and may be incorporated once the contents of the sealed container have been dispensed therefrom. For example, after a determination is made in step 1050 that the mixture of the first compound and isocyanate is reacting to form polyurethane/polyurea components at a desired rate, the process may proceed from step 1050 to an optional step 1070 (shown in FIG. 10B) wherein the reacting mixture is dispensed from the sealed container, and then may proceed to an optional step 1080 (shown in FIG. 10D) wherein at least one optional additive is mixed with the dispensed reacting mixture and permitted to remain within it as the mixture finishes reacting to form polyurethane/polyurea components, after which the process may proceed to end.

In certain embodiments, one or more optional additives may be present in a separate reservoir (e.g., reservoir 199 shown in FIG. 4B), and optional step 1047 may comprise flowing the additives from the separate reservoir into the sealed container.

Figure 10E:
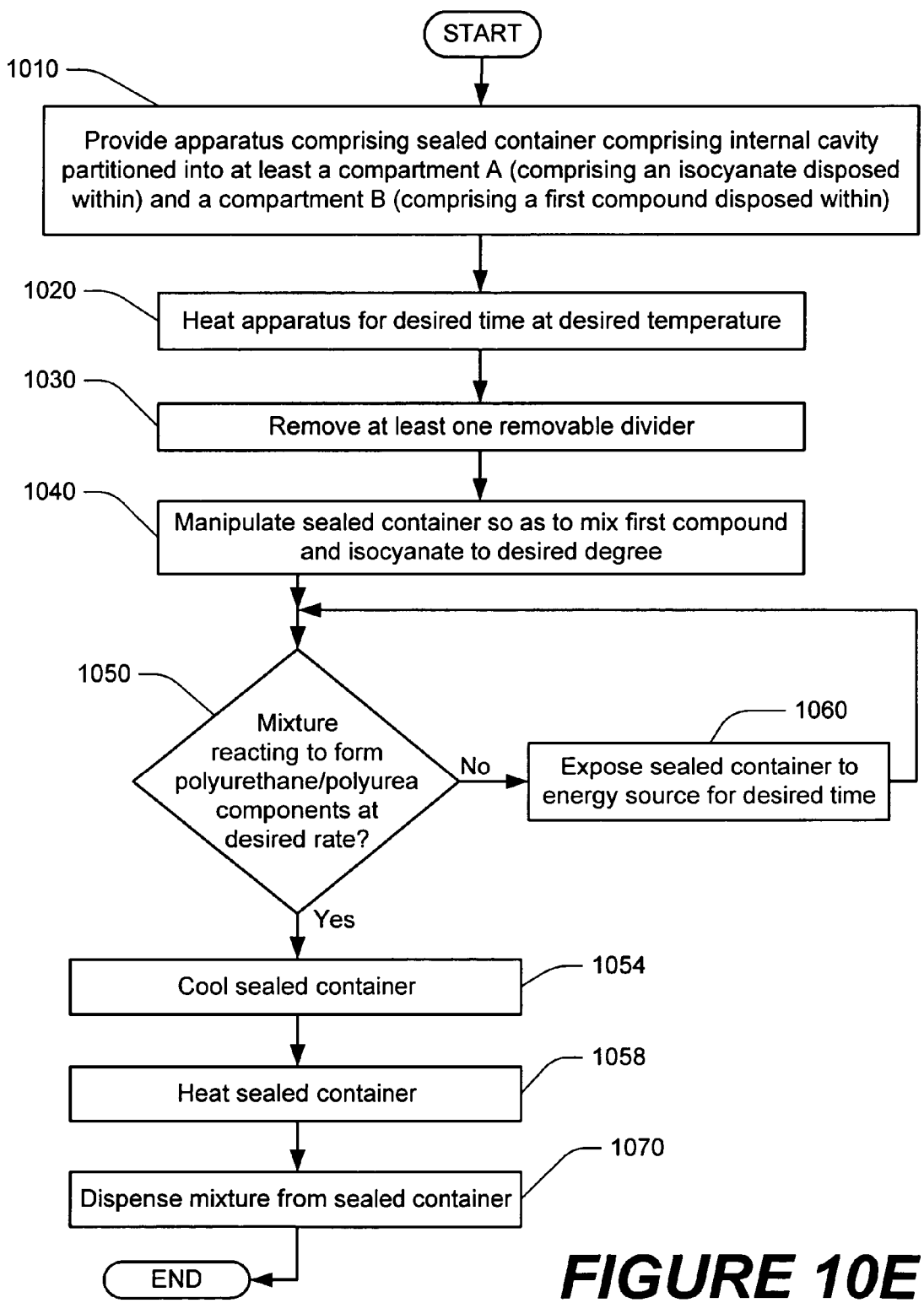

Furthermore, FIG. 10E illustrates the use of an optional step 1054 wherein the sealed container may be cooled for a desired period of time, so as to halt the reaction between the first compound and the isocyanate. For example, when the methods exemplified by FIGS. 10A-10D are being used to generate a composition that may be placed within the body of a mammal as part of a method of the present invention for performing a medical procedure (examples of such methods of performing medical procedures are discussed in greater detail infra), it occasionally may be desirable to pause the reaction between the first compound and the isocyanate at some point after the reaction has begun. For example, if, while the composition is being prepared, the patient into whom the composition is to be placed suffers from, e.g., a burst blood vessel, then the placement of the composition into the patient may be delayed until such time as the patient's condition improves; in such circumstances, the sealed container may be cooled (e.g., by placement of the sealed container in a container of ice water) until such time as it is desired to re-initiate the reaction. In certain of the embodiments wherein the sealed container is cooled in optional step 1054 (shown in FIG. 10E) for a desired time, after which it becomes desirable to re-initiate the reaction, the process then may proceed from step 1054 to step 1058 (shown in FIG. 10E), wherein the sealed container may be heated for a desired time at a desired temperature, and the first compound and the isocyanate may resume reacting to form polyurethane/polyurea components.

Figure 10F:
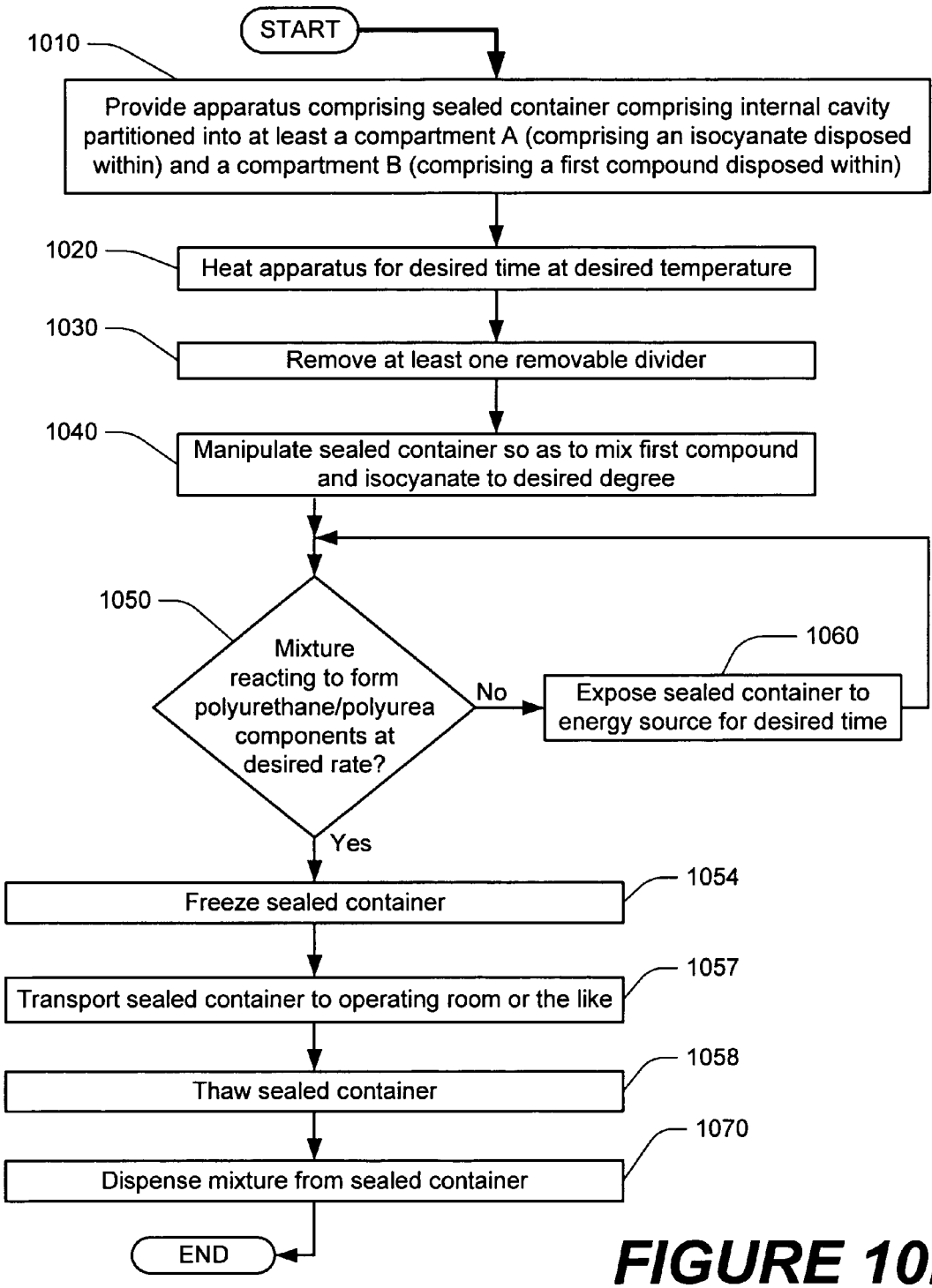

Moreover, as illustrated in FIG. 10F, the present invention further contemplates that optional step 1054 (as shown in FIG. 10F) may involve freezing the sealed container, e.g., by immersing the sealed container in, e.g., liquid nitrogen, so as to suspend the reaction occurring within the sealed container. In certain embodiments of the present invention, this may occur after the contents within the sealed container have been permitted to react for about half the expected reaction time (e.g., the contents may have been permitted to react for about 20 minutes, in certain embodiments). The process then may proceed to step 1057 (shown in FIG. 10F), in which the sealed container is transported to an operating room packed in a suitable medium (e.g., dry ice). Next, the process may proceed to optional step 1058 (shown in FIG. 10F), in which the sealed container is thawed (e.g., in a bath of warm or hot water) without further mixing, after which the contents of the sealed container are dispensed and implanted within the body, wherein the contents of the sealed container may finish reacting (e.g., "cure") to form polyurethane/polyurea components. In certain embodiments of the present invention, a variety of additives such as progenitor cells may be present within the sealed container (e.g., present in a compartment within the sealed container in which a liquid component is disposed) and generally will not suffer adverse effects from being frozen, transported and thawed.

FIGS. 11A through 12F illustrate additional exemplary methods of the present invention comprising reacting isocyanates and polyols/polyamines to form compositions that comprise polyurethane/polyurea components. Because certain features and advantages of these embodiments of the present invention are substantially similar to certain features and advantages of the embodiments described with reference to FIGS. 10A-10F, such similar features and advantages are not discussed further with respect to the embodiments of the present invention illustrated in FIGS. 11A through 12F.

Figure 11A:
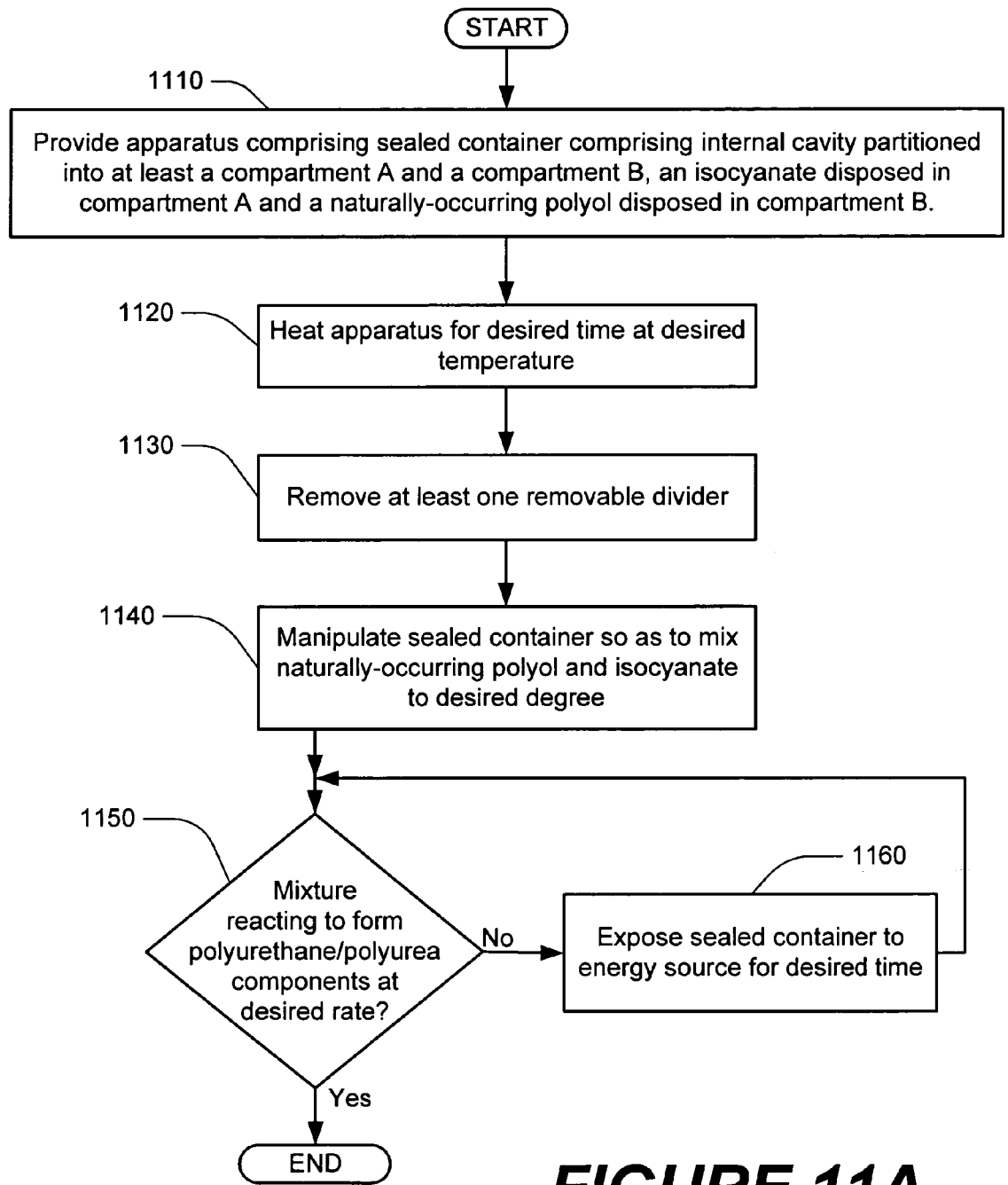
Figure 11B:
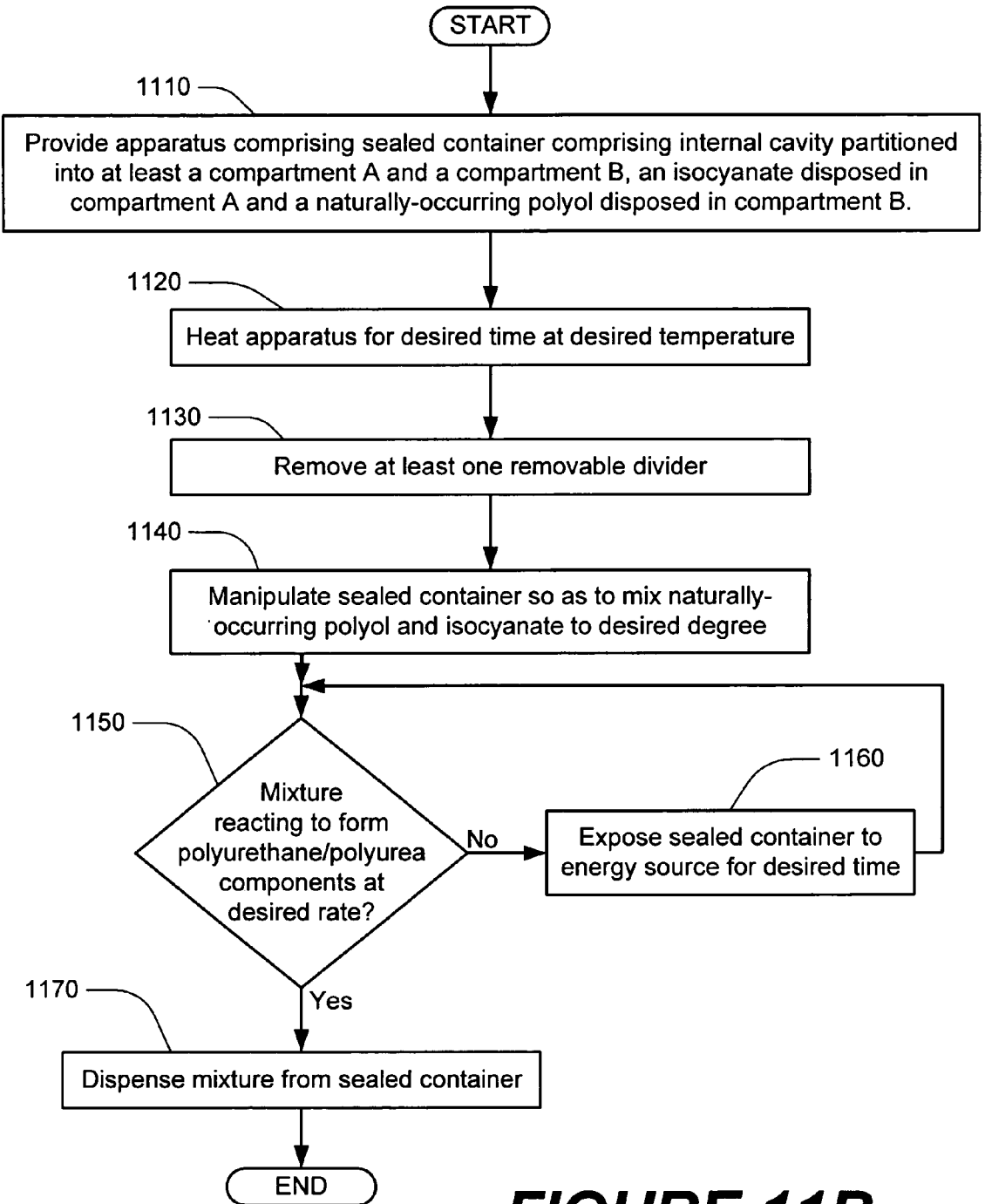
Figure 11C:
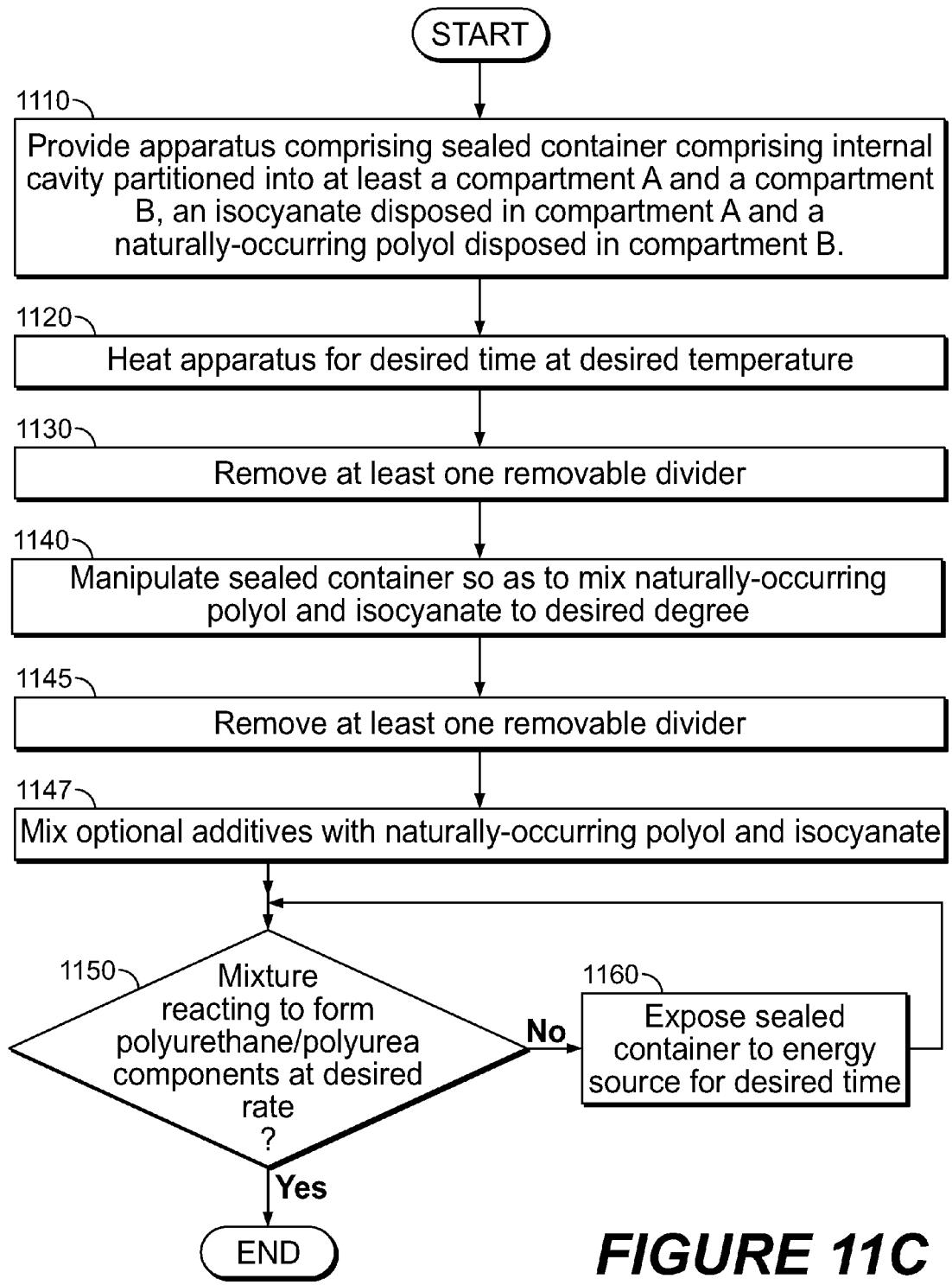
Figure 11D:
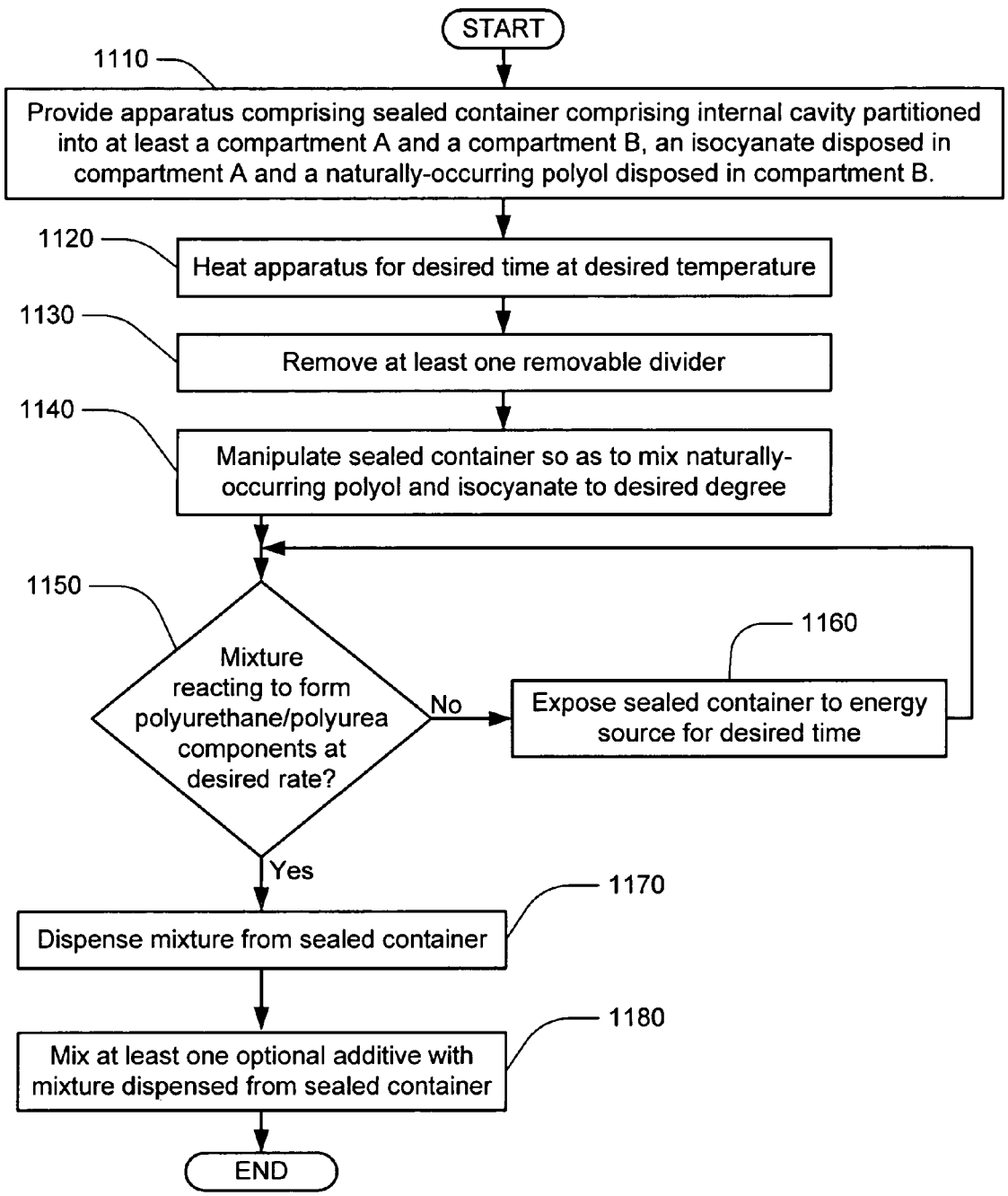
Figure 11E:
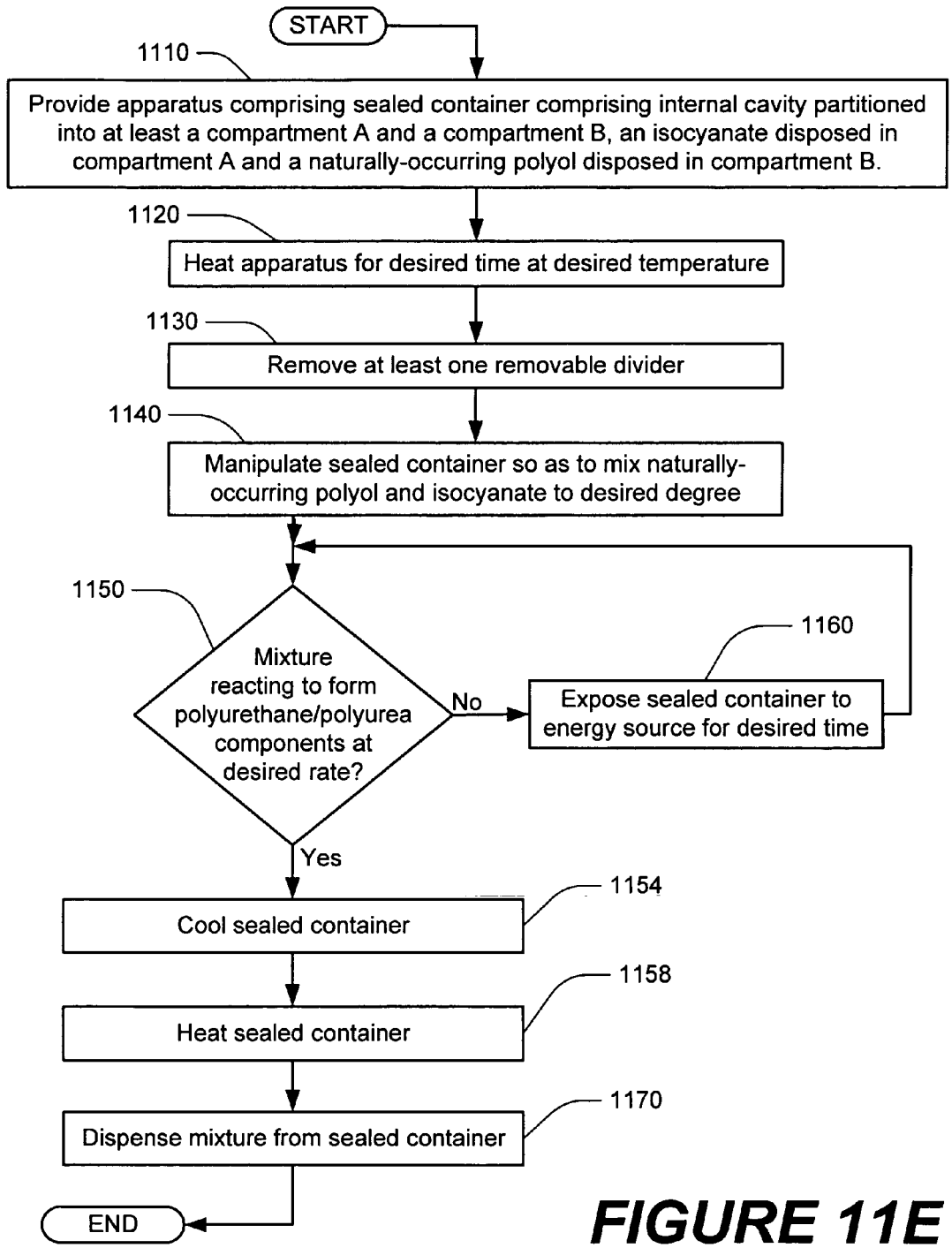
Figure 11F:
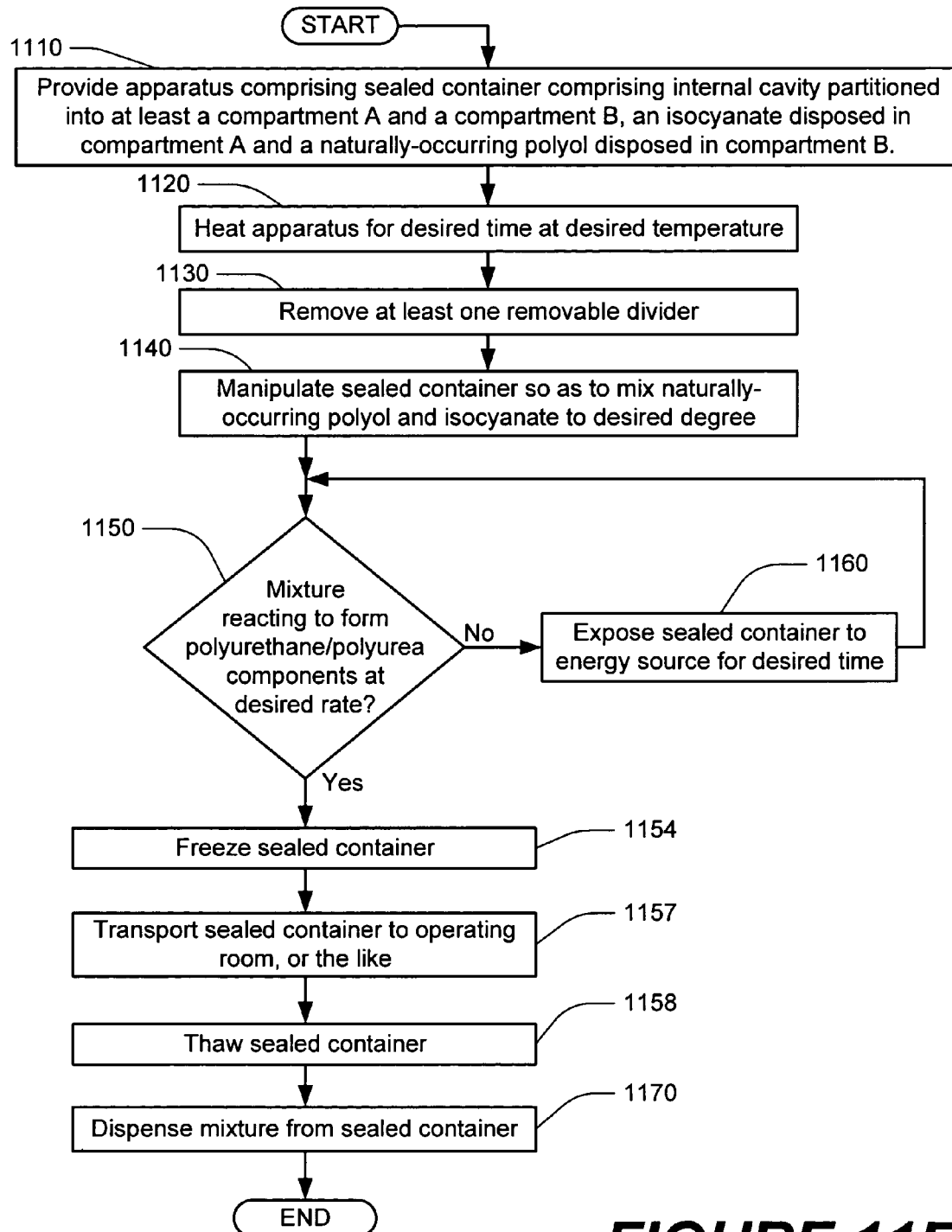

Referring now to FIG. 11A, in step 1110, an apparatus is provided that comprises a sealed container comprising an internal cavity, the internal cavity being separated by a removable divider into a compartment A and a compartment B, an isocyanate being disposed in compartment A and a naturally occurring polyol being disposed in compartment B. In certain embodiments, the isocyanate and the naturally occurring polyol both may be liquids at room temperature. In certain embodiments of the present invention, a polyamine may be disposed in compartment B along with the naturally occurring polyol. Further description of the steps that may be used to react these compounds to form a composition that comprises polyurethane/polyurea components is set forth in FIGS. 11A-11F, and will not be further elaborated upon here. In certain embodiments of the present invention, optional additives may be incorporated into the composition; suitable additives, and the ways in which they may become incorporated, have been previously described in greater detail herein with reference to the discussion of FIGS. 10A-10F (including, inter alia, the discussion of optional steps such as steps 1045, 1047, 1070, 1080, and the like). Moreover, situations may arise in which an operator desires to cool the sealed container for a desired period of time, so as to halt the reaction between the isocyanate and the naturally occurring polyol (and the polyamine, if present); suitable means by which the sealed container may be cooled (and, when desired, re-heated) previously have been described in greater detail herein with reference to the discussion of FIGS. 10E-10F (including, inter alia, the discussion of optional steps such as steps 1054, 1057, and 1058, and the like).

Figure 12A:
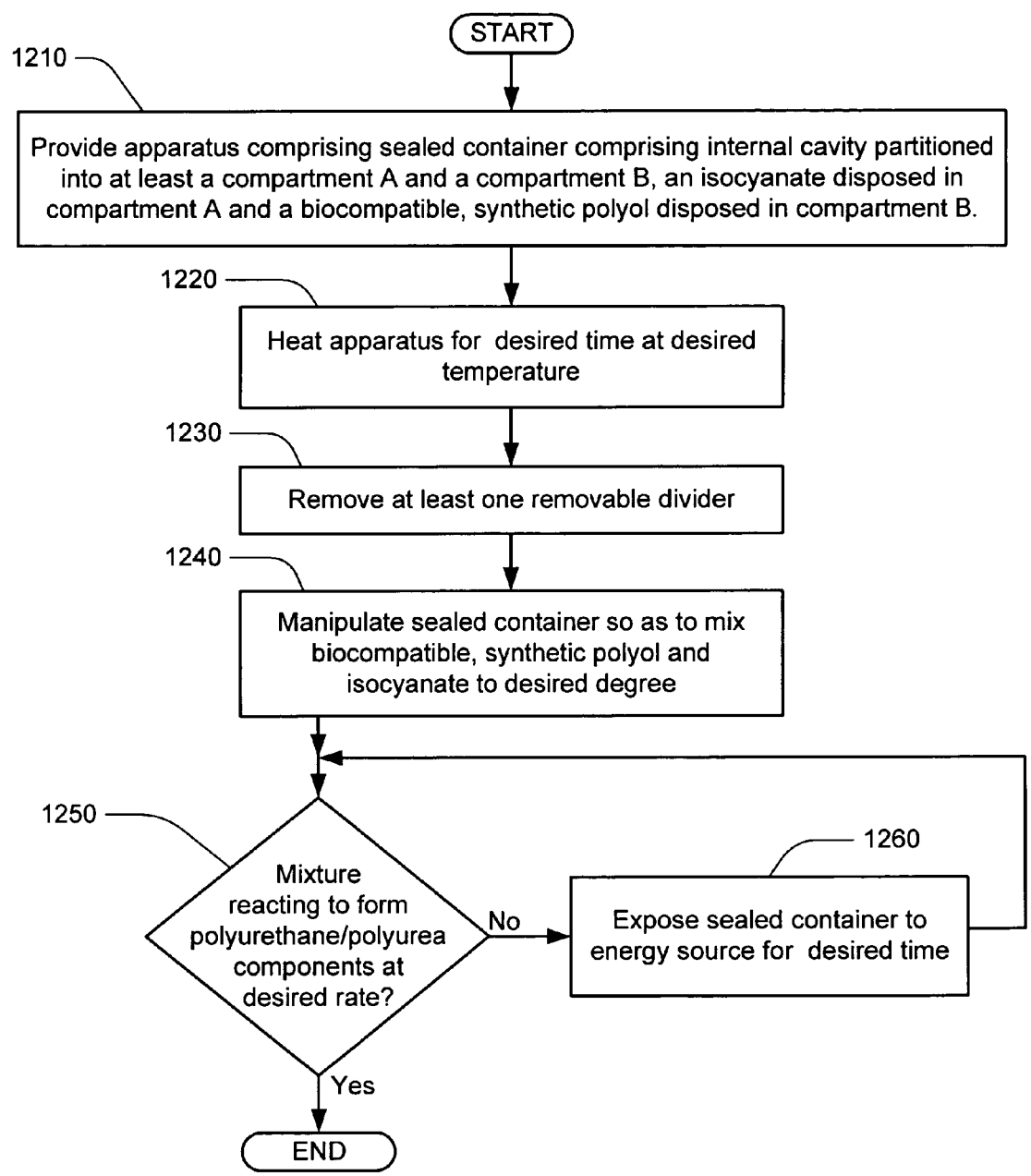
Figure 12B:
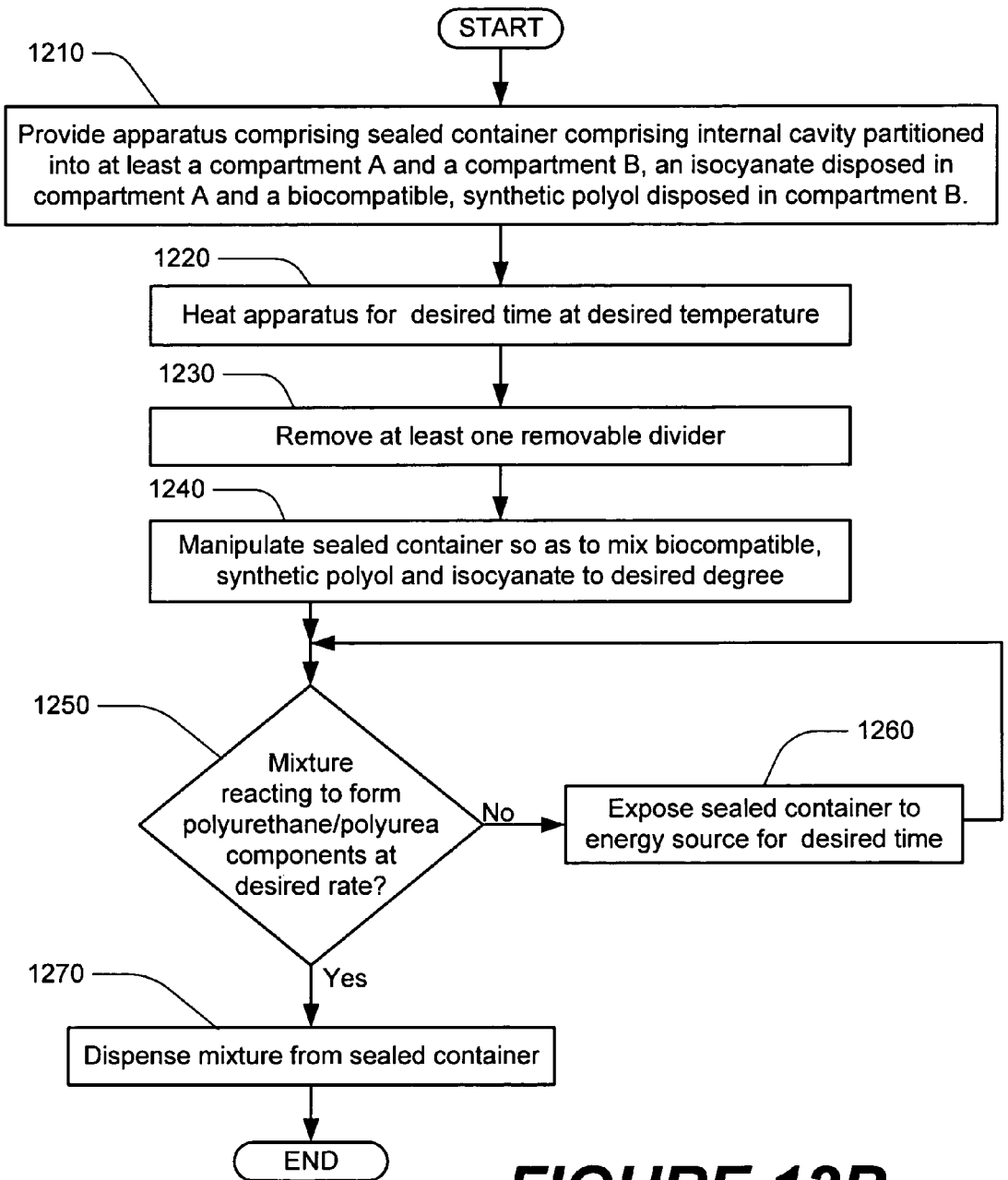
Figure 12C:
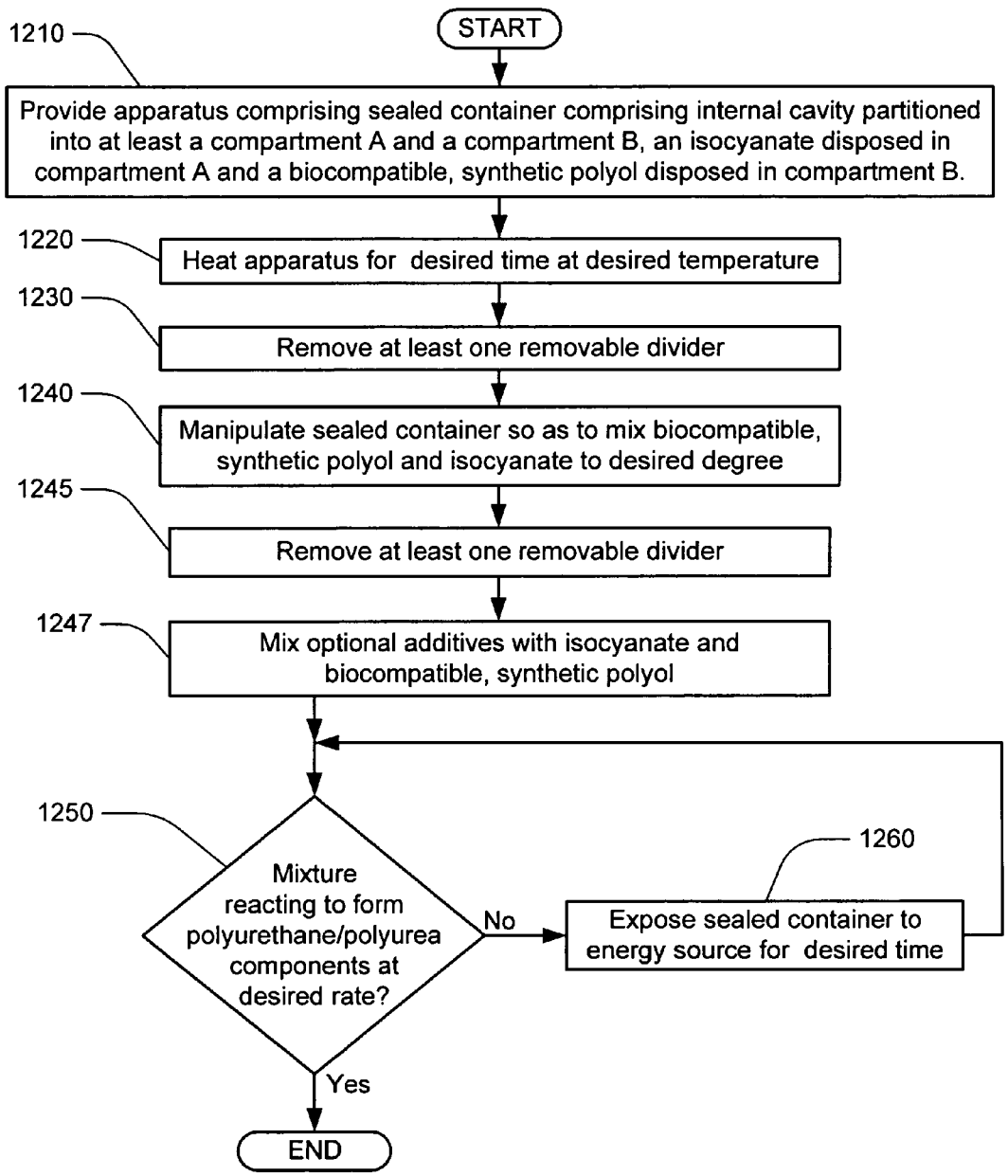
Figure 12D:
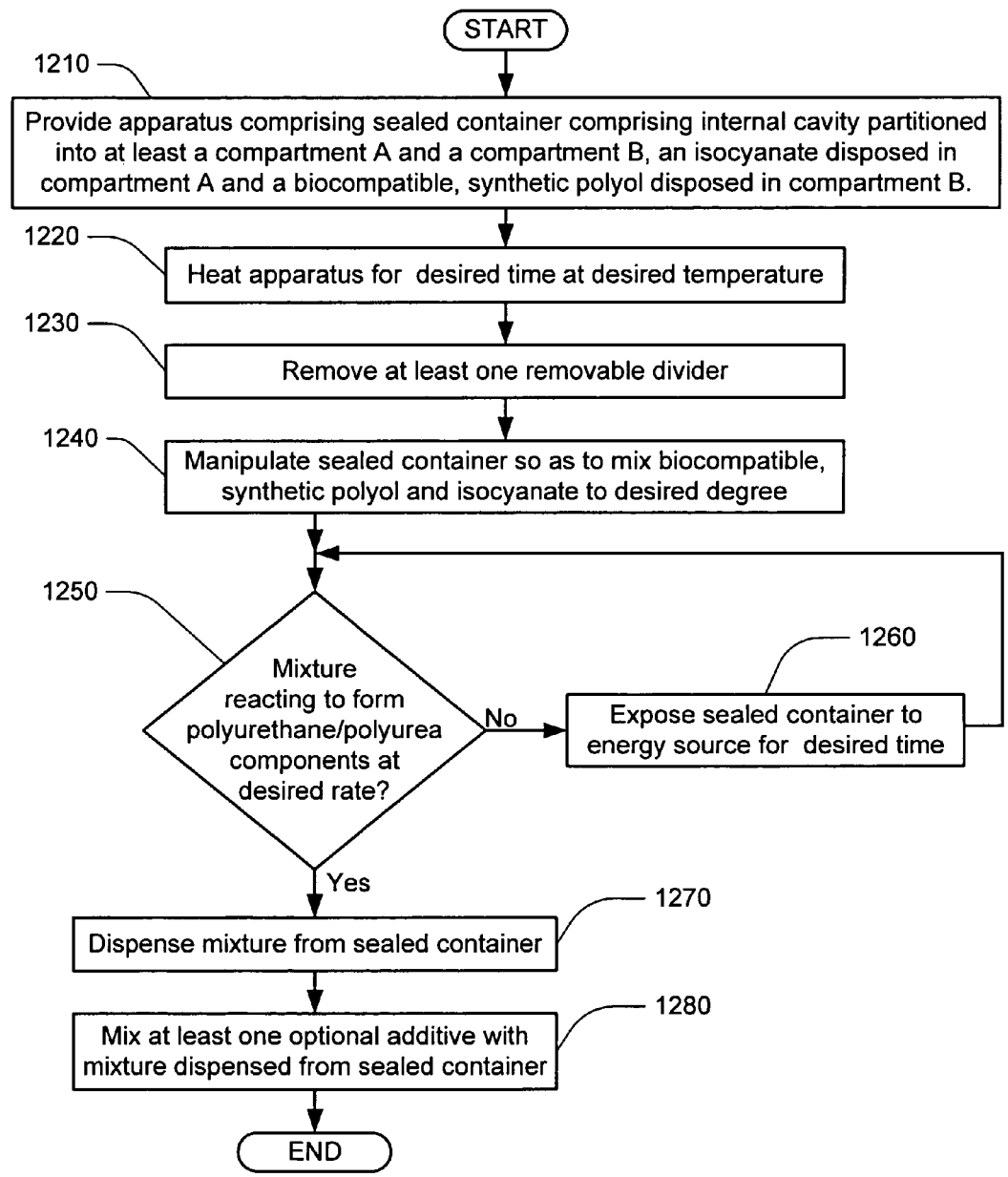
Figure 12E:
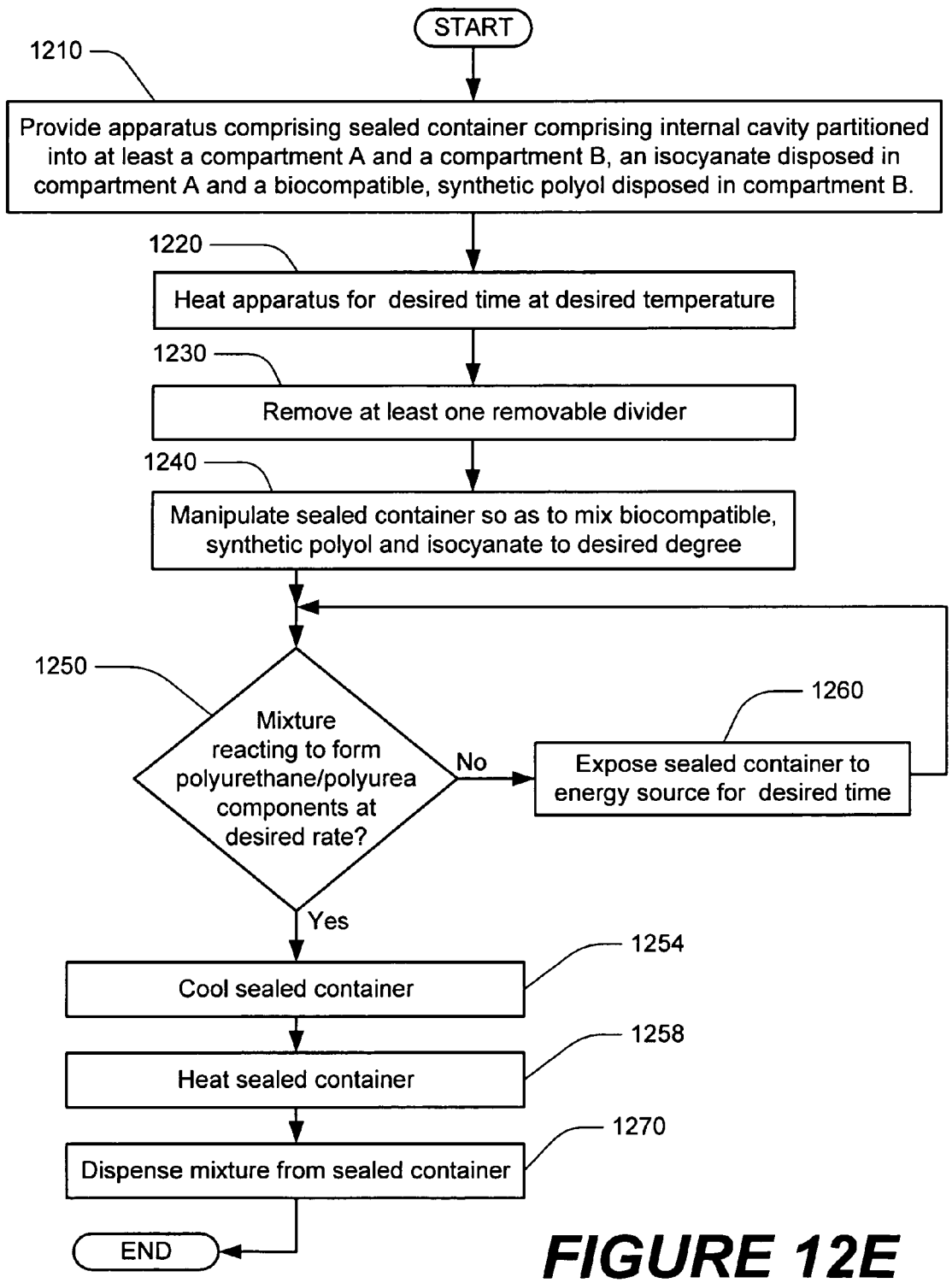
Figure 12F:
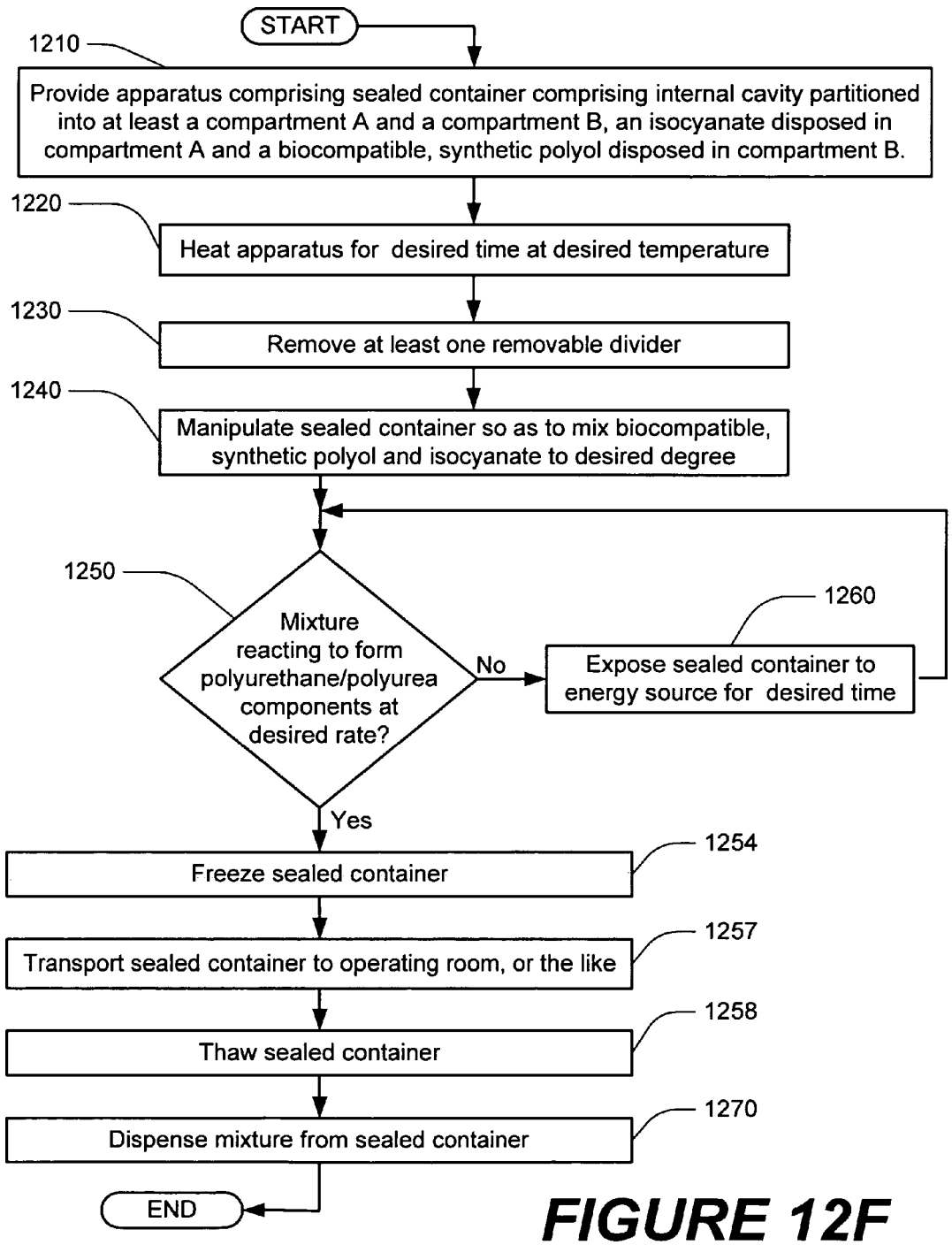

Referring now to FIG. 12A, in step 1210, an apparatus is provided that comprises a sealed container comprising an internal cavity, the internal cavity being separated by a removable divider into a compartment A and a compartment B, an isocyanate being disposed in compartment A and a biocompatible, synthetic polyol being disposed in compartment B. In certain embodiments, the isocyanate and the biocompatible, synthetic polyol both may be liquids at room temperature. In certain embodiments of the present invention, a polyamine may be present in compartment B along with the biocompatible, synthetic polyol. Further description of the steps that may be used to react these compounds to form a composition that comprises polyurethane/polyurea components is set forth in FIGS. 12A-12F, and will not be further elaborated upon here. In certain embodiments of the present invention, optional additives may be incorporated into the composition; suitable additives, and the ways in which they may become incorporated, have been previously described in greater detail herein with reference to the discussion of FIGS. 10A-10F (including, inter alia, the discussion of optional steps such as steps 1045, 1047, 1070, 1080, and the like). Moreover, situations may arise in which an operator desires to cool the sealed container for a desired period of time, so as to halt the reaction between the isocyanate and the naturally occurring polyol (and the polyamine, if present); suitable means by which the sealed container may be cooled (and, when desired, re-heated) previously have been described in greater detail herein with reference to the discussion of FIGS. 10E-10F (including, inter alia, the discussion of optional steps such as steps 1054, 1057, and 1058, and the like).

2. Sealed Inner and Outer Containers

FIGS. 13A-15F describe exemplary methods of the present invention comprising reacting isocyanates and polyols/polyamines to form compositions that comprise polyurethane/polyurea components. Moreover, the methods described in FIGS. 13A-15F employ other embodiments of apparatus of the present invention.

Figure 13A:
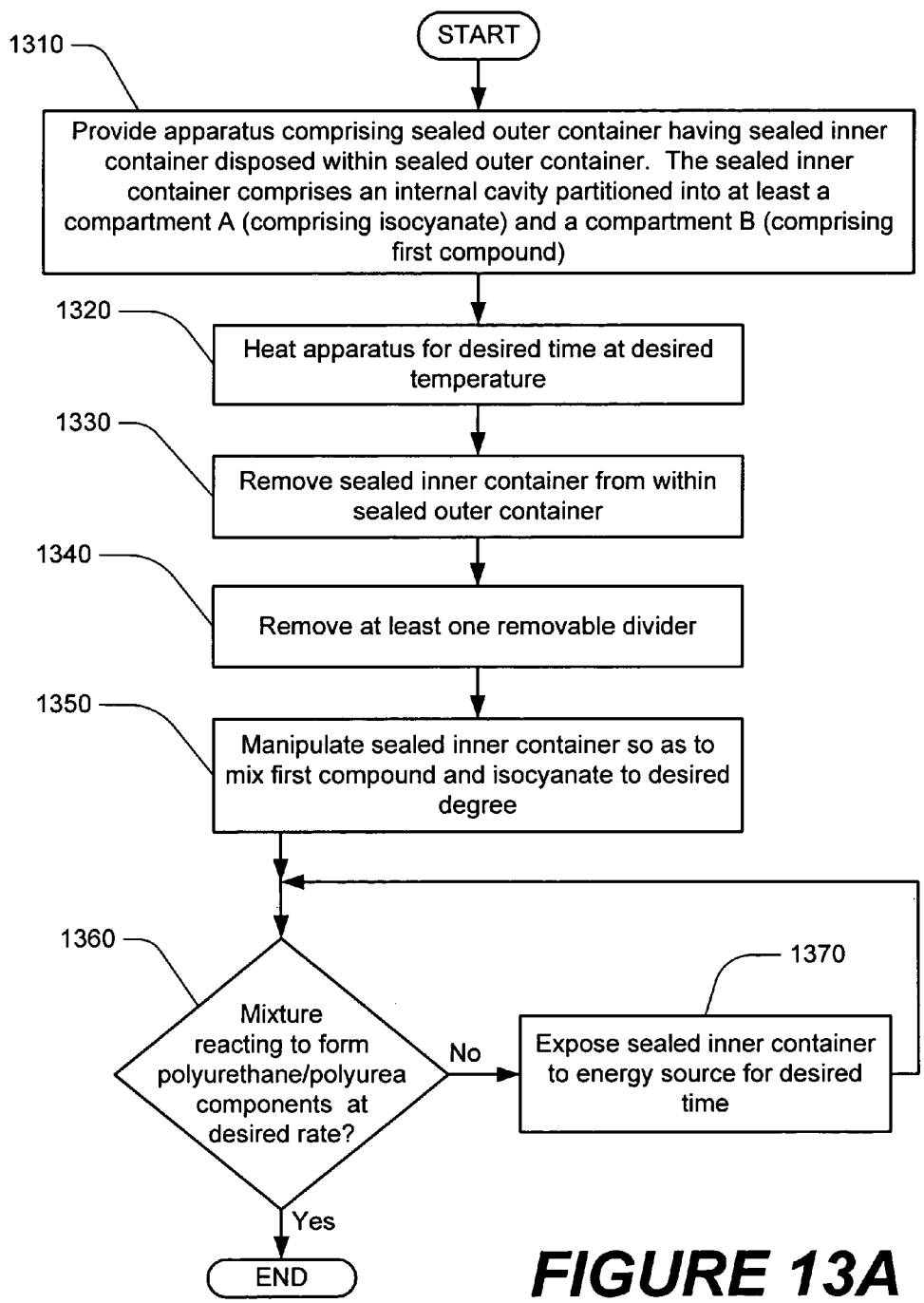
Figure 13B:
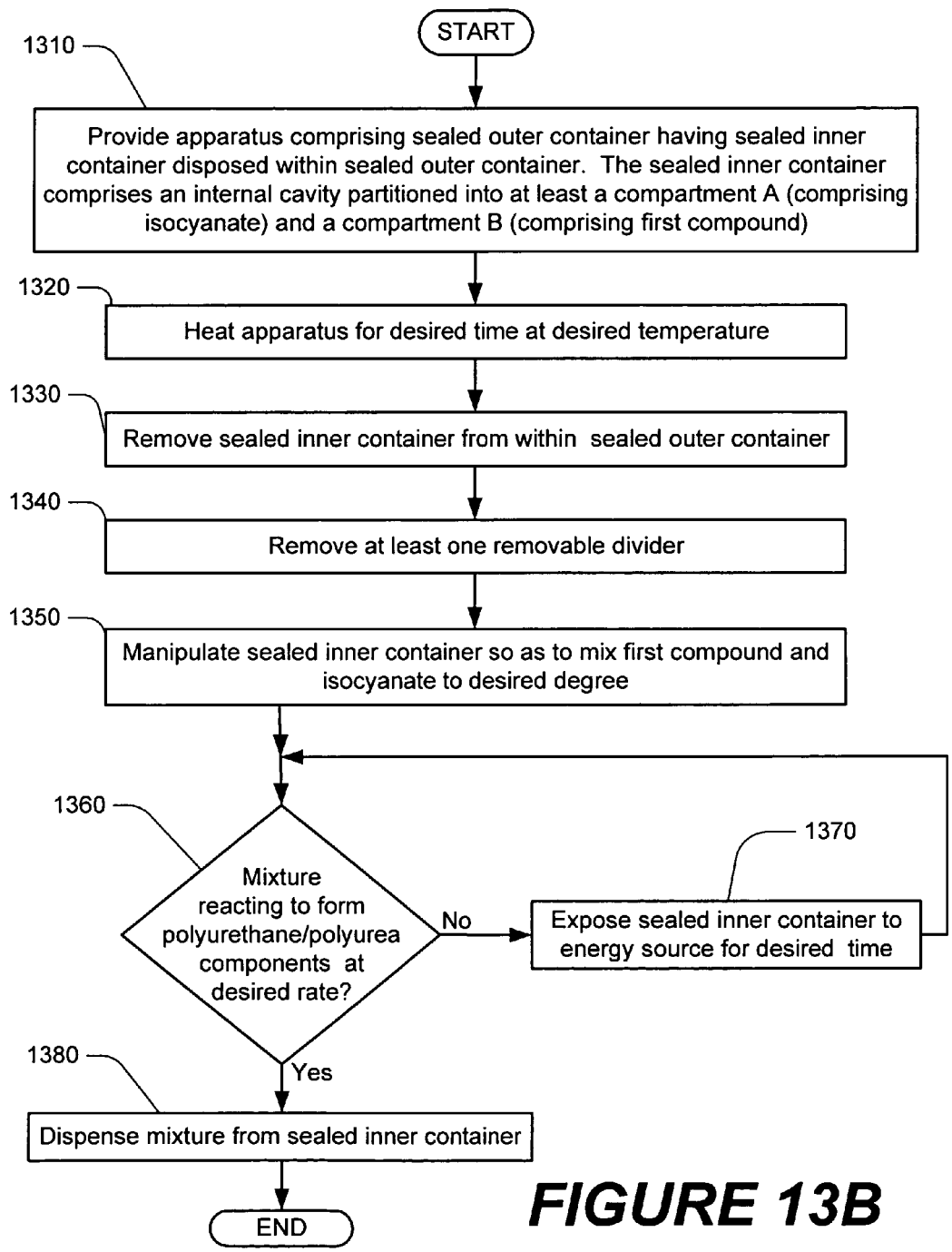
Figure 13C:
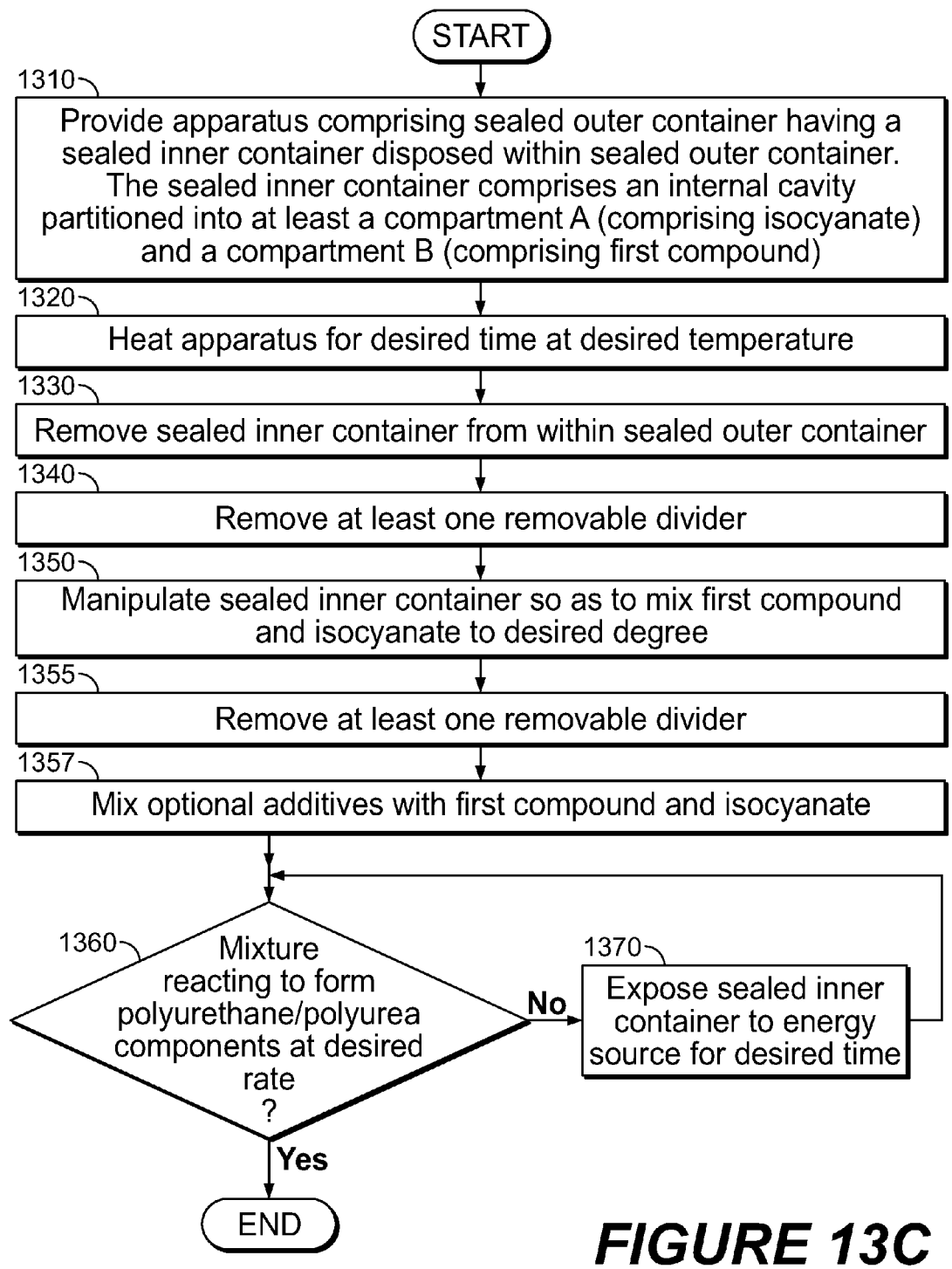
Figure 13D:
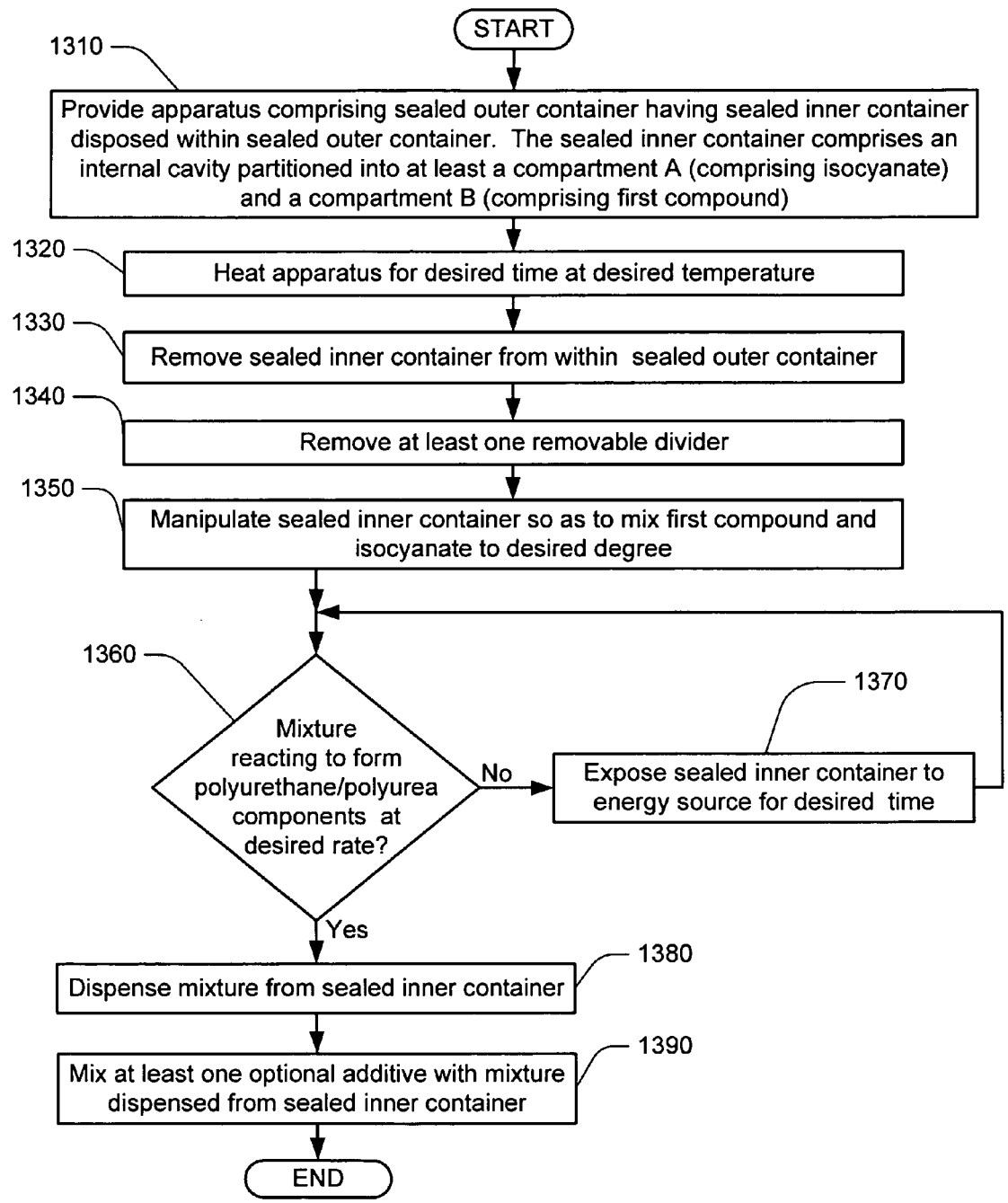
Figure 13E:
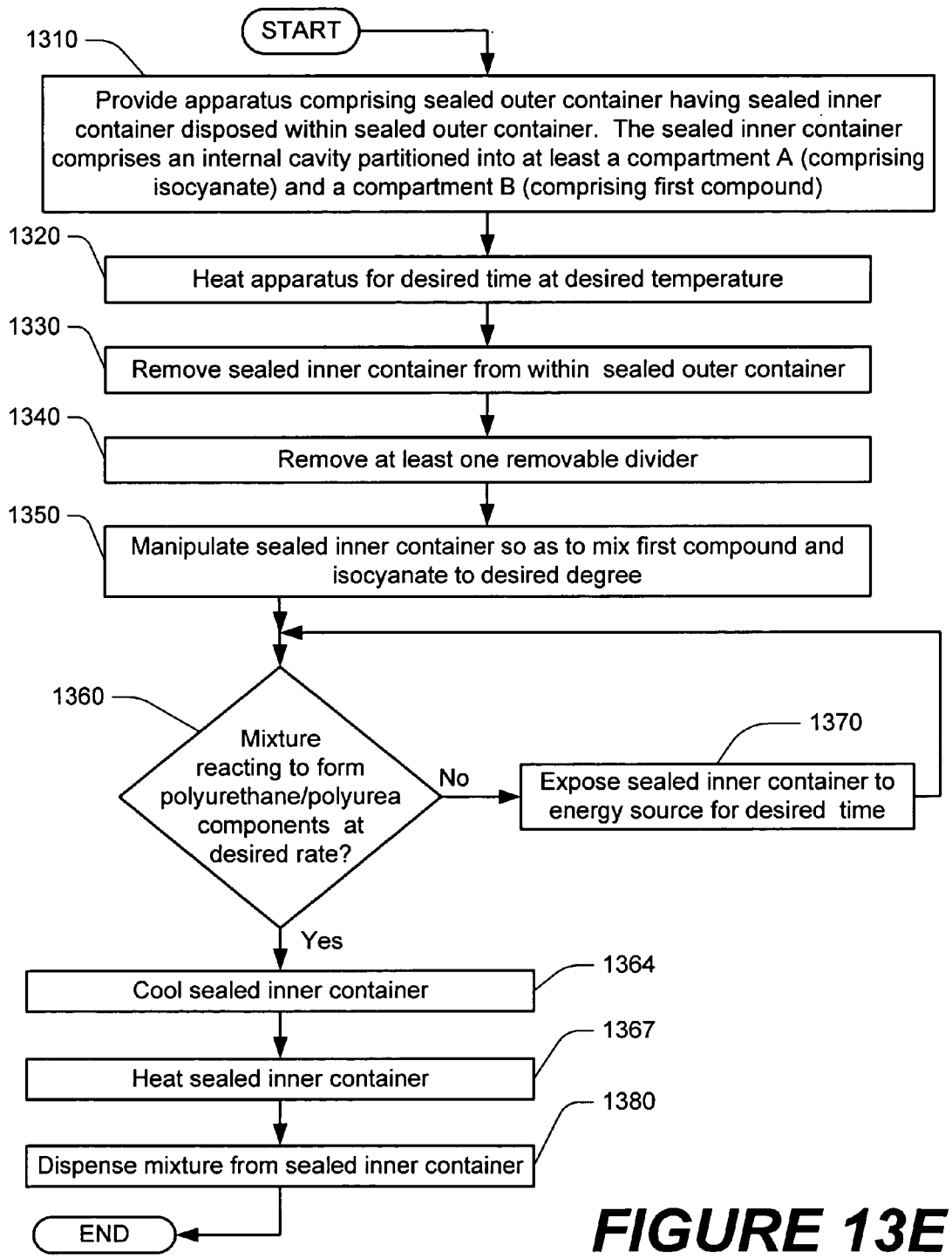

Referring now to FIG. 13A, in step 1310, an apparatus of the present invention is provided that comprises a sealed outer container comprising an internal cavity, wherein a sealed inner container is disposed within the inner cavity of the sealed outer container. The sealed inner container itself comprises an internal cavity that is separated by at least one removable divider into at least a compartment A and a compartment B, an isocyanate being disposed in compartment A and a first compound comprising a mixture of a naturally occurring polyol and a biocompatible, synthetic polyol being disposed in compartment B. In certain embodiments, the first compound may comprise a polyamine and either (or both of) a naturally occurring polyol and a biocompatible, synthetic polyol. In step 1320, the apparatus is heated for a desired time at a desired temperature (e.g., a temperature in the range of from about room temperature to about 150° C.). In certain embodiments, the apparatus may be heated by immersion in boiling water. Among other things, simultaneously heating the sealed outer container and the sealed inner container may be particularly useful in circumstances where the surrounding environment is unsterile; permitting the sealed outer container to remain intact surrounding the sealed inner container may, inter alia, reduce the risk of contamination that otherwise might occur if the sealed inner container alone were heated in the unsterile environment.

In step 1330, the sealed inner container may be removed from within the sealed outer container, and the sealed outer container may be set aside. In step 1340, at least one removable divider (which may be externally affixed to the sealed inner container) may be removed from the sealed inner container, so as to permit fluid communication between the isocyanate and the first compound. In step 1350, the sealed inner container may be manipulated (e.g., manually manipulated) so as to mix the first compound and the isocyanate to a desired degree (e.g., for a time period in the range of from about one minute to about 30 minutes). (The time period for which the sealed inner container may be manipulated has been previously described herein, with reference to the discussion of step 1040 of FIG. 10A.) In step 1360, a determination may be made whether the mixture of the first compound and the isocyanate is reacting to form polyurethane/polyurea components at a desired rate. (This determination has been previously described herein, with reference to the discussion of step 1050 of FIG. 10A.) If the mixture is reacting at a desired rate, the process proceeds to end. Alternatively, in certain optional embodiments of the present invention, after a determination is made in step 1360 that the mixture of the first compound and the isocyanate is reacting at a desired rate, the process may proceed from step 1360 to an optional step 1380 (shown in FIG. 13B) wherein the contents of the sealed inner container are dispensed, after which the process proceeds to end. If, however, the determination is made in step 1360 that the mixture is not reacting at a desired rate, then the process proceeds to step 1370, wherein the sealed inner container is exposed to an energy source for a desired time (e.g., heated in a microwave oven or in boiling water for a desired time, e.g., a time in the range of from about 30 seconds to about 90 seconds). In certain embodiments wherein the mixture comprises optional photo- or light-initiators and other suitable components (e.g., adducts of isocyanates, double-bond-containing isocyanates, double-bond-containing polyols, and the like), the sealed inner container may be exposed to a suitable light source for a desired time. The process then returns to the determination made in step 1360, which has previously been described.

In certain optional embodiments of the present invention, a variety of optional additives may be incorporated into the process. For example, the inner cavity of the sealed inner container optionally further may be separated by removable dividers into at least a compartment A, a compartment B, and a compartment C, wherein one of these compartments (e.g., compartment C) may comprise optional additives including, but not limited to, those that previously have been described herein (e.g., at least one filler material, and/or at least one protein, and the like). In certain of such embodiments the process may comprise optional step 1355 (shown in FIG. 13C) wherein a removable divider is removed, and optional step 1357 (shown in FIG. 13C) wherein the sealed inner container is manipulated (e.g., manually manipulated) so as to mix the optional additives with the mixture of the first compound and the isocyanate. The process then may proceed from optional step 1357 to step 1360, which previously has been described. As an alternative, in certain other optional embodiments of the present invention, certain of the optional additives may be absent from the sealed container, and may be incorporated once the mixture of the first compound and isocyanate is dispensed from the sealed container. For example, after a determination is made in step 1360 that the mixture of the first compound and isocyanate is reacting to form polyurethane/polyurea components at a desired rate, the process may proceed from step 1360 to an optional step 1380 (shown in FIG. 13B) wherein the reacting mixture is dispensed from the sealed container, and then may proceed to an optional step 1390 (shown in FIG. 13D) wherein at least one optional additive is mixed with the dispensed reacting mixture and permitted to remain within it as the mixture finishes reacting to form polyurethane/polyurea components, after which the process may proceed to end.

Furthermore, the present invention also contemplates the optional inclusion of a step 1364 (shown in FIG. 13E) wherein the sealed inner container may be cooled for a desired period of time, so as to halt the reaction between the first compound and the isocyanate. In certain of the embodiments wherein the sealed inner container is cooled in optional step 1364 (shown in FIG. 13E) for a desired time, after which it becomes desirable to re-initiate the reaction, the process then may proceed from optional step 1364 to optional step 1367 (shown in FIG. 13E), wherein the sealed inner container may be heated for a desired time at a desired temperature, and the first compound and the isocyanate may react to form polyurethane/polyurea components.

Figure 13F:
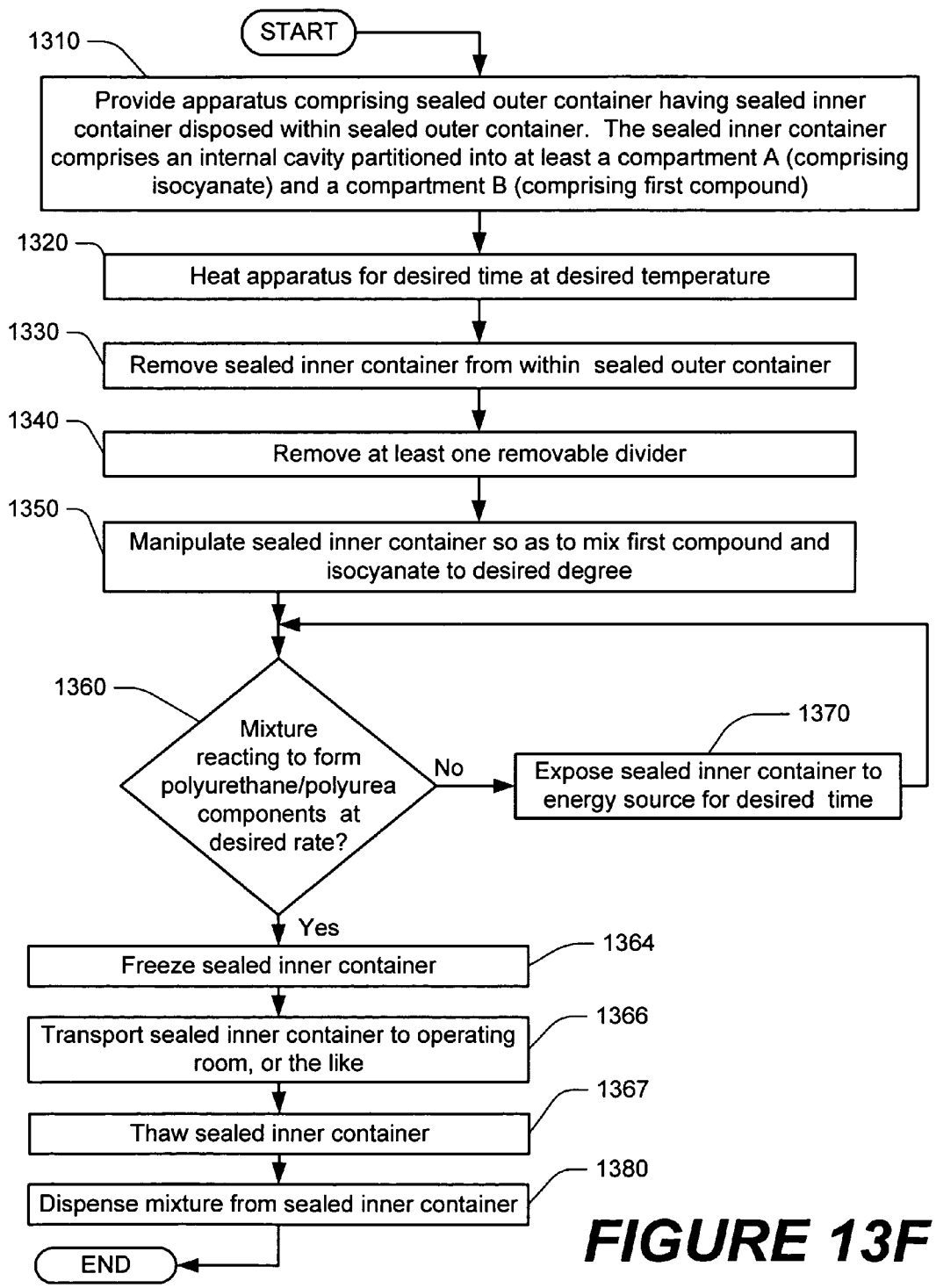

Moreover, as illustrated in FIG. 13F, the present invention further contemplates that optional step 1364 (as shown in FIG. 13F) may involve freezing the sealed inner container, e.g., by immersing the sealed inner container in, e.g., liquid nitrogen, so as to suspend the reaction occurring within the sealed inner container. In certain embodiments of the present invention, this may occur after the contents within the sealed inner container have been permitted to react for about half the expected reaction time (e.g., the contents may have been permitted to react for about 20 minutes, in certain embodiments). The process then may proceed to step 1366 (shown in FIG. 13F), in which the sealed inner container is transported to an operating room packed in a suitable medium (e.g., dry ice). Next, the process may proceed to optional step 1367 (as shown in FIG. 13F), in which the sealed inner container is thawed (e.g., in a bath of warm or hot water) without further mixing, after which the contents of the sealed inner container are dispensed and implanted within the body, wherein the contents of the sealed inner container may finish reacting (e.g., "cure") to form polyurethane/polyurea components.

FIGS. 14A through 15F illustrate additional exemplary methods of the present invention comprising reacting isocyanates and polyols/polyamines to form compositions that comprise polyurethane/polyurea components. Because certain features and advantages of these embodiments of the present invention are substantially similar to certain features and advantages of the embodiments described with reference to FIGS. 13A-F, such similar features and advantages are not discussed further with respect to the embodiments of the present invention illustrated in FIGS. 14A through 15F.

Figure 14A:
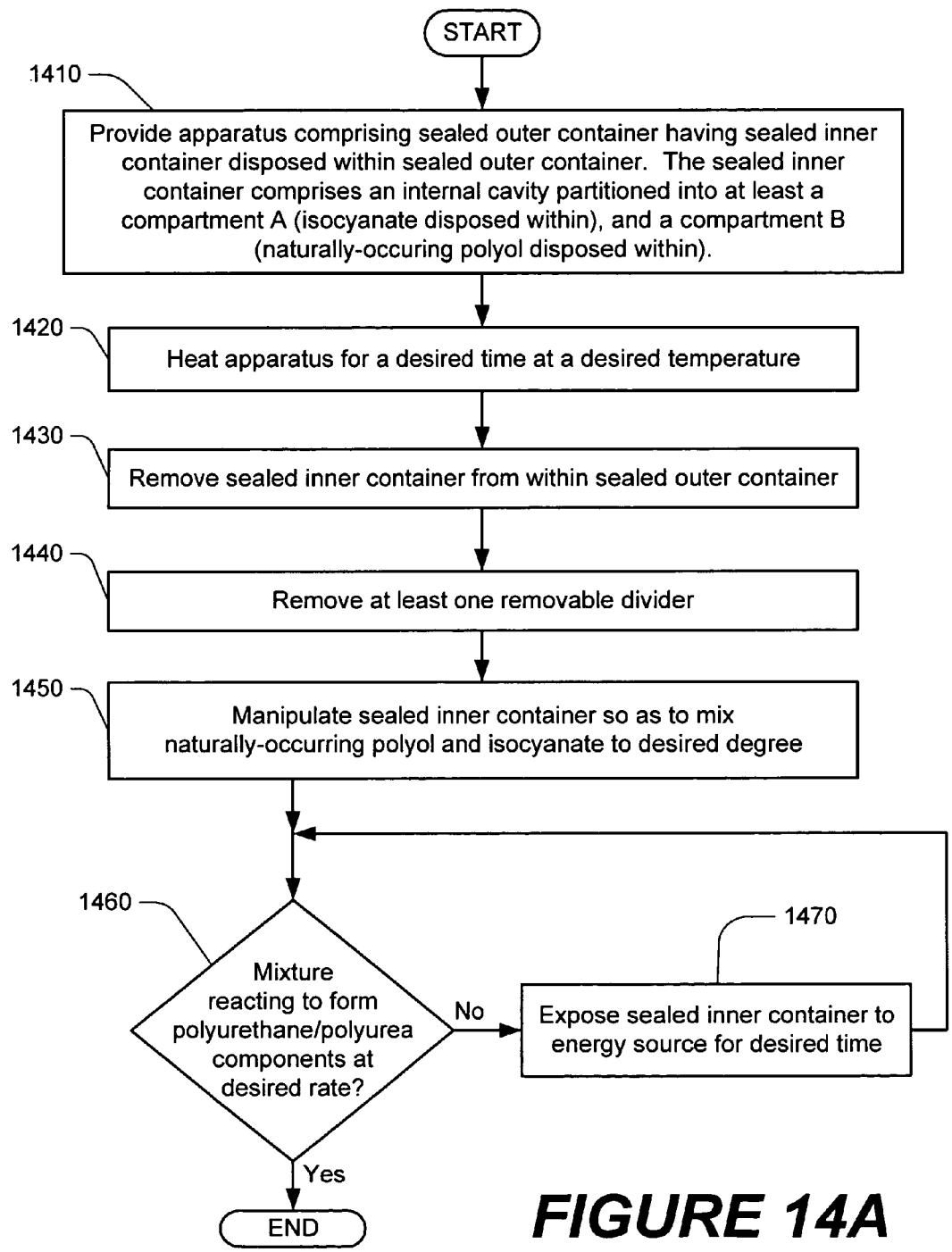
Figure 14B:
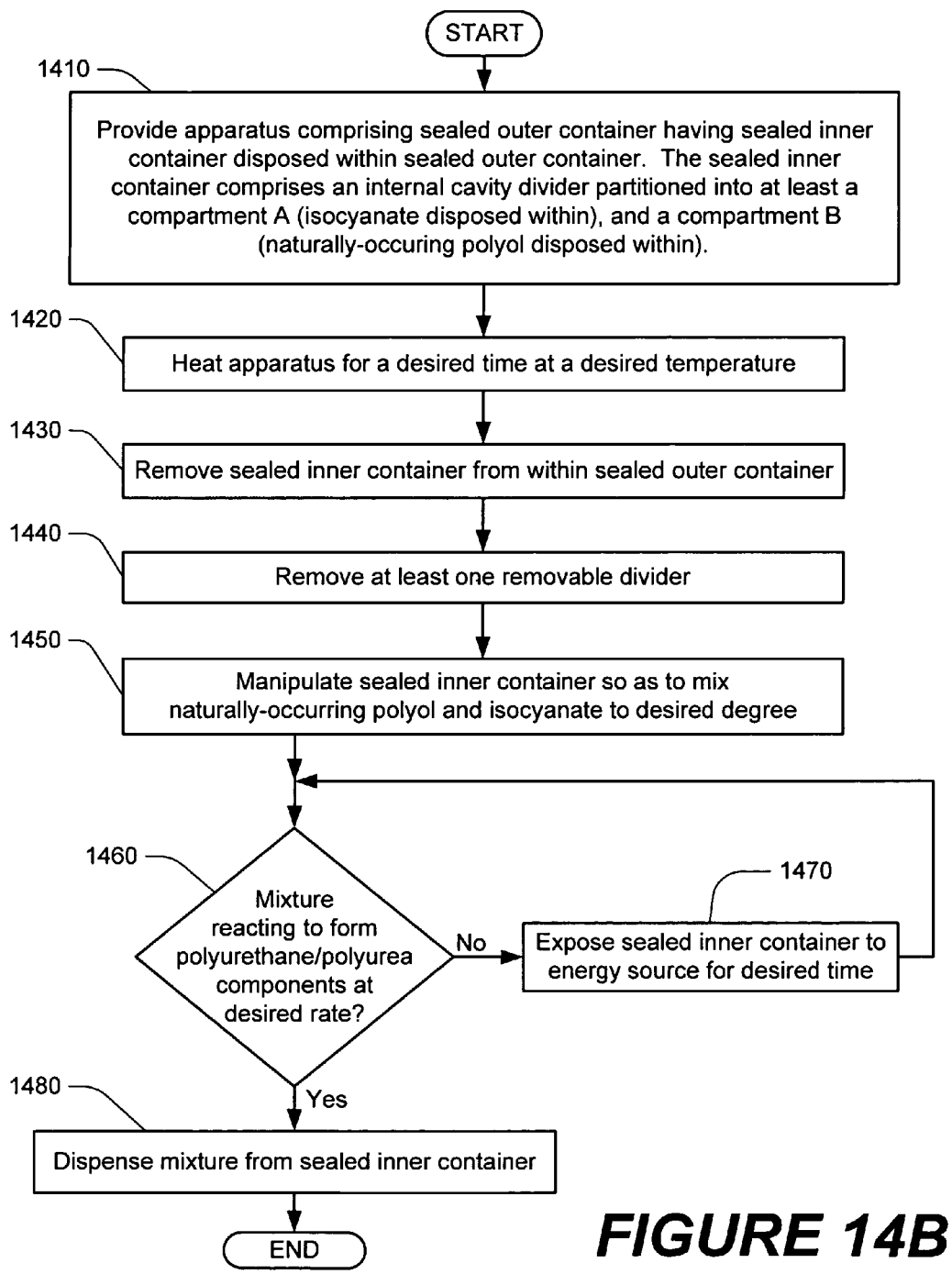
Figure 14C:
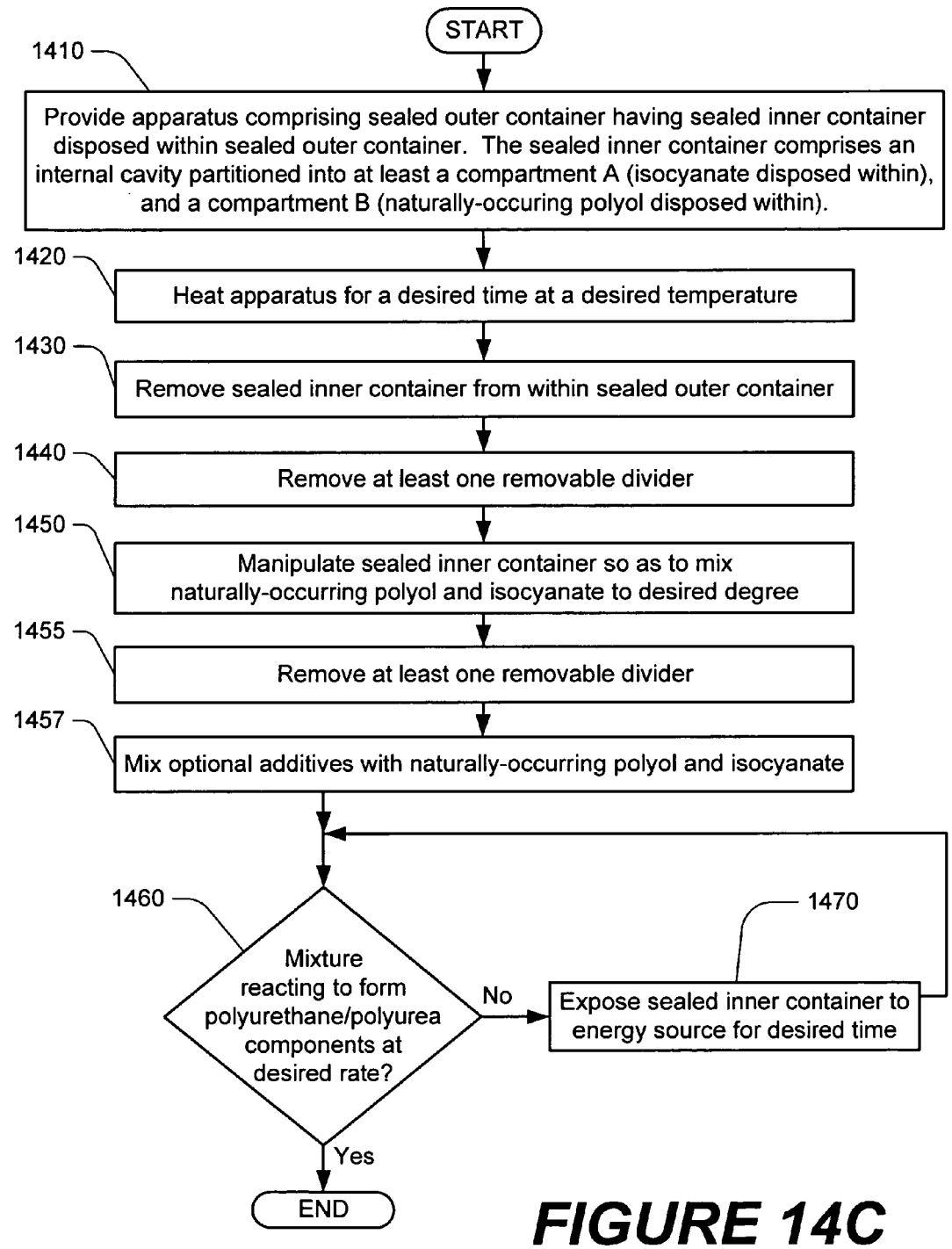
Figure 14D:
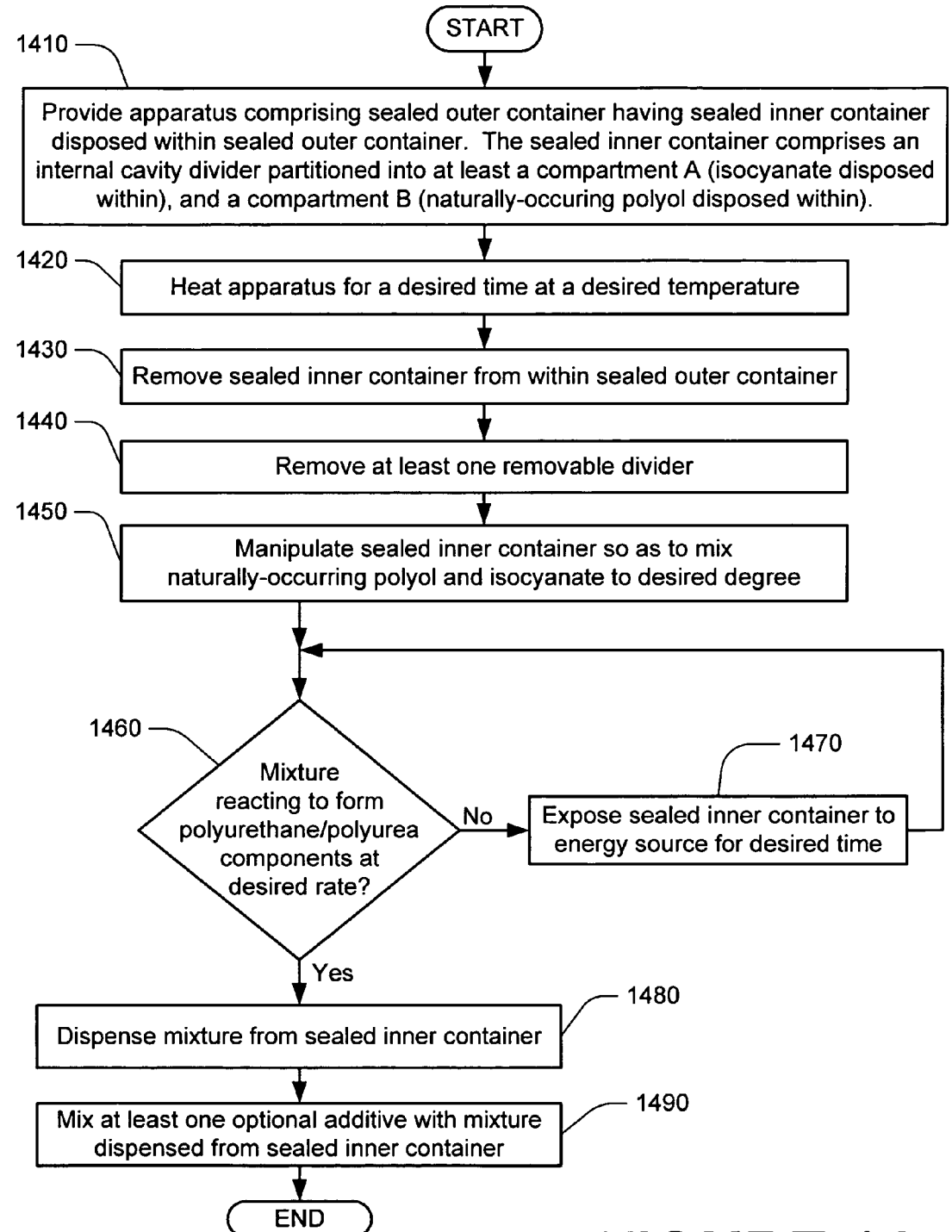
Figure 14E:
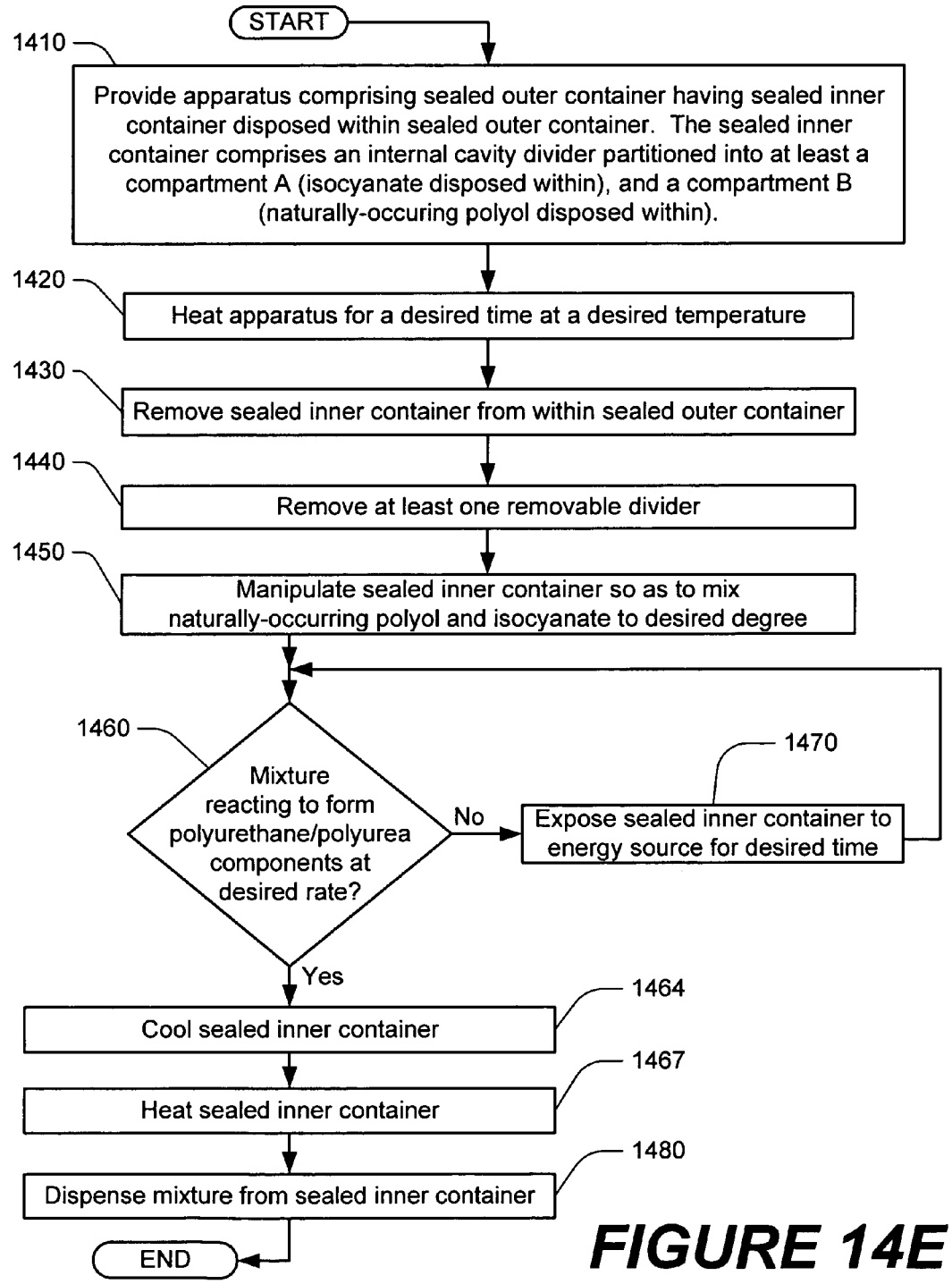
Figure 14F:
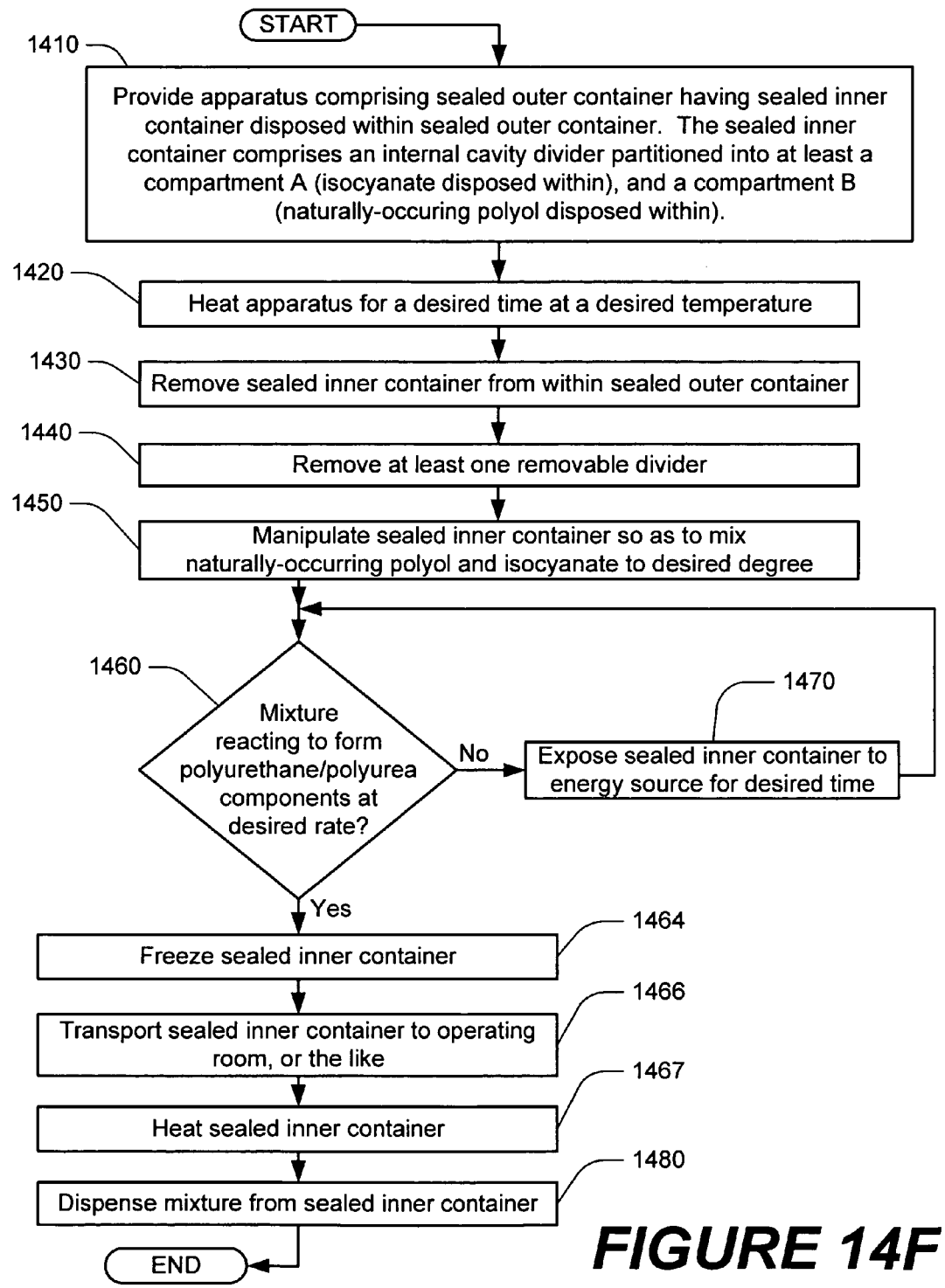

Referring now to FIG. 14A, in step 1410, an apparatus is provided that comprises a sealed outer container comprising an internal cavity, wherein a sealed inner container is disposed within the inner cavity of the sealed outer container. The sealed inner container itself comprises an internal cavity that is separated by at least one removable divider into at least a compartment A and a compartment B, an isocyanate being disposed in compartment A and a naturally occurring polyol being disposed in compartment B. In certain embodiments, the isocyanate and the naturally occurring polyol both may be liquids at room temperature. In certain embodiments of the present invention, a polyamine may be disposed in compartment B along with naturally occurring polyol. Further description of the steps that may be used to react these compounds to form a composition that comprises polyurethane/ polyurea components is set forth in FIGS. 14A-14F, and will not be further elaborated upon here. In certain embodiments of the present invention, optional additives may be incorporated into the composition; suitable additives, and the ways in which they may become incorporated, have been previously described in greater detail herein with reference to the discussion of FIGS. 13A-13F (including, inter alia, the discussion of optional steps such as steps 1355, 1357, 1380, 1390, and the like). Moreover, situations may arise in which an operator desires to cool the sealed inner container for a desired period of time, so as to halt the reaction between the isocyanate and the naturally occurring polyol; suitable means by which the sealed inner container may be cooled (and, when desired, re-heated) previously have been described in greater detail herein with reference to the discussion of FIGS. 13E-13F (including, inter alia, the discussion of optional steps such as steps 1364, 1367, and the like).

Figure 15A:
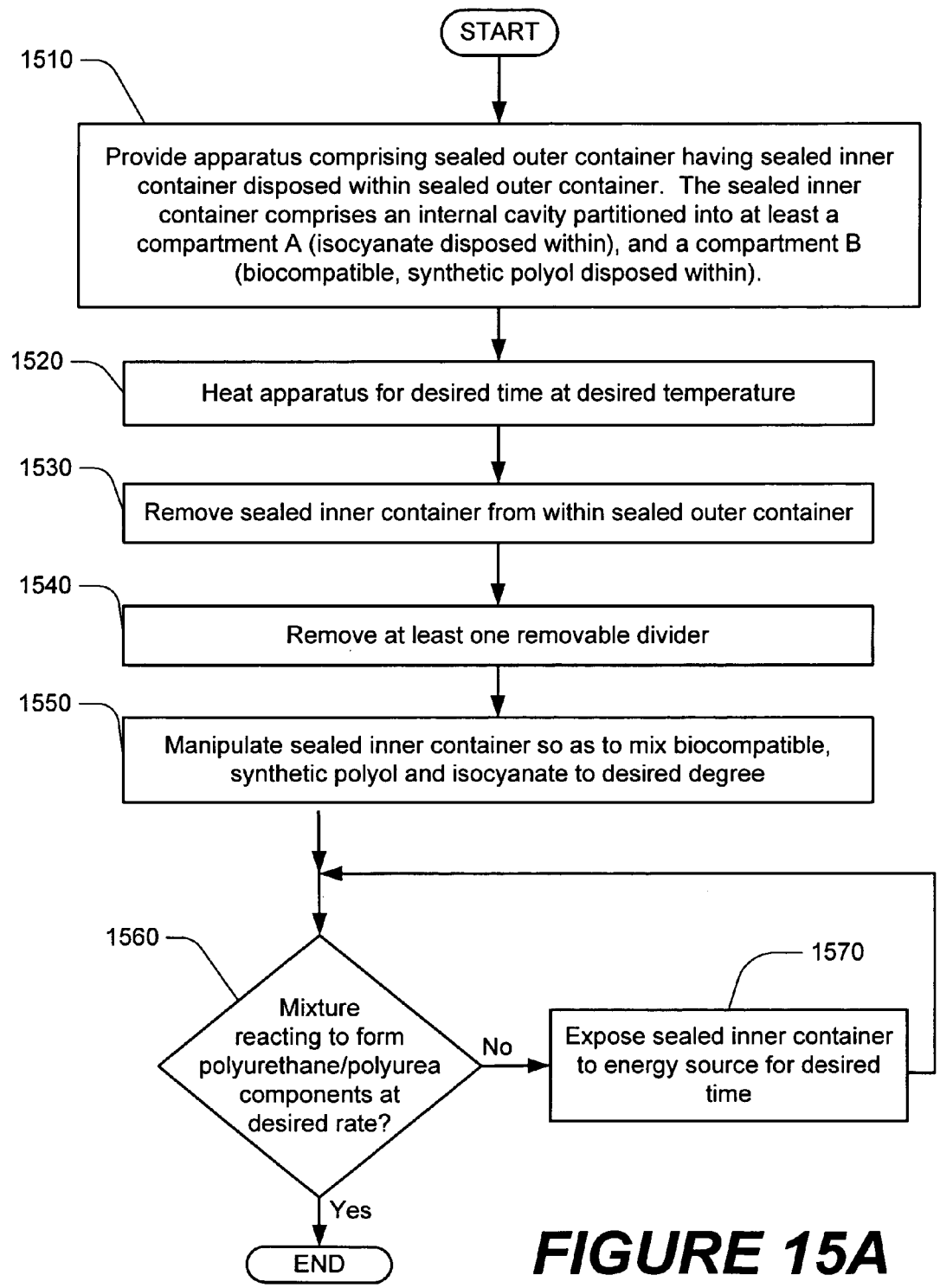
Figure 15B:
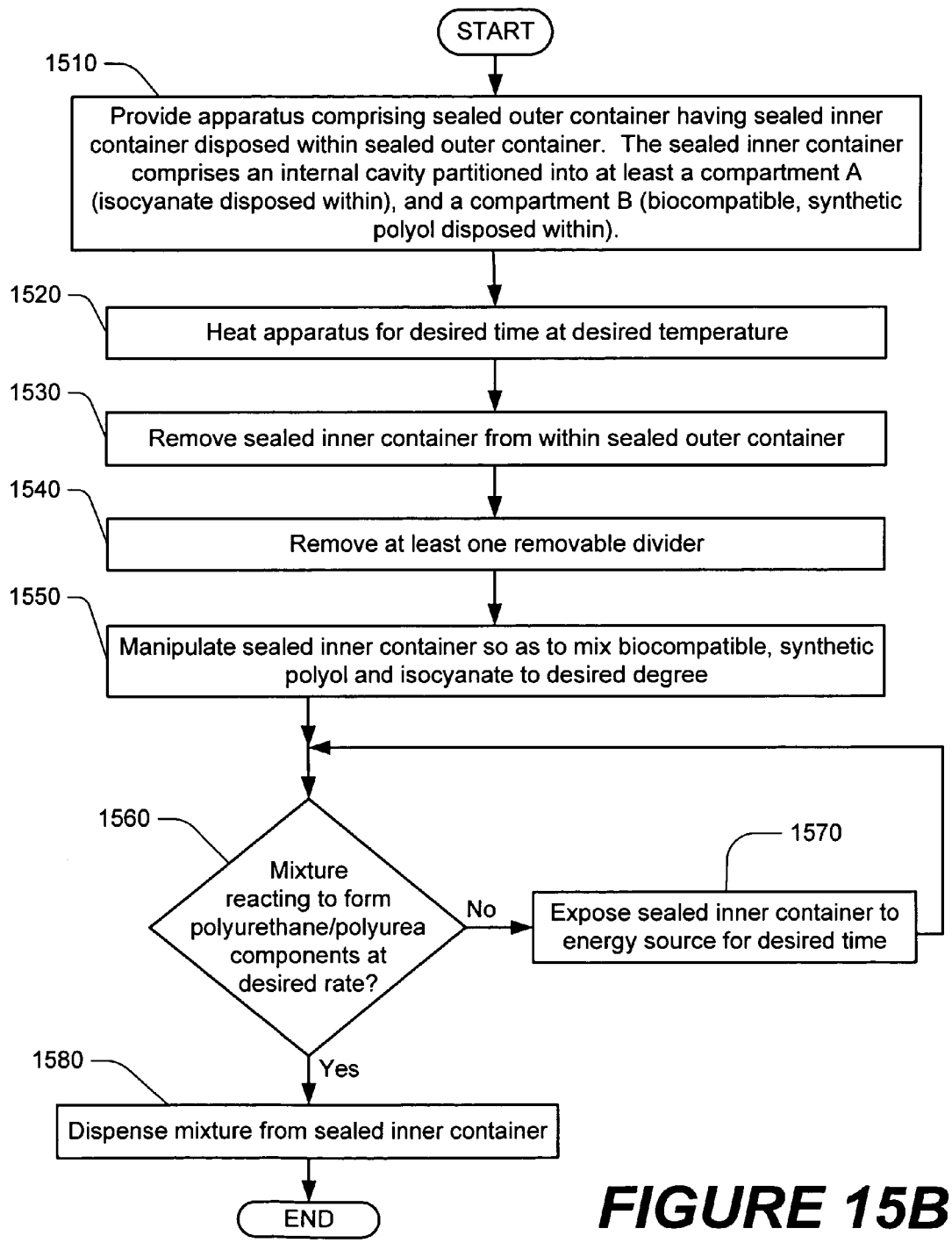
Figure 15C:
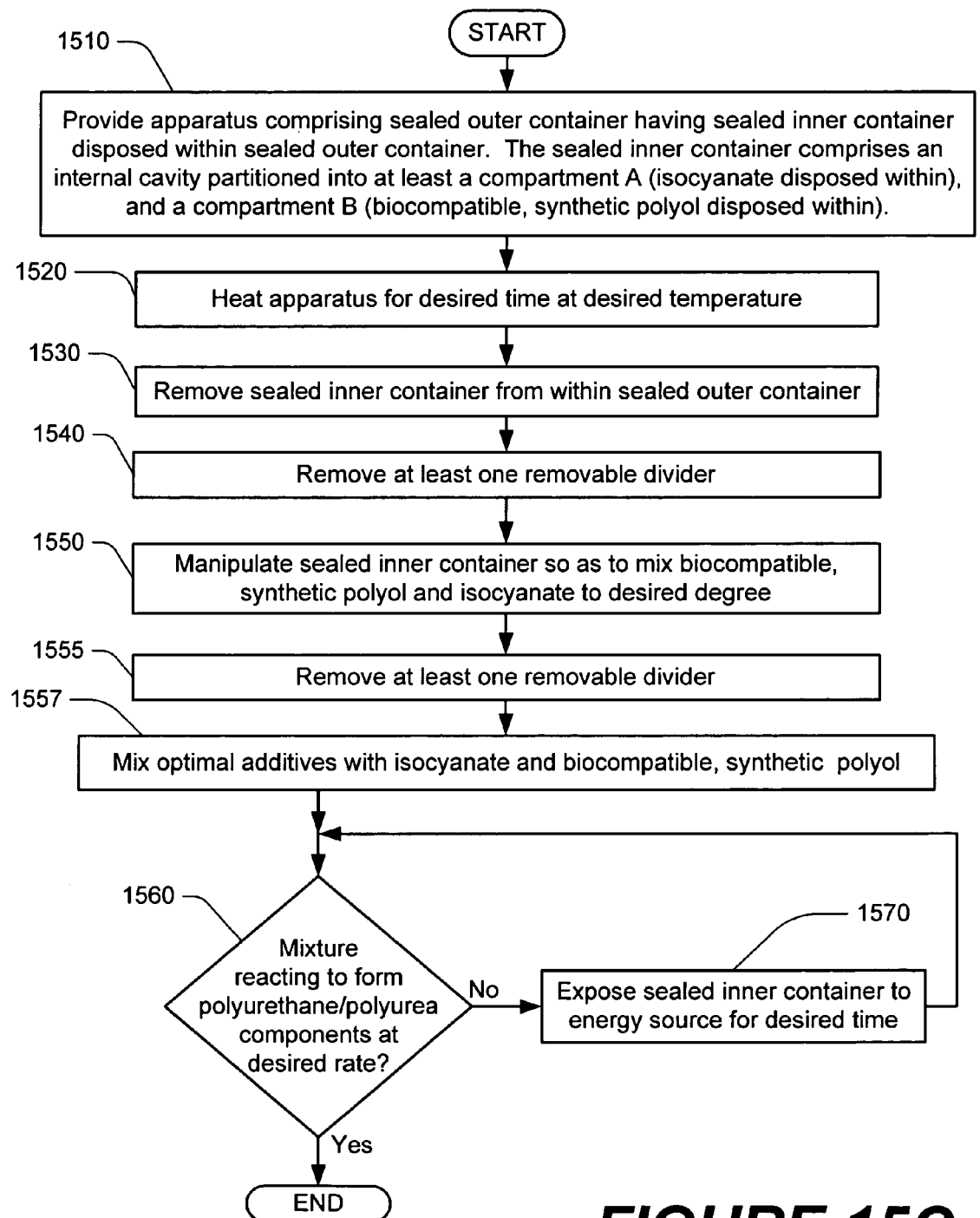
Figure 15D:
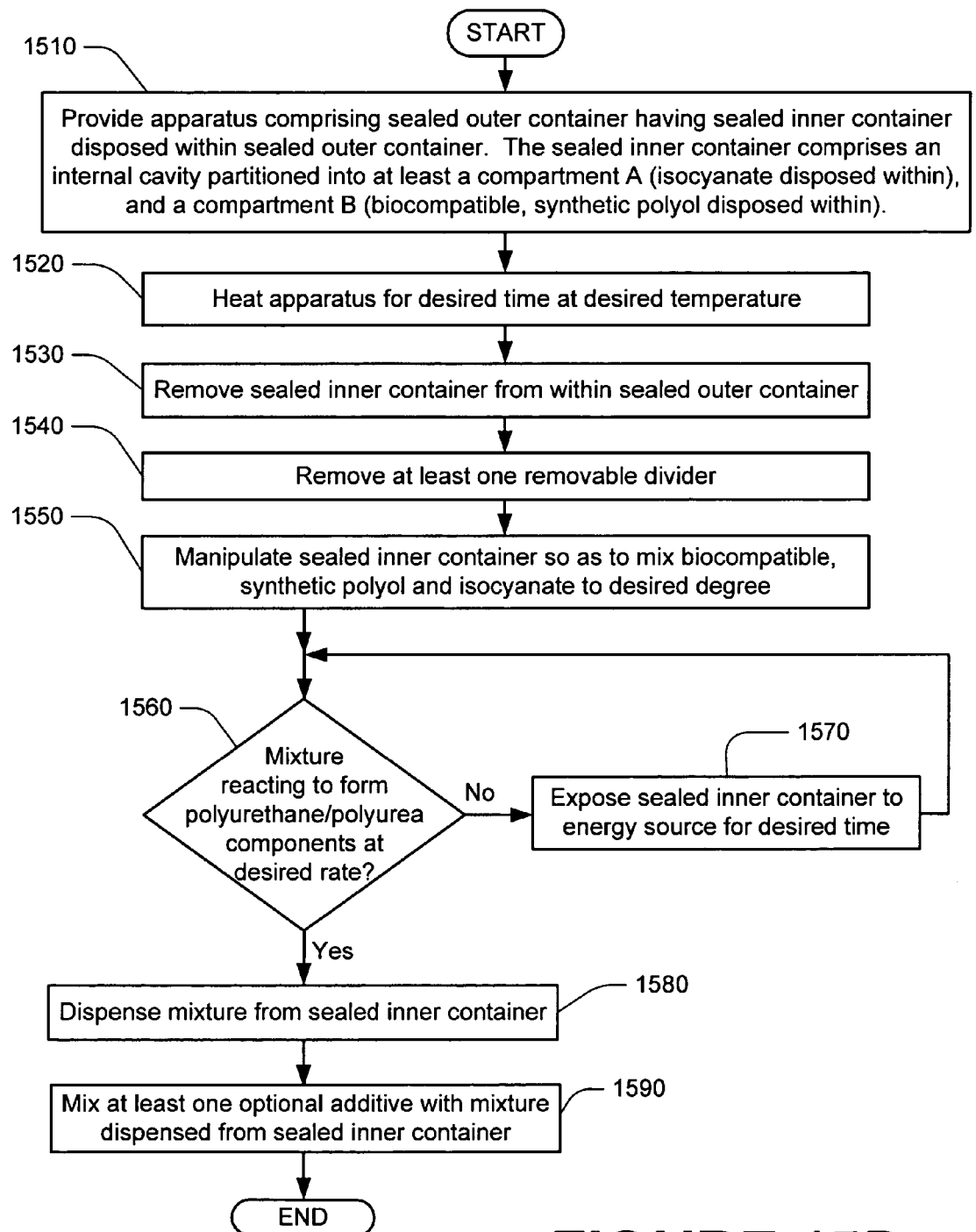
Figure 15E:
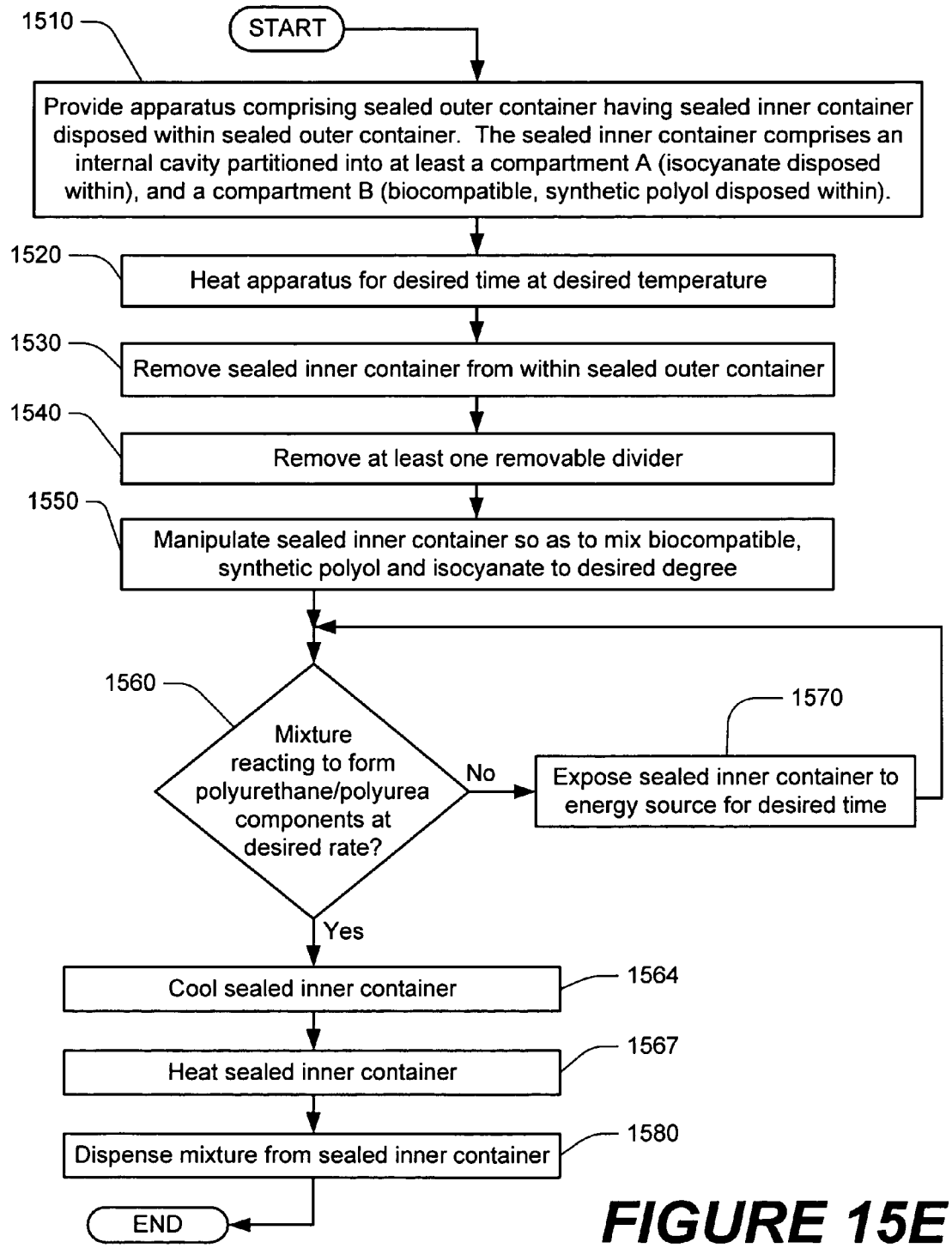
Figure 15F:
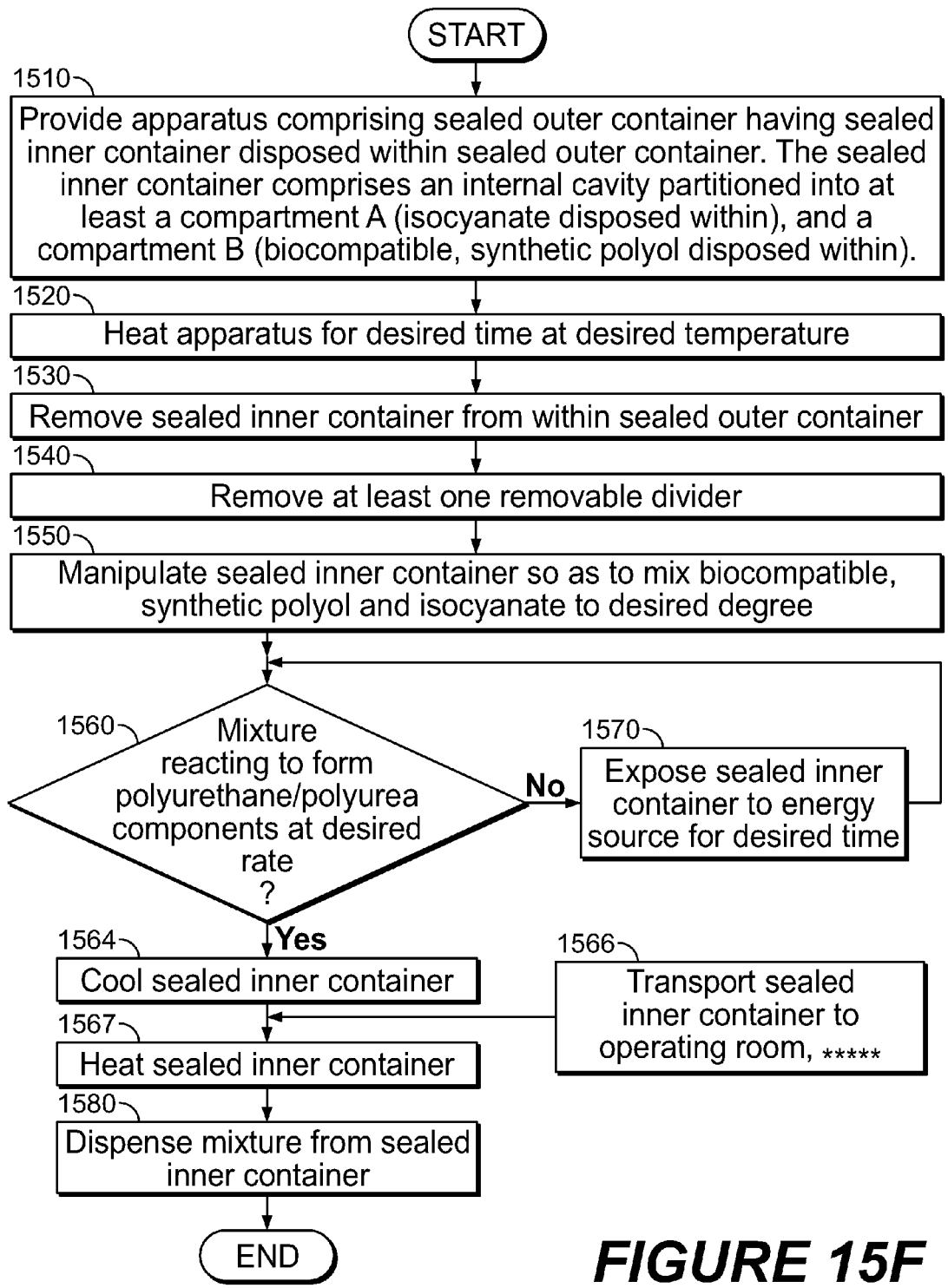

Referring now to FIG. 15A, in step 1510, an apparatus is provided that comprises a sealed outer container comprising an internal cavity, wherein a sealed inner container is disposed within the inner cavity of the sealed outer container. The sealed inner container itself comprises an internal cavity that is separated by at least one removable divider into at least a compartment A and a compartment B, an isocyanate being disposed in compartment A and a biocompatible, synthetic polyol being disposed in compartment B. In certain embodiments, the isocyanate and the biocompatible, synthetic polyol both may be liquids at room temperature. In certain embodiments, a polyamine may be disposed in compartment B along with the biocompatible, synthetic polyol. Further description of the steps that may be used to react these compounds to form a composition that comprises polyurethane/polyurea components is set forth in FIGS. 15A-15F, and will not be further elaborated upon here. In certain embodiments of the present invention, optional additives may be incorporated into the composition; suitable additives, and the ways in which they may become incorporated, have been previously described in greater detail herein with reference to the discussion of FIGS. 13A-13F (including, inter alia, the discussion of optional steps such as steps 1355, 1357, 1380, 1390, and the like). Moreover, situations may arise in which an operator desires to cool the sealed inner container for a desired period of time, so as to halt the reaction between the isocyanate and the naturally occurring polyol; suitable means by which the sealed inner container may be cooled (and, when desired, re-heated) previously have been described in greater detail herein with reference to the discussion of FIGS. 13E-13F (including, inter alia, the discussion of optional steps such as steps 1364, 1367, and the like).

C. Modified "Pre-Polymer" Embodiments

Figure 16A:
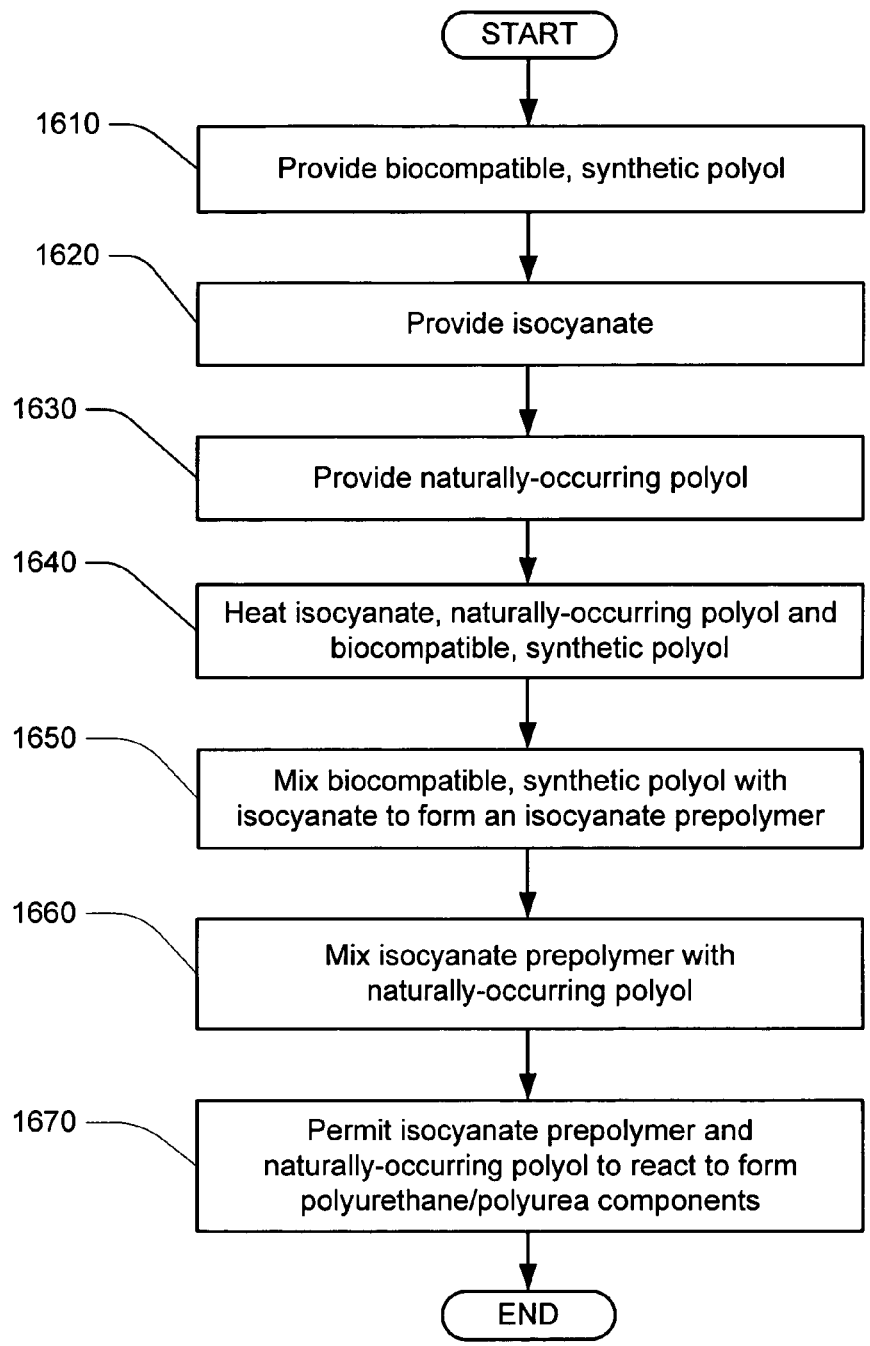
Figure 16B:
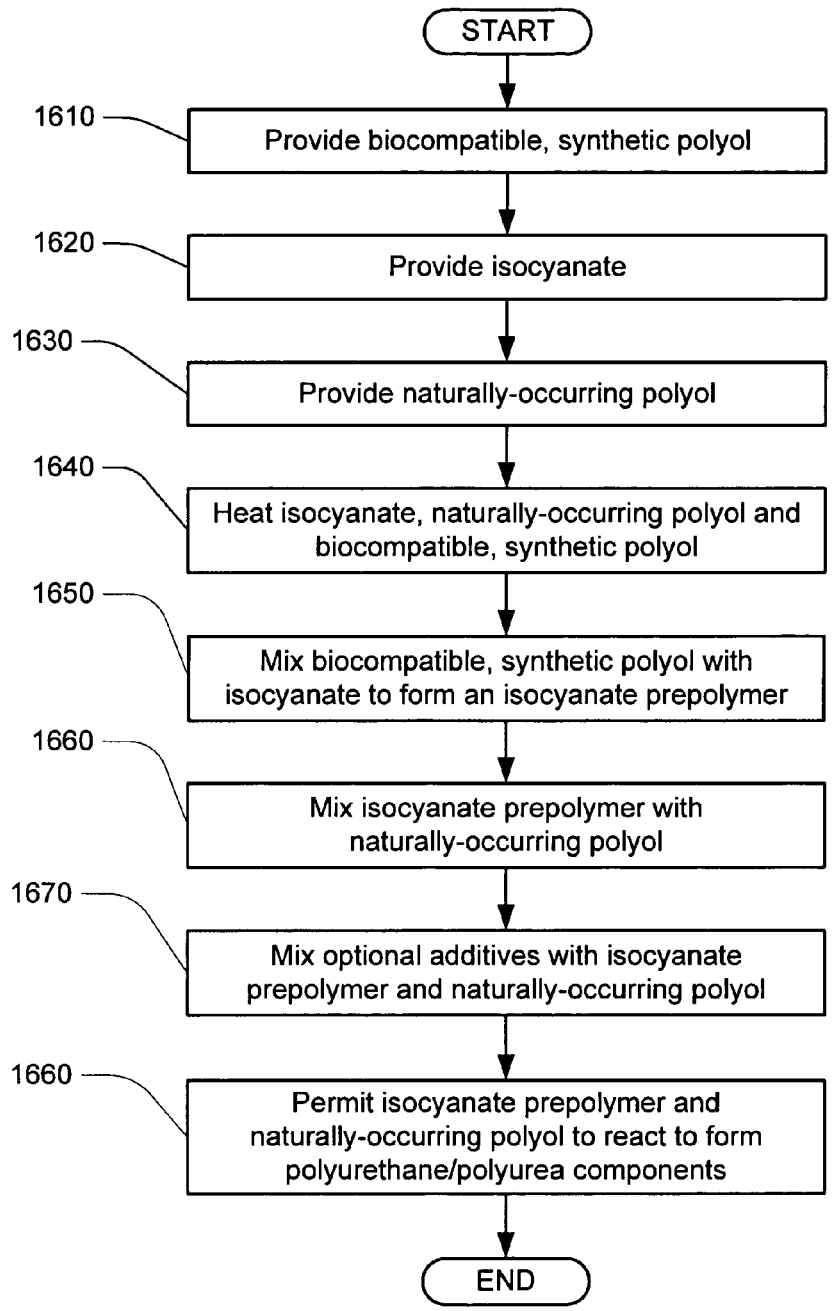
Figure 16C:
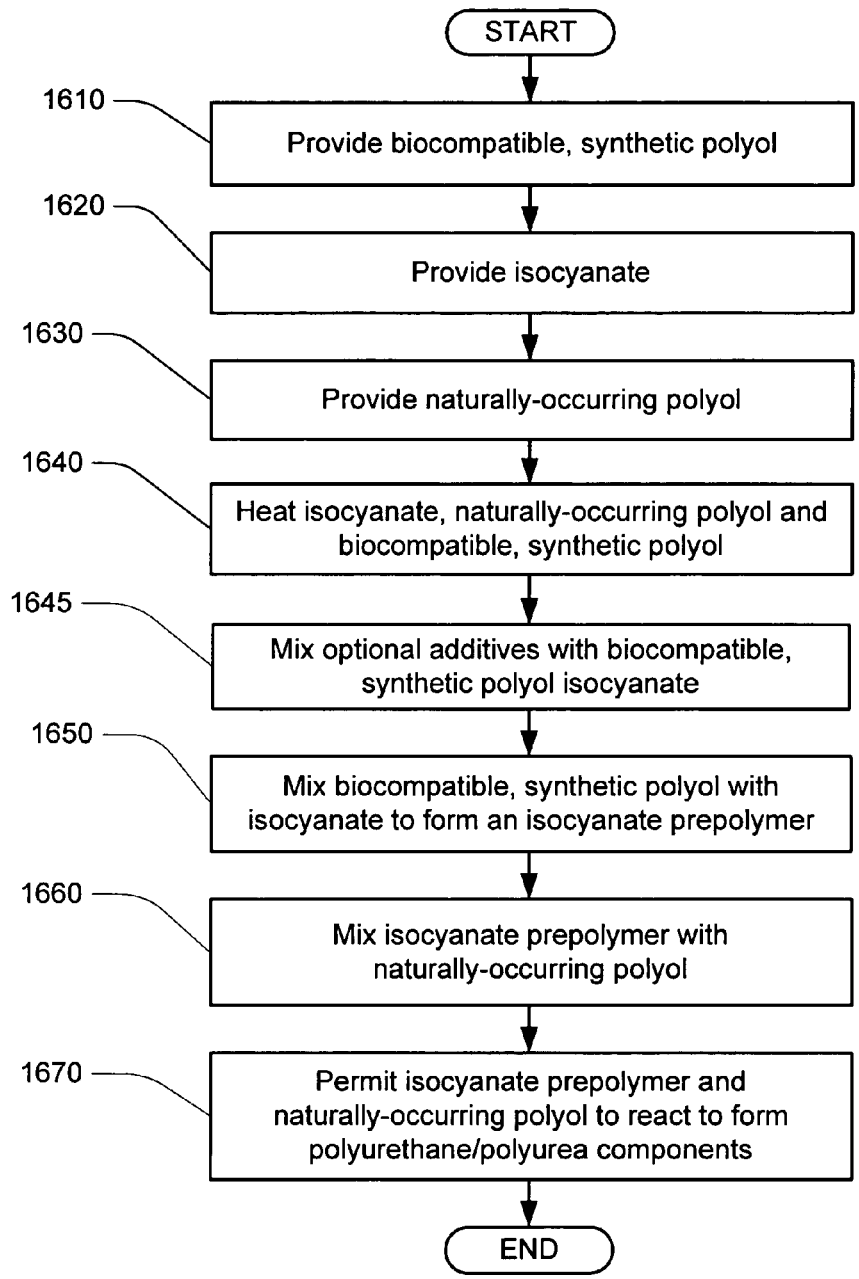

FIGS. 16A-17D set forth exemplary embodiments of methods of the present invention comprising reacting isocyanates with polyols/polyamines to produce isocyanate prepolymers, and subsequently further reacting the isocyanate prepolymers with other compounds to produce compositions comprising polyurethane/polyurea components. Referring now to FIG. 16A, in step 1610, a biocompatible, synthetic polyol is provided. In step 1620, an isocyanate is provided. In step 1630, a naturally occurring polyol is provided. In step 1640, the isocyanate, the biocompatible, synthetic polyol, and the naturally occurring polyol may be heated for a desired time at a desired temperature. In certain embodiments of the present invention, the desired temperature may be in the range of from room temperature to about 150° C., but other temperatures may be selected, as will be recognized by one of ordinary skill in the art, with the benefit of this disclosure. In certain embodiments of the present invention, the desired temperature may be in the range of from about 50° C. to about 100° C. In step 1650, an isocyanate prepolymer is formed by mixing the biocompatible, synthetic polyol with the isocyanate. In certain embodiments of the present invention, the isocyanate may become chemically bound within the isocyanate prepolymer to an extent sufficient to prevent the release of free isocyanate when the composition formed by this method is placed in the body of a mammal. In step 1660, the isocyanate prepolymer formed in step 1650 may be mixed with the naturally occurring polyol to a desired degree. In certain embodiments of the present invention, the naturally occurring polyol may comprise an amount of water. In step 1670, the mixture of the isocyanate prepolymer and the naturally occurring polyol are permitted to react to form polyurethane/polyurea components.

In certain embodiments of the present invention, optional additives may be incorporated into the compositions; examples of such optional additives include, inter alia, those that previously have been described herein (e.g., at least one filler material, and/or at least one protein, and the like). For example, such optional additives may be incorporated in a step 1665 (shown in FIG. 16B) that involves mixing them in with the mixture of isocyanate prepolymer and naturally occurring polyol; such optional step 1665 may be performed after step 1660 and before step 1670. Alternatively, such optional additives may be incorporated in a step 1645 (shown in FIG. 16C) that involves mixing them in with the biocompatible, synthetic polyol and the isocyanate; such optional step 1645 may be performed after step 1640 and before step 1650. Other variations exist as to the moment when the optional additives may be added, as will be recognized by one of ordinary skill in the art, with the benefit of this disclosure.

Figure 16D:
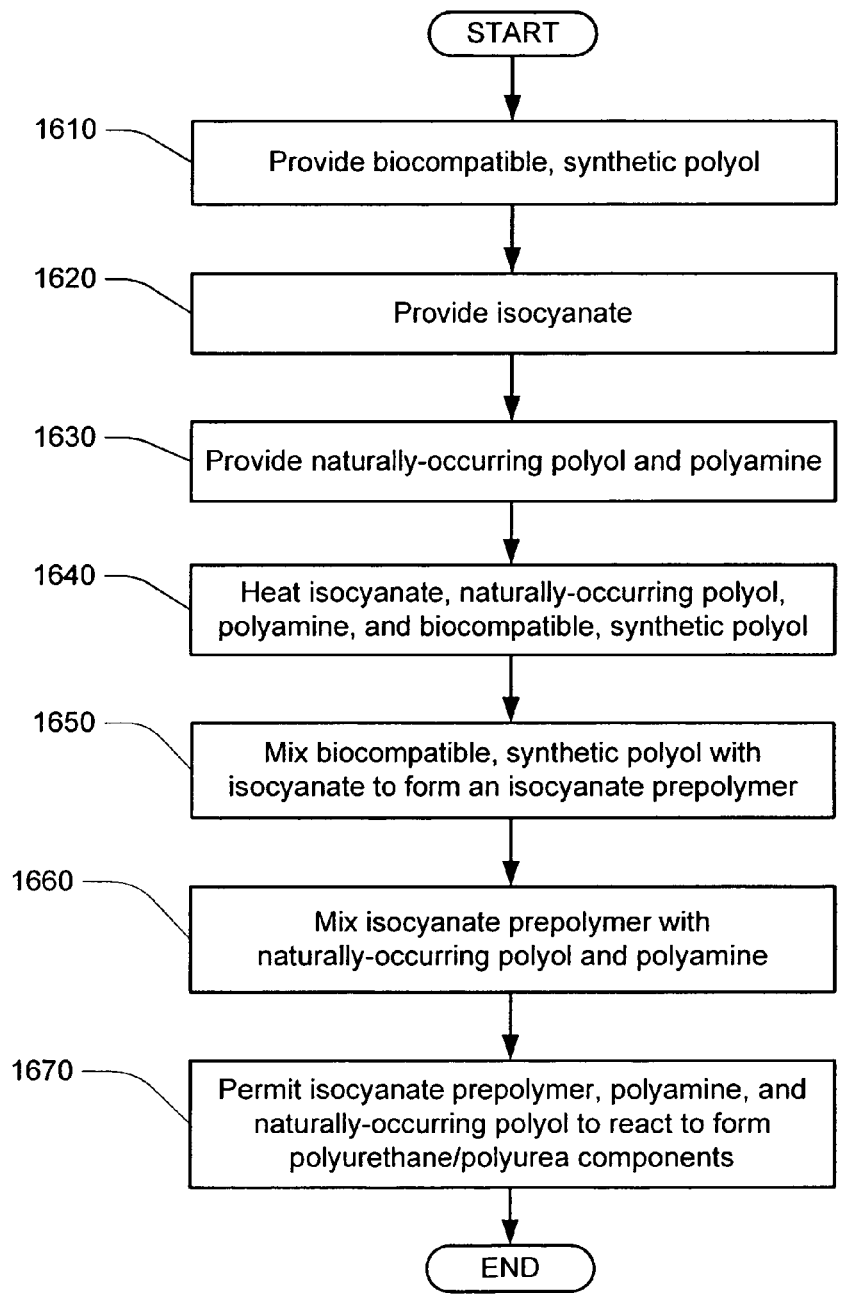

The present invention also contemplates that a polyamine may be provided along with the naturally-occurring polyol, for example by being added during step 1630 as illustrated in FIG. 16D, which demonstrates an exemplary method by which a polyamine may be used in producing polyurethane/polyurea components.

Figure 17A:
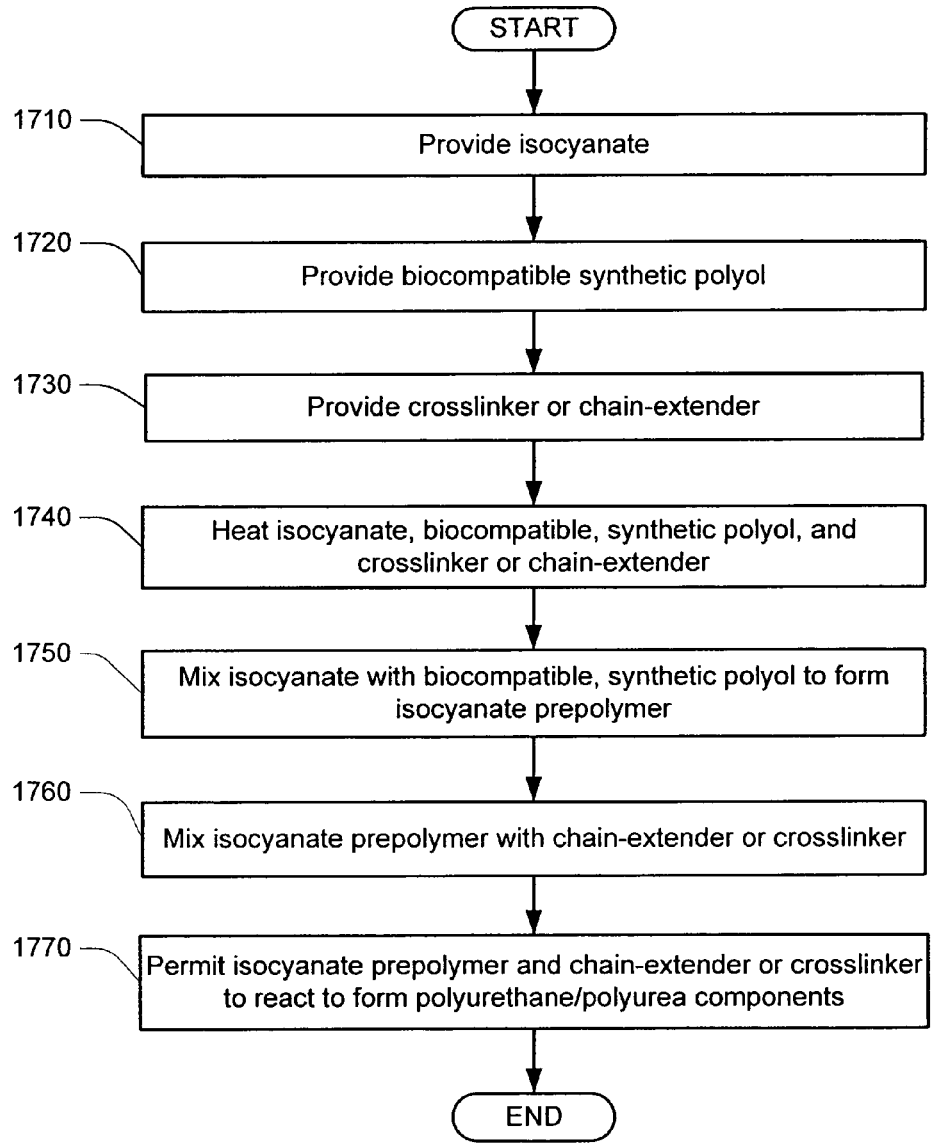
Figure 17B:
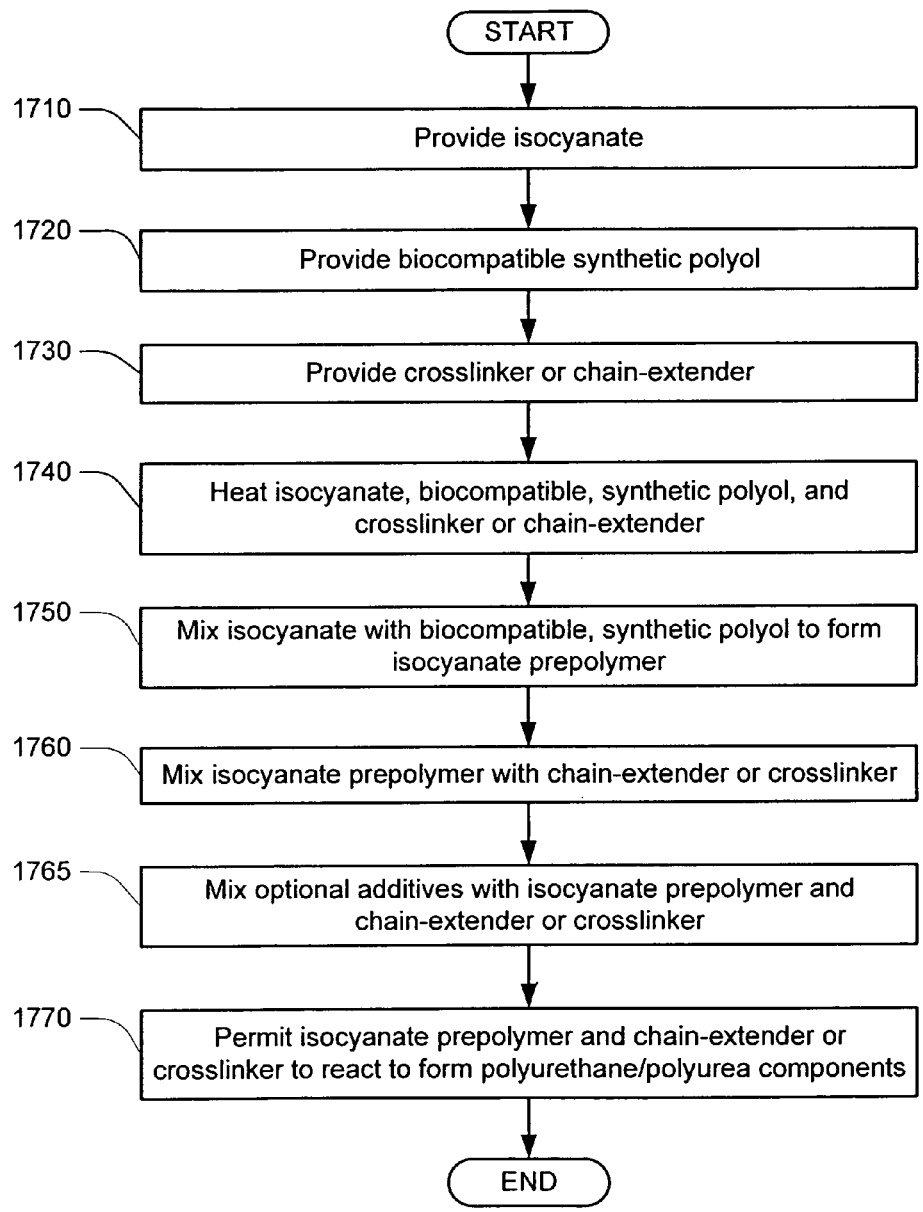
Figure 17C:
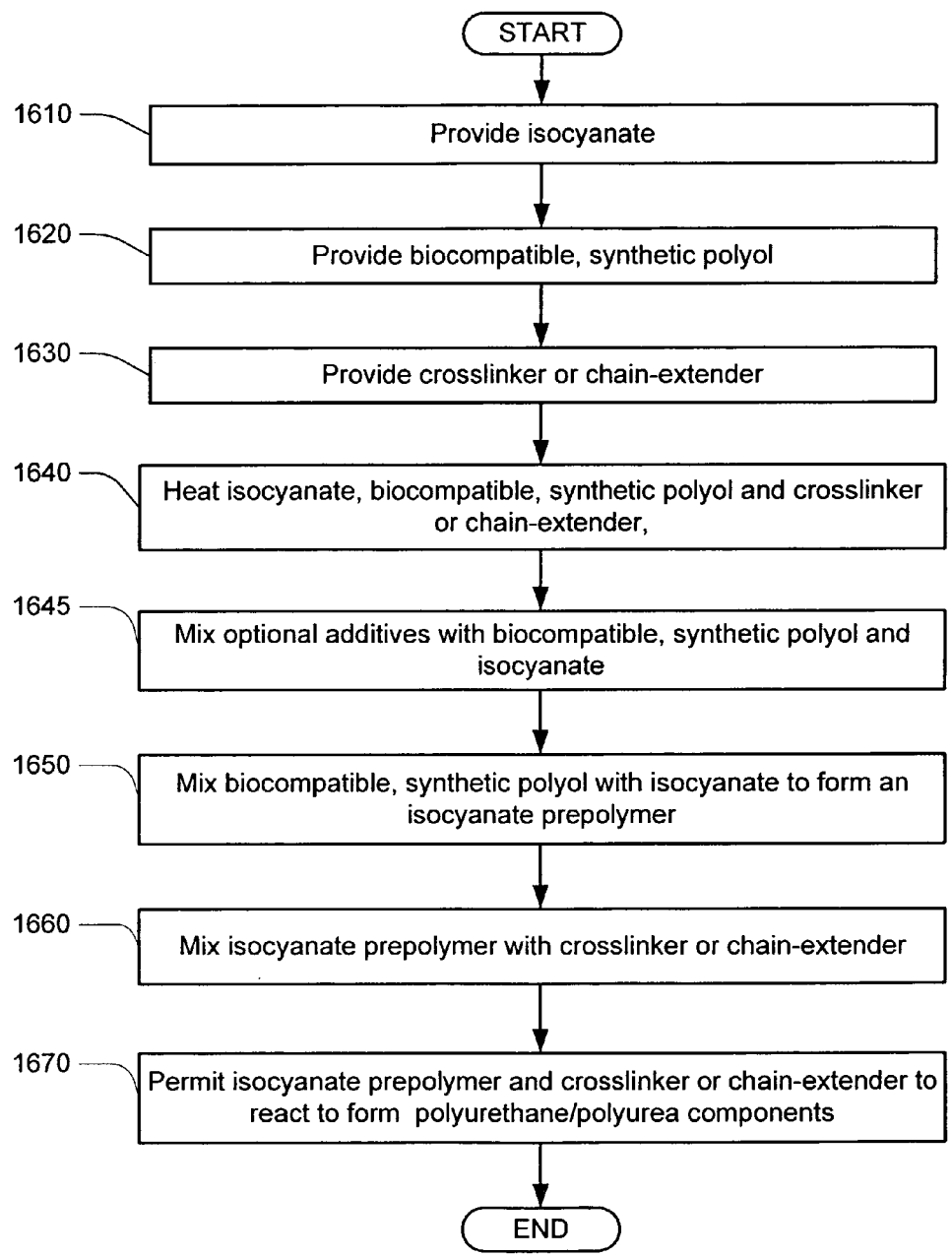
Figure 17D:
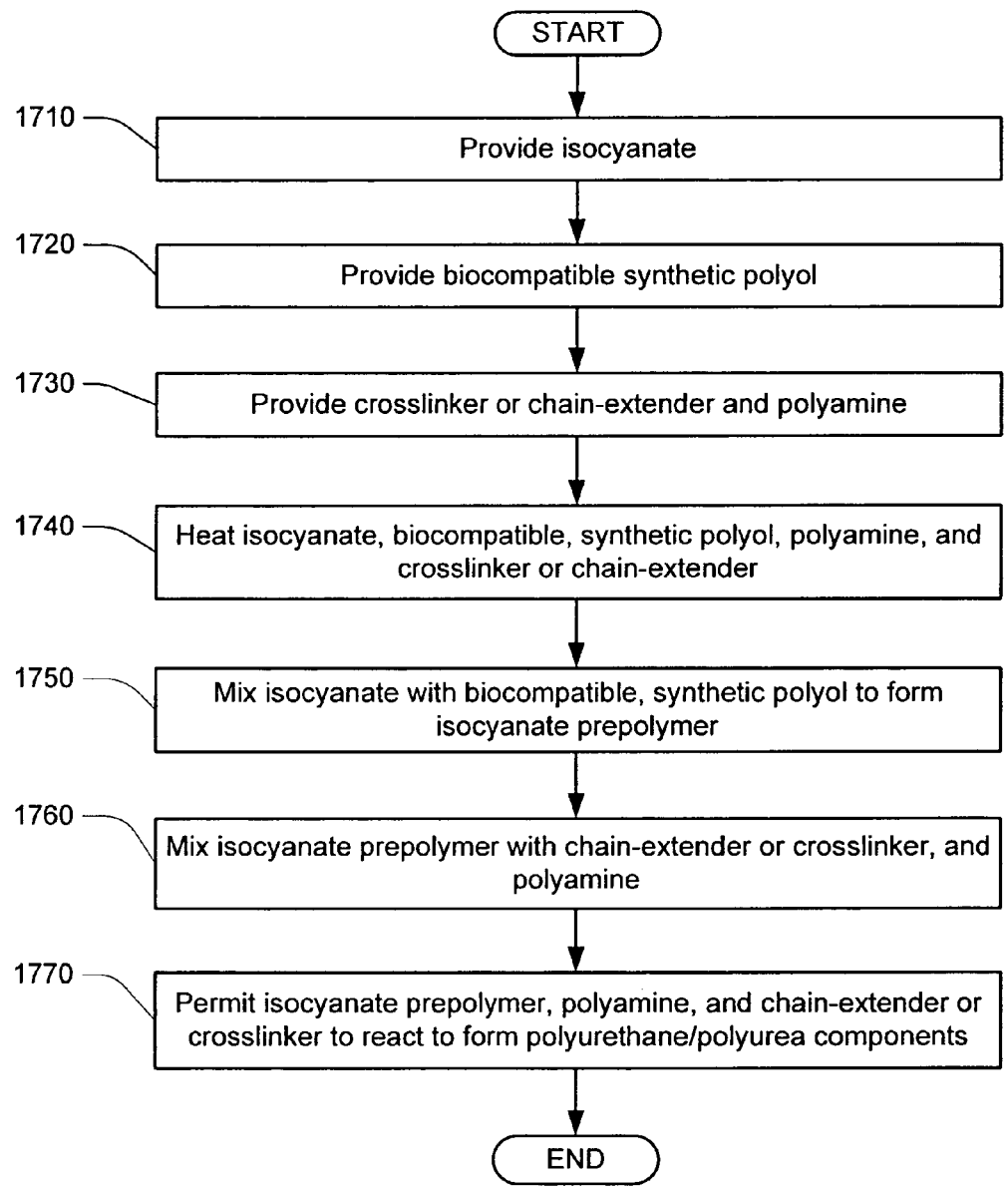

FIG. 17A illustrates another exemplary method of the present invention comprising reacting isocyanates with polyols/polyamines to produce isocyanate prepolymers, and subsequently further reacting the isocyanate prepolymer with other compounds to produce compositions comprising polyurethane/polyurea components. Because certain features and advantages of these embodiments of the present invention are substantially similar to certain features and advantages of the embodiments described with reference to FIGS. 16A-17D, such similar features and advantages are not discussed further with respect to the embodiments of the present invention illustrated in FIGS. 17A-17D.

Referring now to FIG. 17A, in step 1710, an isocyanate may be provided. In step 1720, a biocompatible, synthetic polyol may be provided. In step 1730, a crosslinker or chain-extender may be provided. Exemplary steps that may be used to react these compounds to form a composition that comprises polyurethane/polyurea components are set forth in FIGS. 17A-17D; these steps are substantially similar to corresponding steps that have been described in FIGS. 16A-16D and will not be further elaborated upon here. In certain embodiments of the present invention, optional additives may be incorporated into the composition; suitable additives, and the ways in which they may become incorporated, have been previously described in greater detail herein with reference to the discussion of FIGS. 16B-16C (including, inter alia, the discussion of optional steps such as steps 1645, 1665, and the like). Moreover, in certain embodiments of the present invention, a polyamine may be incorporated, as illustrated, for example, in FIG. 16D.

D. Modified "Prepolymer" Embodiments Employing Apparatus of the Present Invention FIGS. 18A-19F describe exemplary embodiments of the present invention comprising reacting isocyanates with polyols/polyamines to produce isocyanate prepolymers, and subsequently further reacting the isocyanate prepolymers with other compounds to produce compositions comprising polyurethane/polyurea components. Moreover, the methods described in FIGS. 18A-19F employ embodiments of apparatus of the present invention.

1. Sealed Container

Figure 18A:
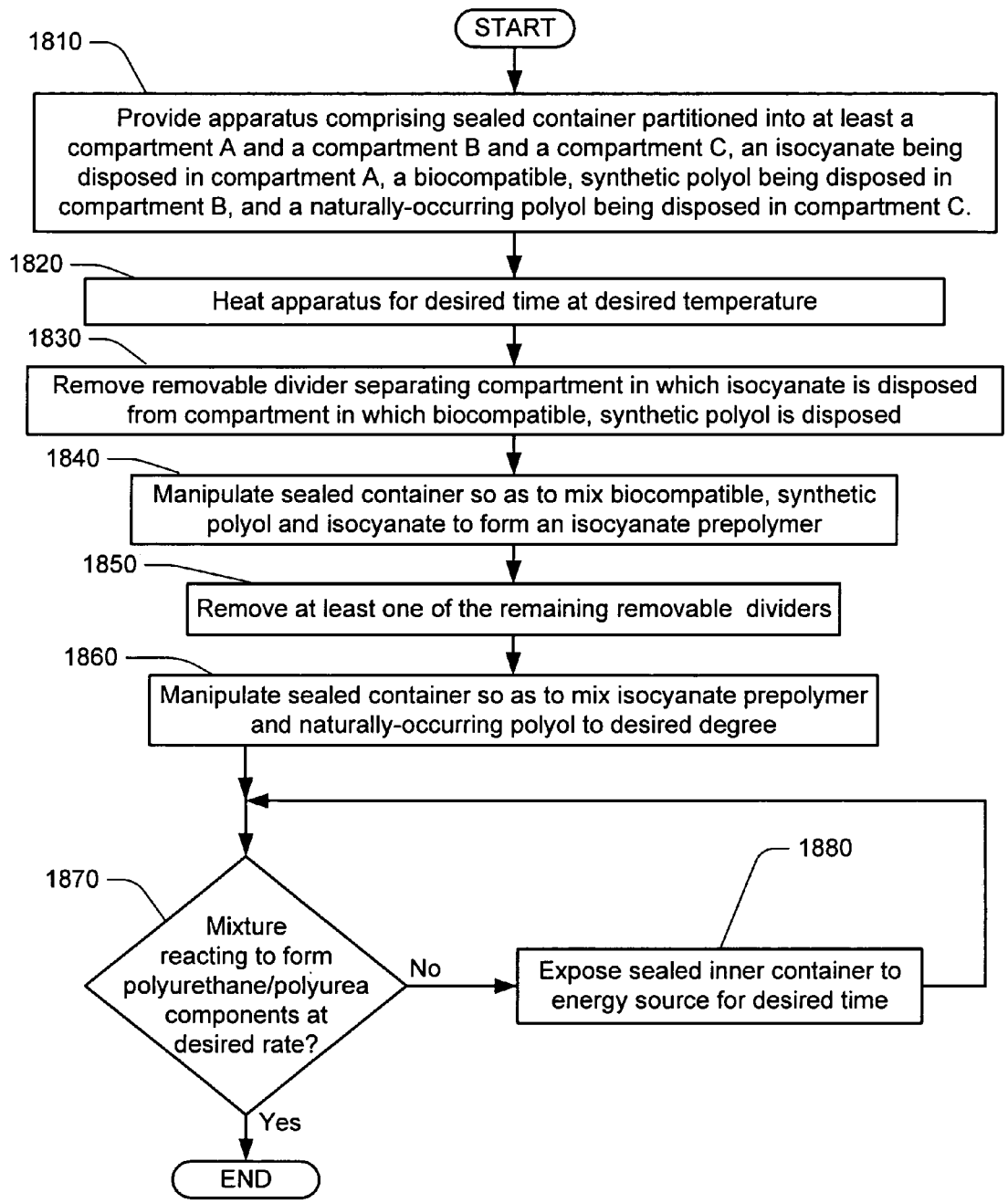
Figure 18B:
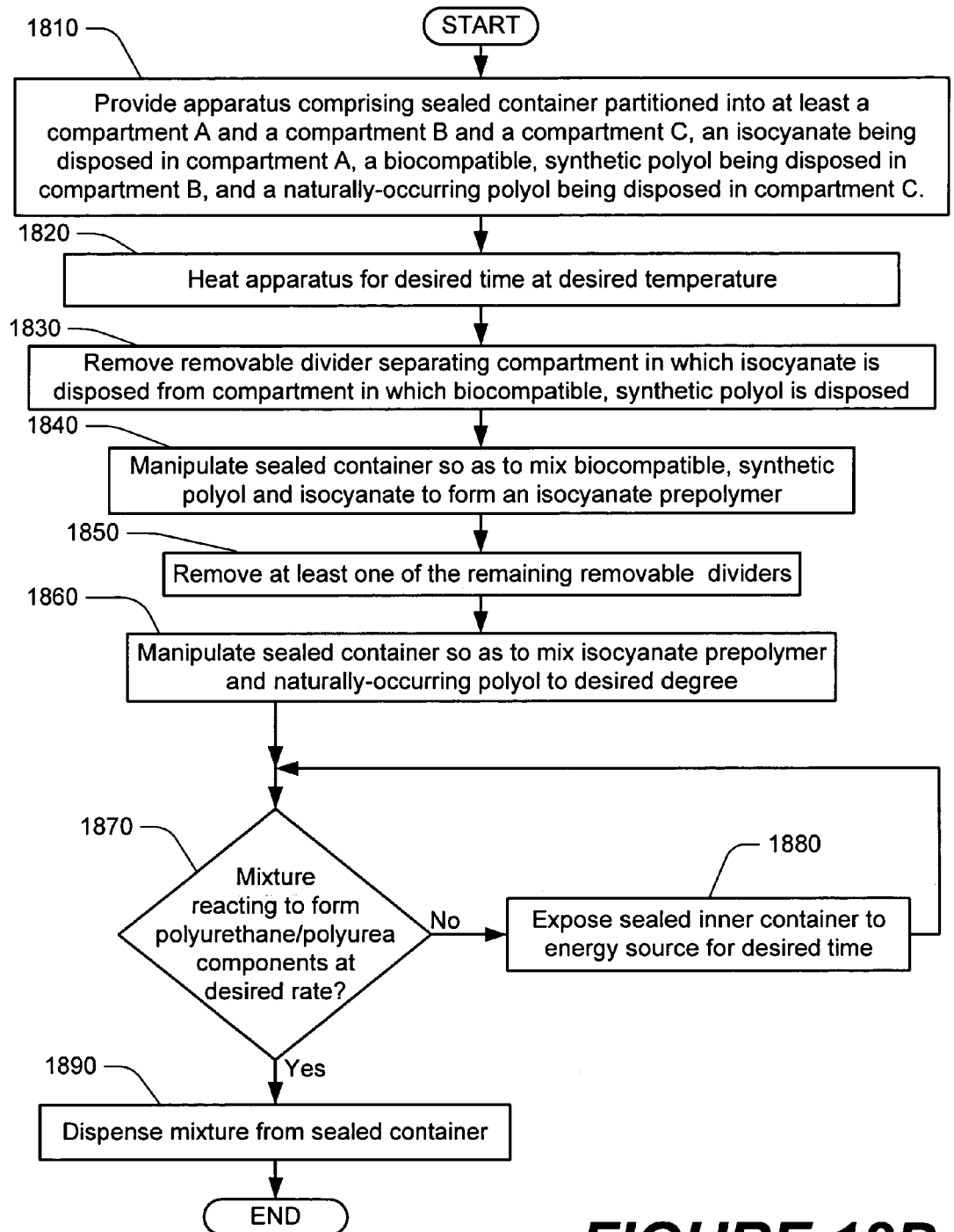
Figure 18C:
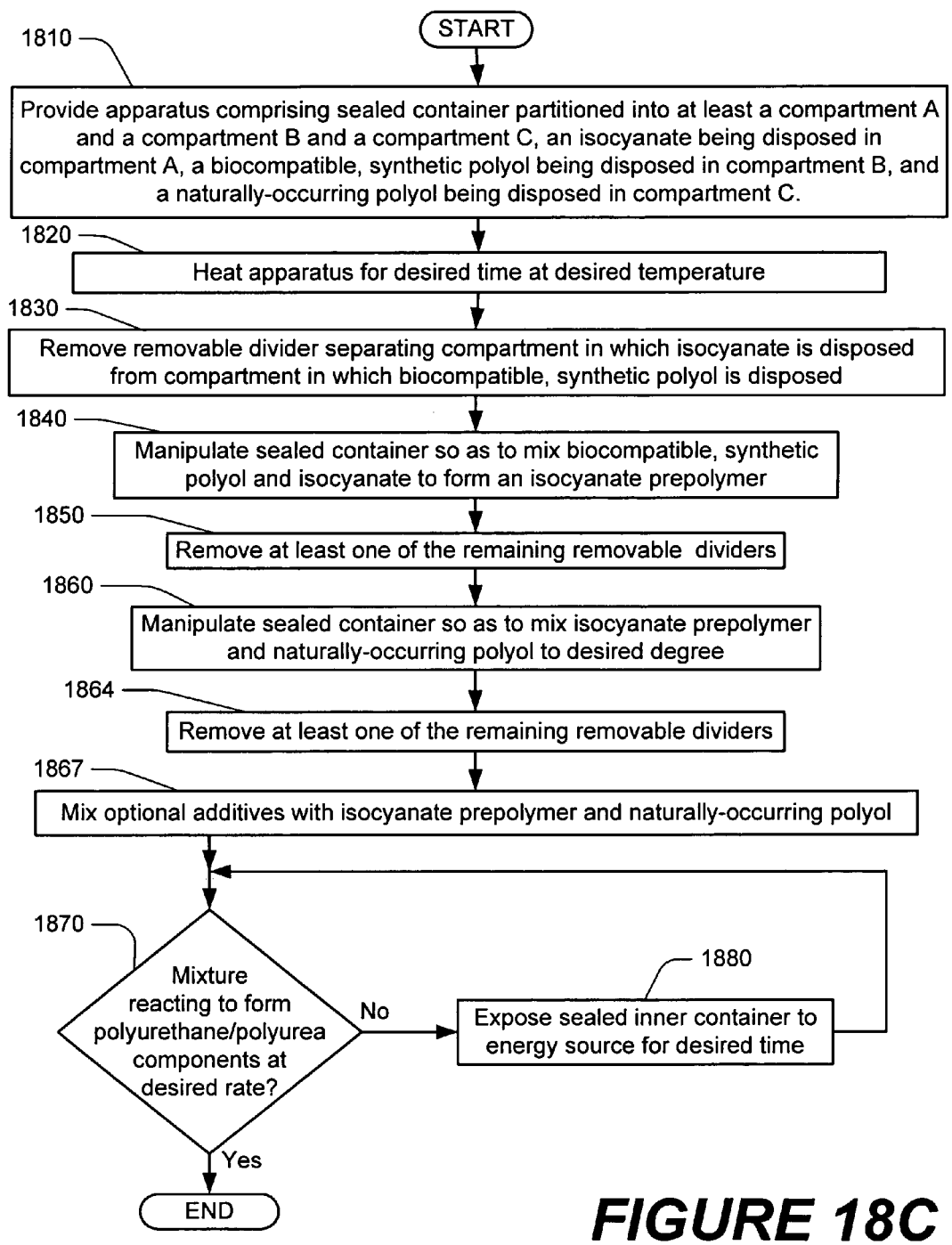
Figure 18D:
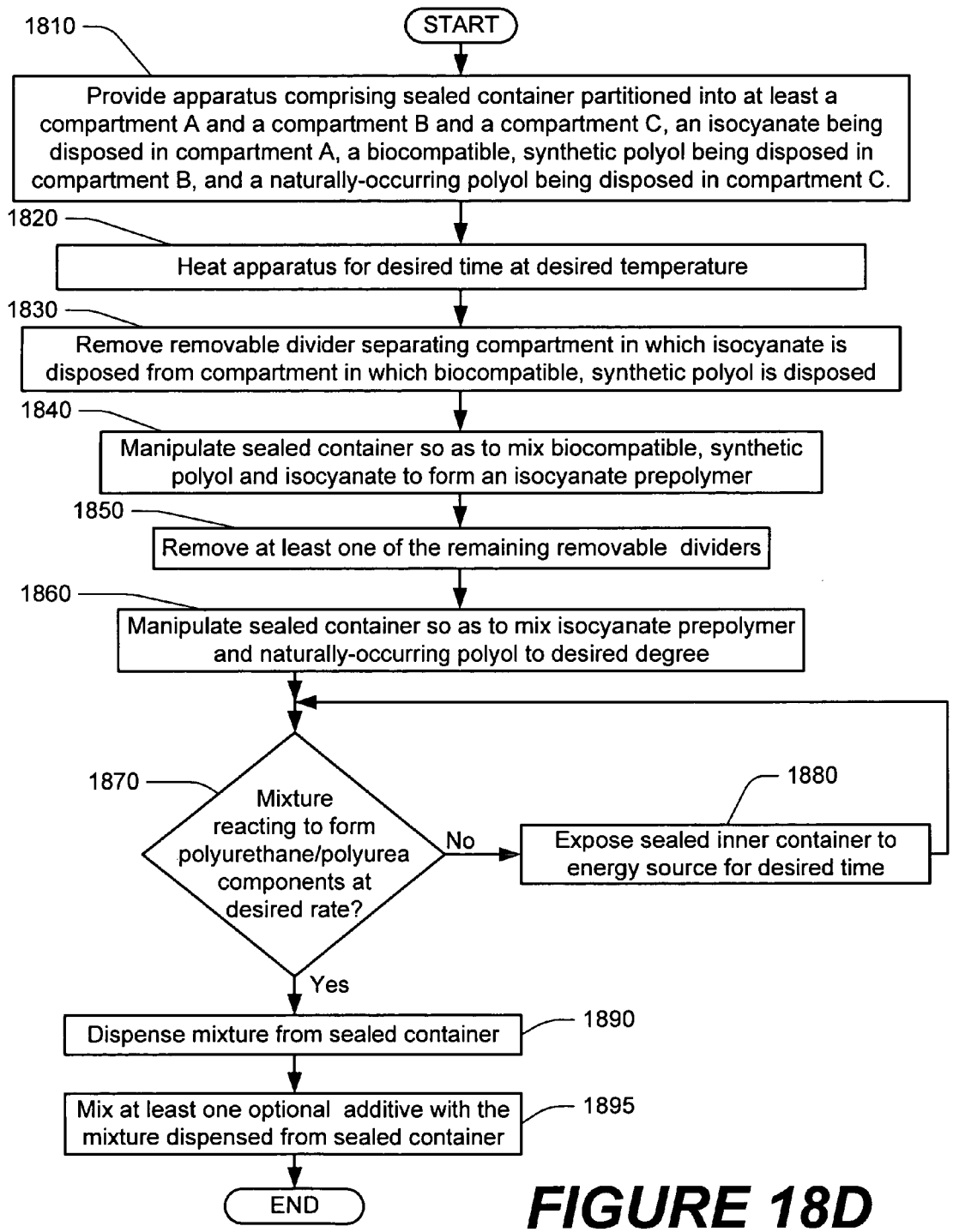

Referring now to FIG. 18A, in step 1810, an apparatus of the present invention is provided that comprises a sealed container comprising an internal cavity, the internal cavity being separated by a removable divider into at least a compartment A, a compartment B, and a compartment C, an isocyanate being disposed in compartment A, a biocompatible, synthetic polyol being disposed in compartment B, and a naturally occurring polyol being disposed in compartment C. In certain embodiments of the present invention, a polyamine may be disposed in compartment C along with the naturally occurring polyol. In step 1820, the sealed container is heated for a desired time at a desired temperature (e.g., in the range of from about room temperature to about 150° Celsius, for certain embodiments). In certain embodiments of the present invention, the sealed container may be heated in boiling water for a desired time (e.g., in the range of from about 30 seconds to about 90 seconds); alternatively, the sealed container may be heated in a microwave oven (e.g., on "HIGH" for a time in the range of from about 30 seconds to about 90 seconds). The desired time and temperature to which the sealed container is heated will depend on how rapidly the operator desires the compounds within the sealed container to react (after having been combined) to form polyurethane/polyurea components. Generally, the closer the temperature of the components approaches 150° Celsius, the faster the reaction will proceed. The desired time and temperature to which the sealed container is heated also may depend on the temperature limitations of the material used to form the sealed container and the removable dividers; if, for example, either the sealed container or the removable dividers are made from a material that may degrade at about 150° C., then the sealed container may be heated to a lower temperature at which the sealed container or removable divider may not degrade (e.g., about 140° C., for example). In step 1830, a removable divider is removed so as to permit fluid communication between the isocyanate and the biocompatible, synthetic polyol. In step 1840, the sealed container is manipulated (e.g., manually manipulated) so as to mix the biocompatible, synthetic polyol and the isocyanate to a desired degree (e.g., to facilitate the formation of an isocyanate prepolymer from the reaction between the biocompatible, synthetic polyol and the isocyanate). In certain embodiments, the sealed container may be manipulated for a time in the range of from about 1 minute to about 30 minutes. The time period during which the sealed container may be manually manipulated may depend on factors including, inter alia, the temperature to which the sealed container may have been heated, whether an optional catalyst has been included, and the type of isocyanate used. For example, if an aromatic isocyanate has been used, the mixture within the sealed container may exotherm and react relatively quickly. Alternatively, if a cycloaliphatic isocyanate has been used, the reaction time may take longer. In step 1850, another divider is removed so as to permit fluid communication between the isocyanate prepolymer and the naturally occurring polyol. In step 1860, the sealed container is manipulated (e.g., manually manipulated) so as to mix the naturally occurring polyol and the isocyanate prepolymer to a desired degree.

In step 1870, a determination may be made whether the mixture of the naturally occurring polyol and the isocyanate prepolymer is reacting at a desired rate. For example, the progress of the reaction may be assessed through tactile feedback, as the viscosity of the mixture within the sealed container may be felt to increase, and as the mixture may be felt, and seen, to progress towards, and through, a "taffy-like" state. In certain embodiments, an FTIR probe may be used to determine whether the mixture of the naturally occurring polyol and the isocyanate prepolymer is reacting at a desired rate; exemplary embodiments of the manner in which an FTIR probe may be used have been previously described herein, with reference to step 1050 of FIG. 10A. Alternatively, other means may be used to determine the progress of the reaction between the naturally occurring polyol and the isocyanate prepolymer, including, inter alia, the use of a small weight; exemplary embodiments of the manner in which a small weight may be used have been previously described herein, with reference to step 1050 of FIG. 10A. If, in step 1870, the mixture is determined to be reacting at a desired rate, the process proceeds to end.

Alternatively, in certain optional embodiments of the present invention, after a determination is made in step 1870 that the mixture of the naturally occurring polyol and the isocyanate prepolymer is reacting at a desired rate, the process may proceed from step 1870 to an optional step 1890 (shown in FIG. 18B) wherein the contents of the sealed container are dispensed therefrom, after which the process may proceed to end. If, however, in step 1870 the determination is made that the mixture is not reacting at a desired rate, then the process proceeds to step 1880, wherein the sealed container is exposed to an energy source for a desired time (e.g., heated in boiling water for 30-90 seconds, or heated on "HIGH" in a microwave oven for a similar time, or the like). In certain embodiments wherein the mixture comprises optional photo- or light-initiators and other suitable components (e.g., adducts of isocyanates, double-bond-containing isocyanates, double-bond containing polyols, and the like), the sealed container may be exposed to a suitable light source for a desired time (e.g., in the range of from a few seconds to about 5 minutes, depending on factors including, inter alia, the intensity of the light source, the concentration of light- or photo-initiators, the concentration of double-bond containing compounds in the composition, and the type of light source). The process then returns to the determination made in step 1870, which has previously been described.

In certain optional embodiments of the present invention, a variety of optional additives may be incorporated into the process. For example, the inner cavity optionally further may be separated by removable dividers into at least a compartment A, a compartment B, a compartment C, and a compartment D, wherein one of these compartments (e.g., compartment D) may comprise optional additives including, but not limited to, those that previously have been described herein (e.g., at least one filler material, and/or at least one protein, and the like). In certain of these embodiments wherein optional additives are disposed within one or more compartments, the process may comprise optional step 1864 (shown in FIG. 18C) wherein a removable divider is removed, and optional step 1867 (shown in FIG. 18C) wherein the sealed container is manipulated (e.g., manually manipulated) so as to mix the optional additives with the mixture of the naturally occurring polyol and the isocyanate prepolymer. The process then may proceed from optional step 1867 to step 1870, which previously has been described. As an alternative, in certain other optional embodiments of the present invention, certain of the optional additives may be introduced outside the sealed container, and may be incorporated once the contents of the sealed container are dispensed therefrom. For example, after a determination is made in step 1870 that the mixture of the naturally occurring polyol and the isocyanate prepolymer is reacting at a desired rate, the process may proceed from step 1870 to an optional step 1890 (shown in FIG. 18D) wherein the reacting mixture is dispensed from the sealed container, and then may proceed to an optional step 1895 (shown in FIG. 18D) wherein at least one optional additive is mixed with the dispensed reacting mixture and permitted to remain within it as the mixture finishes reacting, after which the process may proceed to end.

In certain embodiments, one or more optional additives may be present in a separate reservoir (e.g., reservoir 199 shown in FIG. 4B), and optional step 1867 may comprise flowing the additives from the separate reservoir into the sealed container.

Figure 18E:
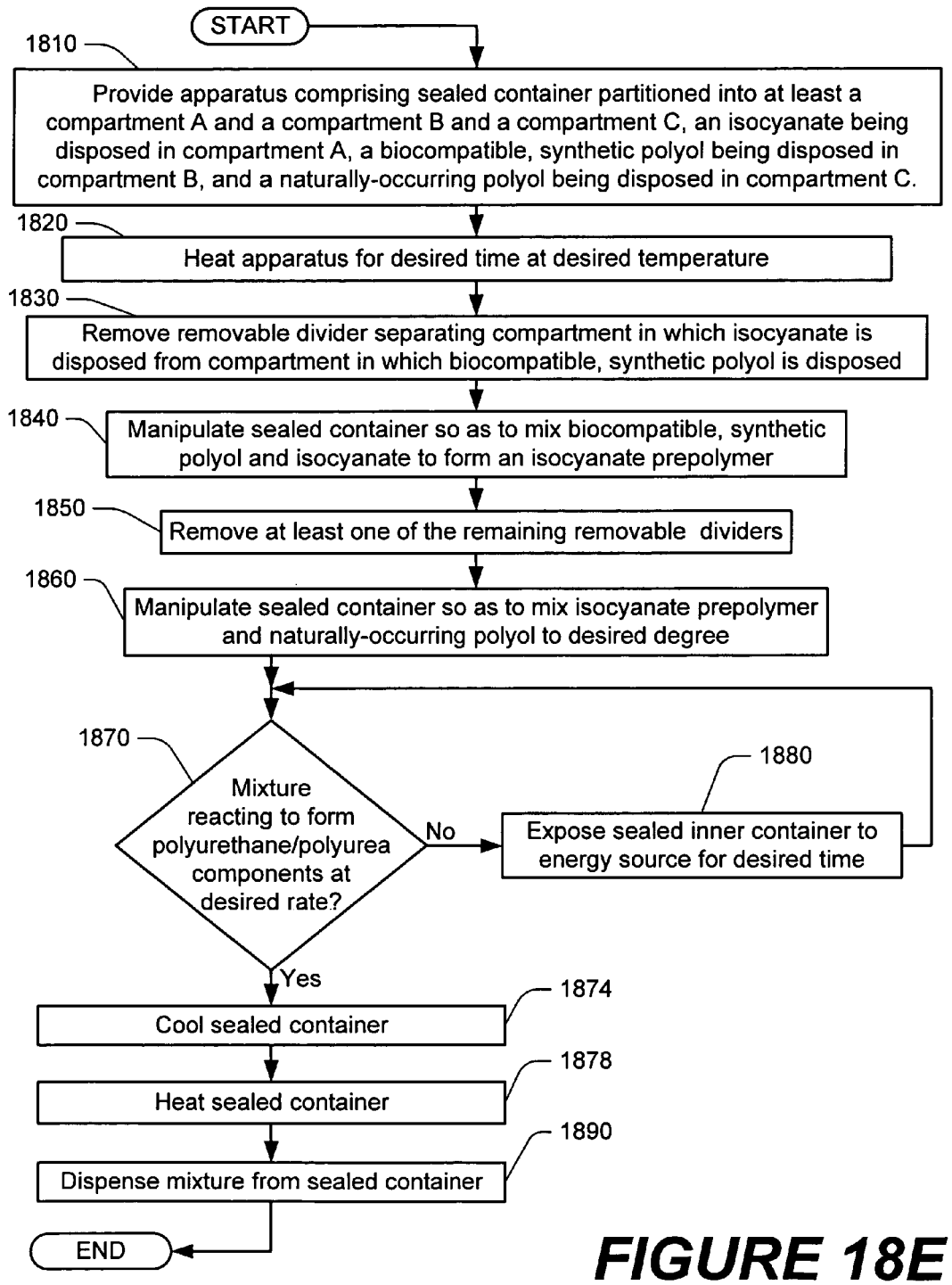

Furthermore, FIG. 18E illustrates the use of an optional step 1874 wherein the sealed container may be cooled for a desired period of time, so as to halt the reaction between the naturally occurring polyol and the isocyanate prepolymer. In certain of the embodiments wherein the sealed container is cooled in optional step 1874 for a desired time, after which it becomes desirable to re-initiate the reaction, the process then may proceed from step 1874 to step 1878, wherein the sealed container may be heated for a desired time at a desired temperature, and the naturally occurring polyol and the isocyanate prepolymer may resume reacting to form polyurethane/polyurea components.

Figure 18F:
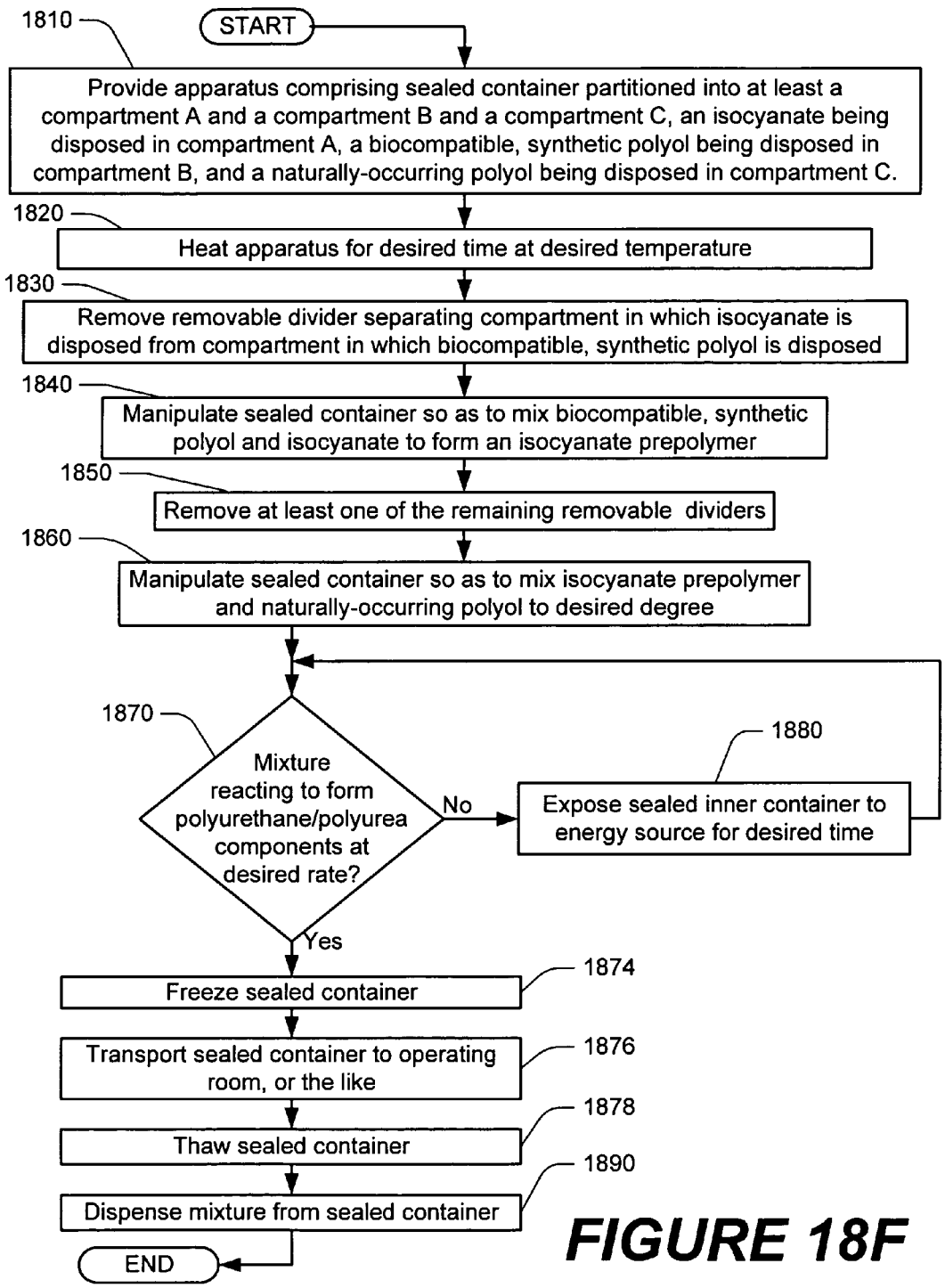

Moreover, as illustrated in FIG. 18F, the present invention further contemplates that optional step 1874 (as shown in FIG. 18F) may involve freezing the sealed container, e.g., by immersing the sealed container in, e.g., liquid nitrogen, so as to suspend the reaction occurring within the sealed container. In certain embodiments of the present invention, this may occur after the contents within the sealed container have been permitted to react for about half the expected reaction time (e.g., the contents may have been permitted to react for about 20 minutes, in certain embodiments). The process then may proceed to step 1876 (shown in FIG. 18F), in which the sealed container is transported to an operating room, or the like, packed in a suitable medium (e.g., dry ice). Next, the process may proceed to optional step 1878 (shown in FIG. 18F), in which the sealed container is thawed (e.g., in a bath of warm or hot water) without further mixing, after which the contents of the sealed container are dispensed and implanted within the body, wherein the contents of the sealed container may finish reacting (e.g., "cure") to form polyurethane/polyurea components.

FIGS. 19A-19F illustrates another exemplary method of the present invention for making compositions. Because certain features and advantages of these embodiments of the present invention are substantially similar to certain features and advantages of the embodiments described with reference to FIGS. 18A-18F, such similar features and advantages are not discussed further with respect to the embodiments of the present invention illustrated in FIGS. 19A-19F.

Figure 19A:
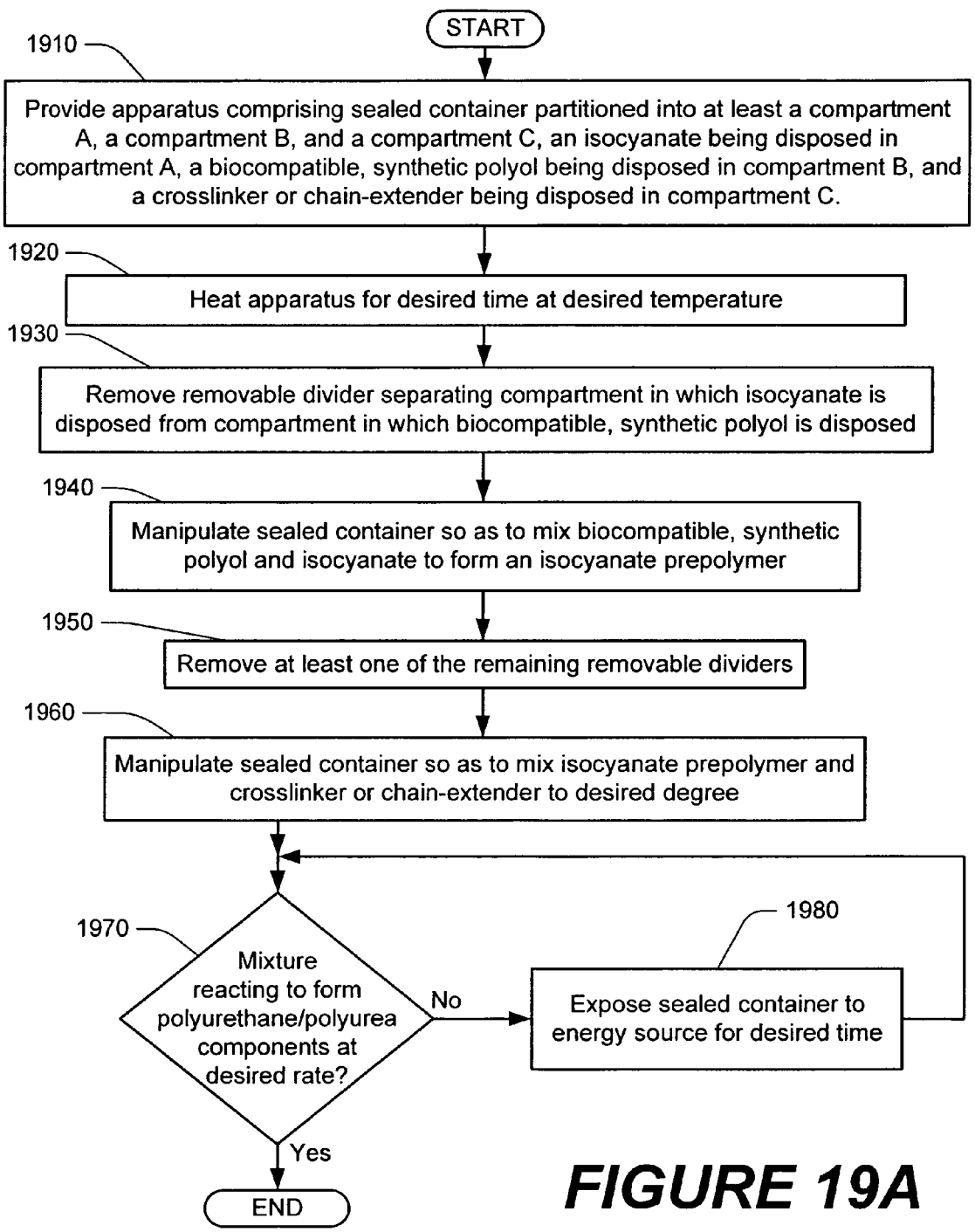
Figure 19B:
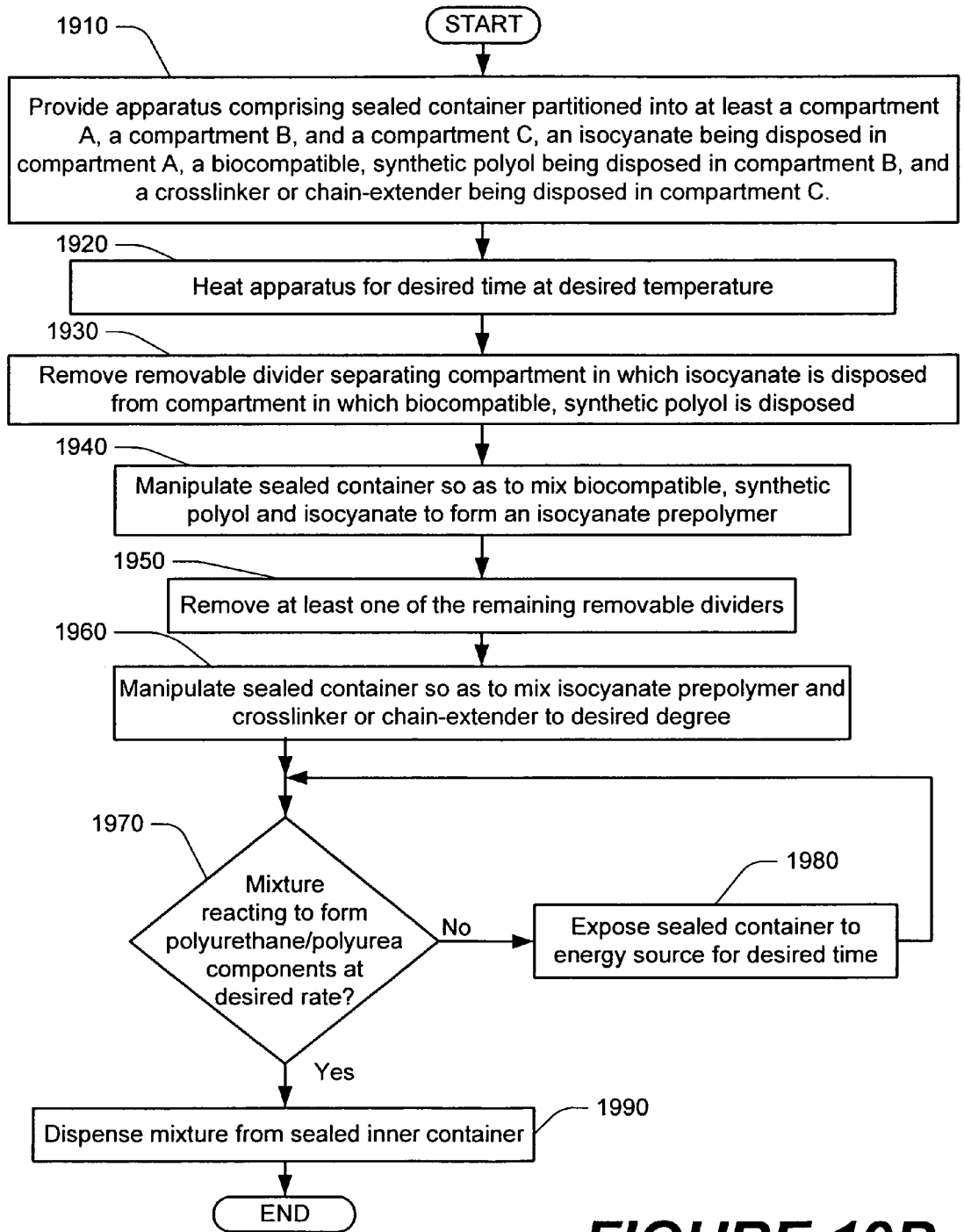
Figure 19C:
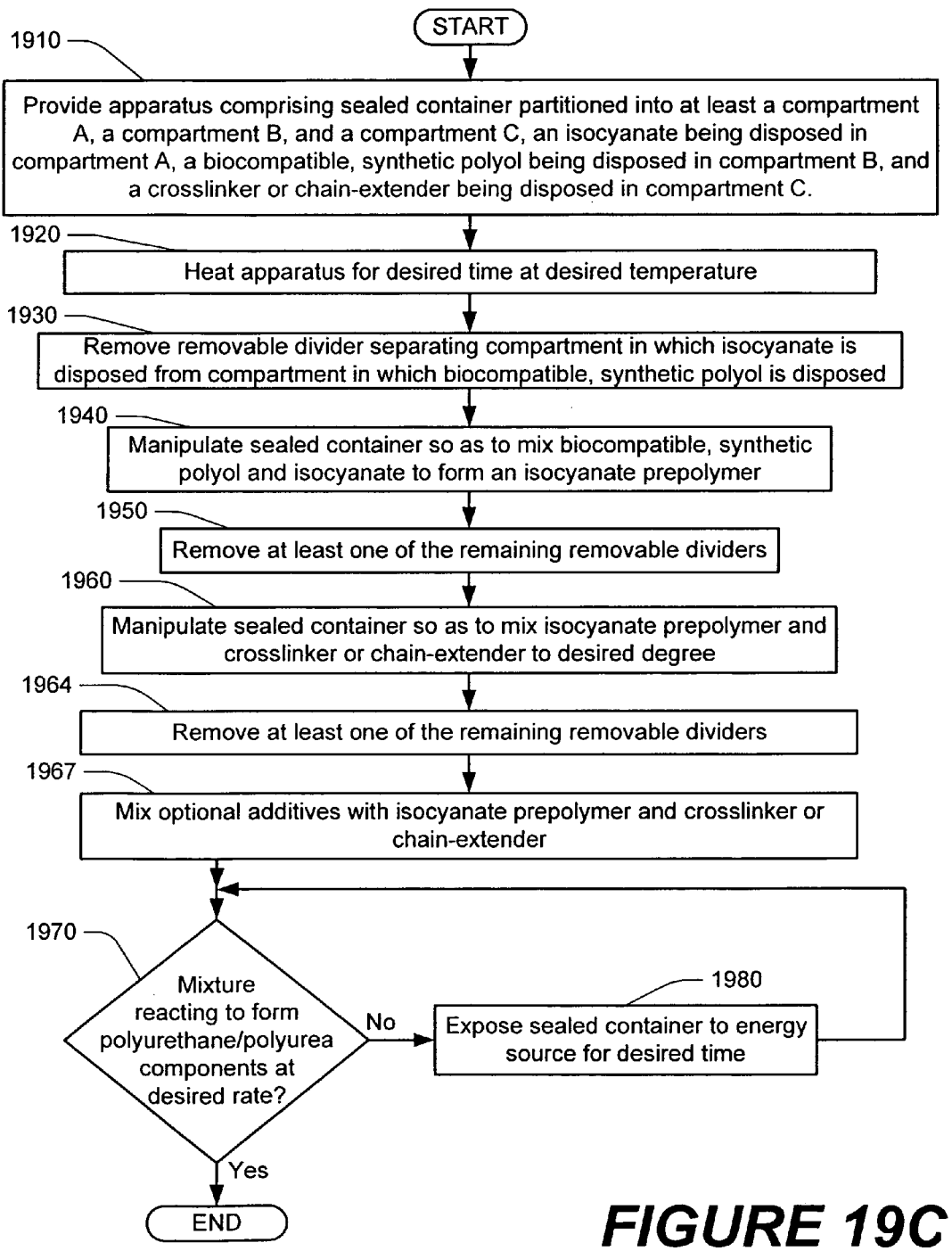
Figure 19D:
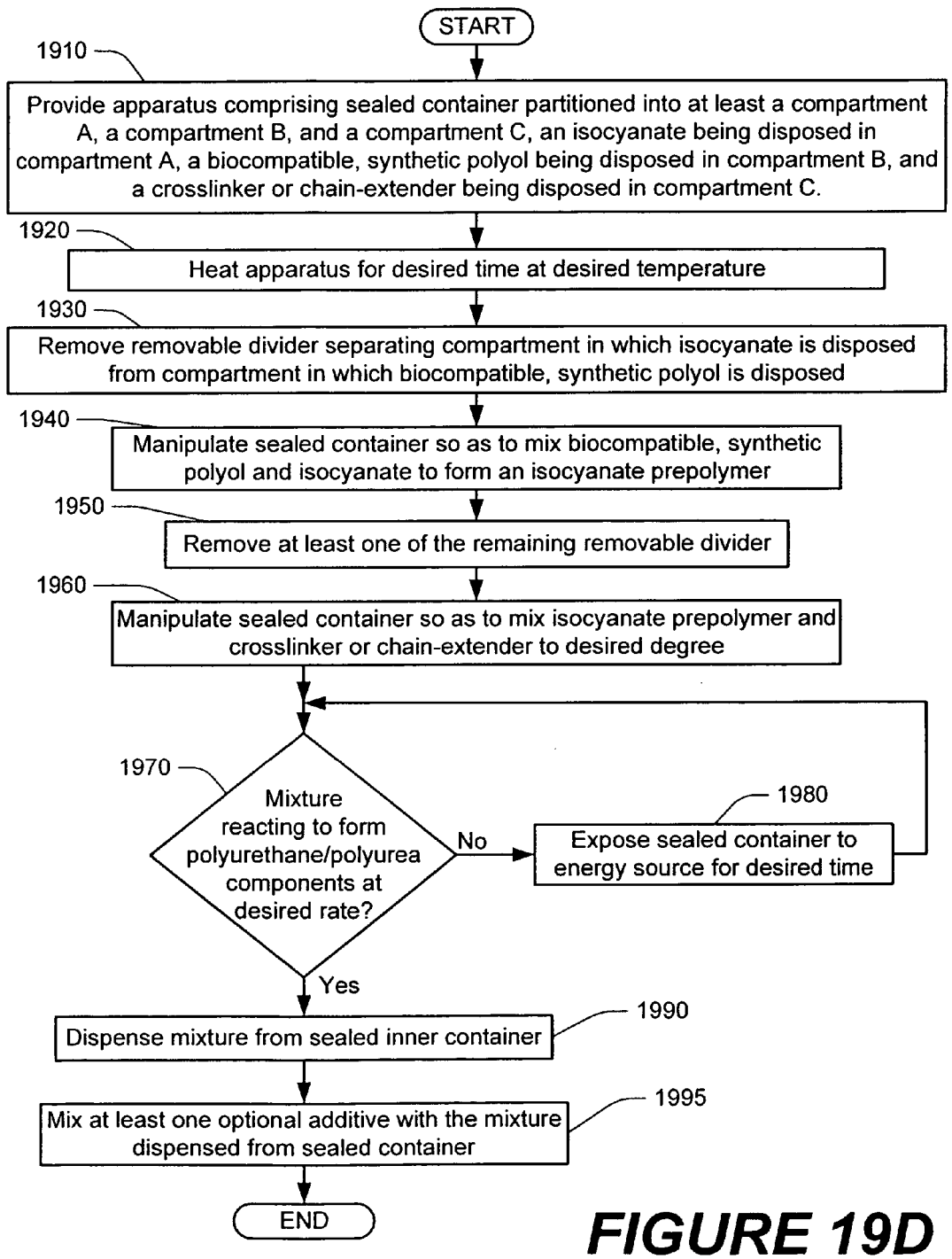
Figure 19E:
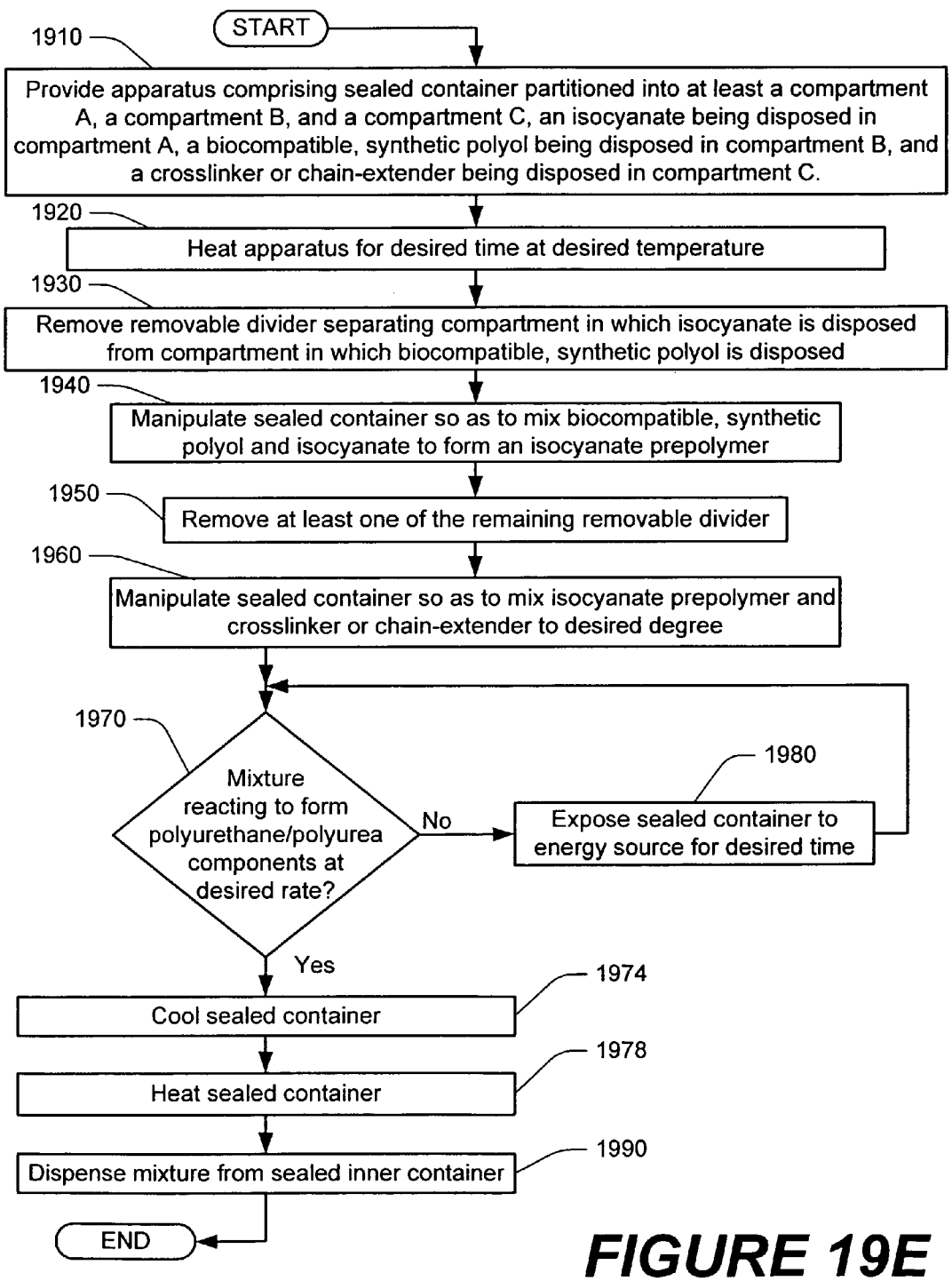
Figure 19F:
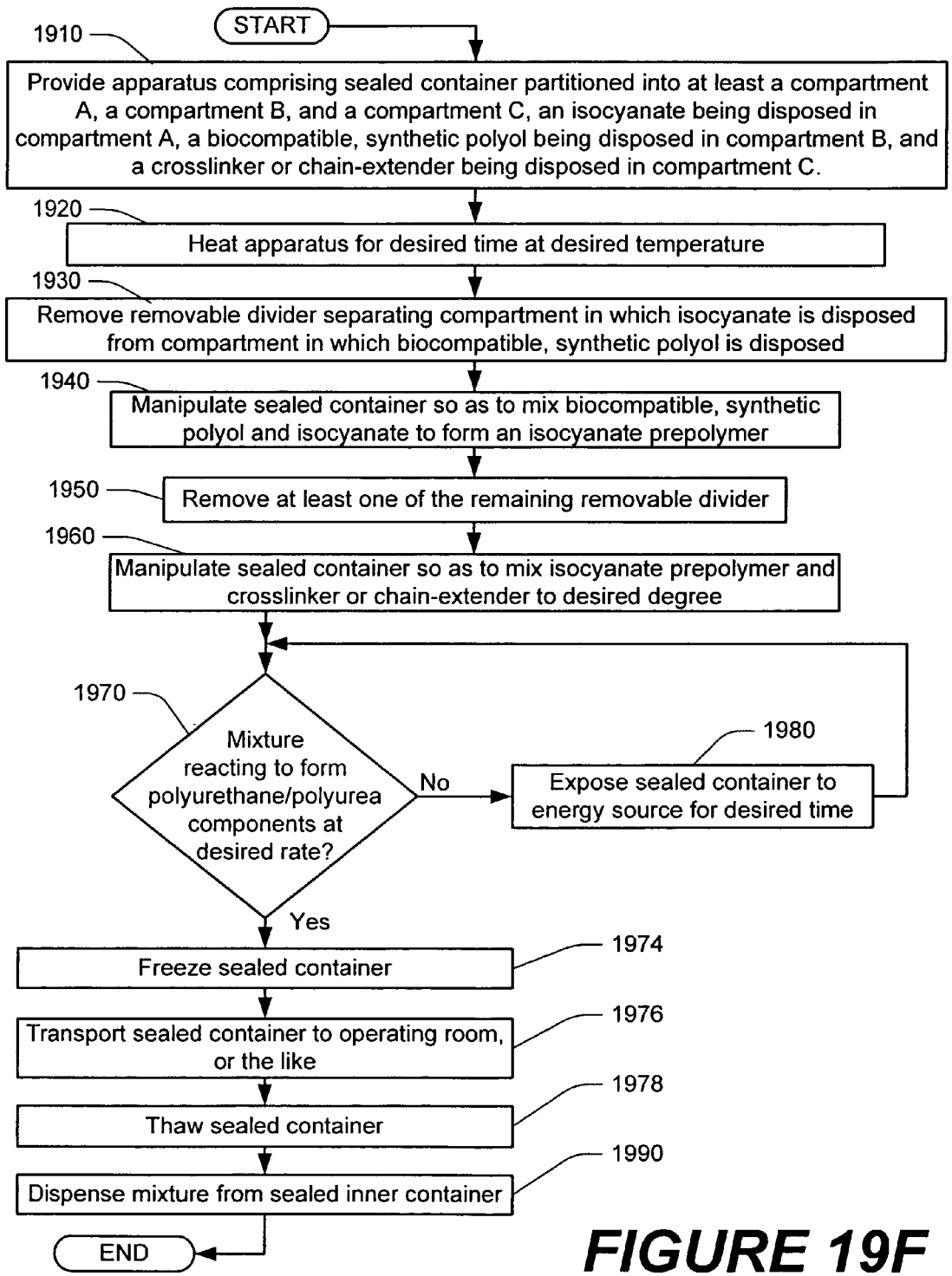

Referring now to FIG. 19A, in step 1910, an apparatus is provided that comprises a sealed container comprising an internal cavity, the internal cavity being separated by a removable divider into a compartment A, a compartment B, and a compartment C, an isocyanate being disposed in compartment A, a biocompatible, synthetic polyol being disposed in compartment B, and a crosslinker or chain-extender being disposed in compartment C. In certain embodiments of the present invention, a polyamine may be disposed in compartment C along with the crosslinker or chain extender. Further description of the steps that may be used to react these compounds to form a composition that comprises polyurethane/polyurea components is set forth in FIGS. 19A-19F, and will not be further elaborated upon here. In certain embodiments of the present invention, optional additives may be incorporated into the composition; suitable additives, and the ways in which they may become incorporated, have been previously described in greater detail herein with reference to the discussion of FIGS. 18A-18D (including, inter alia, the discussion of optional steps such as steps 1864, 1867, 1890, 1895, and the like). Moreover, situations may arise in which an operator desires to cool the sealed container for a desired period of time, so as to halt the reaction occurring therein; suitable means by which the sealed container may be cooled (and, when desired, re-heated) previously have been described in greater detail herein with reference to the discussion of FIGS. 18E-18F (including, inter alia, the discussion of optional steps such as steps 1874, 1876, 1878, and the like).

2. Sealed Inner and Outer Containers

FIGS. 20A-21F describe exemplary methods of the present invention comprising reacting isocyanates with polyols/polyamines to produce isocyanate prepolymers, and subsequently further reacting the isocyanate prepolymers with other compounds to produce compositions comprising polyurethane/polyurea components. Moreover, the methods described in FIGS. 20A-21F employ other embodiments of apparatus of the present invention.

Figure 20A:
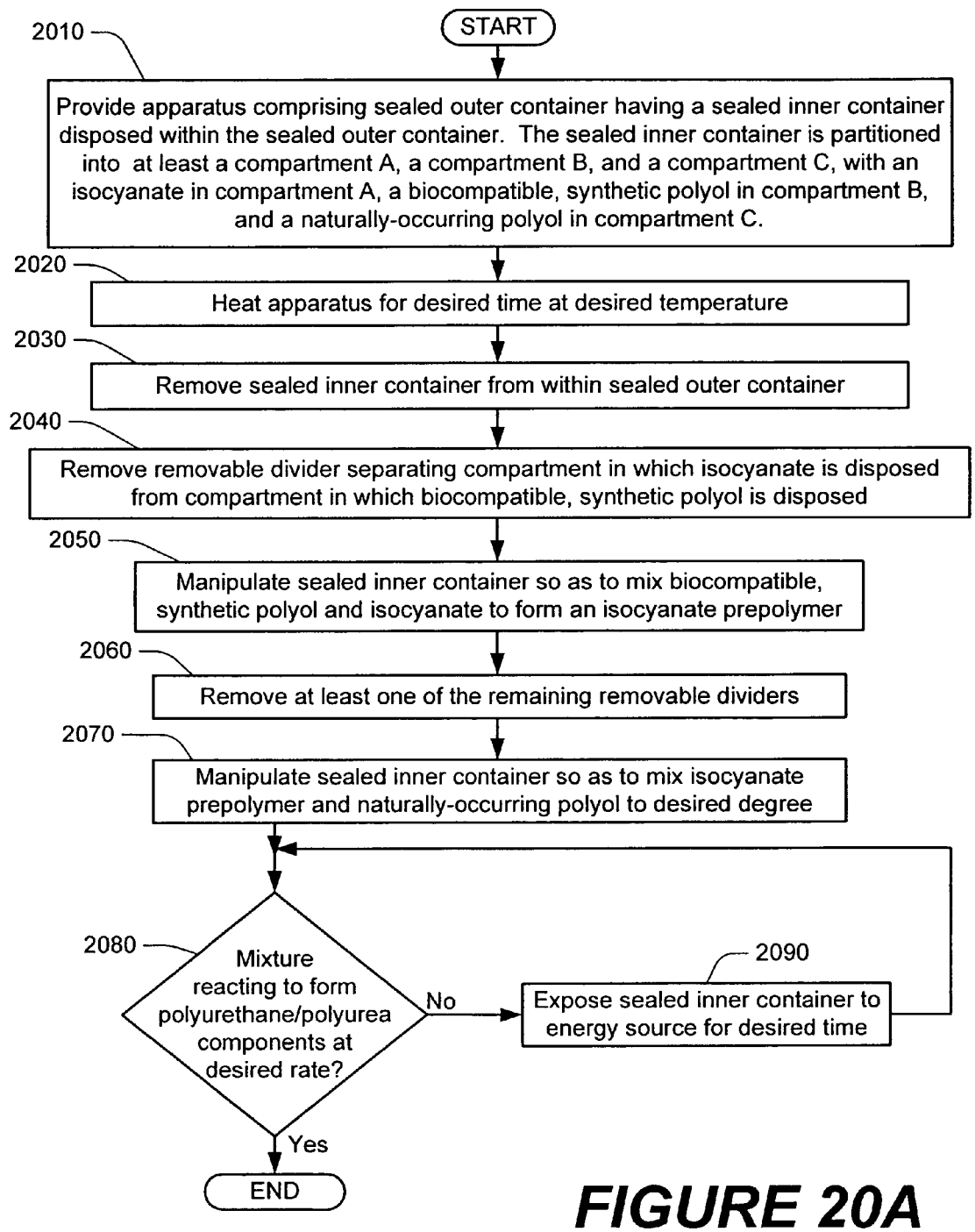
Figure 20B:
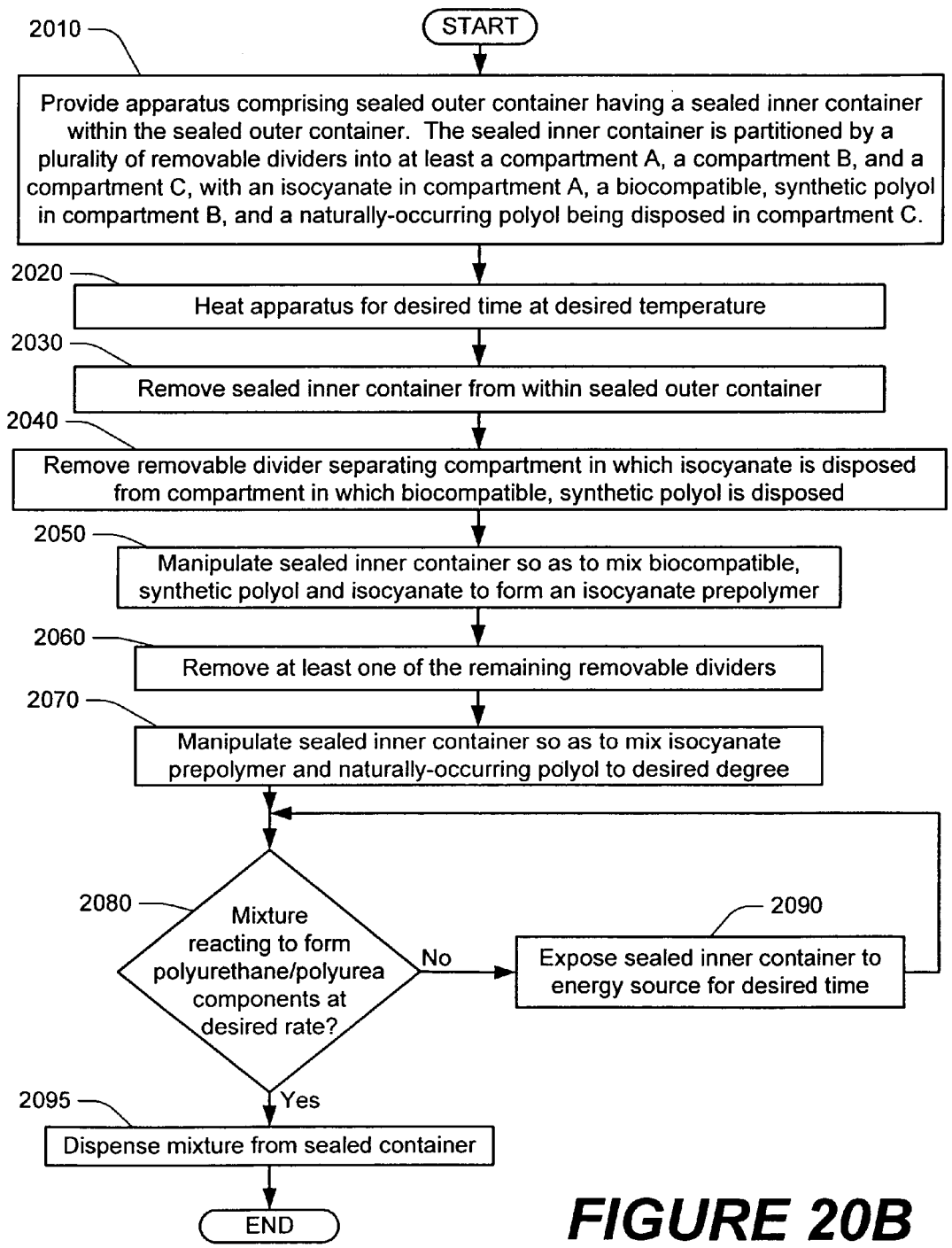
Figure 20C:
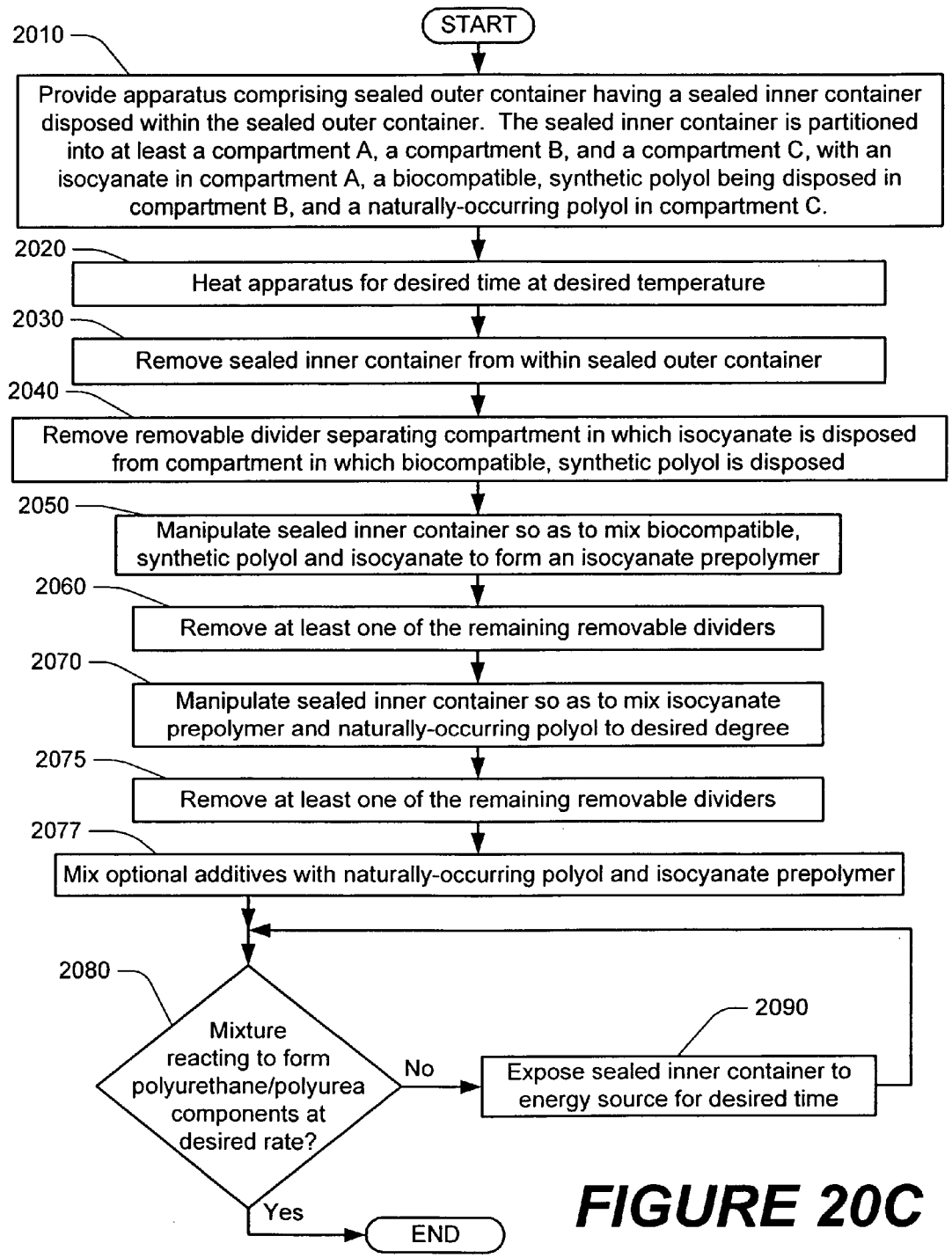
Figure 20D:
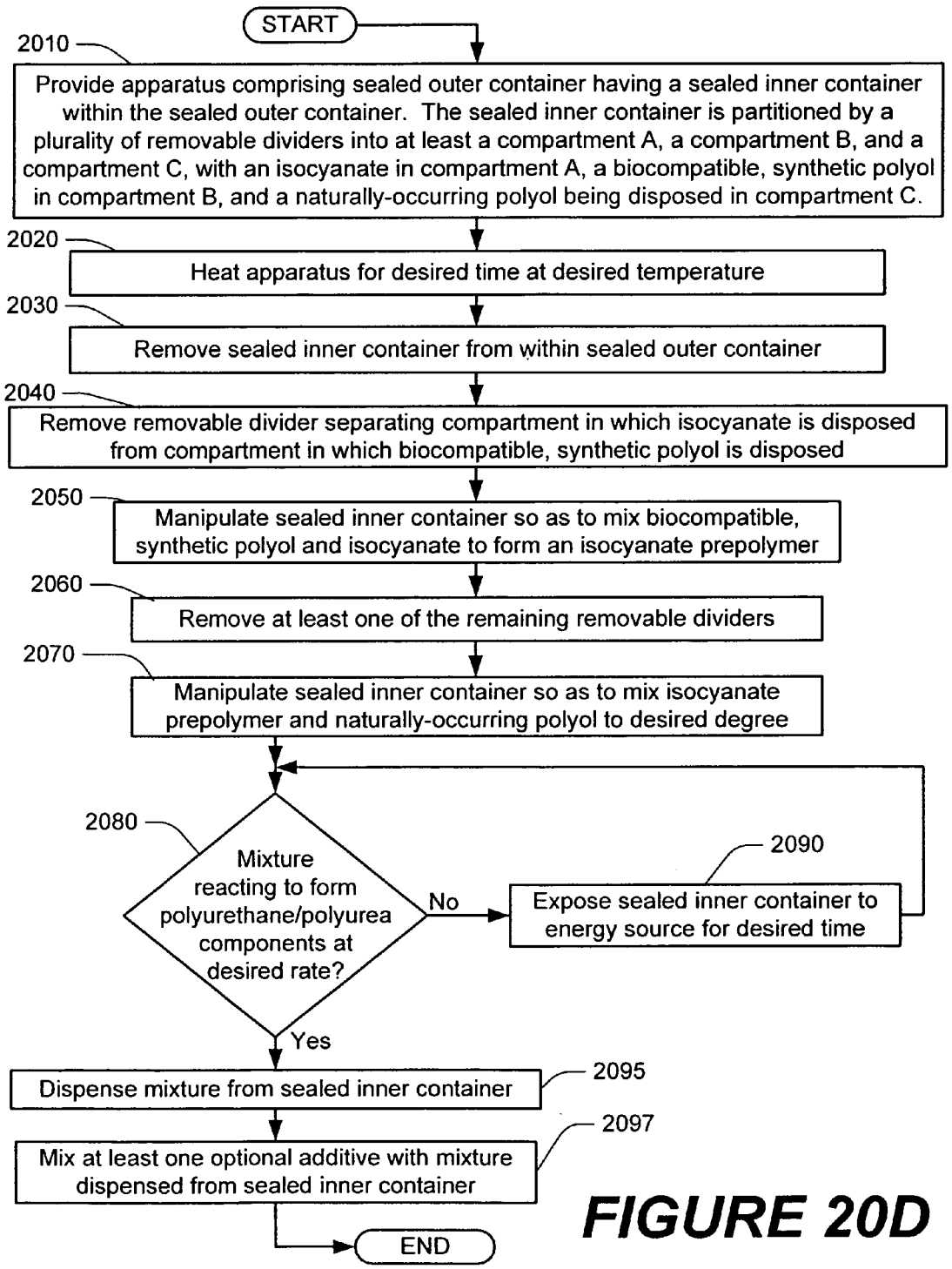

Referring now to FIG. 20A, in step 2010, an apparatus of the present invention is provided that comprises a sealed outer container comprising an internal cavity, wherein a sealed inner container is disposed within the inner cavity of the sealed outer container. The sealed inner container itself comprises an internal cavity that is separated by at least one removable divider into at least a compartment A, a compartment B, and a compartment C, an isocyanate being disposed in compartment A, a biocompatible, synthetic polyol being disposed in compartment B, and a naturally occurring polyol being disposed in compartment C. In certain embodiments of the present invention, a polyamine may be present in compartment C along with the naturally occurring polyol. In step 2020, the apparatus is heated for a desired time at a desired temperature (e.g., a temperature in the range of from about room temperature to about 150° Celsius). In certain embodiments of the present invention, the apparatus may be heated in boiling water for a desired time (e.g., in the range of from about 30 seconds to about 90 seconds). The advantages of simultaneously heating the sealed outer container and the sealed inner container have been set forth previously herein, with reference to, e.g., step 1320 of FIG. 13A.

In step 2030, the sealed inner container may be removed from within the sealed outer container, and the sealed outer container may be set aside. In step 2040, at least one removable divider (which may be externally affixed to the sealed inner container) may be removed from the sealed inner container, so as to permit fluid communication between the isocyanate and the biocompatible, synthetic polyol. In step 2050, the sealed inner container may be manipulated (e.g., manually manipulated) so as to mix the biocompatible, synthetic polyol and the isocyanate to a desired degree (e.g., to facilitate the formation of an isocyanate prepolymer from the reaction between the biocompatible, synthetic polyol and the isocyanate). In certain embodiments of the present invention, the sealed inner container may be manually manipulated for a time in the range of from about one minute to about 30 minutes. The time period during which the sealed inner container may be manually manipulated may depend on factors including, inter alia, the temperature to which the sealed inner container may have been heated, whether an optional catalyst has been included, and the type of isocyanate used. For example, if an aromatic isocyanate has been used, the mixture within the sealed inner container may exotherm and react relatively quickly. Alternatively, if a cycloaliphatic isocyanate has been used, the reaction time may take longer. In step 2060, another divider is removed so as to permit fluid communication between the isocyanate prepolymer and the naturally occurring polyol. In step 2070, the sealed inner container is manipulated (e.g., manually manipulated) so as to mix the naturally occurring polyol and the isocyanate prepolymer to a desired degree.

In step 2080, a determination may be made whether the mixture of the naturally occurring polyol and the isocyanate prepolymer is reacting at a desired rate. For example, the progress of the reaction may be assessed through tactile feedback, as the viscosity of the mixture within the sealed inner container may be felt to increase, and as the mixture may be felt, and seen, to progress towards, and through, a "taffy-like" state. In certain embodiments, an FTIR probe may be used to determine whether the mixture of the naturally occurring polyol and the isocyanate prepolymer is reacting at a desired rate; exemplary embodiments of the manner in which an FTIR probe may be used have been previously described herein, with reference to step 1050 of FIG. 10A. Alternatively, other means may be used to determine the progress of the reaction between the naturally occurring polyol and the isocyanate prepolymer, including, inter alia, the use of a small weight; exemplary embodiments of the manner in which a small weight may be used have been previously described herein, with reference to step 1050 of FIG. 10A. If, in step 2080, the mixture is reacting at a desired rate, the process proceeds to end.

Alternatively, in certain optional embodiments of the present invention, after a determination is made in step 2080 that the mixture of the naturally occurring polyol and the isocyanate prepolymer is reacting at a desired rate, the process may proceed from step 2080 to an optional step 2095 (shown in FIG. 20B) wherein the contents of the sealed inner container are dispensed therefrom, after which the process proceeds to end. If, however, the determination is made in step 2080 that the mixture is not reacting at a desired rate, then the process proceeds to step 2090, wherein the sealed inner container is exposed to an energy source for a desired time (e.g., heated in a microwave oven on "HIGH" or in boiling water for a desired time, e.g., in the range of from about 30 to about 90 seconds). In certain embodiments wherein the mixture comprises optional photo- or light-initiators and other suitable components (e.g., adducts of isocyanates, double-bond-containing isocyanates, double-bond containing polyols, and the like), the sealed container may be exposed to a suitable light source for a desired time (e.g., in the range of from a few seconds to about 5 minutes, depending on factors including, inter alia, the intensity of the light source, the concentration of light- or photo-initiators, the concentration of double-bond containing compounds in the composition, and the type of light source). The process then returns to the determination made in step 2080, which has previously been described.

In certain optional embodiments of the present invention, a variety of optional additives may be incorporated into the process. For example, the inner cavity of the sealed inner container optionally further may be separated by removable dividers into at least a compartment A, a compartment B, a compartment C, and a compartment D, wherein one of these compartments (e.g., compartment D) may comprise optional additives including, but not limited to, those that have been previously described herein (e.g., at least one filler material, and/or at least one protein, and the like). In certain of these embodiments wherein optional additives are disposed within one or more compartments, the process may comprise optional step 2075 (shown in FIG. 20C) wherein a removable divider is removed, and optional step 2077 (shown in FIG. 20C) wherein the sealed inner container is manipulated (e.g., manually manipulated) so as to mix the optional additives with the mixture of the naturally occurring polyol and the isocyanate prepolymer. The process then may proceed from optional step 2077 to step 2080, which previously has been described. As an alternative, in certain other optional embodiments of the present invention, certain of the optional additives may be introduced outside the sealed inner container, and may be incorporated once the contents of the sealed inner container have been dispensed therefrom. For example, after a determination is made in step 2080 that the mixture of the naturally occurring polyol and the isocyanate prepolymer is reacting at a desired rate, the process may proceed from step 2080 to an optional step 2095 (shown in FIG. 20D) wherein the reacting mixture is dispensed from the sealed container, and then may proceed to an optional step 2097 (shown in FIG. 20D) wherein at least one optional additive is mixed with the dispensed reacting mixture and permitted to remain within it as the mixture finishes reacting, after which the process may proceed to end.

In certain embodiments, one or more optional additives may be present in a separate reservoir (e.g., reservoir 199 shown in FIG. 4B), and optional step 2077 may comprise flowing the additives from the separate reservoir into the sealed container.

Figure 20E:
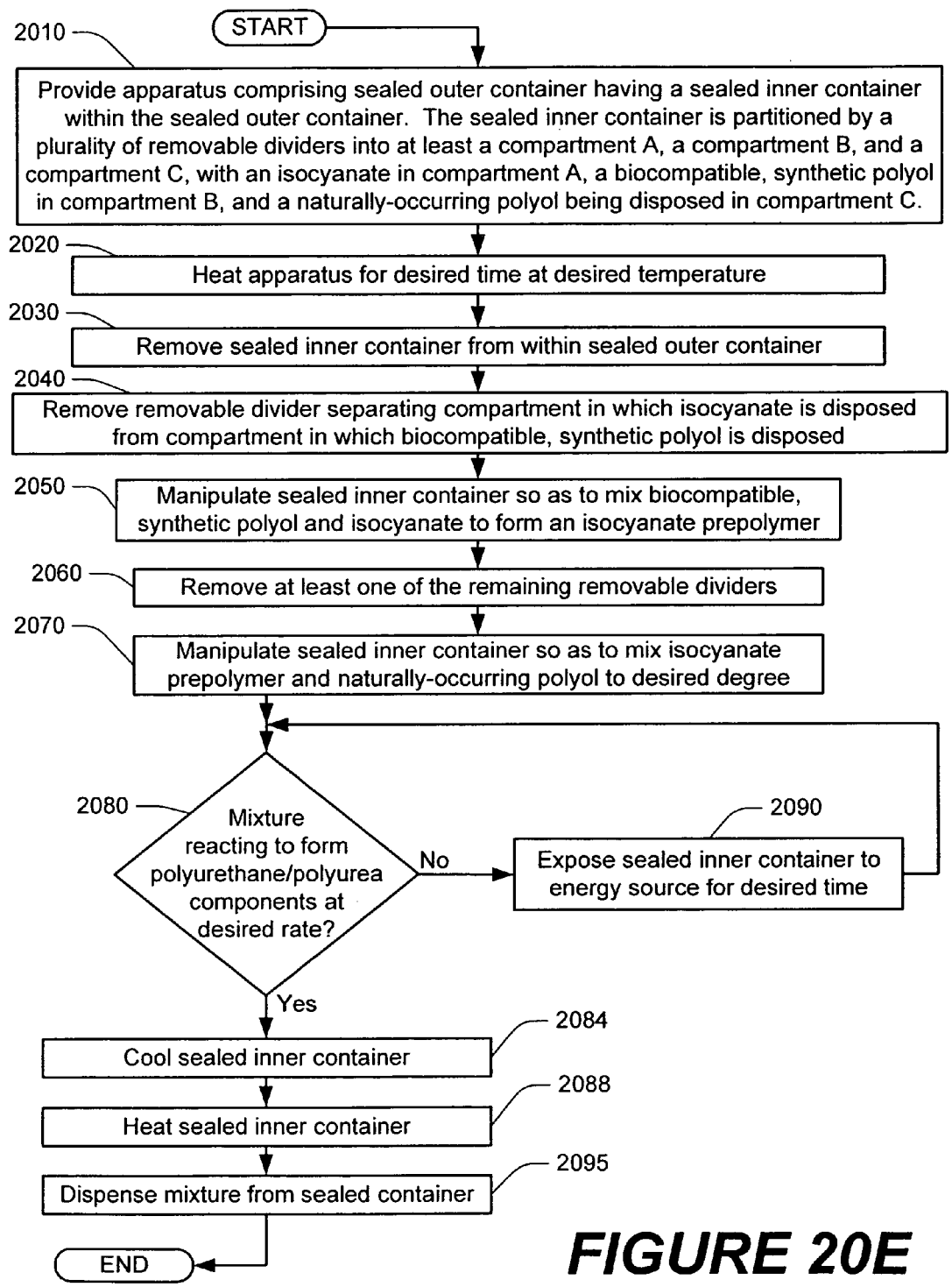

Furthermore, FIG. 20E illustrates the use of an optional step 2084 wherein the sealed inner container may be cooled for a desired period of time, so as to halt the reaction between the naturally occurring polyol and the isocyanate prepolymer. In certain of the embodiments wherein the sealed inner container is cooled in optional step 2084 for a desired time, after which it becomes desirable to re-initiate the reaction, the process then may proceed from step 2084 to step 2088, wherein the sealed inner container may be heated for a desired time at a desired temperature, and the naturally occurring polyol and the isocyanate prepolymer may resume reacting to form polyurethane/polyurea components.

Figure 20F:
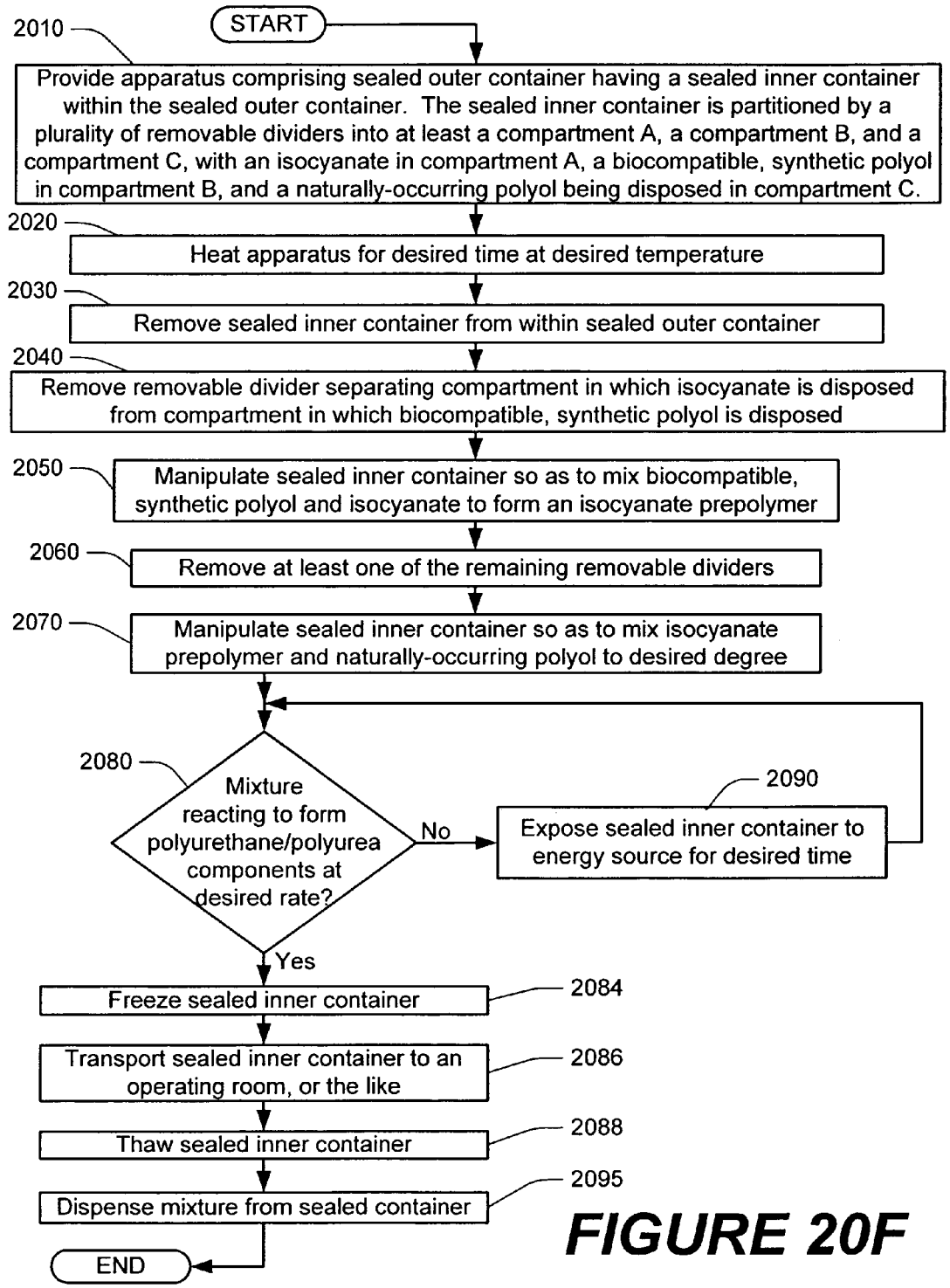

Moreover, as illustrated in FIG. 20F, the present invention further contemplates that optional step 2084 (as shown in FIG. 20F) may involve freezing the sealed container, e.g., by immersing the sealed inner container in, e.g., liquid nitrogen, so as to suspend the reaction occurring within the sealed inner container. In certain embodiments of the present invention, this may occur after the contents within the sealed inner container have been permitted to react for about half the expected reaction time (e.g., the contents may have been permitted to react for about 20 minutes, in certain embodiments). The process then may proceed to step 2086 (shown in FIG. 20F), in which the sealed inner container is transported to an operating room, or the like, packed in a suitable medium (e.g., dry ice). Next, the process may proceed to optional step 2088 (shown in FIG. 20F), in which the sealed inner container is thawed (e.g., in a bath of warm or hot water) without further mixing, after which the contents of the sealed inner container are dispensed and implanted within the body, wherein the contents of the sealed inner container may finish reacting (e.g., "cure") to form polyurethane/polyurea components.

FIGS. 21A-21F illustrates additional exemplary methods of the present invention comprising reacting isocyanates with polyols/polyamines to produce isocyanate prepolymers, and subsequently further reacting the isocyanate prepolymers with other compounds to produce compositions comprising polyurethane/polyurea components. Because certain features and advantages of these embodiments of the present invention are substantially similar to certain features and advantages of the embodiments described with reference to FIGS. 20A-20F, such similar features and advantages are not discussed further with respect to the embodiments of the present invention illustrated in FIGS. 21A-21F.

Figure 21A:
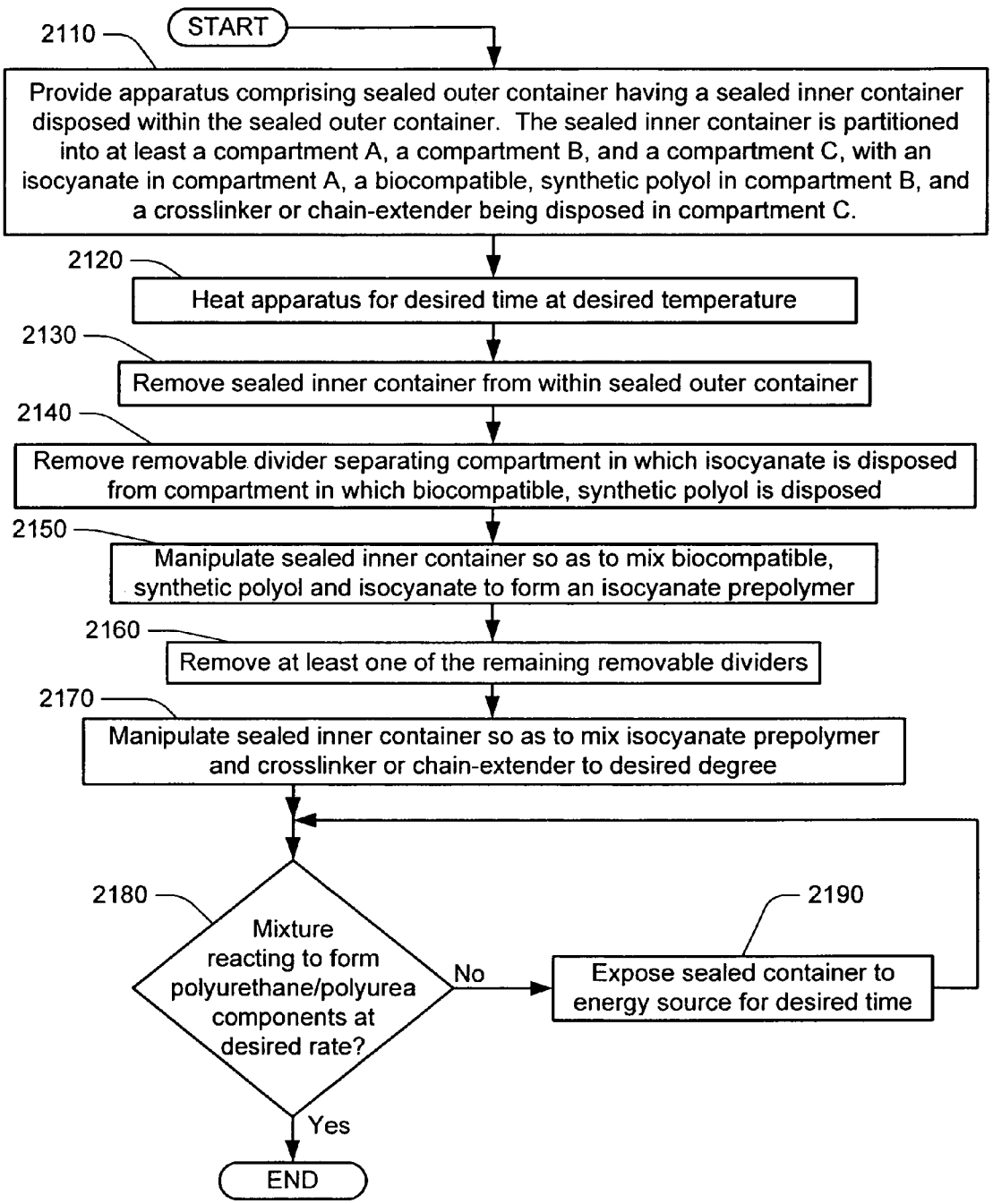
Figure 21B:
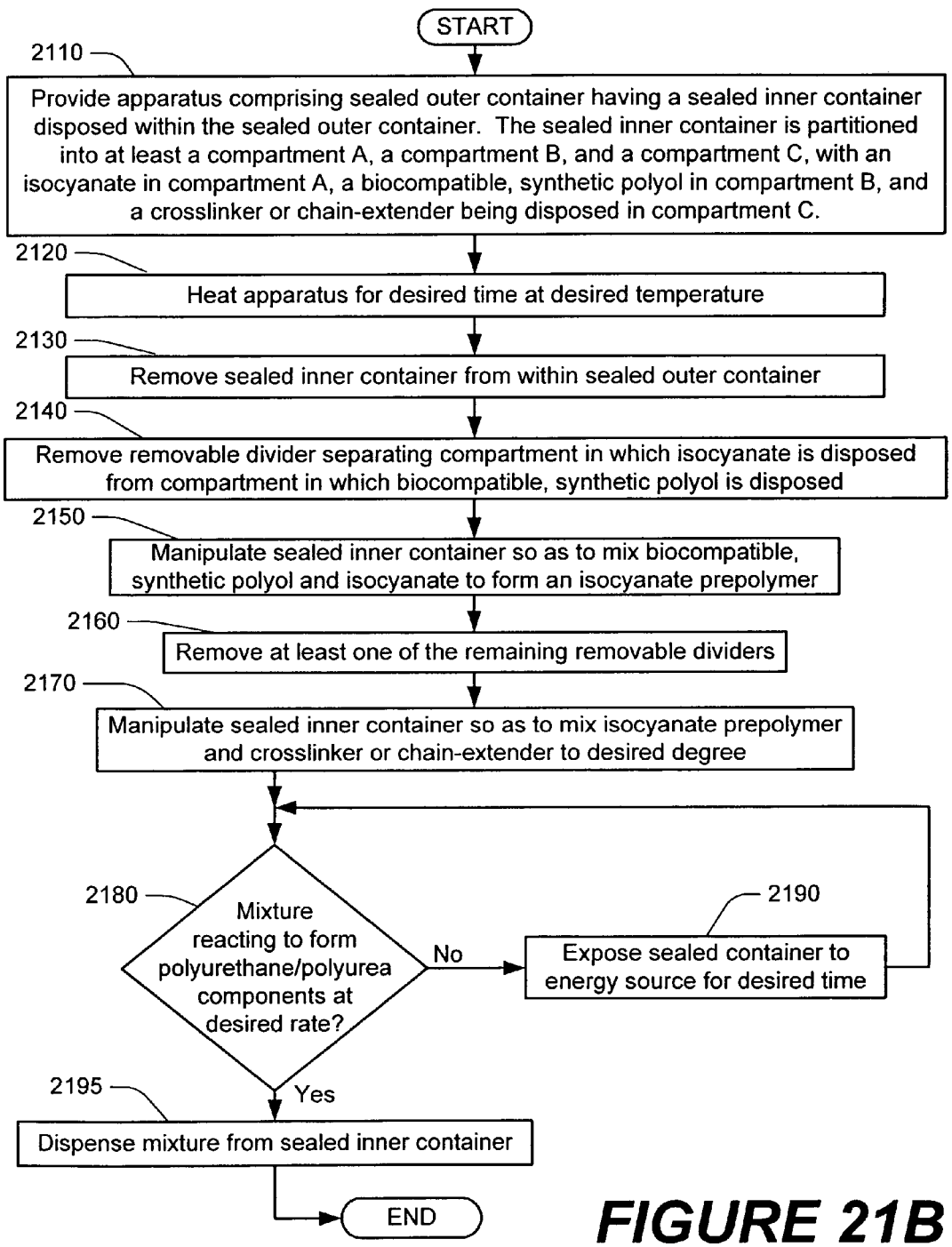
Figure 21C:
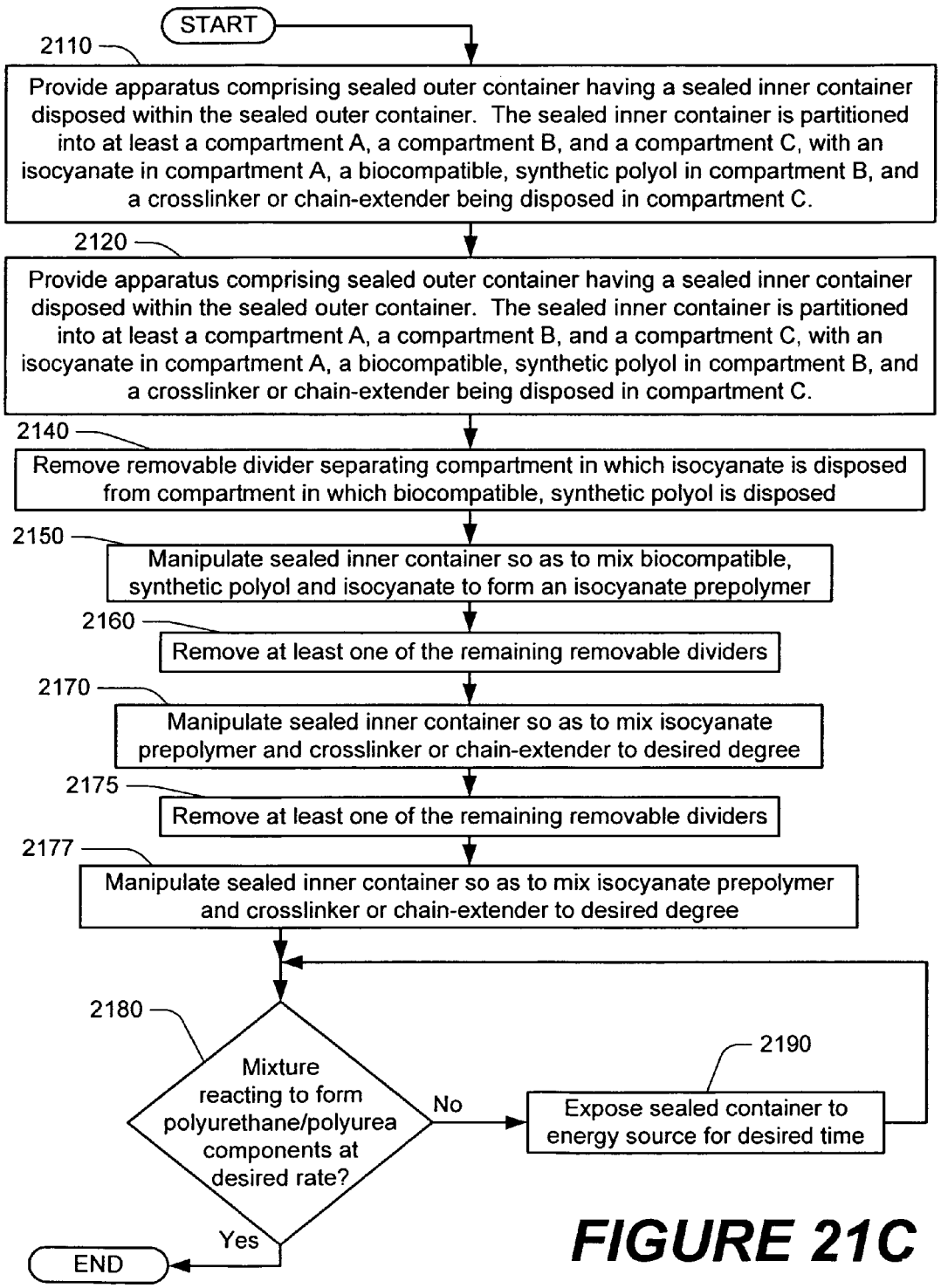
Figure 21D:
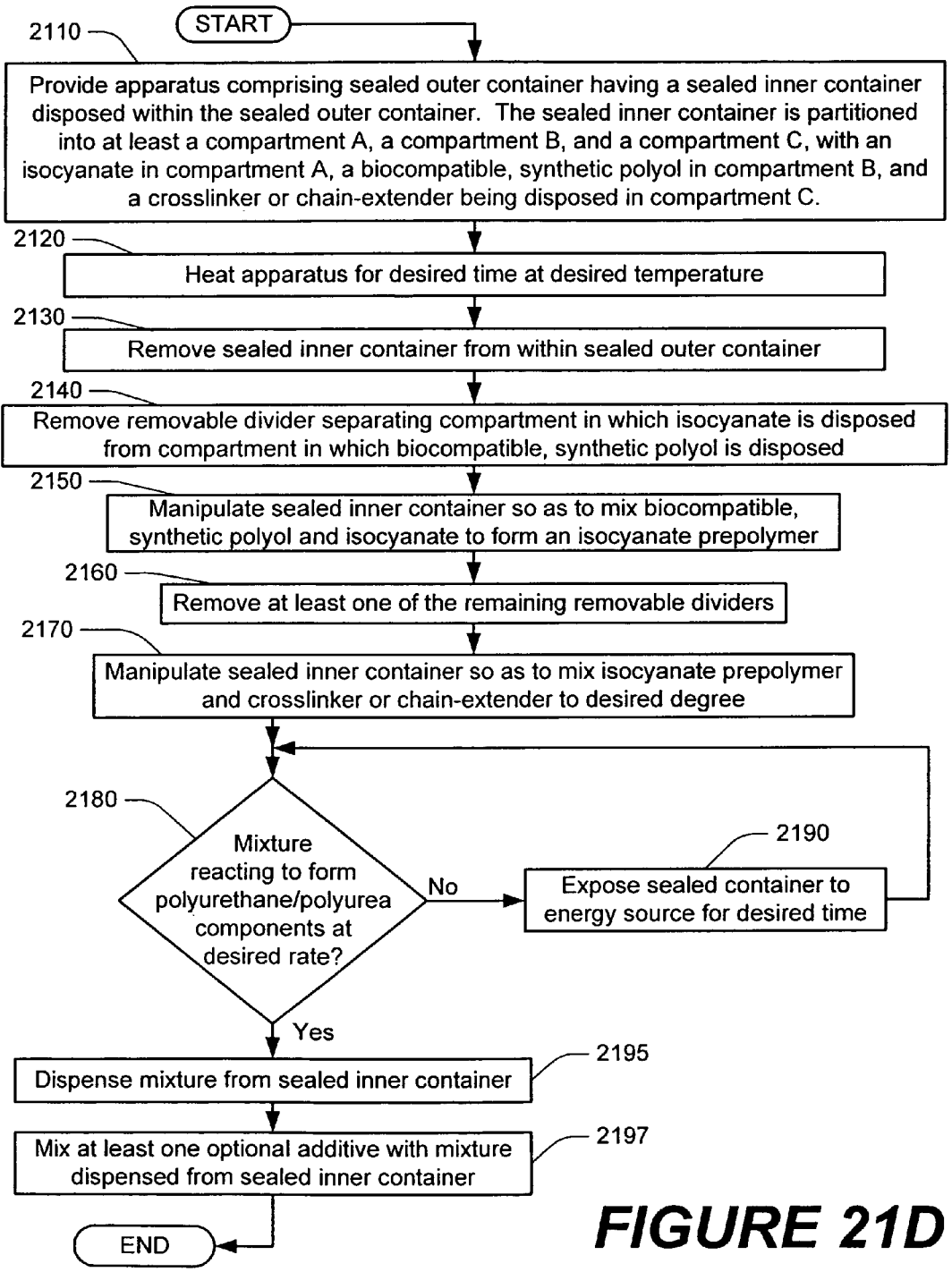
Figure 21E:
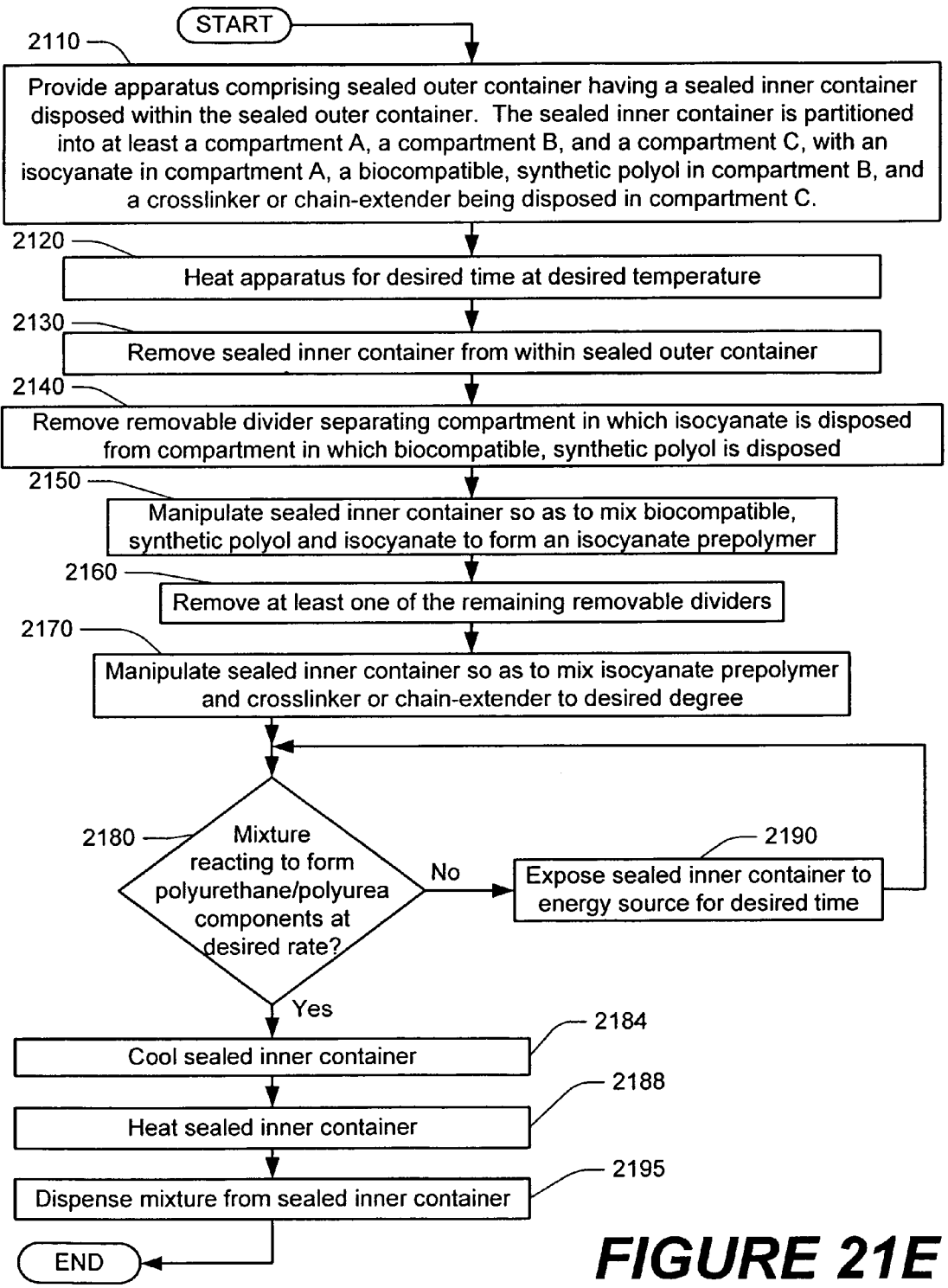
Figure 21F:
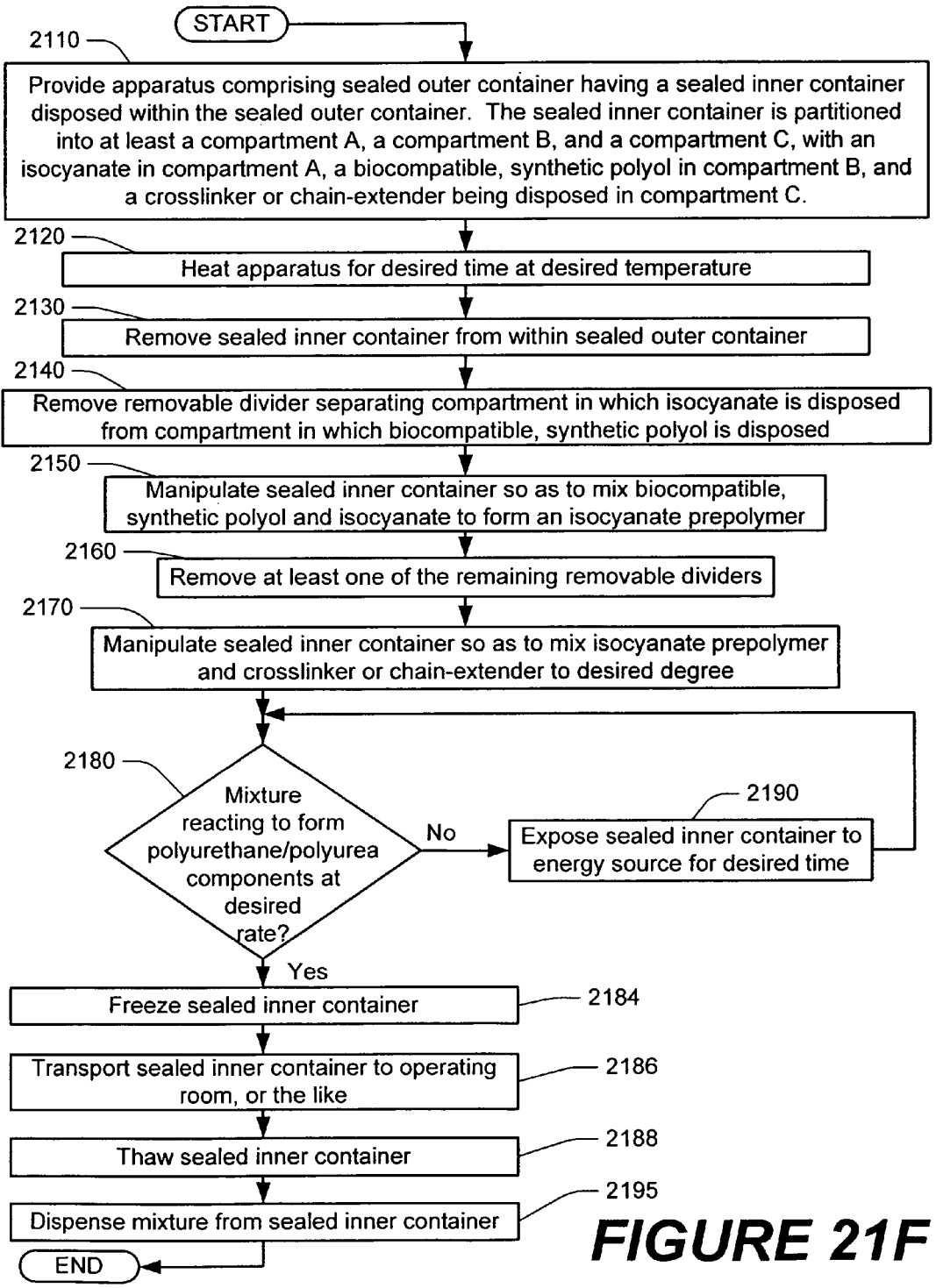

Referring now to FIG. 21A, in step 2110, an apparatus is provided that comprises a sealed outer container comprising an internal cavity, wherein a sealed inner container is disposed within the inner cavity of the sealed outer container. The sealed inner container itself comprises an internal cavity that is separated by at least one removable divider into at least a compartment A, a compartment B, and a compartment C, an isocyanate being disposed in compartment A, a biocompatible, synthetic polyol being disposed in compartment B, and a crosslinker or chain-extender being disposed in compartment C. In certain embodiments of the present invention, a polyamine may be disposed in compartment C along with the crosslinker or chain extender. Further description of the steps that may be used to react these compounds to form a composition that comprises polyurethane/polyurea components is set forth in FIGS. 21A-21F, and will not be further elaborated upon here. In certain embodiments of the present invention, optional additives may be incorporated into the composition; suitable additives, and the ways in which they may become incorporated, have been previously described in greater detail herein with reference to the discussion of FIGS. 20A-20D (including, inter alia, the discussion of optional steps such as steps 2075, 2077, 2090, 2095, and the like). Moreover, situations may arise in which an operator desires to cool the sealed inner container for a desired period of time, so as to halt the reaction occurring therein; suitable means by which the sealed inner container may be cooled (and, when desired, re-heated) previously have been described in greater detail herein with reference to the discussion of FIGS. 20E-20F (including, inter alia, the discussion of optional steps such as steps 2084, 2086, 2088, and the like).

Figure 22A:
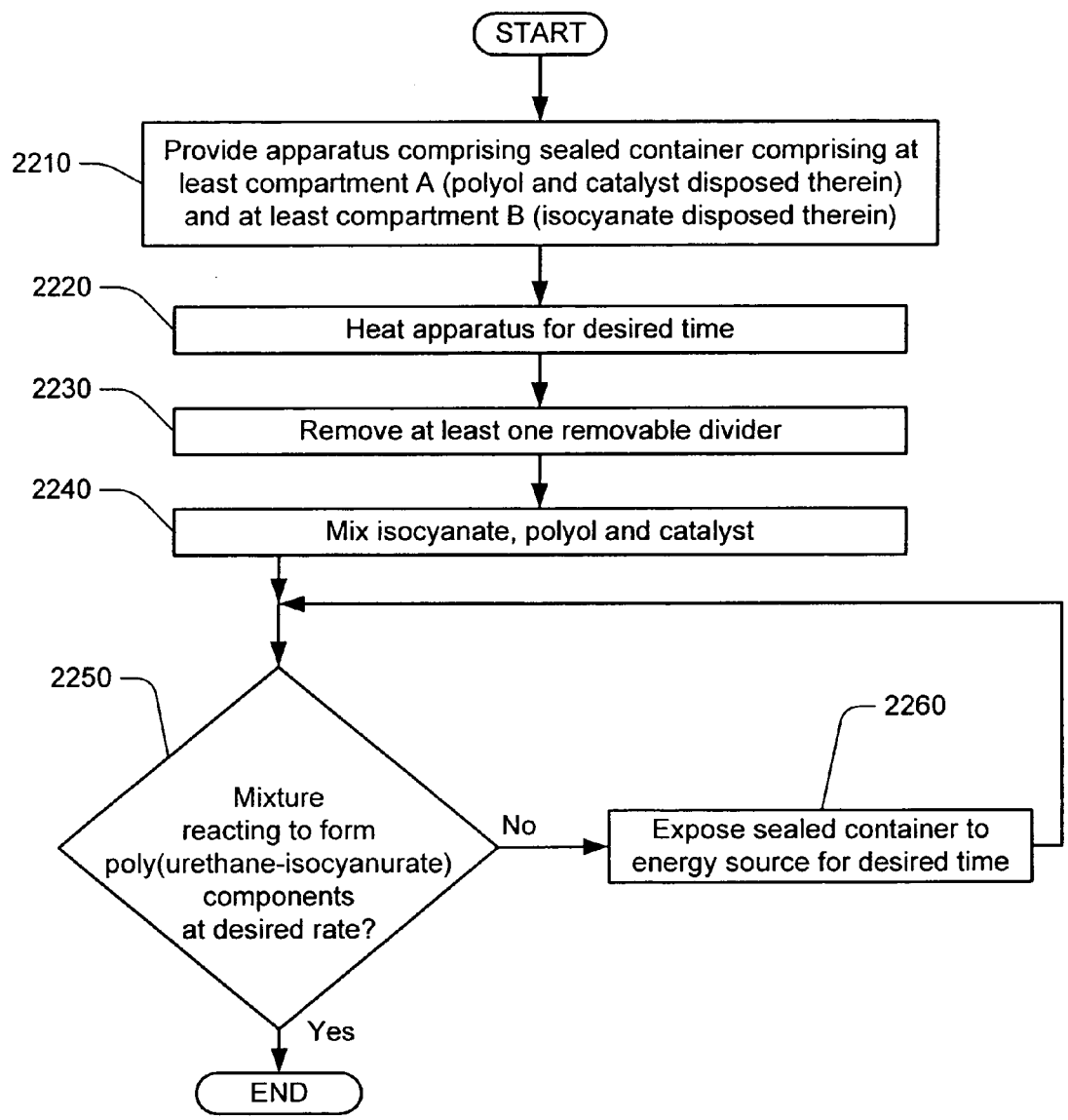
Figure 22B:
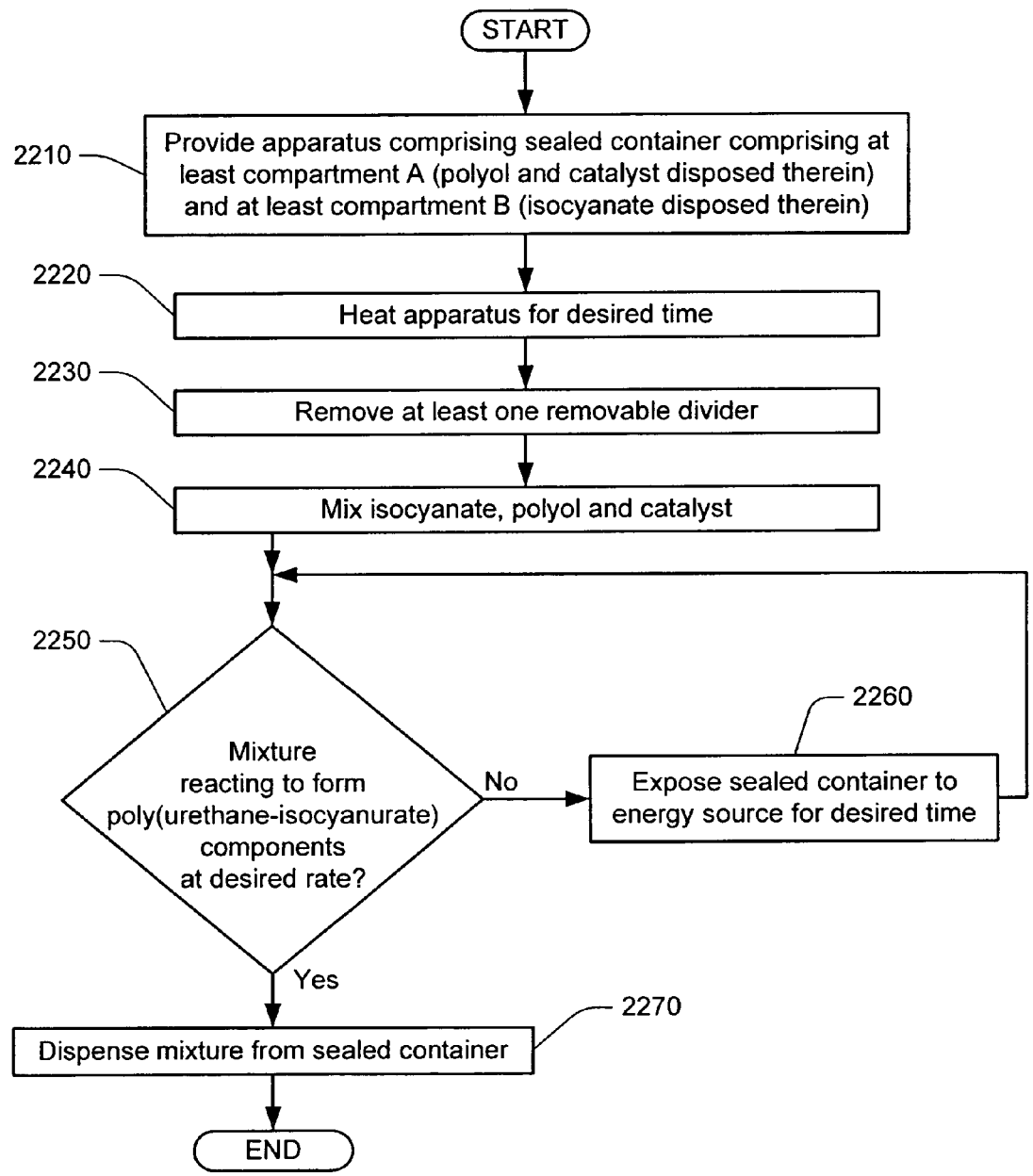
Figure 22C:
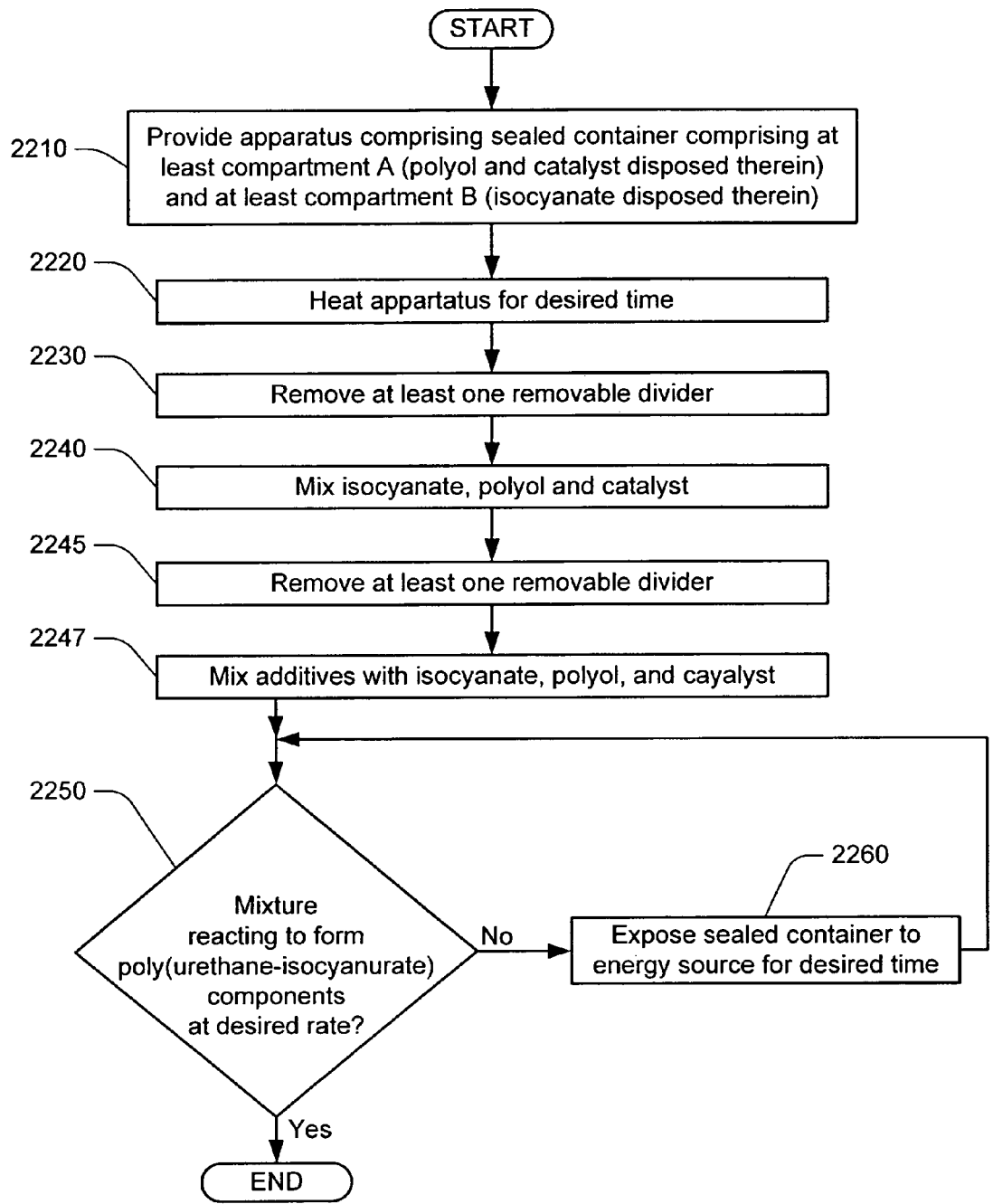
Figure 22D:
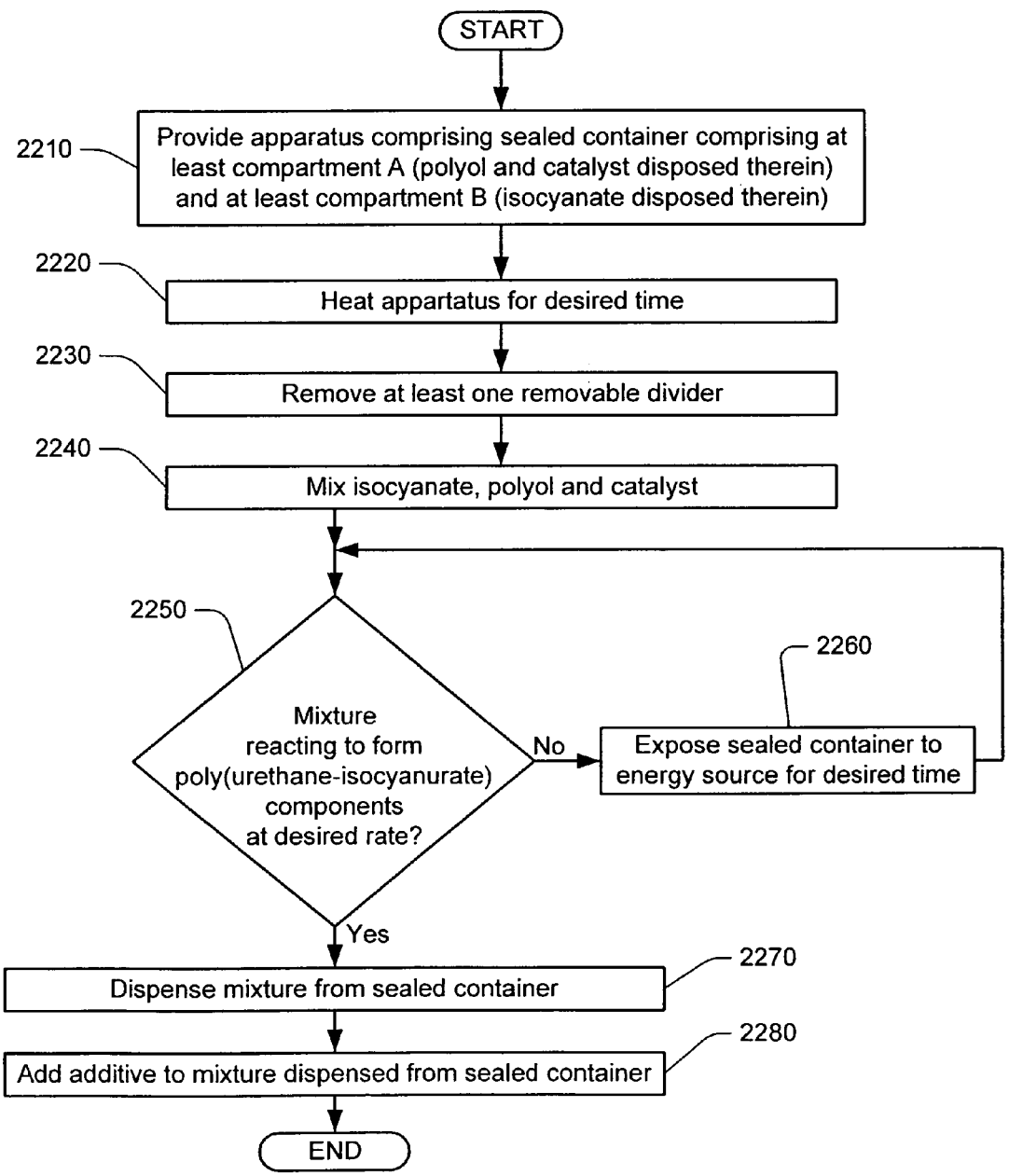

E. Methods for Making Compositions Comprising Poly(Urethane-Isocyanurate) Components and Poly(Urethane-Urea-Isocyanurate) Components FIGS. 22A-25F illustrate exemplary methods of the present invention for making compositions comprising poly(urethane-isocyanurate) components, along with, in certain embodiments, poly(urethane-urea-isocyanurate) components. Referring now to FIG. 22A, in step 2210, an apparatus is provided comprising a sealed container comprising an internal cavity, the internal cavity being separated by at least one removable divider into at least a compartment A and a compartment B. An isocyanate may be disposed within compartment B. A polyol (either a biocompatible, synthetic polyol or a naturally occurring polyol) and a catalyst may be disposed within compartment A. Examples of suitable catalysts include, inter alia, potassium carboxylates, quaternary ammonium carboxylates, tertiary amines, and the like. The equivalent ratio of isocyanate groups to total hydroxyl groups (e.g., the sum of the hydroxyl groups contributed by the biocompatible, synthetic polyol and the naturally-occurring polyol) may be in the range of from about 1.05:1 to about 8:1. In certain embodiments, the polyol may comprise a portion of water, which may enhance the porosity of the compositions. In step 2220, the apparatus may be heated for a desired time at a desired temperature. In certain embodiments, the apparatus may be heated to a temperature in the range of from slightly above room temperature to about 120° C. In step 2230, at least one removable divider is removed from the sealed container. In step 2240, the isocyanate, the polyol and catalyst are mixed to a desired degree. In step 2250, a determination is made whether the mixture is reacting to form poly(urethane-isocyanurate) components (along with poly(urethane-urea-isocyanurate) components, in embodiments wherein water is present) at a desired rate. If the mixture is reacting at a desired rate, the process proceeds to end. If, however, the determination is made in step 2250 that the mixture is not reacting at a desired rate, the process proceeds to step 2260, in which the sealed container is exposed to an energy source for a desired time, after which the process returns to step 2250, which previously has been described.

In certain optional embodiments, a variety of optional additives may be incorporated into the process (e.g., the sealed container may comprise additional compartments, in which optional additives may be disposed). Such optional additives include, but are not limited to, those that have been previously disclosed herein. In certain of these embodiments wherein optional additives are disposed within one or more compartments, the process may comprise optional step 2245 (shown in FIG. 22C) wherein a removable divider is removed, and optional step 2247 (shown in FIG. 22C) wherein the sealed container is manipulated (e.g., manually manipulated) to mix the optional additives with the mixture of the isocyanate, polyol, and catalyst. The process then may proceed from step 2247 to step 2250, which previously has been described.

Alternatively, in certain embodiments of the present invention, certain of the optional additives may be introduced outside the sealed container, and may be incorporated once the contents of the sealed container have been dispensed therefrom. For example, after a determination is made in step 2250 that the mixture is reacting to form poly(urethane-isocyanurate) components (along with poly(urethane-urea-isocyanurate) components, in embodiments wherein water is present) at a desired rate, the process may proceed from step 2250 to an optional step 2270 (shown in FIG. 22D) wherein the reacting mixture is dispensed from the sealed container, and then may proceed to an optional step 2280 (shown in FIG. 22D) wherein at least one optional additive is mixed with the dispensed reacting mixture and permitted to remain within it as the mixture finishes reacting to form poly(urethane-isocyanurate) components (along with poly(urethane-urea-isocyanurate) components, in certain embodiments), after which the process may proceed to end.

In certain embodiments, one or more optional additives may be present in a separate reservoir (e.g., reservoir 199 shown in FIG. 4B), and optional step 2247 may comprise flowing the additives from the separate reservoir into the sealed container.

Figure 22E:
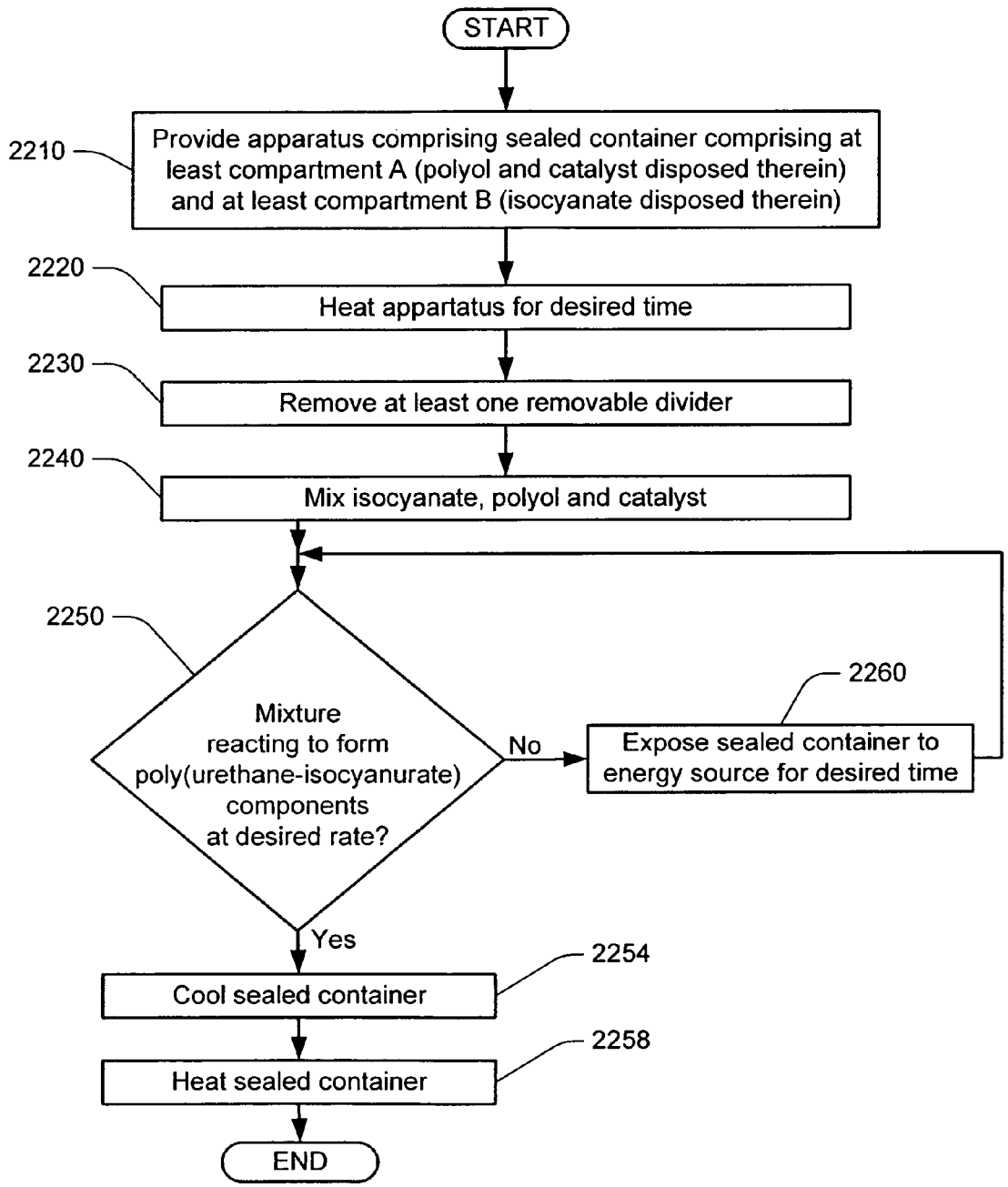

FIG. 22E illustrates that in certain embodiments of the present invention, the sealed container may be cooled at any point in the process so as to suspend or delay, at least temporarily, the reaction occurring therein. In certain of such embodiments, the process may comprise optional step 2254 (shown in FIG. 22E), wherein the sealed container is cooled to a desired temperature (e.g., by immersion within a container of ice water) until such time as re-initiation of the reaction is desired, at which point the process may proceed to optional step 2258 (shown in FIG. 22E), wherein the sealed container may be heated for a desired time to a desired temperature, and the mixture within the sealed container may resume reacting.

Figure 22F:
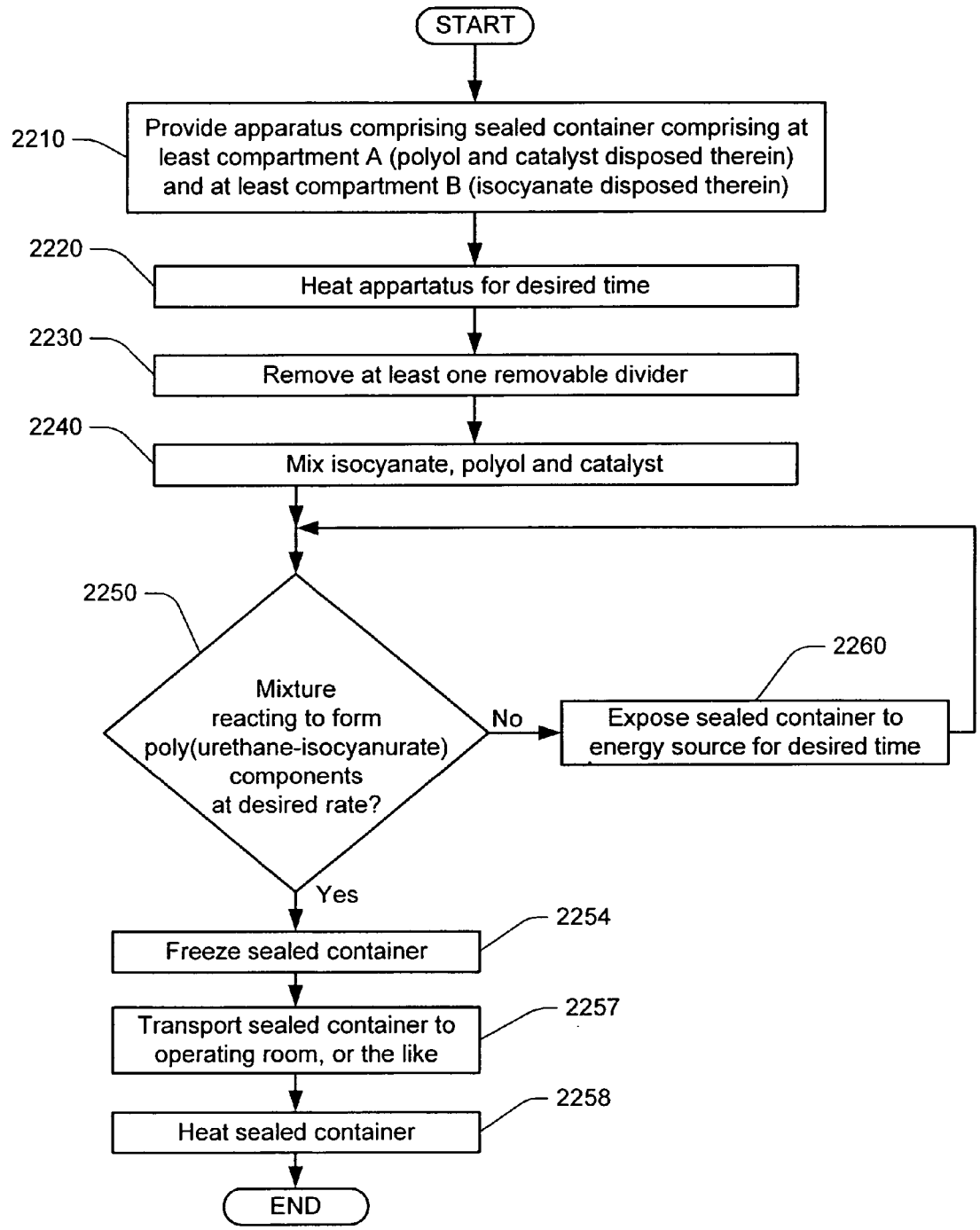

FIG. 22F illustrates that in certain embodiments of the present invention, optional step 2254 (as shown in FIG. 22F) may involve freezing the sealed container (e.g., by immersing it in, for example, liquid nitrogen). In certain embodiments, this may occur after the contents within the sealed container have been permitted to react for about half the time normally allocated for reaction (e.g., the contents may have been permitted to react for a time in the range of from about 5 minutes to about 20 minutes, in certain embodiments, depending upon, inter alia, the amount of catalyst that may be present). The process then may proceed to optional step 2257 (shown in FIG. 22F), in which the sealed container is transported to an operating room, or the like, packed in a suitable medium (e.g., dry ice). The process then may proceed to optional step 2258 (shown in FIG. 22F), in which the sealed container is thawed (e.g., in a bath of warm or hot water) without further mixing, after which the contents of the sealed container are dispensed and implanted within the body of a mammal, wherein the contents of the sealed container may finish reacting (e.g., "cure") to form poly(urethane-isocyanurate) components (along with poly(urethane-urea-isocyanurate) components, in certain embodiments).

FIGS. 23A-23F illustrate how reactions such as those described with reference to FIGS. 22A-22F may be carried out through the use of another embodiment of an apparatus of the present invention, one comprising both a sealed outer container and a sealed inner container. Because certain features and advantages of the embodiments described in FIGS. 23A-23F are substantially similar to certain features and advantages of the embodiments described with reference to FIGS. 22A-22F, such similar features and advantages are not discussed further with respect to the embodiments illustrated in FIGS. 23A-23F.

Figure 23A:
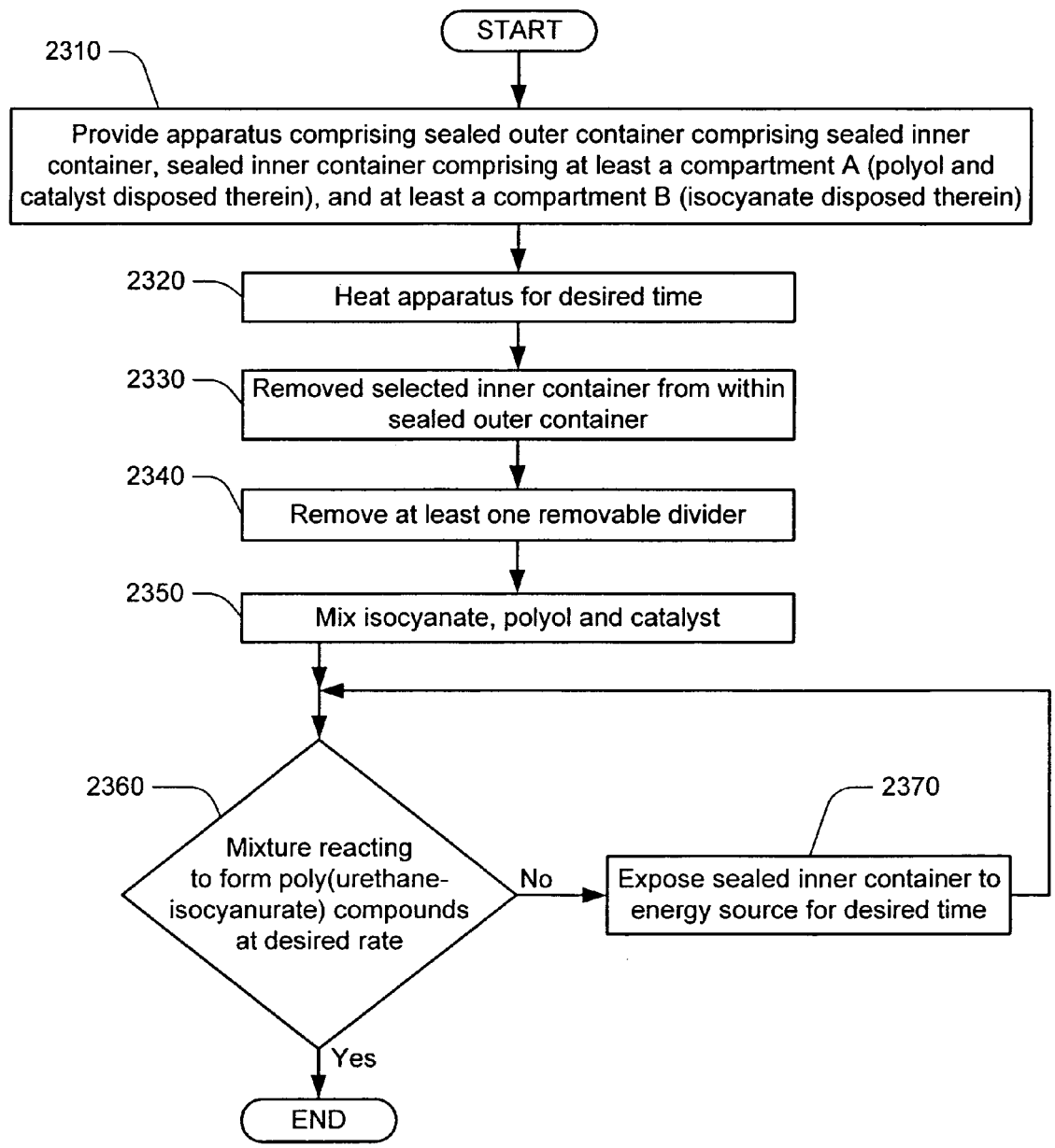

Referring now to FIG. 23A, in step 2310, an apparatus is provided that comprises a sealed outer container comprising a sealed inner container. The sealed inner container itself comprises an internal cavity that is separated by at least one removable divider into at least a compartment A and a compartment B. An isocyanate may be disposed within compartment B. A polyol (either a biocompatible, synthetic polyol or a naturally occurring polyol) and a catalyst may be disposed within compartment A. Examples of suitable catalysts include, inter alia, potassium carboxylates, quaternary ammonium carboxylates, tertiary amines, and the like. The equivalent ratio of isocyanate groups to total hydroxyl groups may be in the range of from about 1.05:1 to about 8:1. In certain embodiments, the polyol may comprise a portion of water, which may enhance the porosity of the compositions. In step 2320, the apparatus may be heated for a desired time at a desired temperature. In certain embodiments, the apparatus may be heated to a temperature in the range of from slightly above room temperature to about 120° C. In step 2330, the sealed inner container may be removed from within the sealed outer container, and in step 2340, at least one removable divider may be removed from the sealed inner container. In step 2350, the isocyanate, polyol, and catalyst may be mixed for a desired time. In step 2360, a determination is made whether the mixture is reacting to form poly(urethane-isocyanurate) components (along with poly(urethane-urea-isocyanurate) components, in embodiments wherein water is present) at a desired rate. If the mixture is reacting at a desired rate, the process proceeds to end. If, however, the determination is made in step 2360 that the mixture is not reacting at a desired rate, the process proceeds to step 2370, in which the sealed inner container is exposed to an energy source for a desired time, after which the process returns to step 2360, which previously has been described.

Figure 23B:
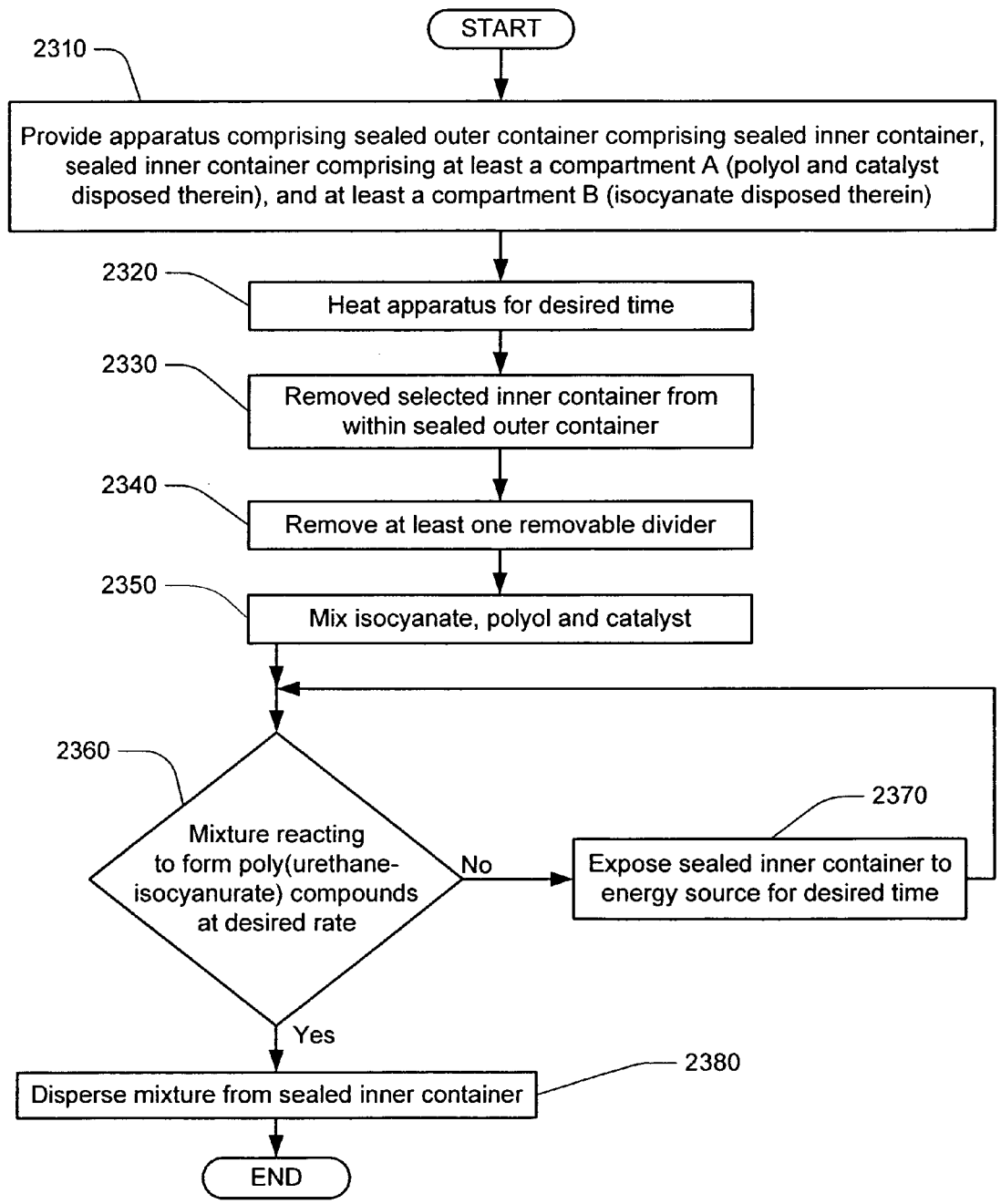
Figure 23C:
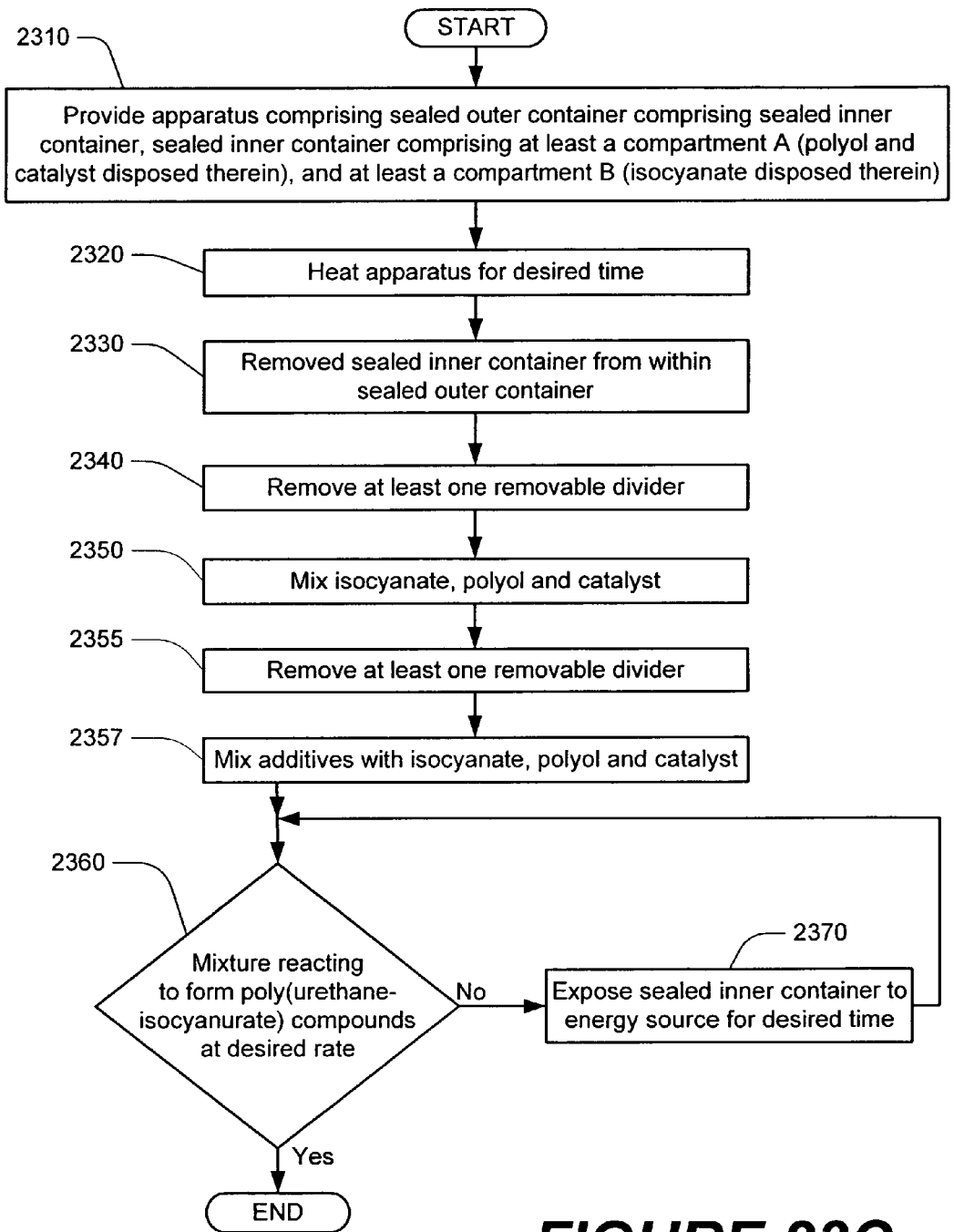
Figure 23D:
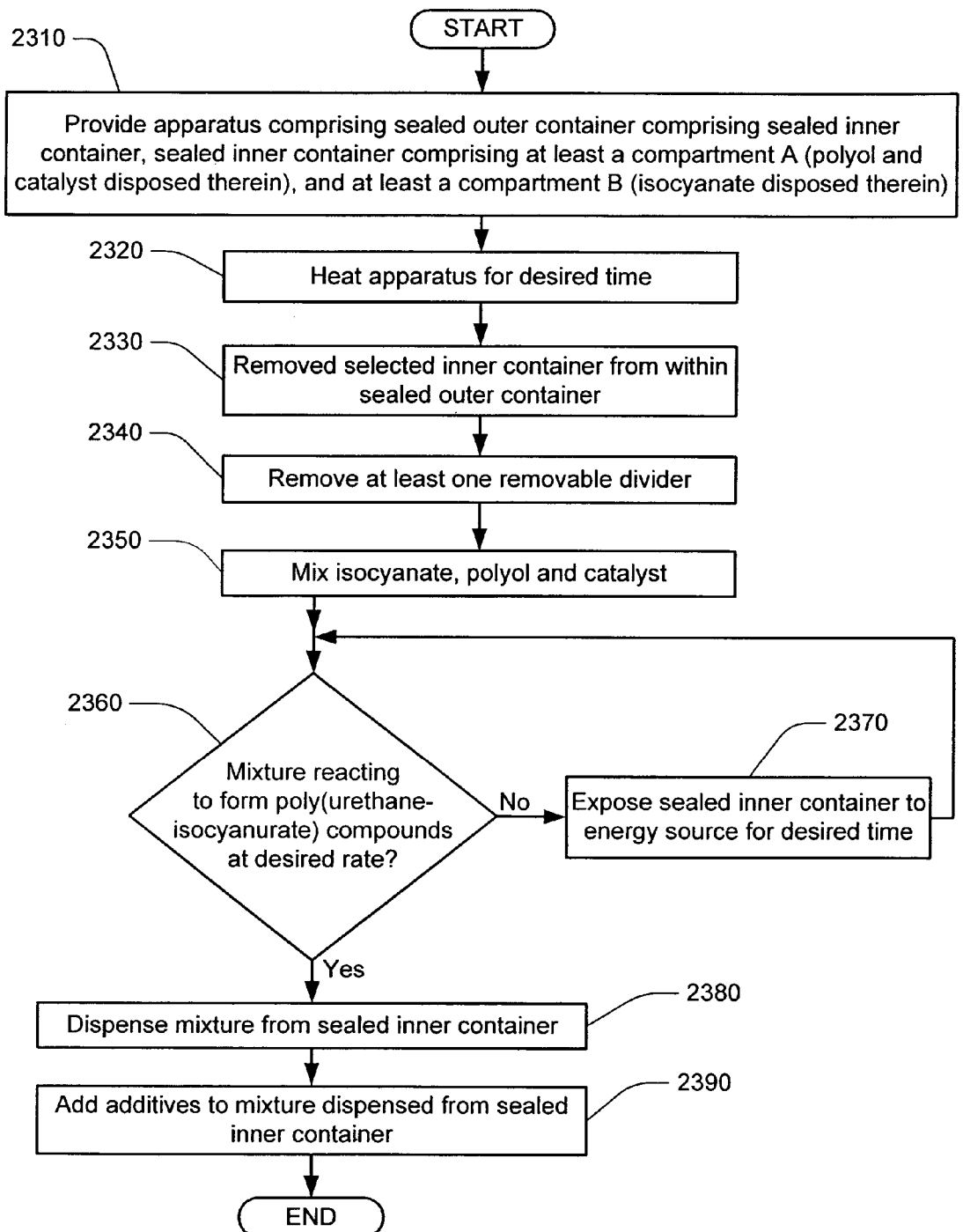

FIG. 23B illustrates the performance of an optional step 2380, wherein the mixture within the sealed inner container is dispensed therefrom. FIG. 23C illustrates that optional additives may be incorporated within the sealed inner container in a variety of ways. As illustrated in FIG. 23C, in certain embodiments, the process may comprise optional step 2355 (shown in FIG. 23C) wherein a removable divider is removed, and optional step 2357 (shown in FIG. 23C) wherein the sealed inner container is manipulated (e.g., manually manipulated) to mix the optional additives with the mixture of the isocyanate, polyol, and catalyst. The process then may proceed from step 2357 to step 2360, which previously has been described.

Alternatively, in certain embodiments of the present invention, certain of the optional additives may be introduced outside the sealed inner container, and may be incorporated once the contents of the sealed inner container have been dispensed therefrom. For example, after a determination is made in step 2360 that the mixture is reacting to form poly(urethane-isocyanurate) components (along with poly(urethane-urea-isocyanurate) components, in embodiments wherein water is present) at a desired rate, the process may proceed from step 2360 to an optional step 2380 (shown in FIG. 23D) wherein the reacting mixture is dispensed from the sealed inner container, and then may proceed to an optional step 2390 (shown in FIG. 23D) wherein at least one optional additive is mixed with the dispensed reacting mixture and permitted to remain within it as the mixture finishes reacting to form poly(urethane-isocyanurate) components (along with poly(urethane-urea-isocyanurate) components, in certain embodiments), after which the process may proceed to end.

Figure 23E:
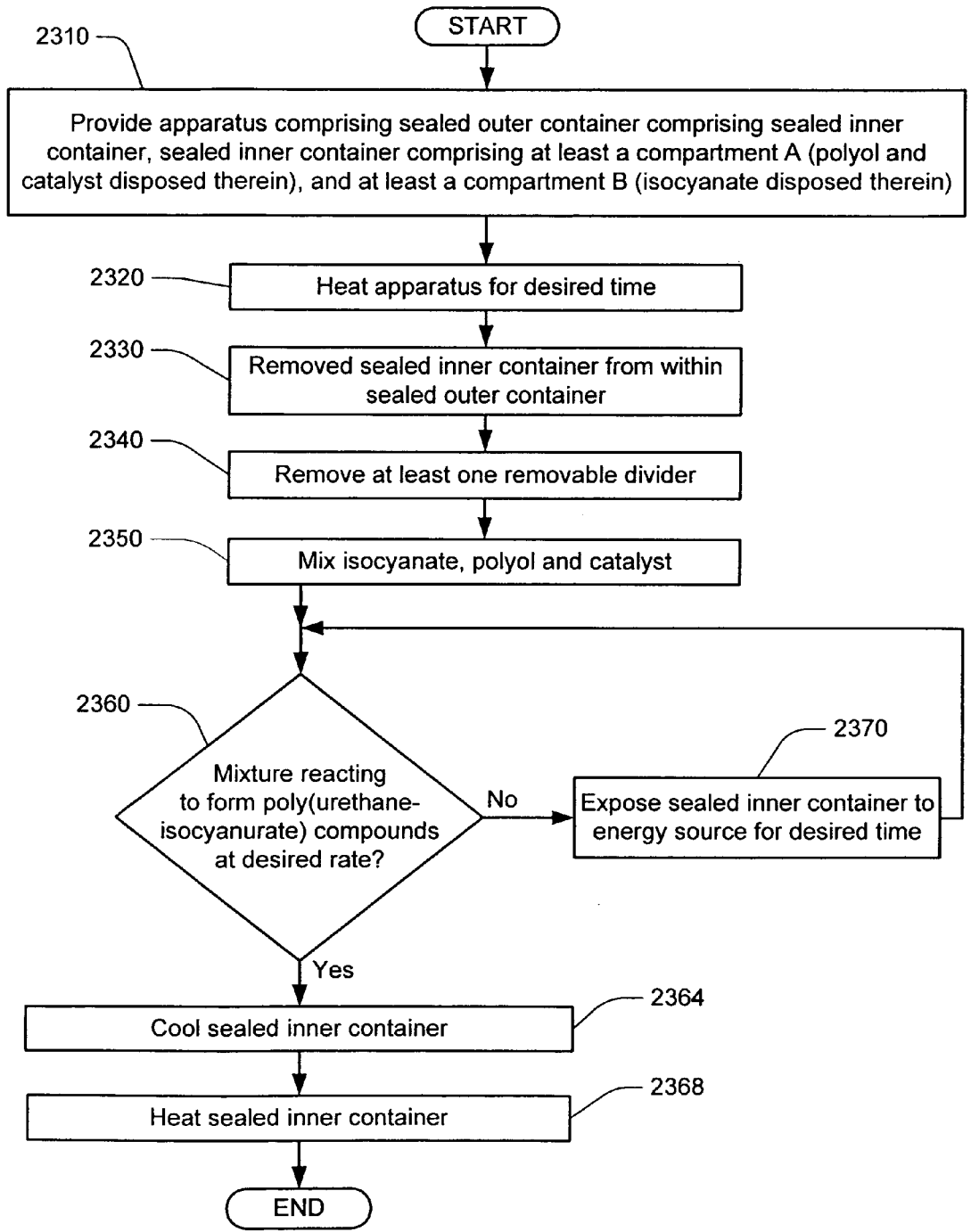

FIG. 23E illustrates that in certain embodiments of the present invention, the sealed inner container may be cooled at any point in the process so as to suspend or delay, at least temporarily, the reaction occurring therein, and illustrates the use of optional cooling step 2364 (shown in FIG. 23E), wherein the sealed inner container is cooled to a desired temperature until such time as re-initiation of the reaction is desired, and optional heating step 2368 (shown in FIG. 23E), wherein the sealed inner container may be heated for a desired time to a desired temperature, and the mixture within the sealed inner container may resume reacting.

Figure 23F:
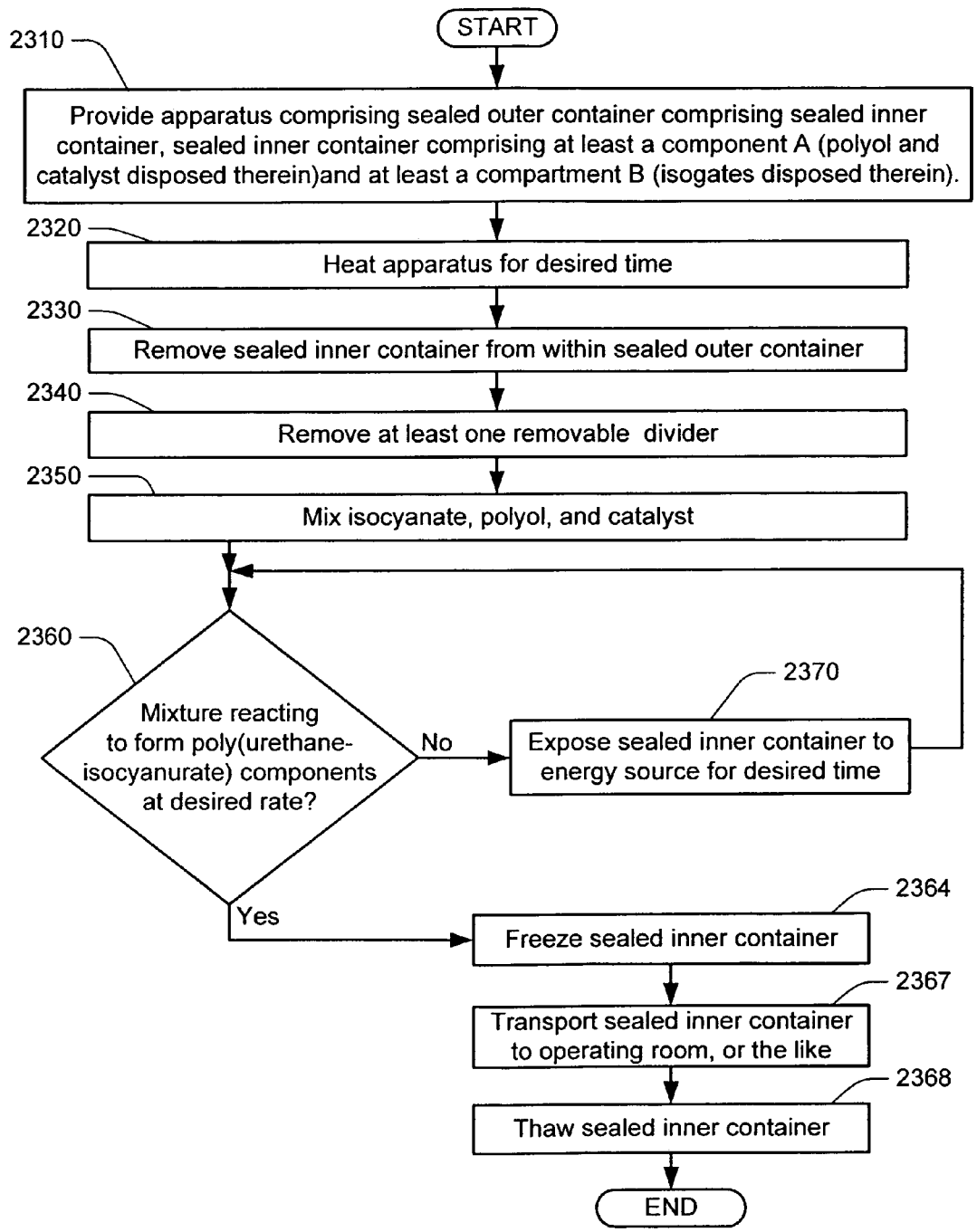

FIG. 23F illustrates that in certain embodiments of the present invention, optional step 2364 (as shown in FIG. 23F) may involve freezing the sealed inner container at a desired time after the container have been permitted to partially react. The process then may proceed to optional step 2367 (shown in FIG. 23F), in which the sealed inner container is transported to an operating room, or the like, and then to optional step 2368 (shown in FIG. 23F), in which the sealed inner container is thawed, after which the contents of the sealed container are dispensed and implanted within the body of a mammal, wherein the contents of the sealed inner container may finish reacting (e.g., "cure") to form poly(urethane-isocyanurate) components (along with poly(urethane-urea-isocyanurate) components, in certain embodiments).

Figure 24A:
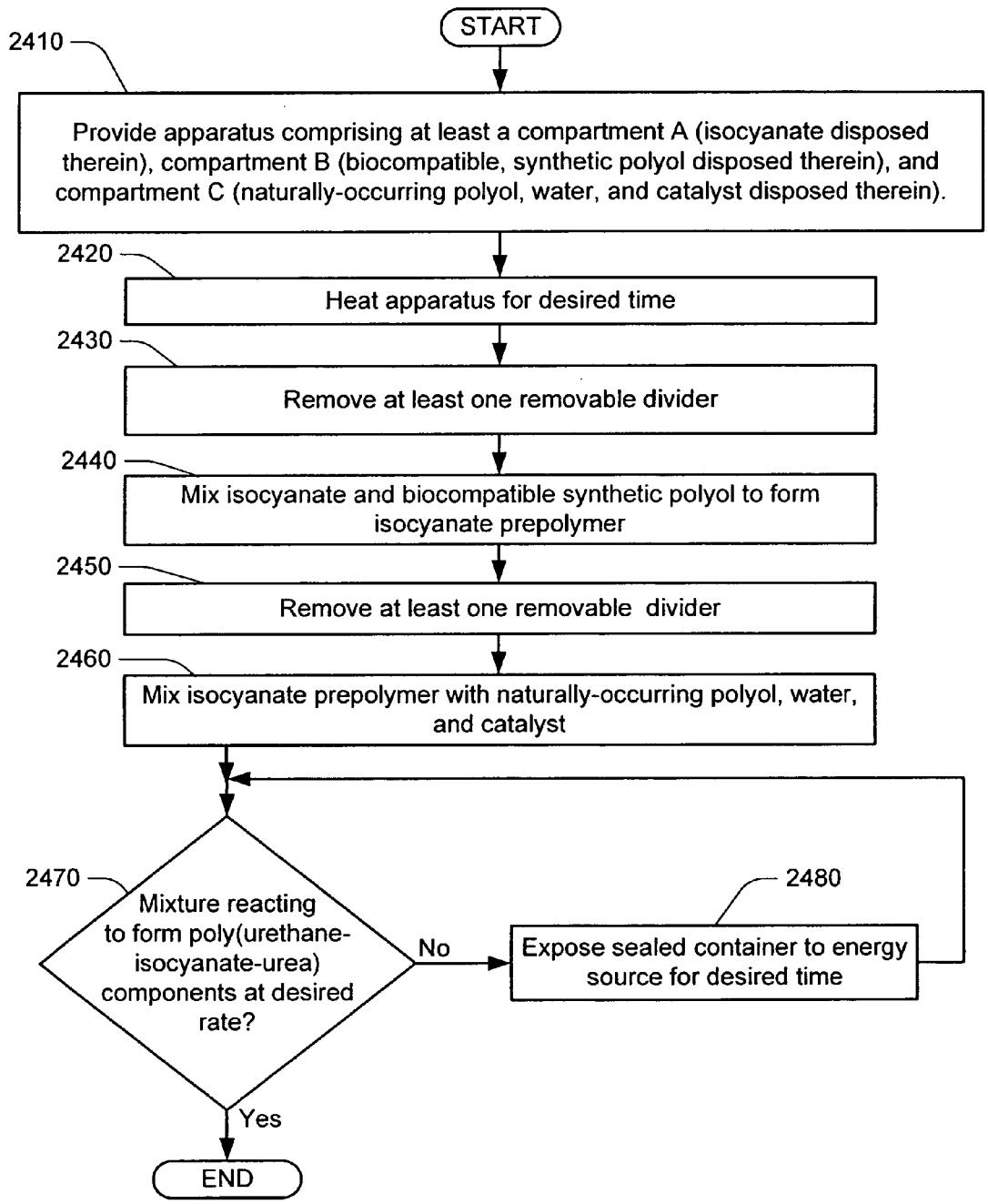

FIGS. 24A-25F illustrate certain embodiments of the present invention that involve the preparation and use of isocyanate prepolymers to prepare compositions comprising poly(urethane-urea-isocyanurate) components. Referring now to FIG. 24A, in step 2410, an apparatus is provided comprising a sealed container comprising an internal cavity, the internal cavity being separated by a plurality of removable dividers into at least a compartment A, a compartment B, and a compartment C. An isocyanate may be disposed within compartment A. A biocompatible, synthetic polyol may be disposed within compartment B. A naturally-occurring polyol, water, and a catalyst may be disposed within compartment C. Examples of suitable catalysts include, inter alia, potassium carboxylates, quaternary ammonium carboxylates, tertiary amines, and the like. The equivalent ratio of isocyanate groups to total hydroxyl groups may be in the range of from about 1.05:1 to about 8:1. In step 2420, the apparatus may be heated for a desired time at a desired temperature. In certain embodiments, the apparatus may be heated to a temperature in the range of from slightly above room temperature to about 100° C., and, in certain preferred embodiments, from slightly above room temperature to about 80° C. In step 2430, at least one removable divider is removed from the sealed container. In step 2440, the isocyanate, and the biocompatible, synthetic polyol are mixed for a time sufficient to form an isocyanate prepolymer. In step 2450, at least one removable divider is removed, and in step 2460 the isocyanate prepolymer is mixed with the naturally-occurring polyol, water, and catalyst. In step 2470, a determination is made whether the mixture is reacting to form poly(urethane-urea-isocyanurate) components at a desired rate. If the mixture is reacting at a desired rate, the process proceeds to end. If, however, the determination is made in step 2470 that the mixture is not reacting at a desired rate, the process proceeds to step 2480, in which the sealed container is exposed to an energy source for a desired time, after which the process returns to step 2470, which previously has been described.

Figure 24B:
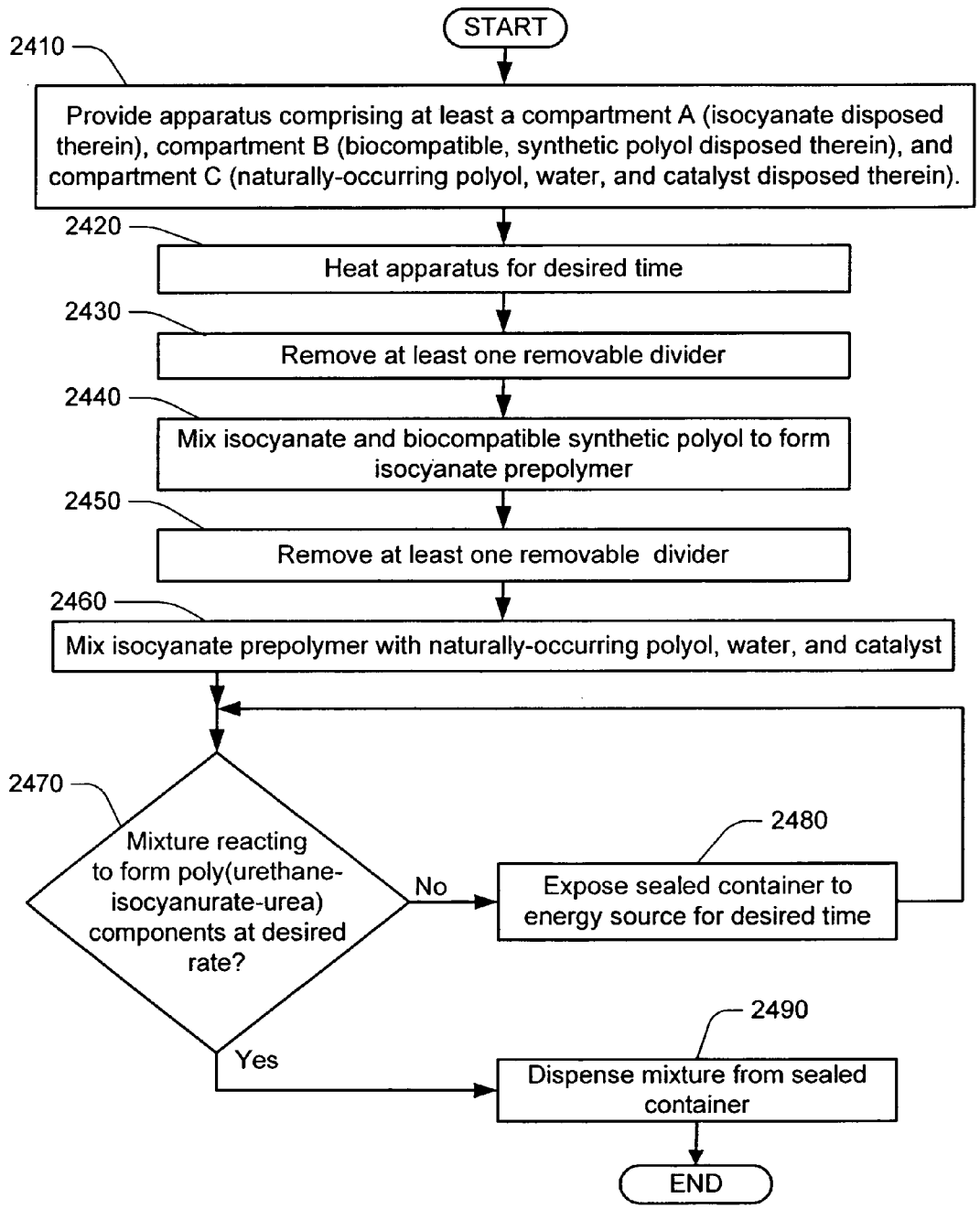
Figure 24C:
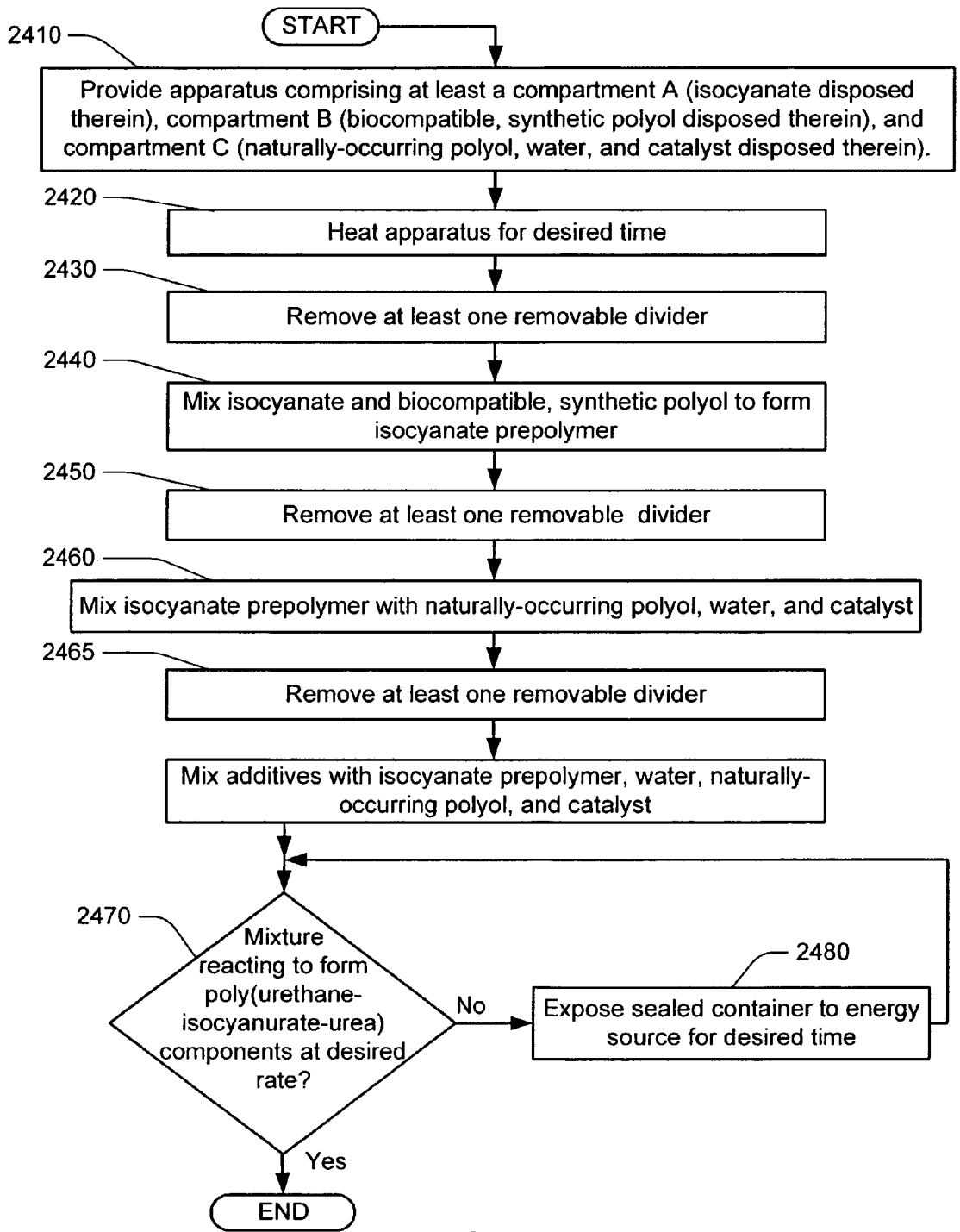
Figure 24D:
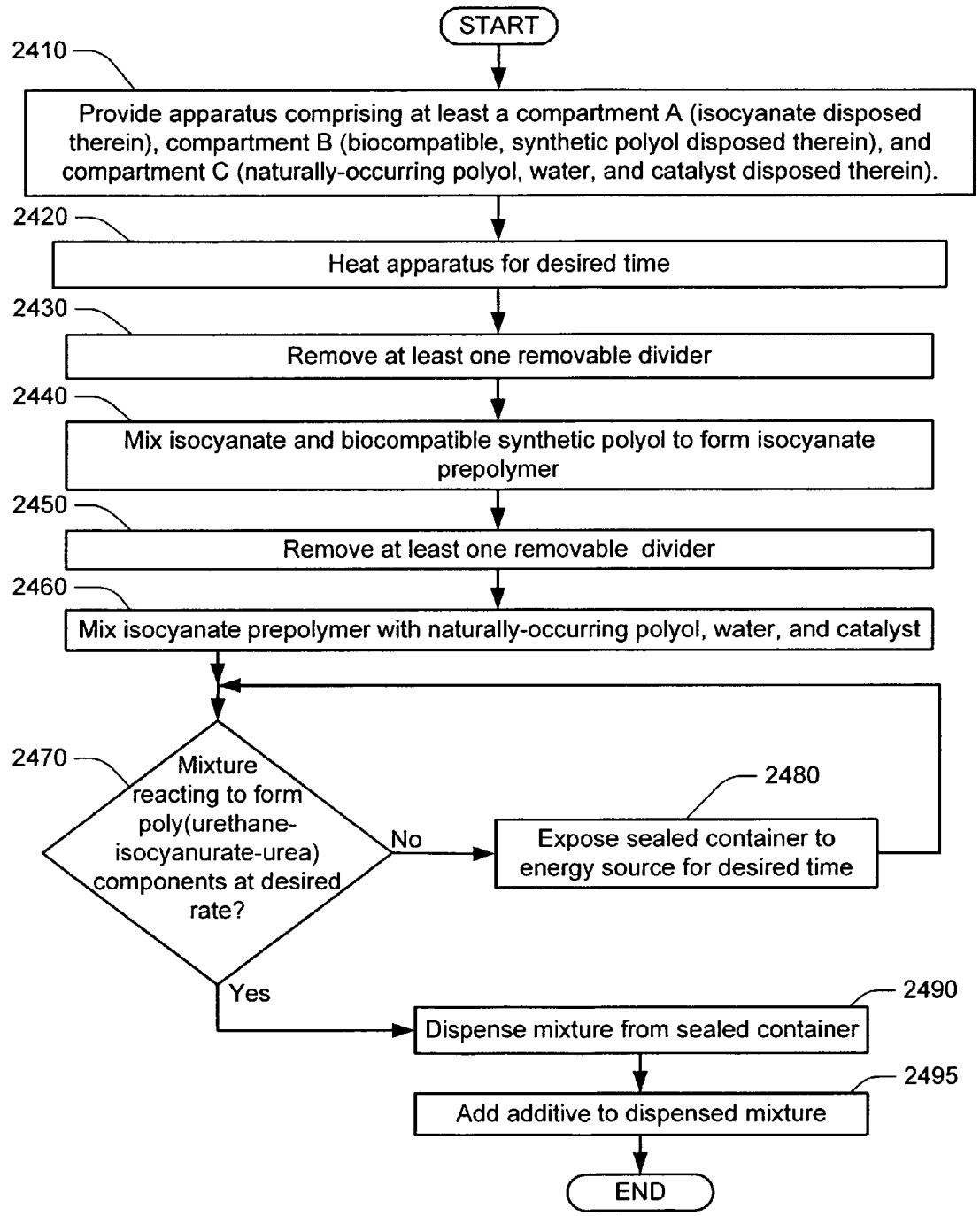

FIG. 24B illustrates the performance of an optional step 2490, wherein the mixture within the sealed container is dispensed therefrom. FIG. 24C illustrates that optional additives may be incorporated within the sealed container in a variety of ways. As illustrated in FIG. 24C, in certain embodiments, the process may comprise optional step 2465 (shown in FIG. 24C) wherein a removable divider is removed, and optional step 2467 (shown in FIG. 24C) wherein the sealed container is manipulated (e.g., manually manipulated) to mix the optional additives with the mixture of the isocyanate prepolymer, water, naturally-occurring polyol, and catalyst. The process then may proceed from step 2467 to step 2470, which previously has been described.

Alternatively, in certain embodiments of the present invention, certain of the optional additives may be introduced outside the sealed container, and may be incorporated once the contents of the sealed container have been dispensed therefrom. For example, after a determination is made in step 2470 that the mixture is reacting to form poly(urethane-urea-isocyanurate) components at a desired rate, the process may proceed from step 2470 to an optional step 2490 (shown in FIG. 24D) wherein the reacting mixture is dispensed from the sealed container, and then may proceed to an optional step 2495 (shown in FIG. 24D) wherein at least one optional additive is mixed with the dispensed reacting mixture and permitted to remain within it as the mixture finishes reacting to form poly(urethane-urea-isocyanurate) components, after which the process may proceed to end.

Figure 24E:
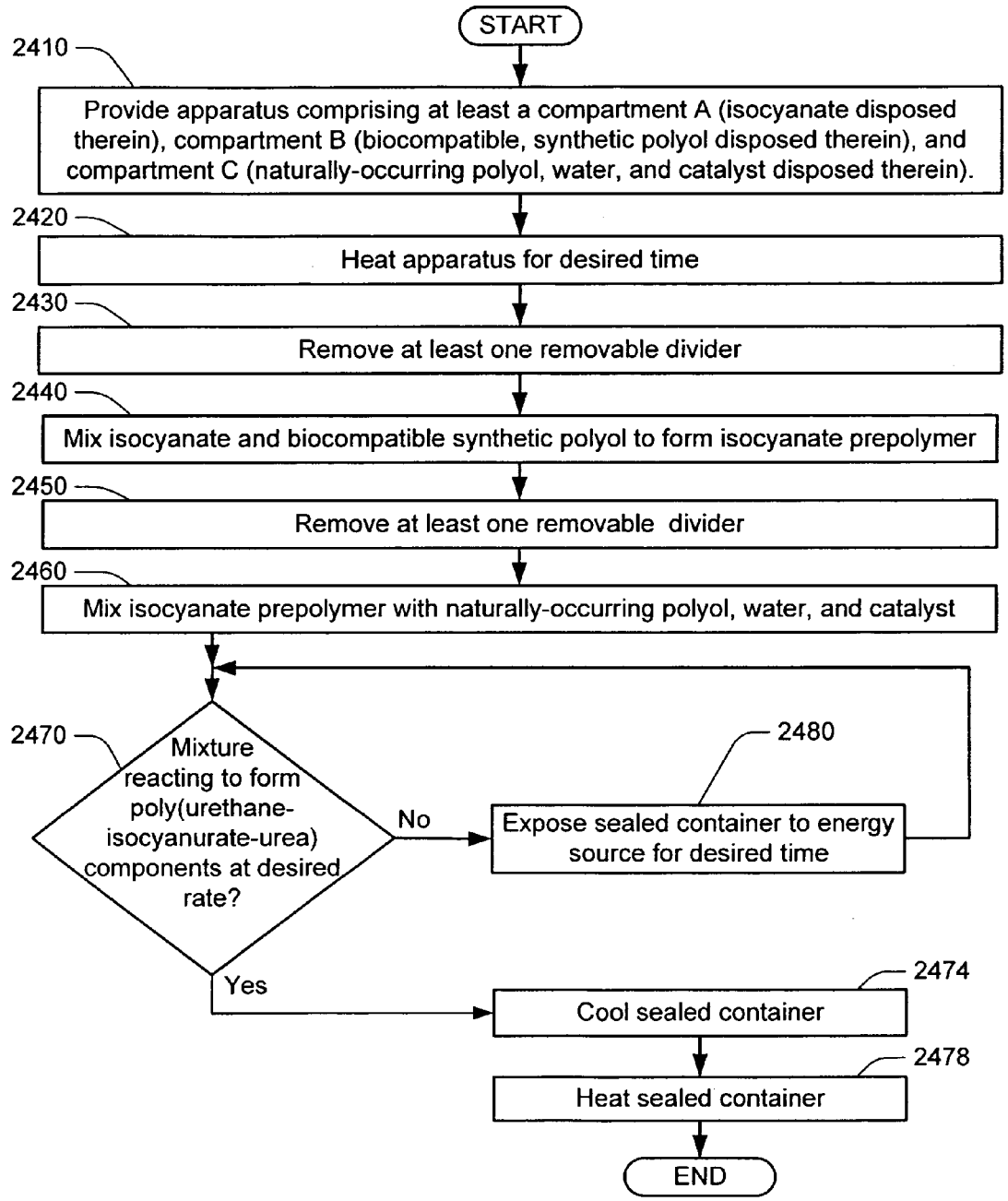

FIG. 24E illustrates that in certain embodiments of the present invention, the sealed container may be cooled at any point in the process so as to suspend or delay, at least temporarily, the reaction occurring therein, and illustrates the use of optional cooling step 2474 (shown in FIG. 24E), wherein the sealed container is cooled to a desired temperature until such time as re-initiation of the reaction is desired, and optional heating step 2478 (shown in FIG. 24E), wherein the sealed container may be heated for a desired time to a desired temperature, and the mixture within the sealed container may resume reacting.

Figure 24F:
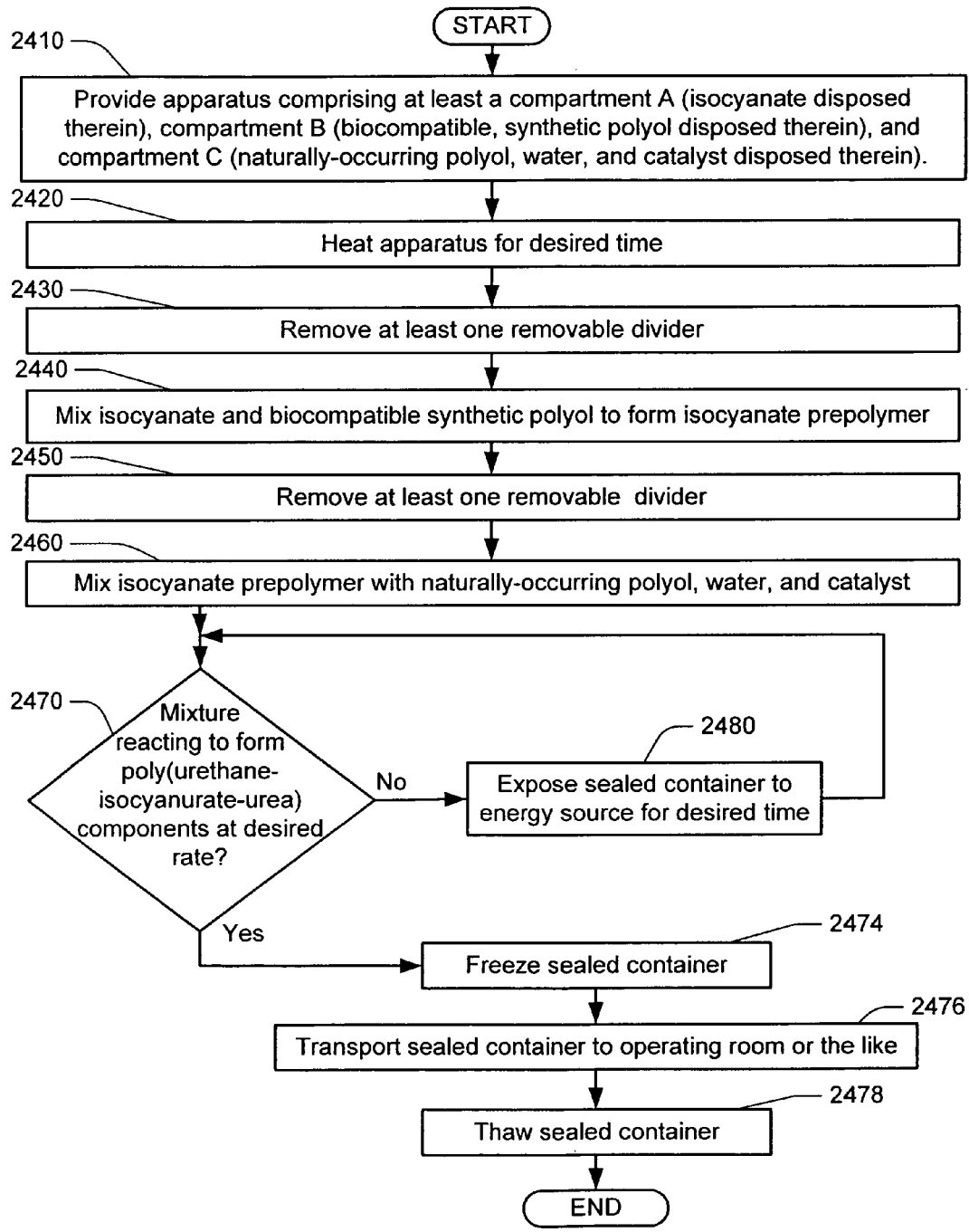

FIG. 24F illustrates that in certain embodiments of the present invention, optional step 2474 (as shown in FIG. 24F) may involve freezing the sealed container at a desired time after the container have been permitted to partially react. The process then may proceed to optional step 2476 (shown in FIG. 24F), in which the sealed container is transported to an operating room, or the like, and then to optional step 2478 (shown in FIG. 24F), in which the sealed container is thawed, after which the contents of the sealed container are dispensed and implanted within the body of a mammal, wherein the contents of the sealed container may finish reacting (e.g., "cure") to form poly(urethane-urea-isocyanurate) components.

FIGS. 25A-25F illustrate how reactions such as those described with reference to FIGS. 24A-24F may be carried out through the use of another embodiment of an apparatus of the present invention, one comprising both a sealed outer container and a sealed inner container. Because certain features and advantages of the embodiments described in FIGS. 25A-25F are substantially similar to certain features and advantages of the embodiments described with reference to FIGS. 24A-24F, such similar features and advantages are not discussed further with respect to the embodiments illustrated in FIGS. 25A-25F.

Figure 25A:
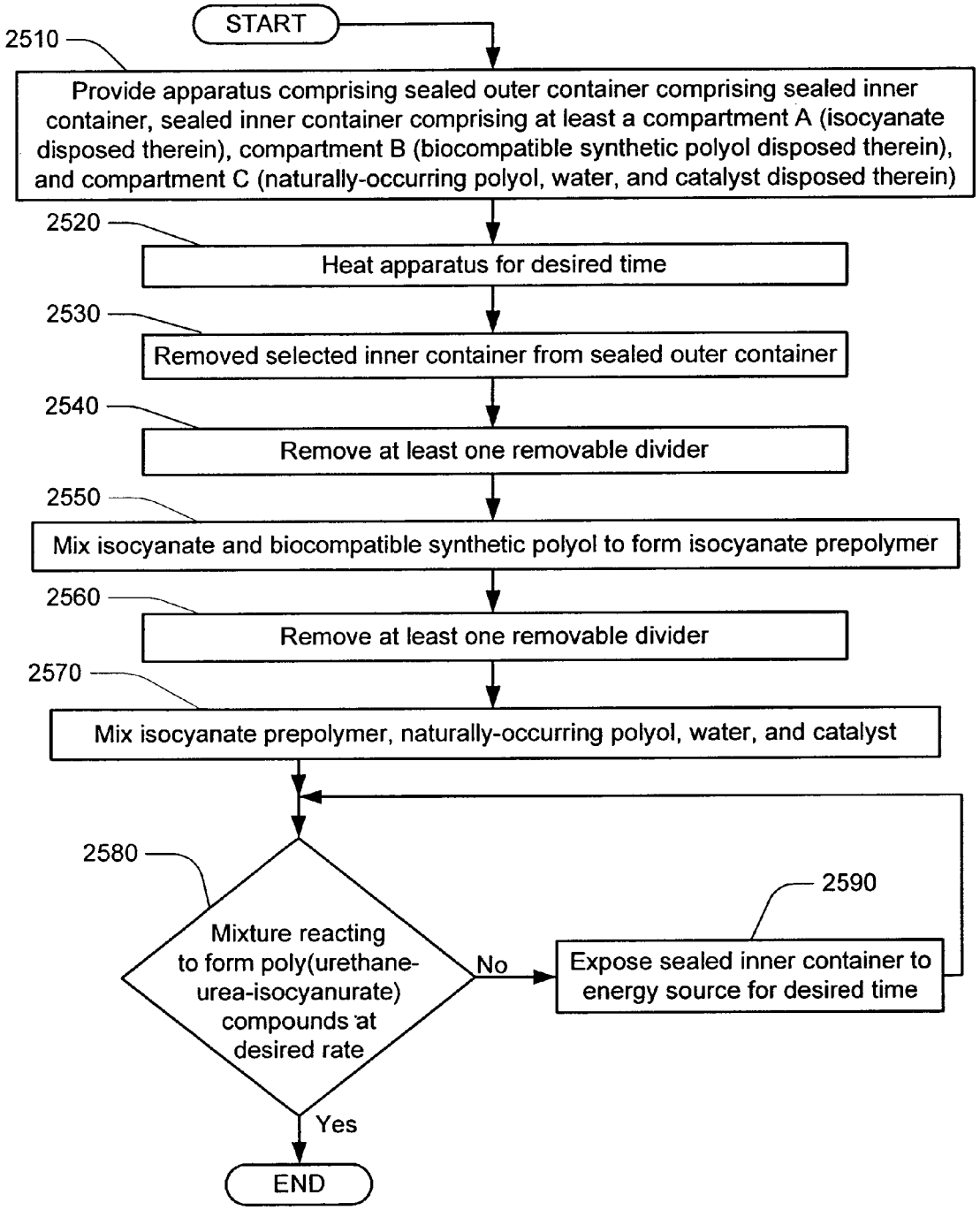

Referring now to FIG. 25A, in step 2510, an apparatus is provided comprising a sealed outer container, within which is disposed a sealed inner container. The sealed inner container itself comprises an internal cavity that is separated by a plurality of removable dividers into at least a compartment A, a compartment B, and a compartment C. An isocyanate may be disposed within compartment A. A biocompatible, synthetic polyol may be disposed within compartment B. A naturally-occurring polyol, water, and a catalyst may be disposed within compartment C. Examples of suitable catalysts include, inter alia, potassium carboxylates, quaternary ammonium carboxylates, tertiary amines, and the like. The equivalent ratio of isocyanate groups to total hydroxyl groups may be in the range of from about 1.05:1 to about 8:1. In step 2520, the apparatus may be heated for a desired time at a desired temperature. In certain embodiments, the apparatus may be heated to a temperature in the range of from slightly above room temperature to about 100° C., and in certain preferred embodiments, in the range of from slightly above room temperature to about 80° C. In step 2530, the sealed inner container may be removed from within the sealed outer container. In step 2540, at least one removable divider is removed from the sealed inner container. In step 2550, the isocyanate, and the biocompatible, synthetic polyol are mixed for a time sufficient to form an isocyanate prepolymer. In step 2560, at least one removable divider is removed, and in step 2570 the isocyanate prepolymer is mixed with the naturally-occurring polyol, water, and catalyst. In step 2580, a determination is made whether the mixture is reacting to form poly(urethane-urea-isocyanurate) components at a desired rate. If the mixture is reacting at a desired rate, the process proceeds to end. If, however, the determination is made in step 2580 that the mixture is not reacting at a desired rate, the process proceeds to step 2590, in which the sealed container is exposed to an energy source for a desired time, after which the process returns to step 2580, which previously has been described.

Figure 25B:
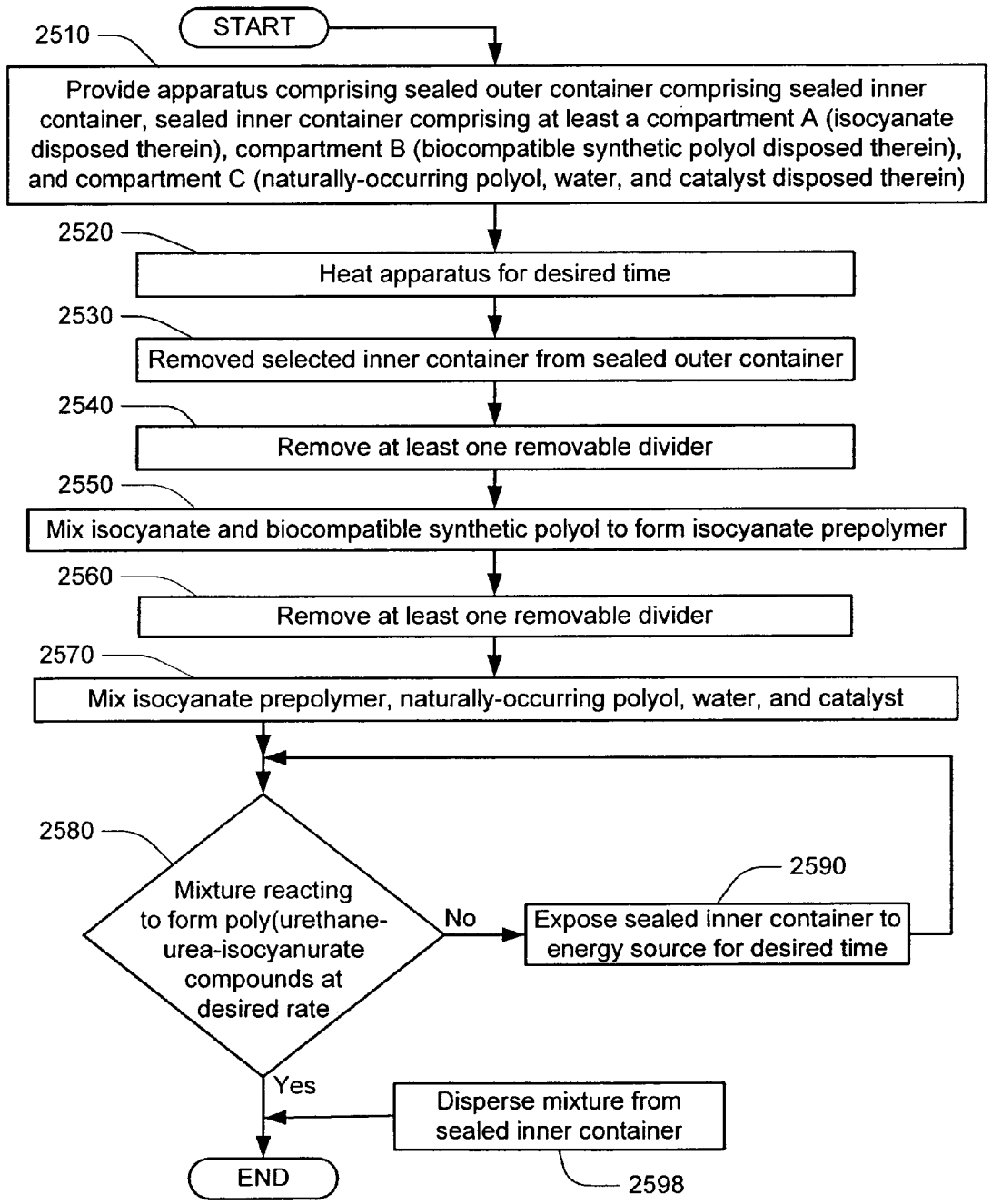
Figure 25C:
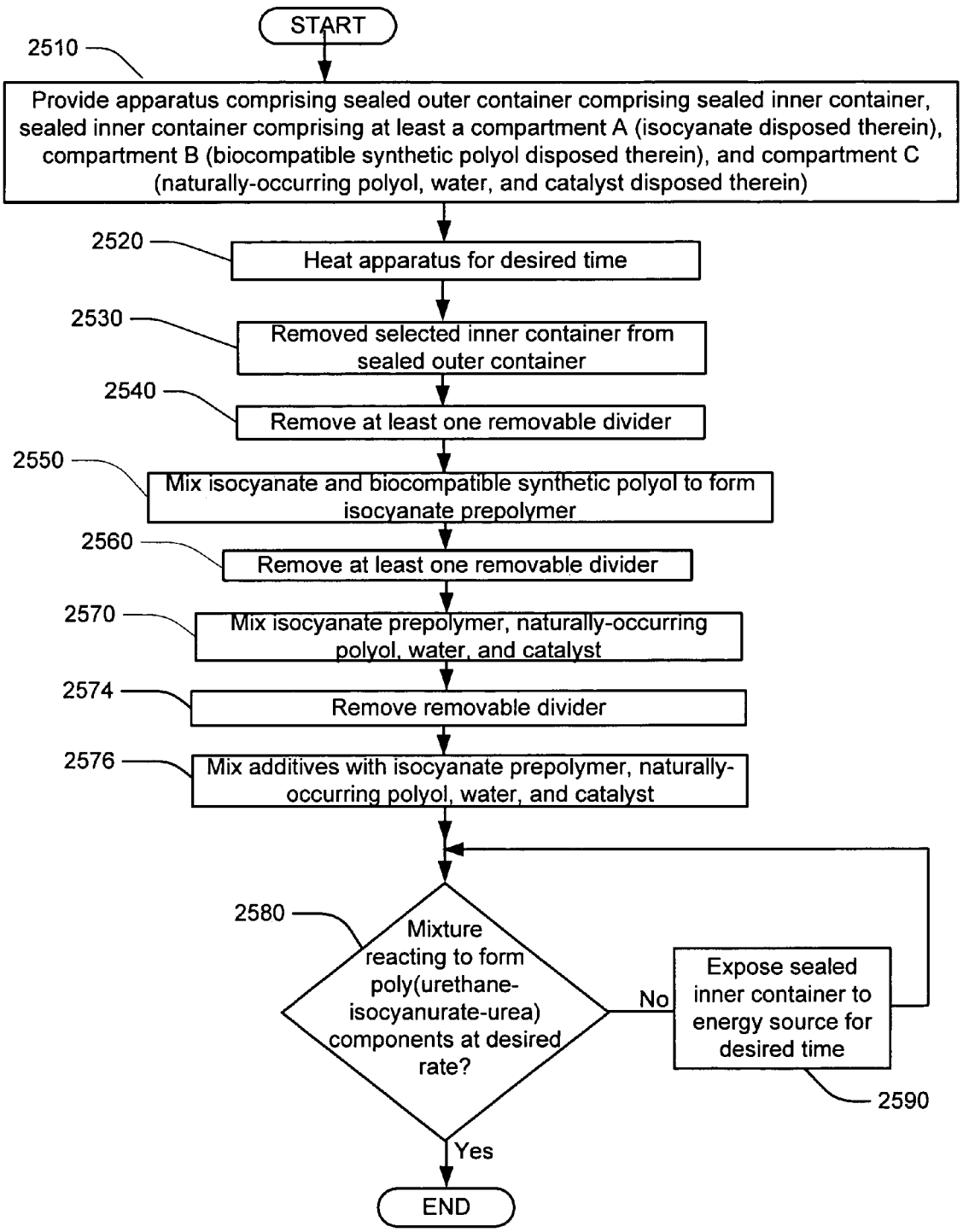
Figure 25D:
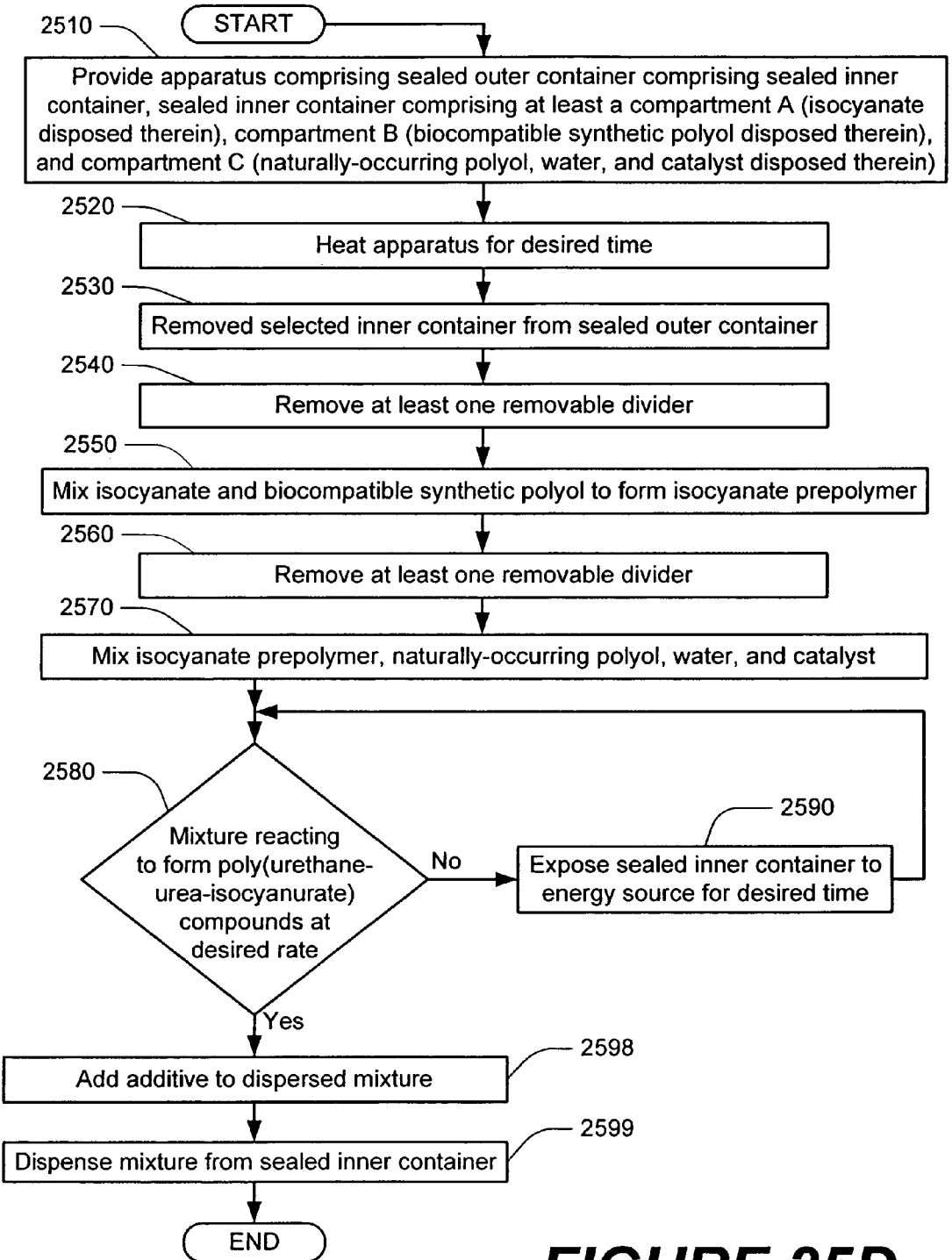

FIG. 25B illustrates the performance of an optional step 2598, wherein the mixture within the sealed inner container is dispensed therefrom. FIG. 25C illustrates that optional additives may be incorporated within the sealed inner container in a variety of ways. As illustrated in FIG. 25C, in certain embodiments, the process may comprise optional step 2574 (shown in FIG. 25C) wherein a removable divider is removed, and optional step 2576 (shown in FIG. 25C) wherein the sealed inner container is manipulated (e.g., manually manipulated) to mix the optional additives with the mixture of the isocyanate prepolymer, water, naturally-occurring polyol, and catalyst. The process then may proceed from step 2576 to step 2580, which previously has been described.

Alternatively, in certain embodiments of the present invention, certain of the optional additives may be introduced outside the sealed inner container, and may be incorporated once the contents of the sealed inner container have been dispensed therefrom. For example, after a determination is made in step 2580 that the mixture is reacting to form poly(urethane-urea-isocyanurate) components at a desired rate, the process may proceed from step 2580 to an optional step 2598 (shown in FIG. 25D) wherein the reacting mixture is dispensed from the sealed inner container, and then may proceed to an optional step 2599 (shown in FIG. 25D) wherein at least one optional additive is mixed with the dispensed reacting mixture and permitted to remain within it as the mixture finishes reacting to form poly(urethane-urea-isocyanurate) components, after which the process may proceed to end.

Figure 25E:
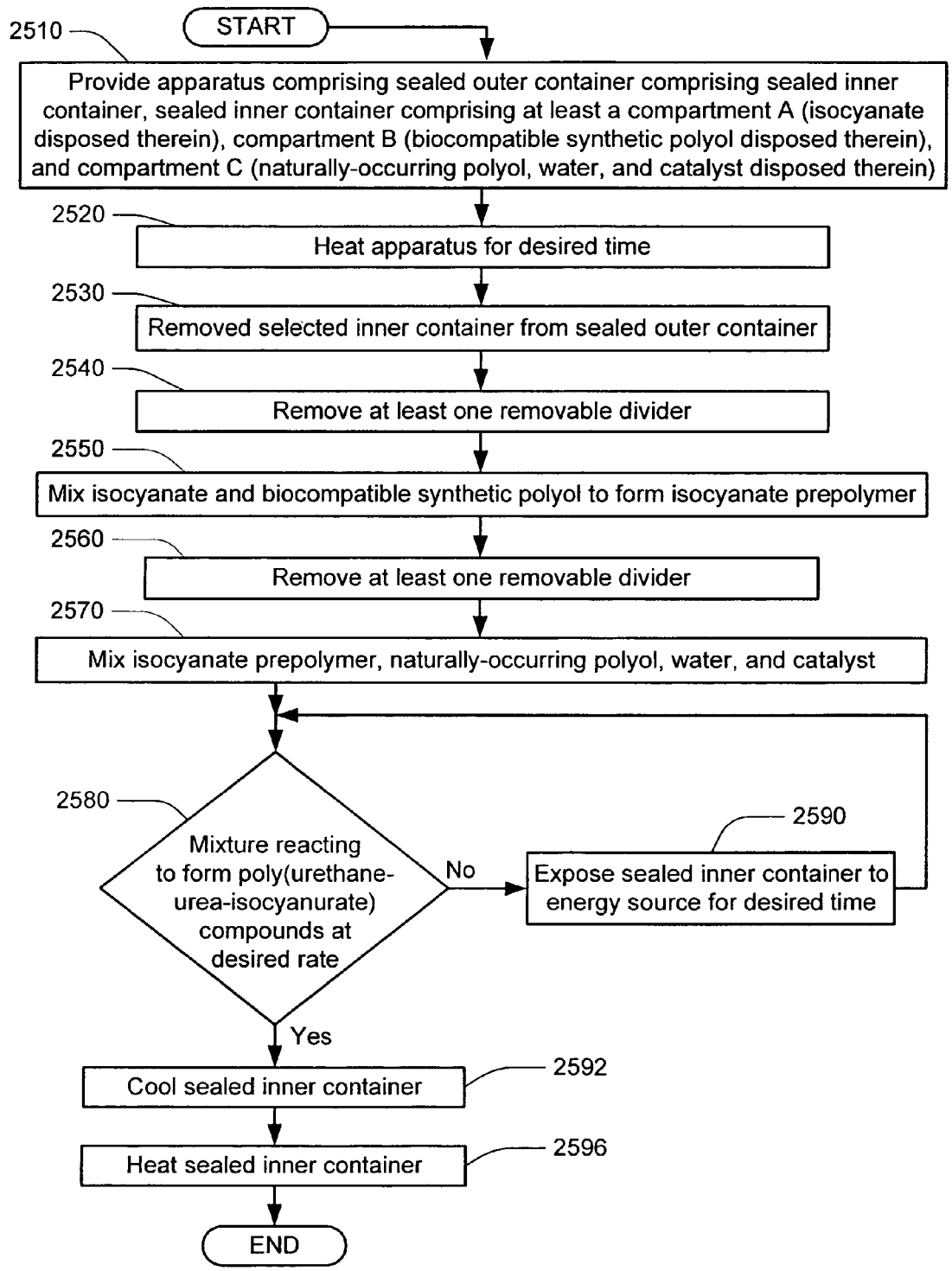

FIG. 25E illustrates that in certain embodiments of the present invention, the sealed inner container may be cooled at any point in the process so as to suspend or delay, at least temporarily, the reaction occurring therein, and illustrates the use of optional cooling step 2592 (shown in FIG. 25E), wherein the sealed inner container is cooled to a desired temperature until such time as re-initiation of the reaction is desired, and optional heating step 2596 (shown in FIG. 25E), wherein the sealed inner container may be heated for a desired time to a desired temperature, and the mixture within the sealed inner container may resume reacting.

Figure 25F:
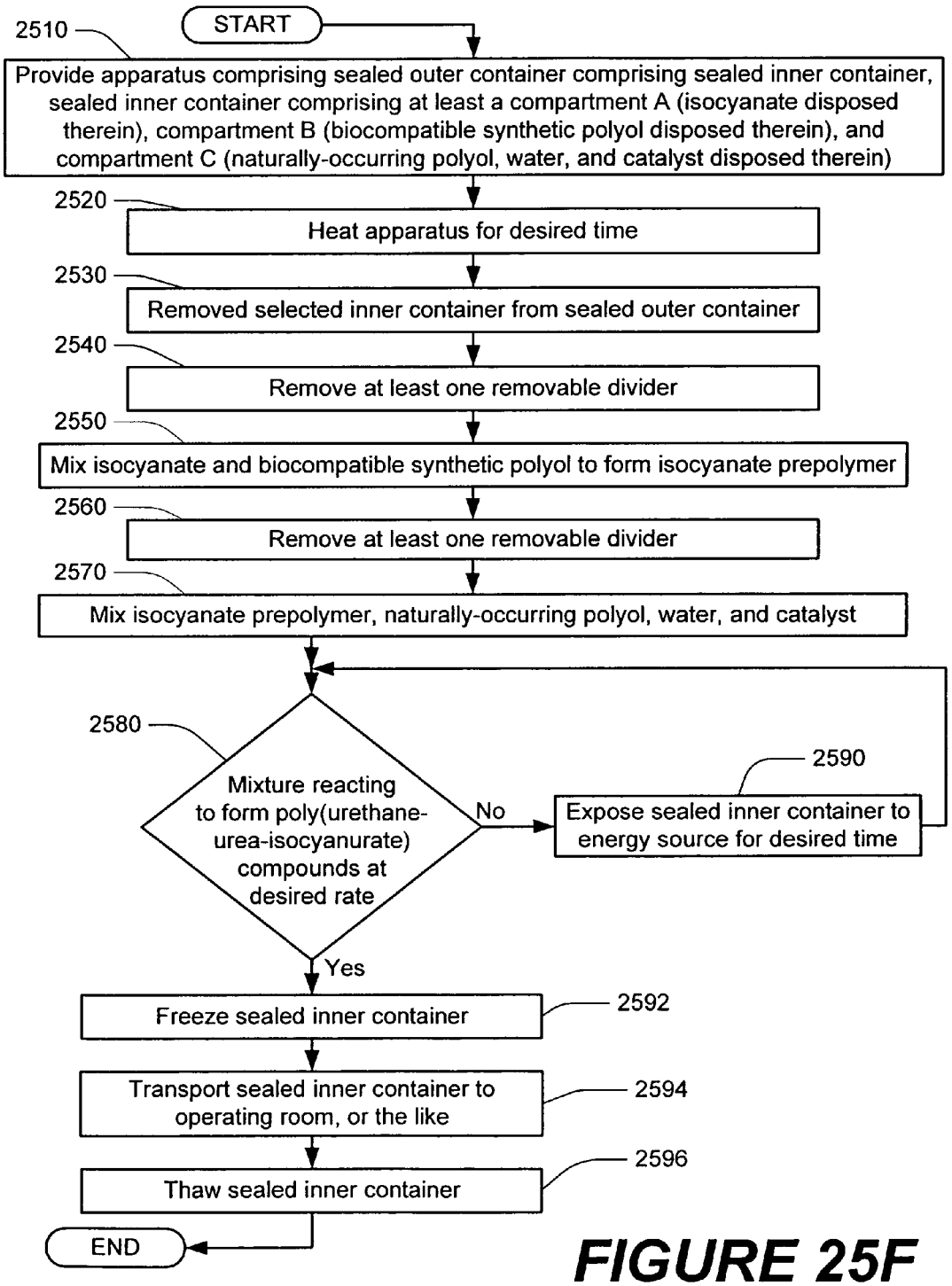

FIG. 25F illustrates that in certain embodiments of the present invention, optional step 2592 (as shown in FIG. 25F) may involve freezing the sealed inner container at a desired time after the container have been permitted to partially react. The process then may proceed to optional step 2594 (shown in FIG. 25F), in which the sealed inner container is transported to an operating room, or the like, and then to optional step 2596 (shown in FIG. 25F), in which the sealed inner container is thawed, after which the contents of the sealed inner container are dispensed and implanted within the body of a mammal, wherein the contents of the sealed inner container may finish reacting (e.g., "cure") to form poly(urethane-urea-isocyanurate) components.

Figure 26A:
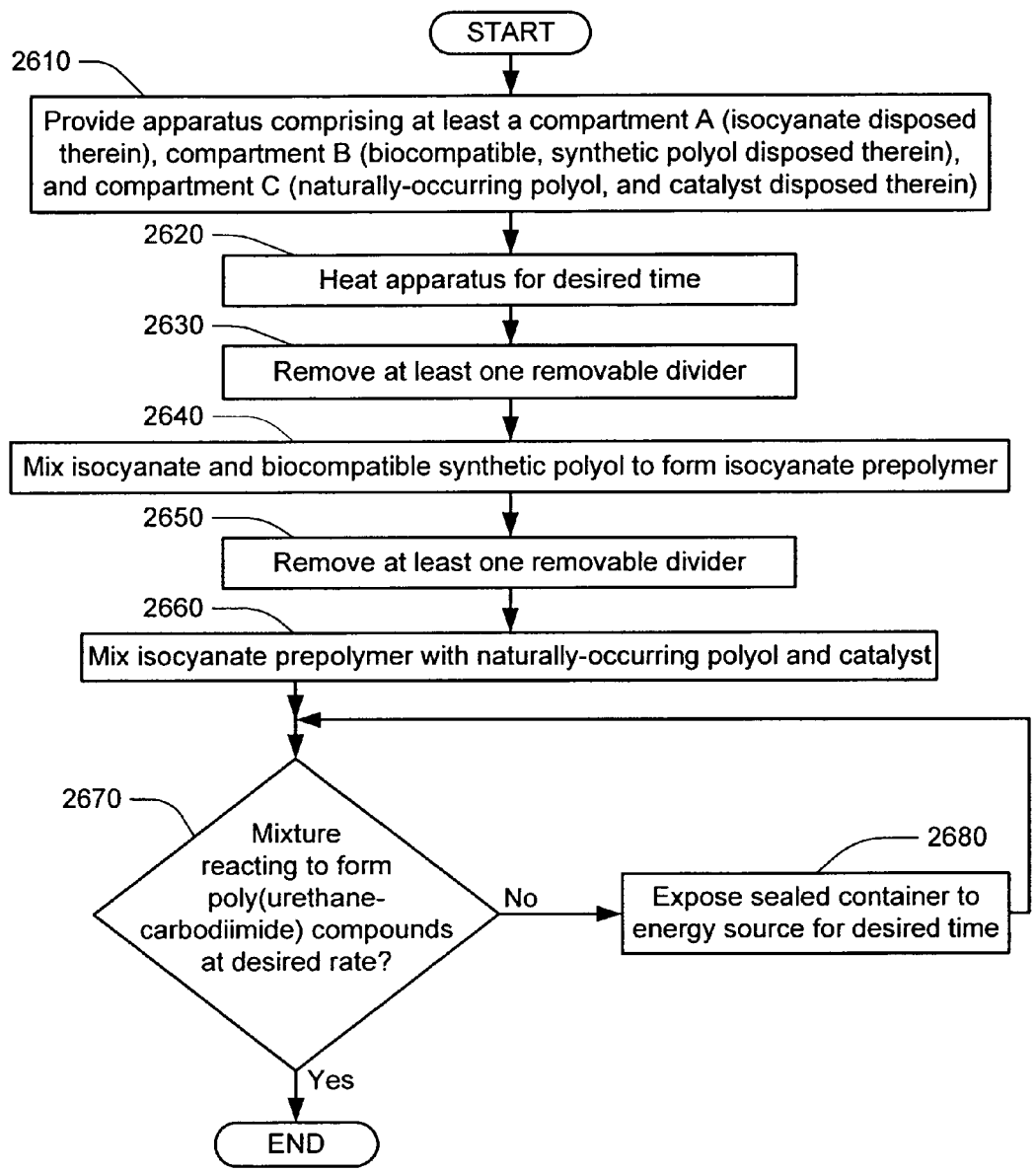

F. Methods for Making Compositions Comprising Poly (Urethane-Carbodiimide) Components FIGS. 26A-27F illustrate certain embodiments of the present invention that involve the preparation and use of isocyanate prepolymers to prepare compositions comprising poly(urethane-carbodiimide) components. Referring now to FIG. 26A, in step 2610, an apparatus is provided comprising a sealed container comprising an internal cavity, the internal cavity being separated by a plurality of removable dividers into at least a compartment A, a compartment B, and a compartment C. An isocyanate may be disposed within compartment A. A biocompatible, synthetic polyol may be disposed within compartment B. A naturally-occurring polyol and a catalyst may be disposed within compartment C. Examples of suitable catalysts include, inter alia, triphenylphosphine oxide, hexamethylphosphoric triamide, and the like. The equivalent ratio of isocyanate groups to total hydroxyl groups may be in the range of from about 1.05:1 to about 4:1. In step 2620, the apparatus may be heated for a desired time at a desired temperature. In certain embodiments, the apparatus may be heated to a temperature in the range of from about 100° C. to about 160° C. In step 2630, at least one removable divider is removed from the sealed container. In step 2640, the isocyanate, and the biocompatible, synthetic polyol are mixed for a time sufficient to form an isocyanate prepolymer. In step 2650, at least one removable divider is removed, and in step 2660 the isocyanate prepolymer is mixed with the naturally-occurring polyol and catalyst. In step 2670, a determination is made whether the mixture is reacting to form poly(urethane-carbodiimide) components at a desired rate. If the mixture is reacting at a desired rate, the process proceeds to end. If, however, the determination is made in step 2670 that the mixture is not reacting at a desired rate, the process proceeds to step 2680, in which the sealed container is exposed to an energy source for a desired time, after which the process returns to step 2670, which previously has been described.

Figure 26B:
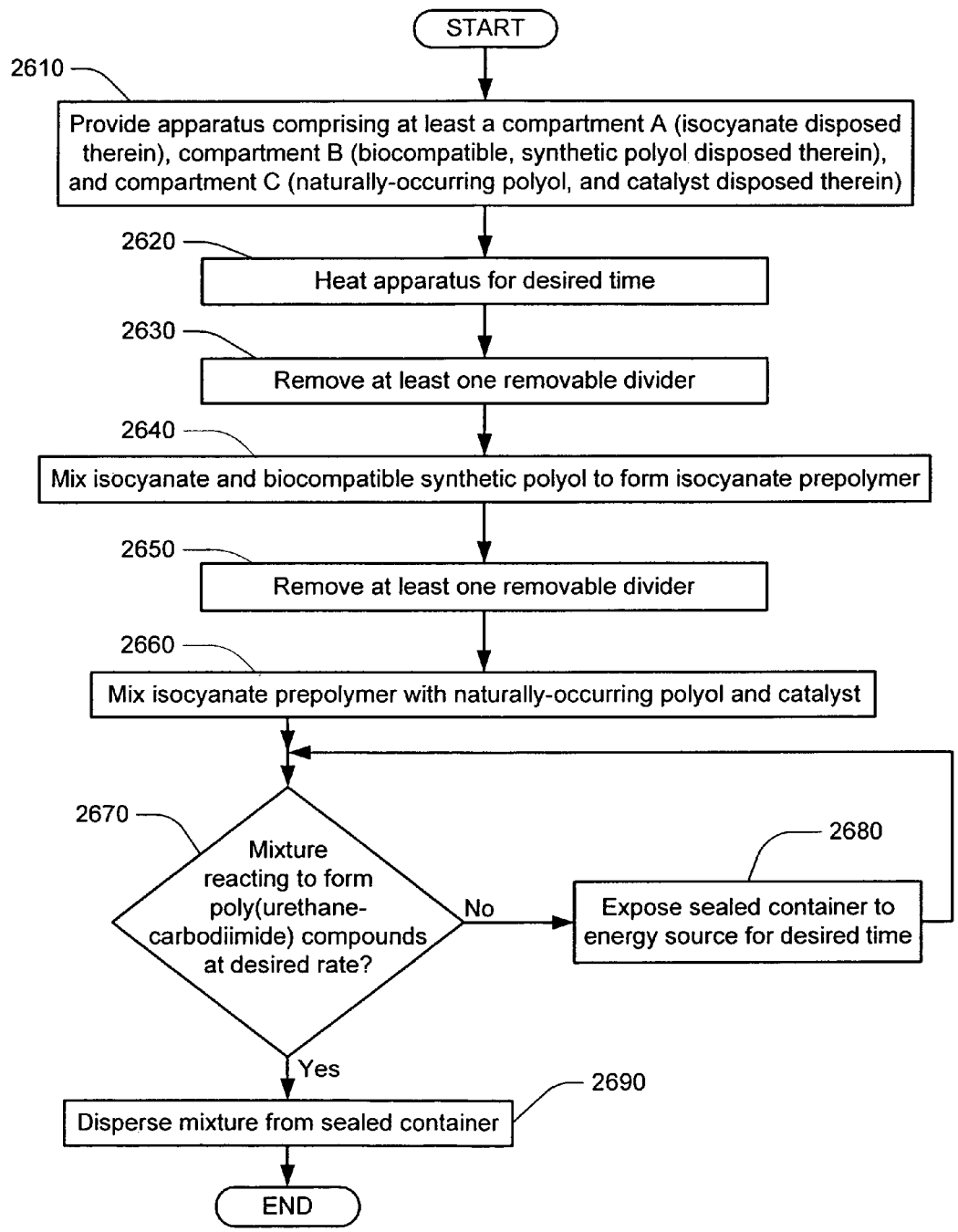
Figure 26C:
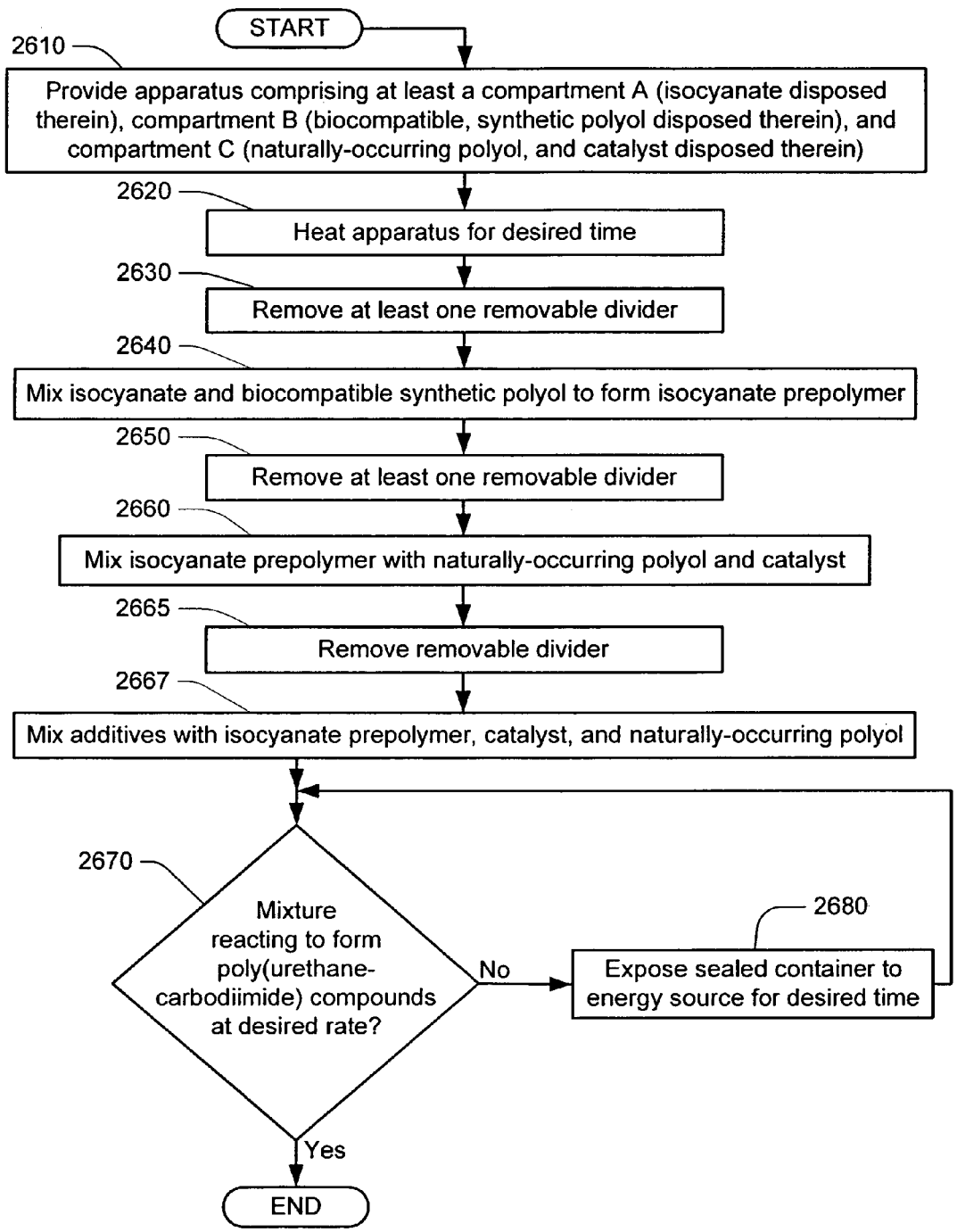
Figure 26D:
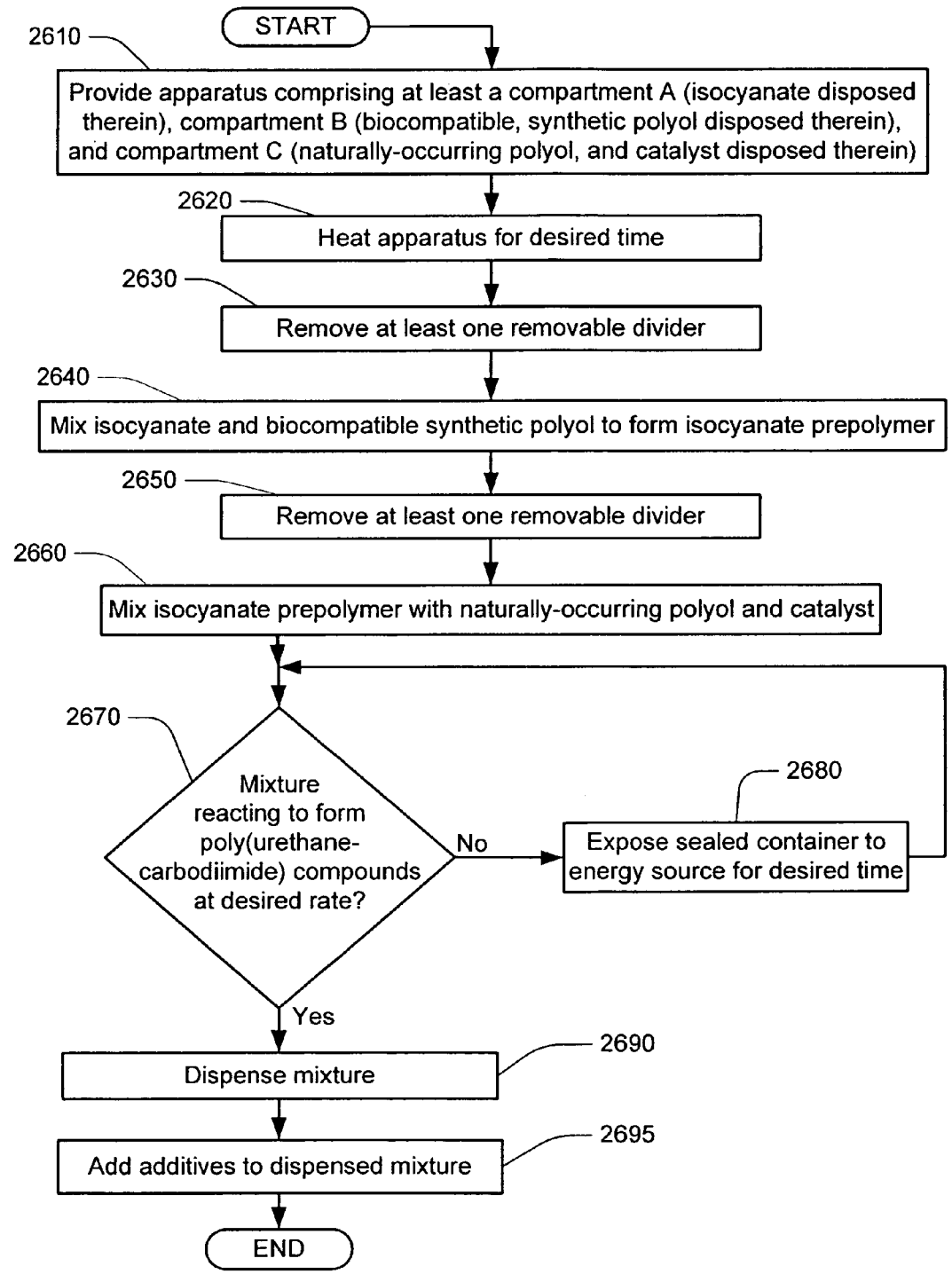

FIG. 26B illustrates the performance of an optional step 2690, wherein the mixture within the sealed container is dispensed therefrom. FIG. 26C illustrates that optional additives may be incorporated within the sealed container in a variety of ways. As illustrated in FIG. 26C, in certain embodiments, the process may comprise optional step 2665 (shown in FIG. 26C) wherein a removable divider is removed, and optional step 2667 (shown in FIG. 26C) wherein the sealed container is manipulated (e.g., manually manipulated) to mix the optional additives with the mixture of the isocyanate prepolymer, naturally-occurring polyol, and catalyst. The process then may proceed from step 2667 to step 2670, which previously has been described.

Alternatively, in certain embodiments of the present invention, certain of the optional additives may be introduced outside the sealed container, and may be incorporated once the contents of the sealed container have been dispensed therefrom. For example, after a determination is made in step 2670 that the mixture is reacting to form poly(urethane-carbodiimide) components at a desired rate, the process may proceed from step 2670 to an optional step 2690 (shown in FIG. 26D) wherein the reacting mixture is dispensed from the sealed container, and then may proceed to an optional step 2695 (shown in FIG. 26D) wherein at least one optional additive is mixed with the dispensed reacting mixture and permitted to remain within it as the mixture finishes reacting to form poly(urethane-carbodiimide) components, after which the process may proceed to end.

Figure 26E:
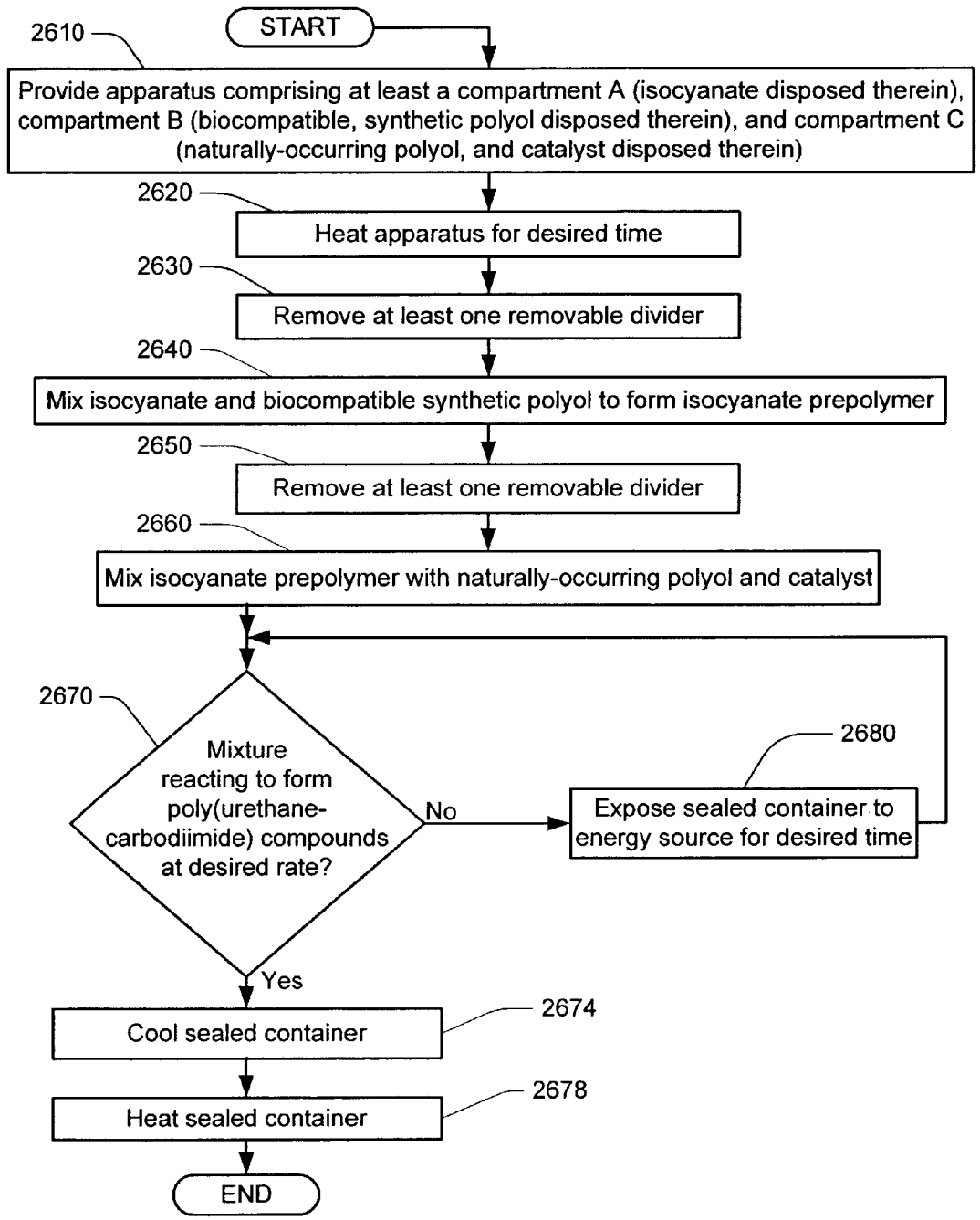

FIG. 26E illustrates that in certain embodiments of the present invention, the sealed container may be cooled at any point in the process so as to suspend or delay, at least temporarily, the reaction occurring therein, and illustrates the use of optional cooling step 2674 (shown in FIG. 26E), wherein the sealed container is cooled to a desired temperature until such time as re-initiation of the reaction is desired, and optional heating step 2678 (shown in FIG. 26E), wherein the sealed container may be heated for a desired time to a desired temperature, and the mixture within the sealed container may resume reacting.

Figure 26F:
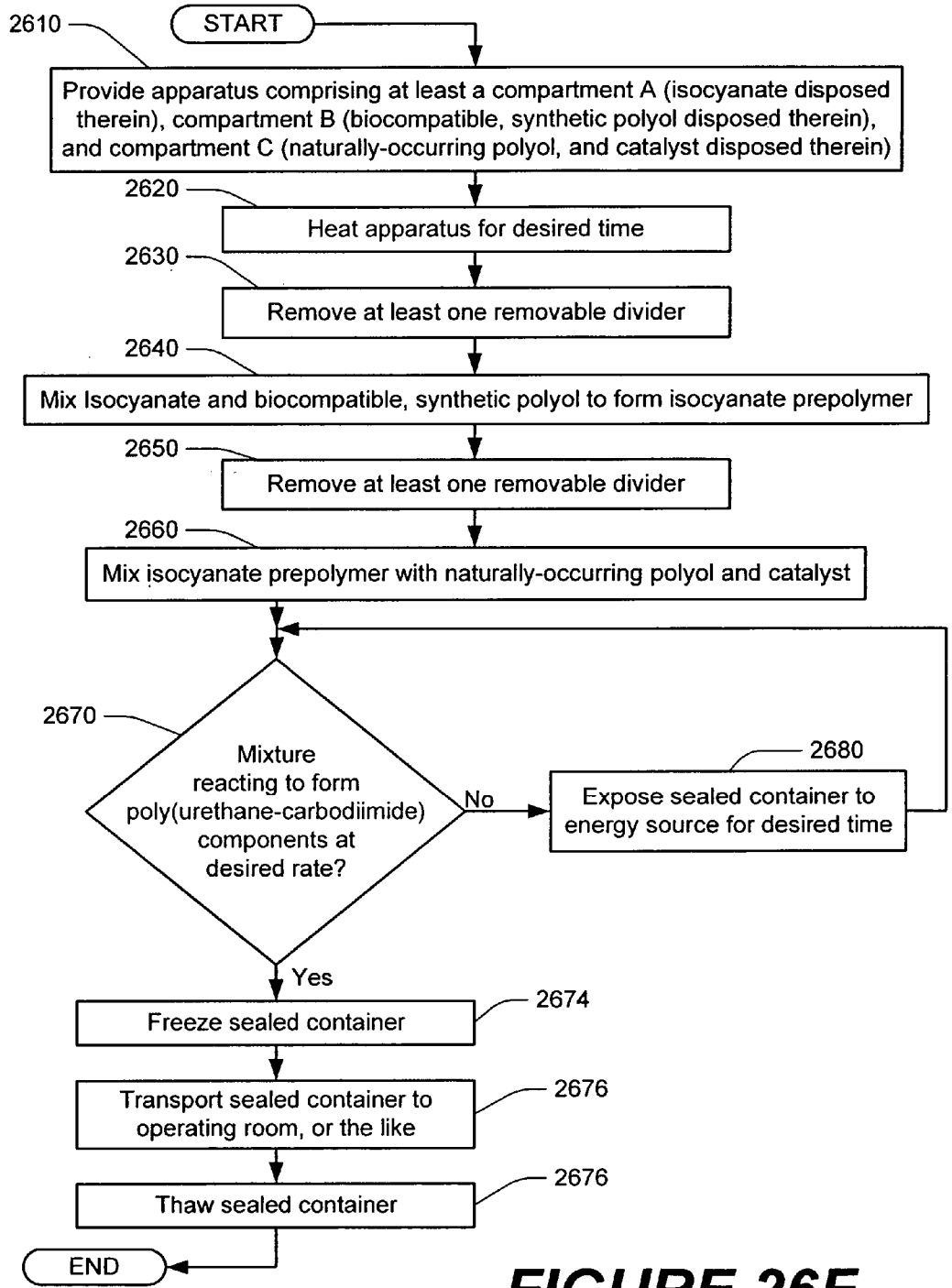

FIG. 26F illustrates that in certain embodiments of the present invention, optional step 2674 (as shown in FIG. 26F) may involve freezing the sealed container at a desired time after the container have been permitted to partially react. The process then may proceed to optional step 2676 (shown in FIG. 26F), in which the sealed container is transported to an operating room, or the like, and then to optional step 2678 (shown in FIG. 26F), in which the sealed container is thawed, after which the contents of the sealed container are dispensed and implanted within the body of a mammal, wherein the contents of the sealed container may finish reacting (e.g., "cure") to form poly(urethane-carbodiimide) components.

FIGS. 27A-27F illustrate how reactions such as those described with reference to FIGS. 26A-26F may be carried out through the use of another embodiment of an apparatus of the present invention, one comprising both a sealed outer container and a sealed inner container. Because certain features and advantages of the embodiments described in FIGS. 27A-27F are substantially similar to certain features and advantages of the embodiments described with reference to FIGS. 26A-26F, such similar features and advantages are not discussed further with respect to the embodiments illustrated in FIGS. 27A-27F.

Figure 27A:
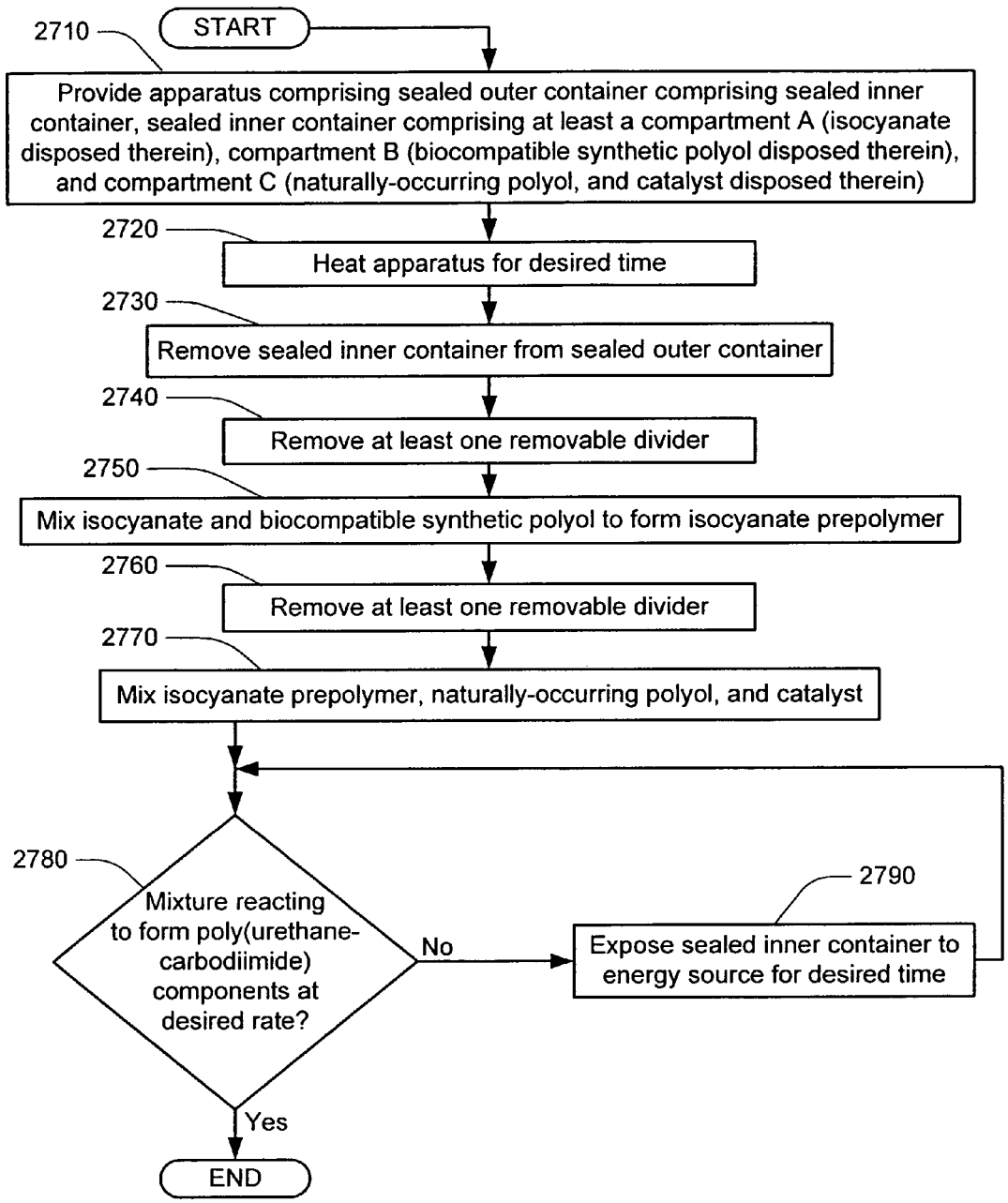

Referring now to FIG. 27A, in step 2710, an apparatus is provided comprising a sealed outer container, within which is disposed a sealed inner container. The sealed inner container itself comprises an internal cavity that is separated by a plurality of removable dividers into at least a compartment A, a compartment B, and a compartment C. An isocyanate may be disposed within compartment A. A biocompatible, synthetic polyol may be disposed within compartment B. A naturally-occurring polyol and a catalyst may be disposed within compartment C. Examples of suitable catalysts include, inter alia, triphenylphosphine oxide, hexamethylphosphoric triamide, and the like. The equivalent ratio of isocyanate groups to total hydroxyl groups may be in the range of from about 1.05:1 to about 4:1. In step 2720, the apparatus may be heated for a desired time at a desired temperature. In certain embodiments, the apparatus may be heated to a temperature in the range of from about 100° C. to about 160° C. In step 2730, the sealed inner container may be removed from within the sealed outer container. In step 2740, at least one removable divider is removed from the sealed inner container. In step 2750, the isocyanate, and the biocompatible, synthetic polyol are mixed for a time sufficient to form an isocyanate prepolymer. In step 2760, at least one removable divider is removed, and in step 2770 the isocyanate prepolymer is mixed with the naturally-occurring polyol and catalyst. In step 2780, a determination is made whether the mixture is reacting to form poly(urethane-carbodiimide) components at a desired rate. If the mixture is reacting at a desired rate, the process proceeds to end. If, however, the determination is made in step 2780 that the mixture is not reacting at a desired rate, the process proceeds to step 2790, in which the sealed container is exposed to an energy source for a desired time, after which the process returns to step 2780, which previously has been described.

Figure 27B:
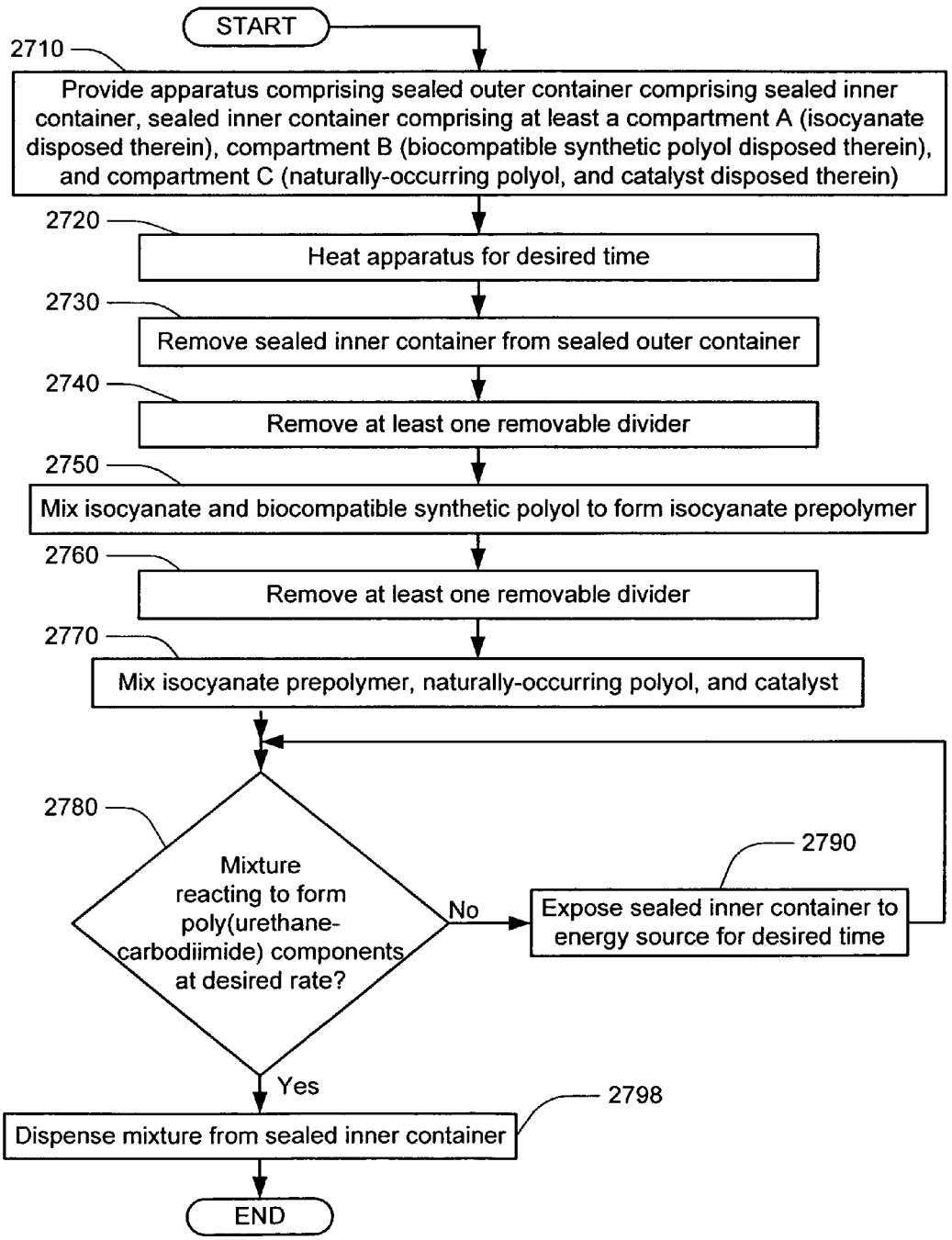
Figure 27C:
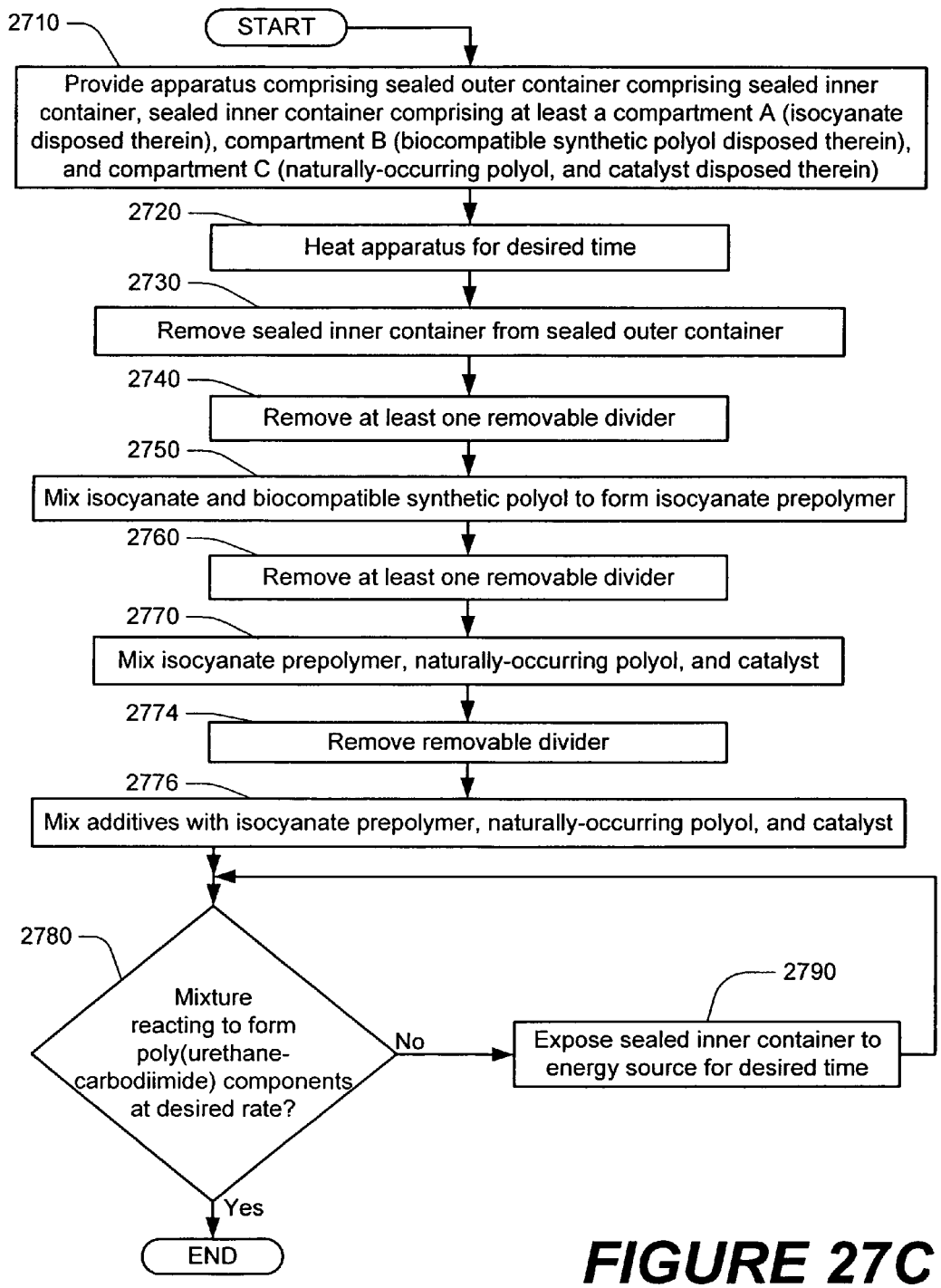
Figure 27D:
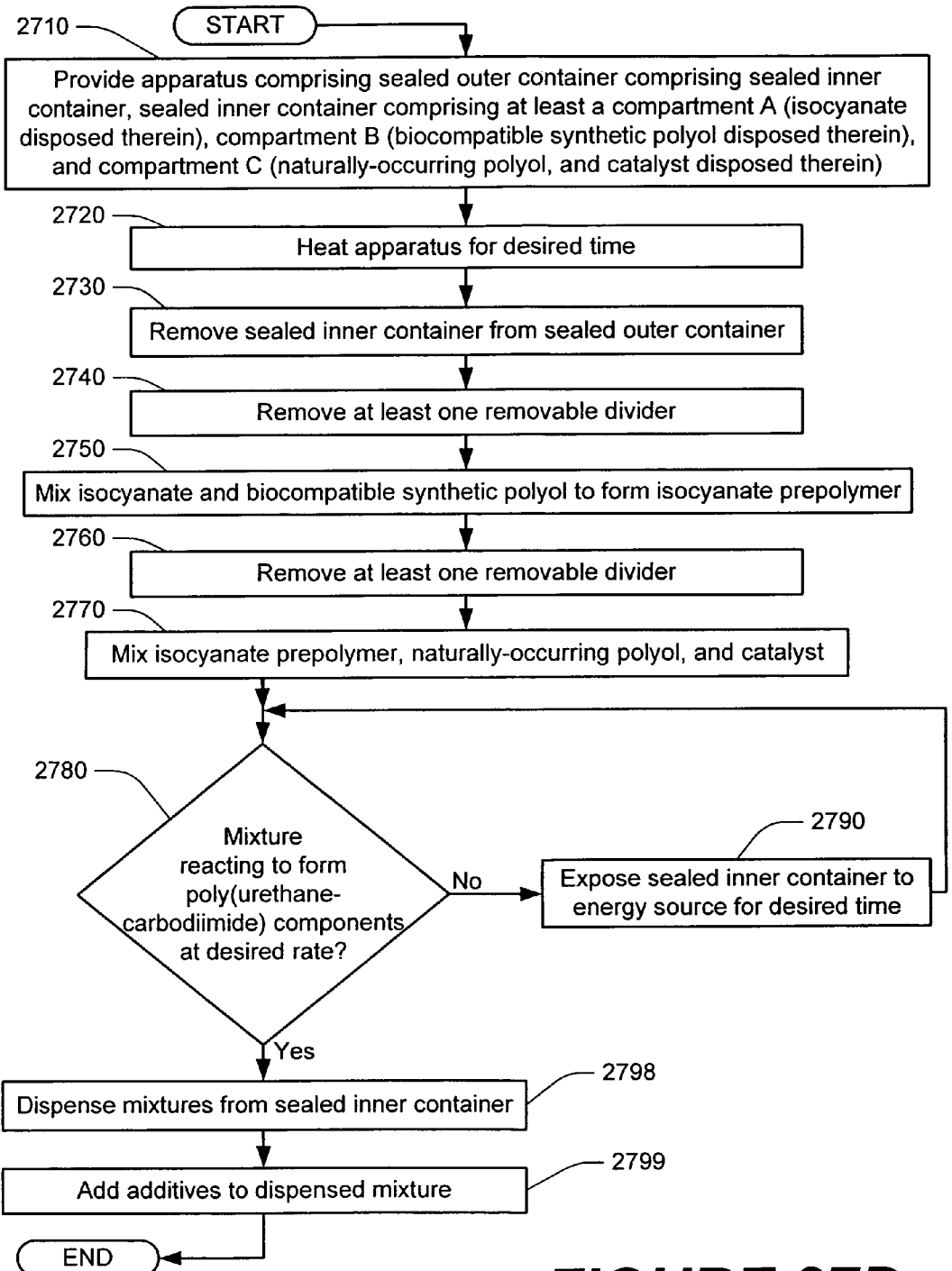

FIG. 27B illustrates the performance of an optional step 2798, wherein the mixture within the sealed inner container is dispensed therefrom. FIG. 27C illustrates that optional additives may be incorporated within the sealed inner container in a variety of ways. As illustrated in FIG. 27C, in certain embodiments, the process may comprise optional step 2774 (shown in FIG. 27C) wherein a removable divider is removed, and optional step 2776 (shown in FIG. 27C) wherein the sealed inner container is manipulated (e.g., manually manipulated) to mix the optional additives with the mixture of the isocyanate prepolymer, naturally-occurring polyol, and catalyst. The process then may proceed from step 2776 to step 2780, which previously has been described.

Alternatively, in certain embodiments of the present invention, certain of the optional additives may be introduced outside the sealed inner container, and may be incorporated once the contents of the sealed inner container have been dispensed therefrom. For example, after a determination is made in step 2780 that the mixture is reacting to form poly(urethane-carbodiimide) components at a desired rate, the process may proceed from step 2780 to an optional step 2798 (shown in FIG. 27D) wherein the reacting mixture is dispensed from the sealed inner container, and then may proceed to an optional step 2799 (shown in FIG. 27D) wherein at least one optional additive is mixed with the dispensed reacting mixture and permitted to remain within it as the mixture finishes reacting to form poly(urethane-carbodiimide) components, after which the process may proceed to end.

Figure 27E:
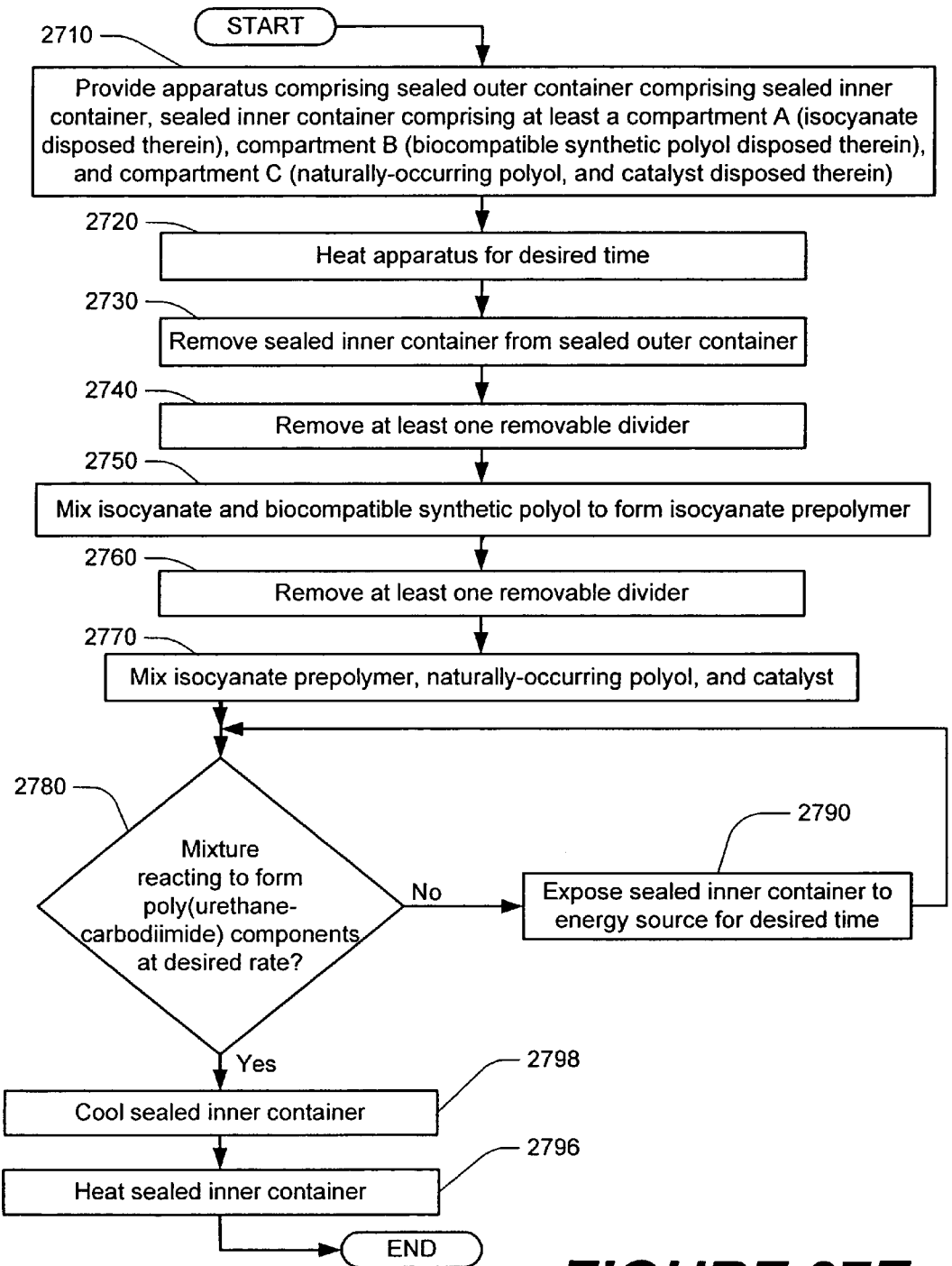

FIG. 27E illustrates that in certain embodiments of the present invention, the sealed inner container may be cooled at any point in the process so as to suspend or delay, at least temporarily, the reaction occurring therein, and illustrates the use of optional cooling step 2792 (shown in FIG. 27E), wherein the sealed inner container is cooled to a desired temperature until such time as re-initiation of the reaction is desired, and optional heating step 2796 (shown in FIG. 27E), wherein the sealed inner container may be heated for a desired time to a desired temperature, and the mixture within the sealed inner container may resume reacting.

Figure 27F:
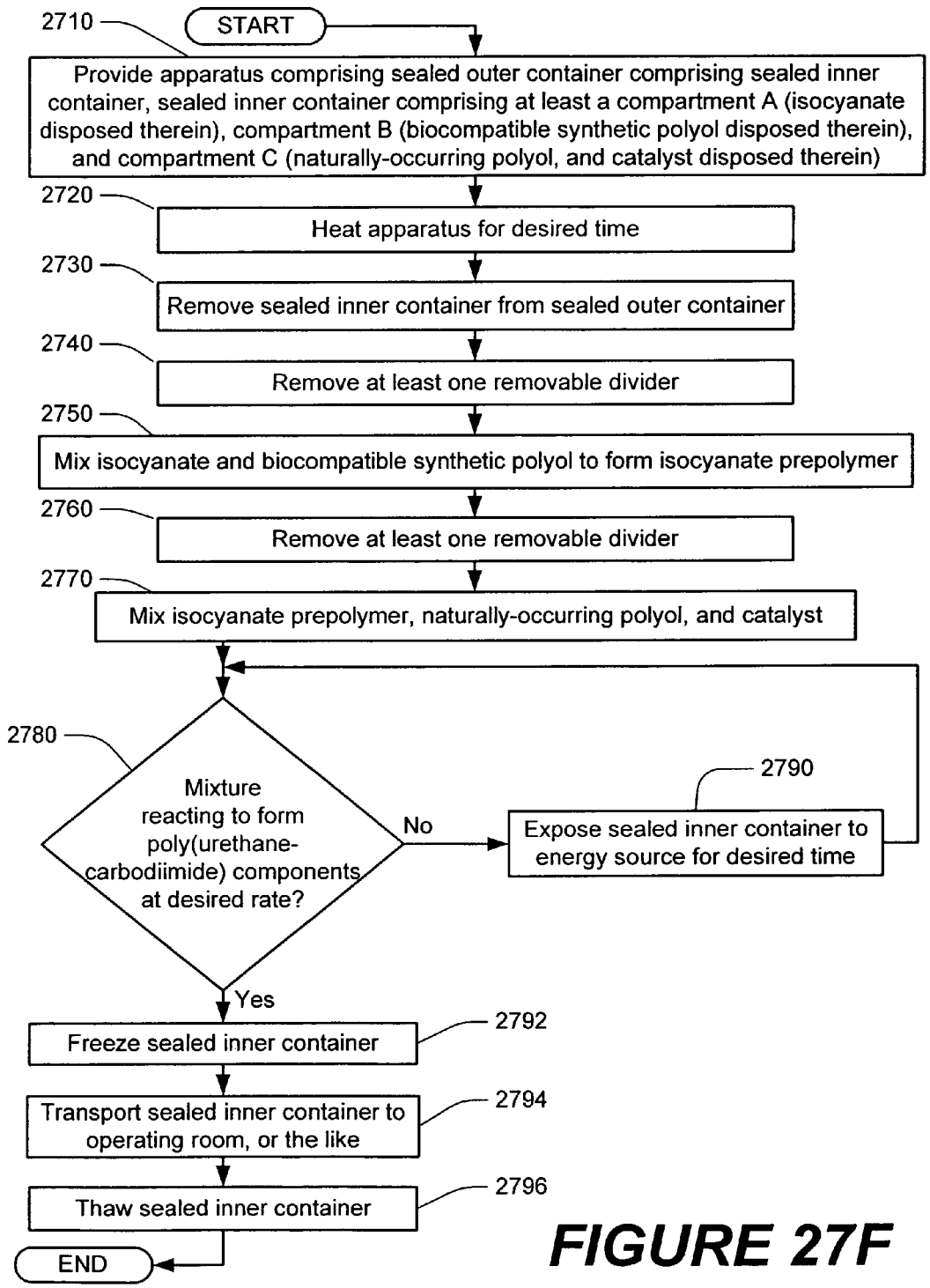

FIG. 27F illustrates that in certain embodiments of the present invention, optional step 2792 (as shown in FIG. 27F) may involve freezing the sealed inner container at a desired time after the container have been permitted to partially react. The process then may proceed to optional step 2794 (shown in FIG. 27F), in which the sealed inner container is transported to an operating room, or the like, and then to optional step 2796 (shown in FIG. 27F), in which the sealed inner container is thawed, after which the contents of the sealed inner container are dispensed and implanted within the body of a mammal, wherein the contents of the sealed inner container may finish reacting (e.g., "cure") to form poly(urethane-carbodiimide) components.

Figure 28:
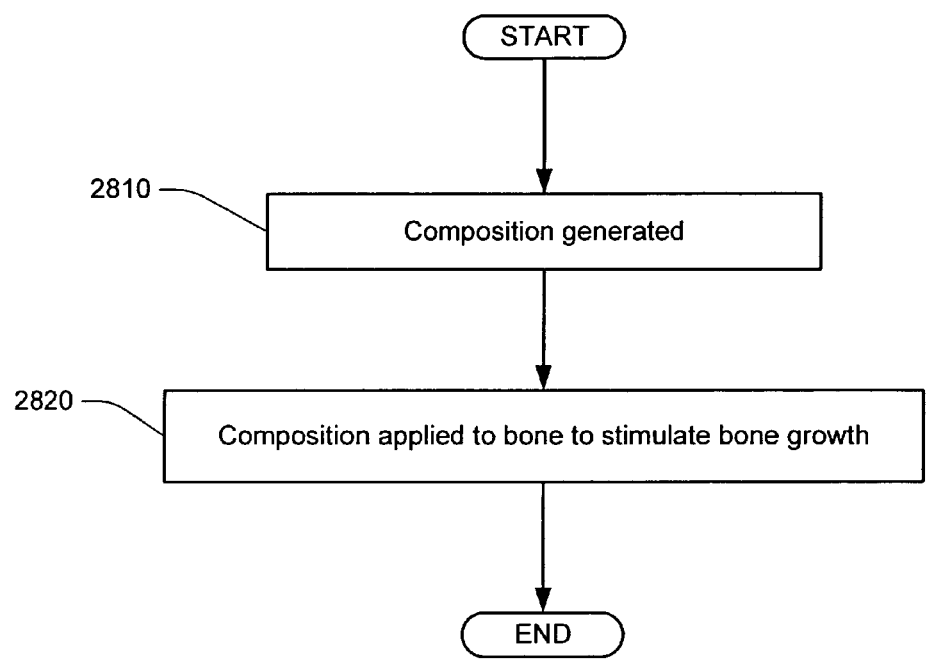
FIGS. 28-35 are top level flow-charts depicting exemplary methods for performing a medical procedure according to exemplary embodiments of the present invention.

G. Methods for Performing Medical Procedures Using Compositions Prepared According to Methods of the Present Invention FIG. 28 depicts an exemplary embodiment of a method 2800 for performing a medical procedure, e.g., a non-invasive or an invasive medical procedure. In step 2810, a composition made according to the methods of the present invention may be generated, which composition may be the same or substantially the same as any of the compositions that are described herein. In certain embodiments, the composition may be a composition that comprises polyurethane/polyurea components; in certain embodiments, the composition may comprise poly(urethane-isocyanurate)s and/or poly(urethane-urea-isocyanurate)s and/or poly(urethane-carbodiimide)s. In step 2820, the composition may be applied to a portion of a bone of a mammal. For example, a needle may be inserted through a skin of the mammal, and the composition may be dispensed onto a surface of the bone, e.g., at a location of a damaged portion of the bone, and the particular composition may stimulate bone growth.

While not willing to be bound by a theory, it is believed that cyclic adenosine monophosphate (cyclic AMP) regulated lipases within the body of a mammal may facilitate the metabolism of the compositions made according to the methods of the present invention after placement of these compositions in contact with, or in the vicinity of, a bone of the mammal. The compositions that comprise polyurethane/polyurea components, poly(urethane-isocyanurate) components, poly(urethane-urea-isocyanurate) components, and/or poly(urethane-carbodiimide) components generally comprise at least one ester group within their chemical structure. Water that naturally is present within the mammal then may react with the at least one ester group so as to be converted, for example, into glycerol, fatty acids, and the conversion of adenosine diphosphate to adenosine triphosphate. While not willing to be bound by theory, it is believed that adenosine triphosphate units within the mammal may support various anabolic activities that may result in the formation of bone.

When a composition made according to the methods of the present invention is placed in contact with, or in the vicinity of, a bone of a mammal, the composition may be a liquid, and may conform to a shape of the bone. The composition may transform into a solid after such placement within the mammal. In another embodiment of the present invention, method 2800 also may comprise the step of increasing or decreasing a temperature of the composition before or after the placement of the composition within the body of the mammal. Increasing the temperature of the composition may decrease an amount of time which it takes for the particular composition to transform or cure from a liquid to a solid. Analogously, decreasing the temperature of the composition may increase an amount of time which it takes for such transformation or curing of the composition to occur.

FIGS. 29 through 36 illustrate additional exemplary methods of the present invention for performing a medical procedure. Because certain features and advantages of these embodiments of the present invention are substantially similar to certain features and advantages of the above-described embodiments of the present invention, such similar features and advantages of the above-described embodiments of the present invention are not discussed further with respect to the embodiments of the present invention illustrated in FIGS. 29 through 36.

Figure 29:
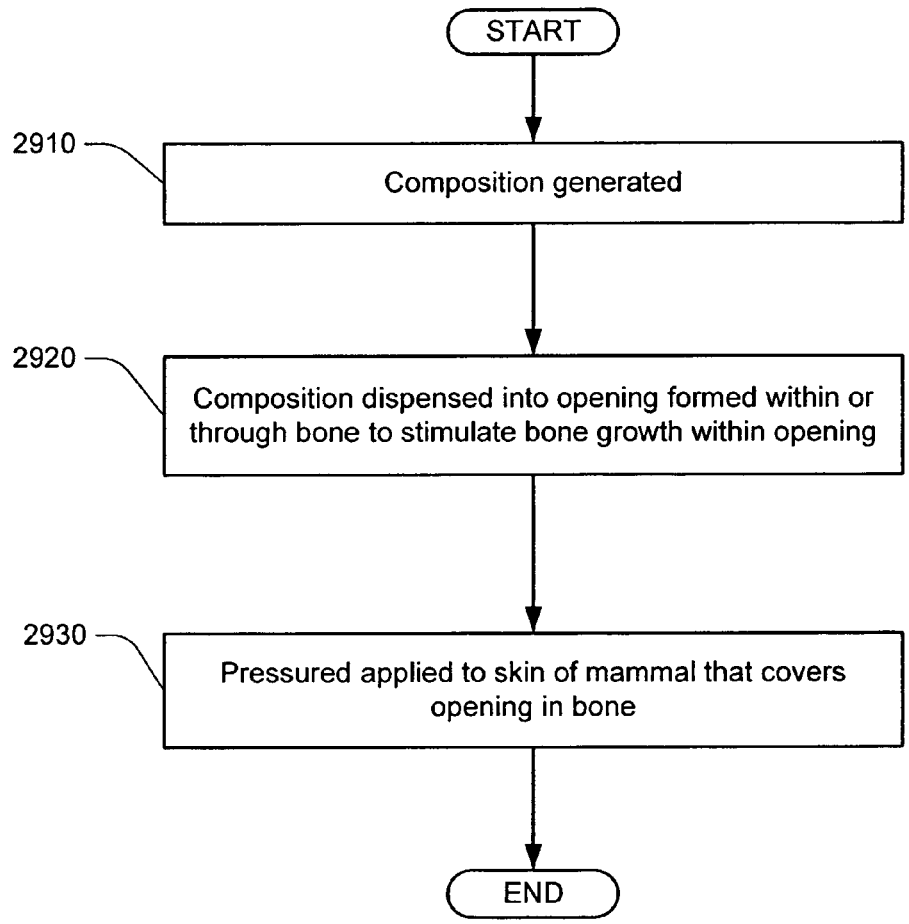

Referring now to FIG. 29, another exemplary embodiment of a method 2900 for performing a medical procedure, e.g., a non-invasive or an invasive medical procedure, is depicted therein. In step 2910, a composition made according to the methods of the present invention may be generated, which composition may be the same or substantially the same as any of the compositions that are described herein. In step 2920, the composition is dispensed into an opening formed within or through at least one portion of a bone of a mammal. In an exemplary embodiment, method 2900 also may comprise step 2930, wherein pressure is applied to a skin of the mammal that covers the opening in the bone, which may alter the shape of the composition of the present invention within the opening.

Figure 30:
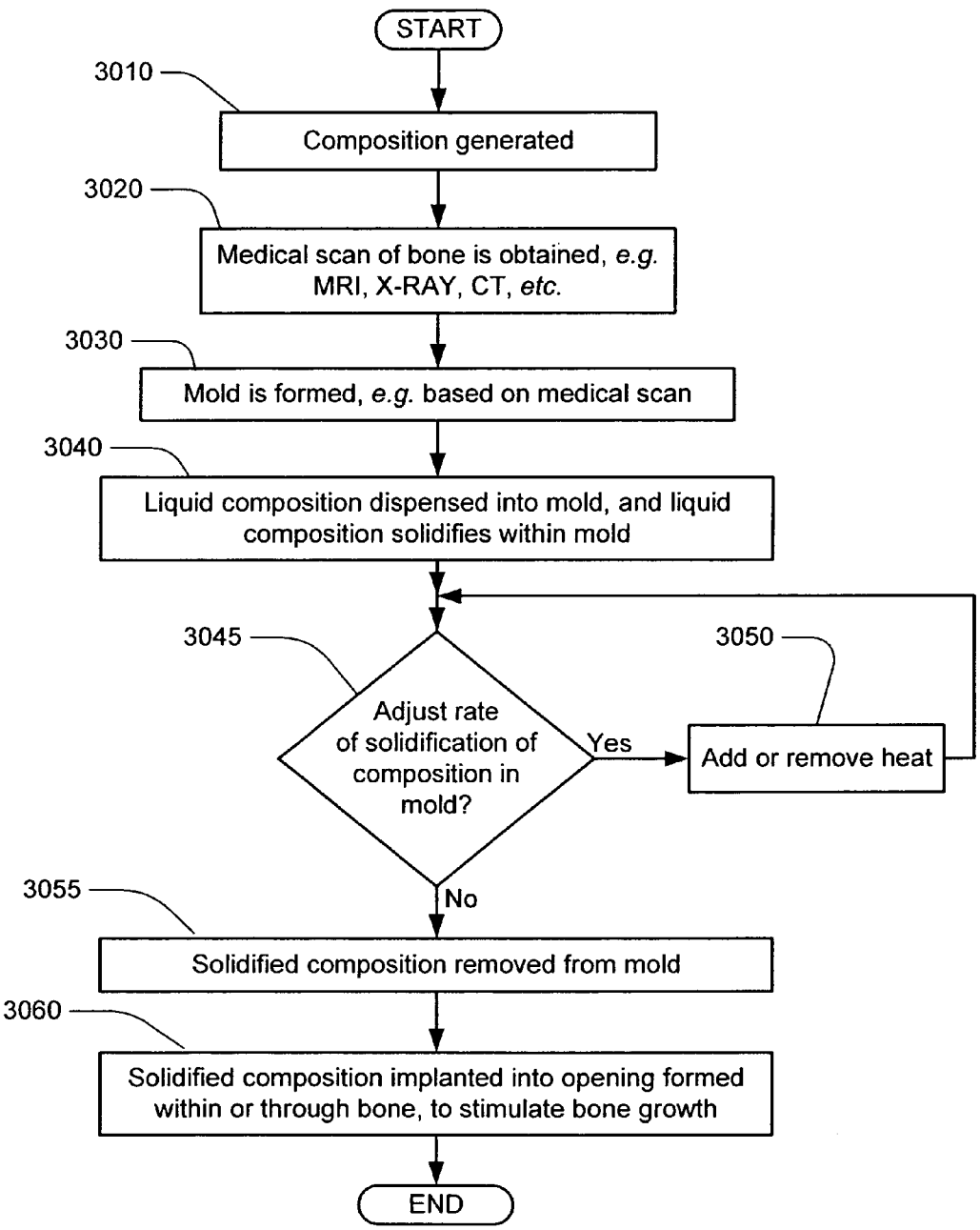

FIG. 30 illustrates still another exemplary embodiment of a method 3000 for performing a medical procedure, e.g., a non-invasive or an invasive medical procedure. In step 3010, a composition made according to the methods of the present invention may be generated, which composition may be the same or substantially the same as any of the compositions that are described herein. In step 3020, a medical scan of a bone of a mammal may be obtained, e.g., a CT scan, an MRI scan, an X-ray scan, or the like. In step 3030, a mold may be formed, e.g., based on the medical scan or based on a generic size for the mold, and in step 3040, the liquid composition of the present invention may be dispensed into the mold, and permitted to solidify therein. In step 3045, the operator determines whether or not to adjust the rate at which the composition solidifies within the mold. If the operator elects to adjust the rate of solidification, the process proceeds to step 3050, wherein the operator adjusts the rate of solidification, e.g., by adding or removing heat. Generally, the addition of heat will increase the rate of solidification, whereas the removal of heat will decrease the rate of solidification. From step 3050, the process returns to the determination in step 3045. If, in step 3045, the operator elects not to adjust the rate of solidification, the process proceeds to step 3055. In step 3055, the solidified composition may be removed from the mold, and in step 3060, the solidified composition may be implanted into an opening formed within or through at least one portion of the bone.

Figure 31:
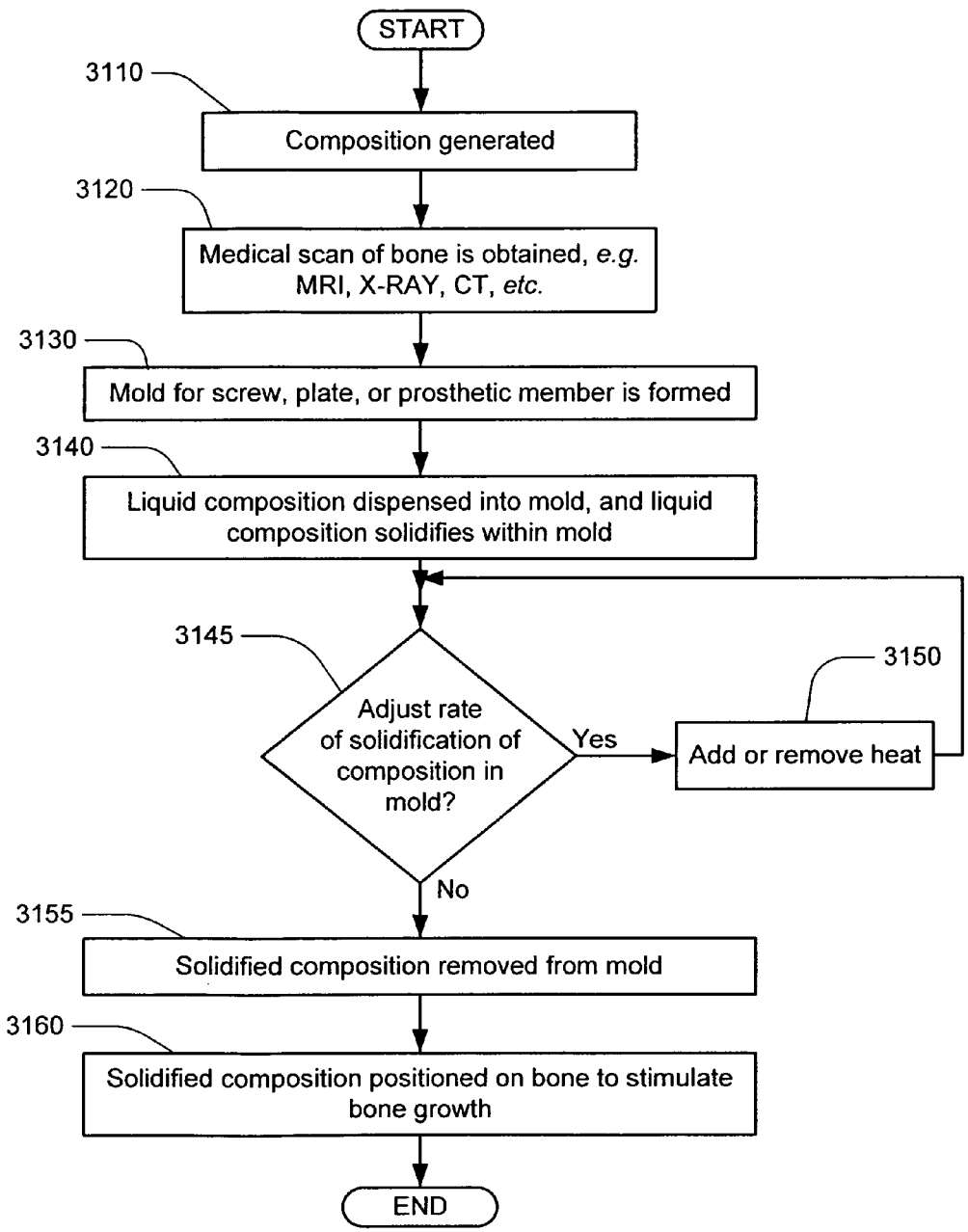

FIG. 31 illustrates another exemplary embodiment of a method 3100 for performing a medical procedure, e.g., a non-invasive or an invasive medical procedure. In step 3110, a composition made according to the methods of the present invention may be generated, which composition may be the same or substantially the same as any of the compositions that are described herein. In step 3120, a medical scan of a bone of a mammal may be obtained, e.g., a CT scan, an MRI scan, an X-ray scan, or the like. In step 3130, a mold may be formed, e.g., based on the medical scan or based on a generic size for the mold, and in step 3140, the liquid composition may be dispensed into the mold, and permitted to solidify therein. In step 3145, the operator determines whether or not to adjust the rate at which the composition solidifies within the mold. If the operator elects to adjust the rate of solidification, the process proceeds to step 3150, wherein the operator adjusts the rate of solidification, e.g., by adding or removing heat. Generally, the addition of heat will increase the rate of solidification, whereas the removal of heat will decrease the rate of solidification. From step 3150, the process returns to the determination in step 3145. If, in step 3145, the operator elects not to adjust the rate of solidification, the process proceeds to step 3155. In step 3155, the solidified composition of the present invention may be removed from the mold, and in step 3160, the solidified composition of the present invention may be positioned on at least one portion of the bone.

Figure 32:
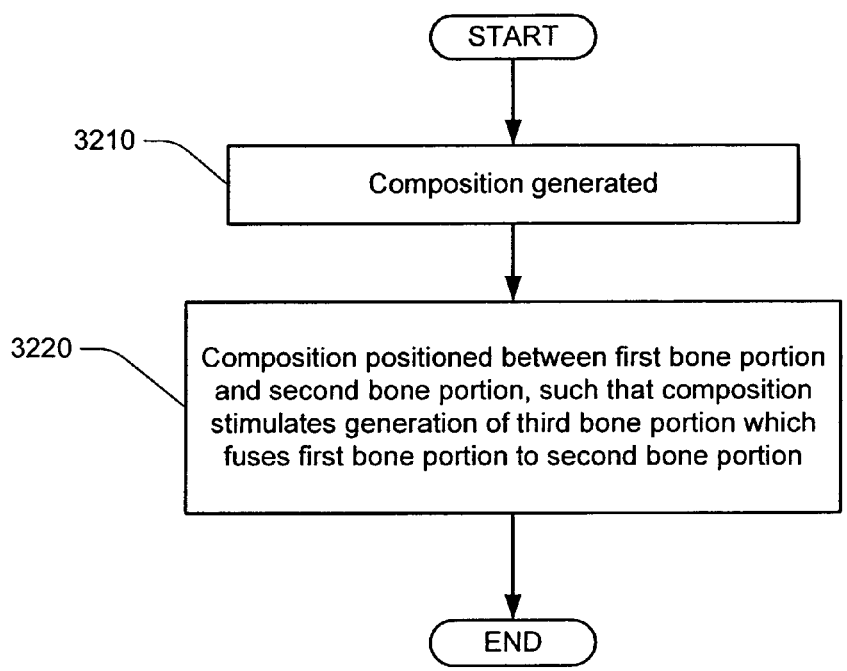

FIG. 32 illustrates still another exemplary embodiment of a method 3200 for performing a medical procedure, e.g., a non-invasive or an invasive medical procedure. In step 3210, a composition made according to the methods of the present invention may be generated, which composition may be the same or substantially the same as any of the compositions that are described herein. In step 3220, the composition may be positioned between a first bone portion of a mammal and a second bone portion of the mammal for fusing the first bone portion to the second bone portion, such that the composition stimulates the growth of a third bone portion that fuses the first bone portion to the second bone portion. For example, the composition may be injected into a balloon, and the balloon may be positioned between the first bone portion and the second bone portion. In an exemplary embodiment, the balloon may rest on tissue of the mammal, and the tissue may degrade the balloon before the composition solidifies. Moreover, the same bone within the mammal may comprise each of the first bone portion and the second bone portion, or a first bone may comprise the first bone portion and a second bone may comprise the second bone portion. For example, the first bone may be a first vertebra of a spine of the mammal and the second bone may be a second vertebra of the spine.

Figure 33:
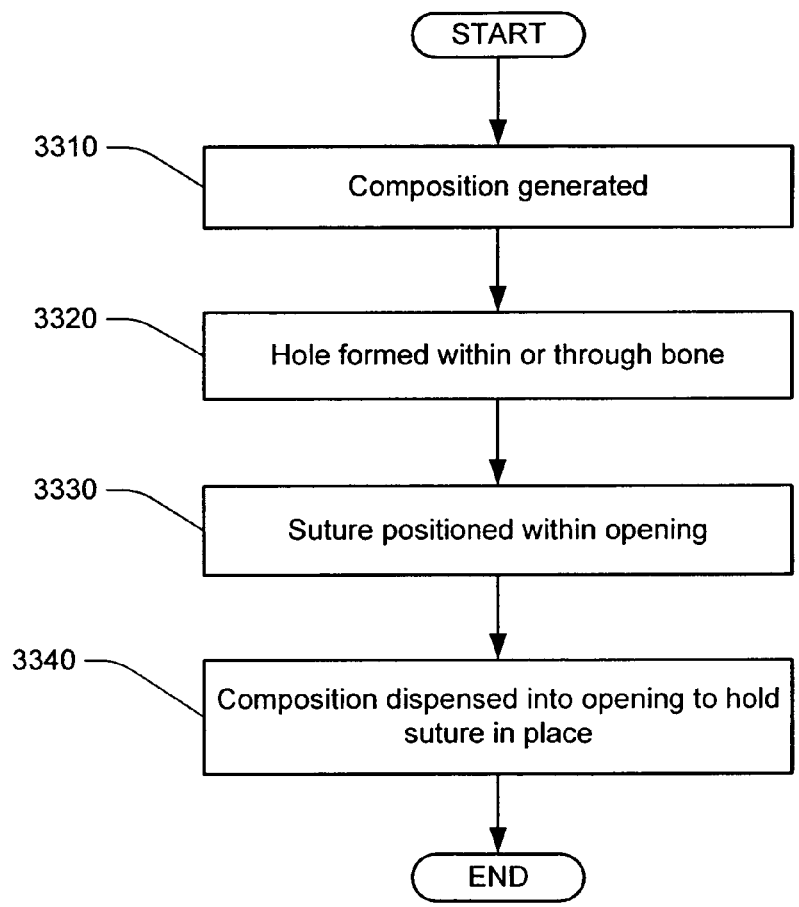

FIG. 33 depicts another exemplary embodiment of a method 3300 for performing a medical procedure, e.g., a non-invasive or an invasive medical procedure. In step 3310, a composition made according to the methods of the present invention may be generated, which composition may be the same or substantially the same as any of the compositions that are described herein. In step 3320, a hole in a bone of a mammal may be formed, e.g., drilled, within or through the bone. In step 3330, at least one suture may be positioned within the opening formed within or through the bone. For example, a fluid or a powder which prevents the suture from adhering to the composition may be applied to the suture, and then the suture may be dispensed in the opening. In step 3340, the composition may be dispensed into the opening to prevent the suture from falling out of the opening.

Figure 34:
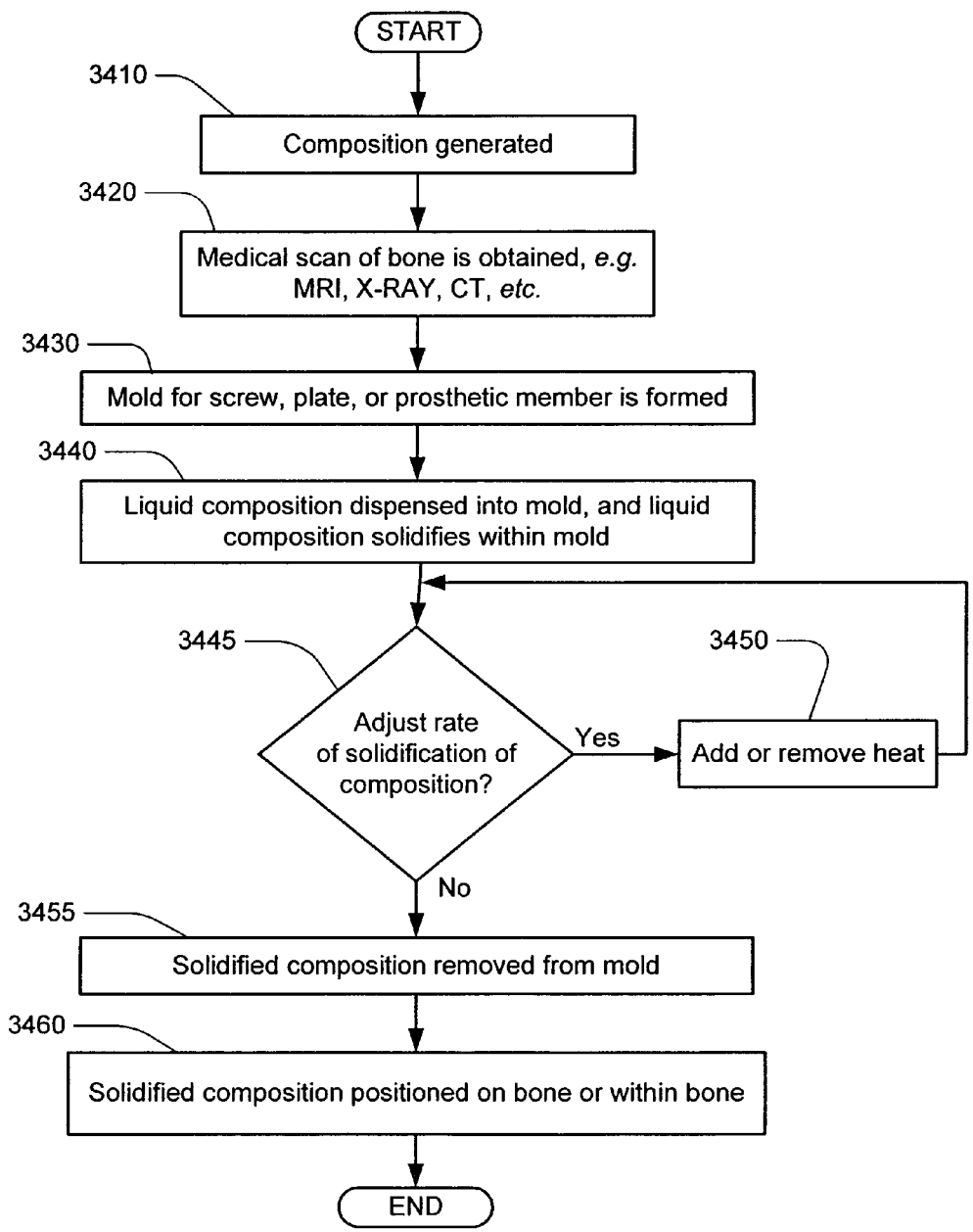

FIG. 34 depicts another exemplary embodiment of a method 3400 for performing a medical procedure, e.g., a non-invasive or an invasive medical procedure. In step 3410, a composition made according to the methods of the present invention may be generated, which composition may be the same or substantially the same as any of the compositions that are described herein. In step 3420, a medical scan of a bone of a mammal may be obtained, e.g., a CT scan, an MRI scan, an X-ray scan, or the like. In step 3430, a mold may be formed, which mold may comprise a mold for a screw, a mold for a plate, a mold for a prosthetic member, or the like. In step 3440, the liquid composition may be dispensed into the mold, and permitted to solidify therein. In step 3445, the operator determines whether or not to adjust the rate at which the composition solidifies within the mold. If the operator elects to adjust the rate of solidification, the process proceeds to step 3450, wherein the operator adjusts the rate of solidification, e.g., by adding or removing heat. Generally, the addition of heat will increase the rate of solidification, whereas the removal of heat will decrease the rate of solidification. From step 3450, the process returns to the determination in step 3445. If, in step 3445, the operator elects not to adjust the rate of solidification, the process proceeds to step 3455. In step 3455, the solidified composition of the present invention may be removed from the mold, and in step 3460, the solidified composition of the present invention may be positioned on a bone of a mammal or within an opening formed within the bone.

Figure 35:
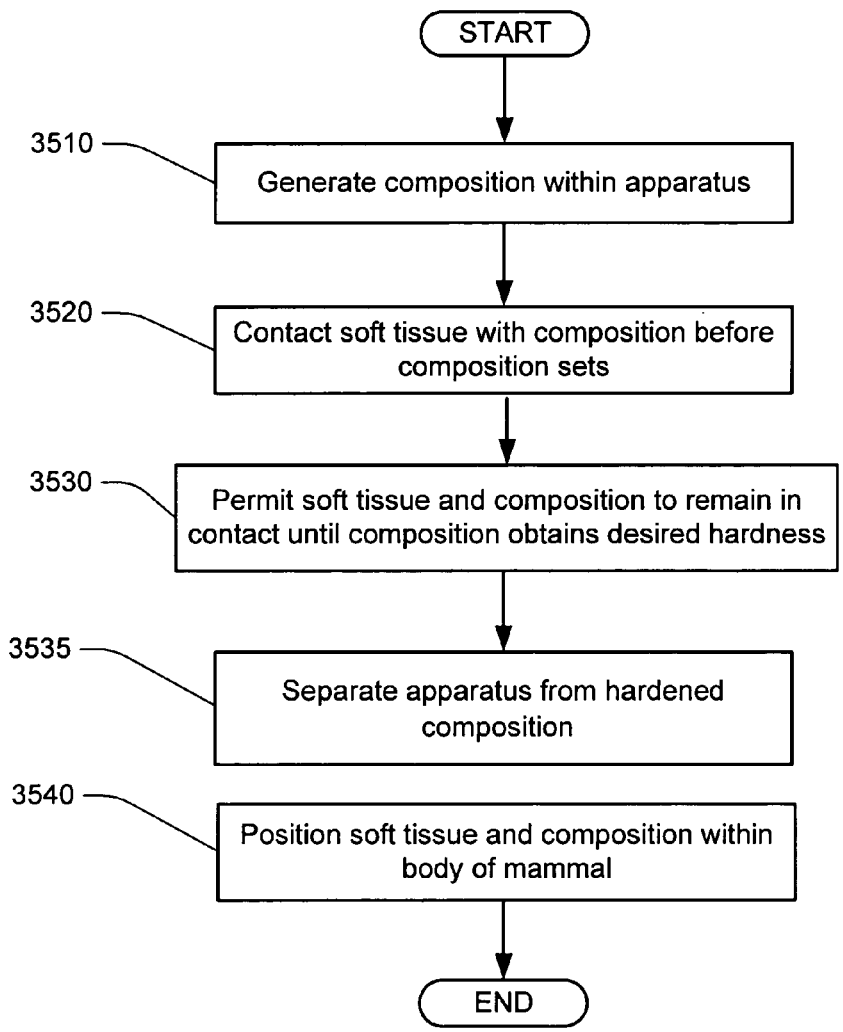

FIG. 35 depicts another exemplary embodiment of a method 3500 for performing a medical procedure, e.g., a non-invasive or an invasive medical procedure. In step 3510, a composition made according to the methods of the present invention may be generated within an apparatus of the present invention, which composition may be the same or substantially the same as any of the compositions that are described herein. In step 3520, a soft tissue (e.g., a tendon, such as a cadaver's tendon or a patient's own tendon) of a mammal may be placed in contact with the composition before the composition has set. The soft tissue may be inserted into an apparatus of the present invention while a composition of the present invention is resident therein, and the soft tissue may thereby contact, and be immersed within, the composition. For example, referring now to FIG. 2, tear notch 130 may be used to form an opening (not shown in FIG. 2) within apparatus 100, and a soft tissue (not shown in FIG. 2) may be inserted into the opening to a desired extent (e.g., about one inch, in some embodiments). Referring again to FIG. 35, in step 3530, the soft tissue is permitted to remain in contact with the composition until the composition has hardened to a desired degree (for example, the composition may be in a "late-taffy" stage, or the composition may be in solid state, and may have fully polymerized). Next, in step 3535, the apparatus of the present invention is separated (e.g., peeled back) from the hardened composition. In step 3540, the solidified composition and the soft tissue resident therein may be positioned within the body of a mammal. Among other benefits, the above-described method 3500 provides an opportunity to mate the compositions of the present invention with soft tissue in an environment separate from an operating room, to therefore simplify subsequent attachment of the composition to the soft tissue during an operation. Another benefit of the above-described method 3500 is that the shape of the implant (e.g., the solidified composition and the soft tissue resident therein) may be controlled by the geometry of the apparatus of the present invention. For example, by placing the soft tissue within a triangular section of the apparatus (e.g., the triangular section at the right-hand side of compartment C in FIG. 1A, for example), the implant will be formed in a triangular shape, without need of a separate step in which the composition is poured into, for example, a triangular mold, to be contacted therein with the soft tissue. Among other things, the above-described method 3500 may reduce the time during which the mammal is required to be in the operating room, and may improve the interface between the soft tissue and existing equipment.

FIG. 36 illustrates an embodiment of the present invention in which partially-cured particles may be formed via a first reaction that is permitted to proceed only partially toward completion, after which the partially-cured particles may be included within an apparatus of the present invention for use in a second reaction that is permitted to proceed to completion. For example, a composition of the present invention (including, by way of example, an isocyanate, a naturally occurring polyol and a biocompatible, synthetic polyol) may be prepared, heated for a time sufficient to at least partially react the components (e.g., about 15-20 minutes, in certain embodiments), at which point the composition may be crushed into small particles that will have been partially cured. Next, these partially-cured particles optionally may be included within another composition of the present invention (for example, a composition that includes, inter alia, an isocyanate prepolymer and a crosslinker or chain-extender), and this composition comprising partially-cured particles may be permitted to react fully to form a composition of the present invention comprising biocompatible polyurethane/polyurea components.

Referring now to FIG. 36, in step 3610 a first compound is provided that comprises a mixture of a naturally-occurring polyol and a biocompatible, synthetic polyol. In step 3615, an isocyanate is provided. In step 3620, the first compound and isocyanate may be heated to a desired degree. In step 3625, the first compound and isocyanate may be mixed for a time sufficient to at least partially react the first compound and isocyanate (e.g., for a time in the range of from about 15-20 minutes, in certain embodiments). In step 3630, the partially-reacted mixture of the first compound and isocyanate may be crushed into partially-cured particles having a desired size; a broad variety of particle sizes may be suitable, and one of ordinary skill in the art, with the benefit of this disclosure, will be able to identify a suitable particle size for a particular application. In step 3635, an unsealed container may be provided (e.g., unsealed container 110u, as illustrated in FIG. 6G), that comprises an internal cavity (e.g., internal cavity 120, as shown in FIG. 6G) partitioned into at least a compartment A, a compartment B, and a compartment C. In step 3640, a desired amount of partially-cured particles may be disposed within compartment C. In step 3645, an isocyanate prepolymer may be disposed within compartment A, and a crosslinker/chain-extender may be disposed within compartment B. In step 3650, the unsealed container 110u may be sealed (e.g., heat sealed) to form a sealed container (e.g., sealed container 110, as shown in FIG. 1A, for example). In step 3655, the sealed container may be heated for a desired time at a desired temperature. In step 3660, removable dividers separating the compartments may be removed. In step 3665, the sealed container may be manipulated so as to mix the isocyanate prepolymer, the crosslinker/chain-extender, and the partially-cured particles to a desired degree. In step 3670, a determination may be made whether the mixture is reacting to form polyurethane/polyurea components at a desired rate. If, in step 3670, the mixture is not determined to be reacting at a desired rate, then the process may proceed to step 3675, in which the sealed container is exposed to an energy source for a desired time, after which the process proceeds back to step 3670. If, in step 3670, the mixture is determined to be reacting at a desired rate, then the process proceeds to end.

In still another embodiment of the present invention, laser-beam polymerization may be used. For example, compositions of the present invention that comprise suitable components (e.g., adducts of isocyanates, double-bond-containing isocyanates, double-bond-containing polyols, and the like), may be polymerized by exposure to an energy source, such as a laser beam progressing through a predetermined path (e.g., stereolithography fabrication). Software, such as that which is commercially available from Materilize, may be used to fabricate or recreate 2-dimensional and 3-dimensional shapes. A computer-aided-drawing (CAD) may be used as a template, and the composition comprising the above-mentioned components. The energy source (e.g., laser beam) may be manipulated using the template so as to draw within the polymerized composition a desired shape; once the shape has been drawn, the polymerized composition having that shape may be extracted from the remainder of the composition.

Therefore, the present invention is well adapted to carry out the objects and attain the ends and advantages mentioned as well as those that are inherent therein. While the invention has been depicted and described by reference to certain embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. For example, referring to FIG. 10A, an operator may elect not to perform step 1020 (which discloses heating an apparatus of the present invention before mixing components disposed therein), and instead may elect to perform an optional step 1041 (not shown in FIG. 10A), which optional step 1041 may involve heating the apparatus after having mixed the components disposed therein. As another example, the present invention contemplates that apparatus of the present invention may be used with breakable dividers; in such embodiments wherein breakable dividers are used to separate compartments within, e.g., a sealed inner container, the portions in this disclosure that describe "removing at least one removable divider" will be understood to contemplate breaking at least one breakable divider. As another example, the present invention contemplates that a sealed container may be provided that has a plurality of ampoules (e.g., glass or plastic ampoules) disposed therein, each ampoule having disposed therein a component (e.g., an isocyanate, a polyol, an additive, an isocyanate prepolymer, partially-cured particles, and the like); in such embodiments wherein a sealed container is provided having ampoules disposed therein, the ampoules themselves may be construed as dividers that may separate or partition components within the sealed container, and portions in this disclosure that describe "removing at least one removable divider" will be understood to contemplate breaking the ampoules so as to permit communication, within the sealed container, between the components disposed within the ampoules (compounds made in such fashion may be dispensed from the sealed container through a strainer or filter so as to filter out any particles of broken plastic or glass). The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A bone-growth promoting composition, comprising: an osteoconductive polyurethane composition having in its cured state an average pore size ranging from about 5 microns to about 500 microns and a compressive strength consistent for use in bone repair, wherein the polyurethane composition is suitable for use in vivo; calcium carbonate present in an amount ranging from about 0.01% to about 55% by weight of the composition, wherein the polyurethane composition is made by the process of combining a polyol, an isocyanate, and water, and the water is present in an amount ranging from about 0.05% to about 1% by weight of the composition.

2. The composition of claim 1, wherein the water is present in an amount ranging from about 0.1% to about 1% by weight of the composition.

3. The composition of claim 1, wherein the polyol is a naturally-occurring polyol, a biocompatible, synthetic polyol or both.

4. The composition of claim 1, further comprising one or more of bone, calcium phosphate, calcium pyrophosphate, hydroxyapatite, poly methyl methacrylate, glass-ionomer, calcium sulfate, or tricalcium phosphate.

5. The composition of claim 1, wherein the isocyanate is an aromatic isocyanate.

6. The composition of claim 1, wherein the compressive strength is at least 50 MPa.

7. The composition of claim 1, wherein the composition is initially in a moldable state and cures into a solid state.

8. The composition of claim 7, wherein the composition cures into a solid state at room temperature about 20 minutes to about 30 minutes after formulation.

9. The composition of claim 1, wherein the composition in its cured state has a tensile strength of at least 40 MPa.

10. The composition of claim 1, wherein the composition in its cured state has a Modulus of Elasticity of at least 1,500 MPa.

11. The composition of claim 1, wherein the calcium carbonate is present in an amount ranging from about 25% to about 35% by weight of the composition.

12. The composition of claim 1, wherein the process further comprises the inclusion of a cross-linker.

13. The composition of claim 12, wherein the cross-linker is a trifunctional castor-oil based polyol.

14. The composition according claim 1, wherein the calcium carbonate is an osteoconductive component.

15. The composition according to claim 1, wherein the calcium carbonate contributes to the generation of the porosity in the composition.

16. The composition according to claim 1, wherein the calcium carbonate has a particle size distribution that enhances resorption of calcium or bone remodeling within the body of a mammal after implantation.

* * * * *

UNITED STATES PATENT AND TRADEMARK OFFICE
CERTIFICATE OF CORRECTION

| | | |
|---|---|---|
| PATENT NO. | : 7,964,207 B2 | Page 1 of 1 |
| APPLICATION NO. | : 11/089489 | |
| DATED | : June 21, 2011 | |
| INVENTOR(S) | : Richard Joseph Deslauriers | |

It is certified that error appears in the above-identified patent and that said Letters Patent is hereby corrected as shown below:

On the Title Page, Item (54) Title, please delete "METHOD" and insert --METHODS-- therefor;

Column 1, Title, please delete "METHOD" and insert --METHODS-- therefor;

Column 60, line 51 (Claim 14), please delete "according" and insert --according to-- therefor.

Signed and Sealed this
Eighteenth Day of October, 2011

David J. Kappos
*Director of the United States Patent and Trademark Office*